(12) United States Patent
Nett et al.

(10) Patent No.: US 10,787,500 B2
(45) Date of Patent: Sep. 29, 2020

(54) METHODS FOR PURIFYING HETERODIMERIC MULTISPECIFIC ANTIBODIES FROM PARENTAL HOMODIMERIC ANTIBODY SPECIES

(71) Applicant: Adimab, LLC, Lebanon, NH (US)

(72) Inventors: Juergen Hermann Nett, Lebanon, NH (US); K. Dane Wittrup, Lebanon, NH (US); Maximiliano Vasquez, Lebanon, NH (US)

(73) Assignee: Adimab, LLC, Lebanon, NH (US)

( * ) Notice: Subject to any disclaimer, the term of this patent is extended or adjusted under 35 U.S.C. 154(b) by 216 days.

(21) Appl. No.: 15/565,494

(22) PCT Filed: Apr. 8, 2016

(86) PCT No.: PCT/US2016/026620
§ 371 (c)(1),
(2) Date: Oct. 10, 2017

(87) PCT Pub. No.: WO2016/164708
PCT Pub. Date: Oct. 13, 2016

(65) Prior Publication Data
US 2018/0079797 A1    Mar. 22, 2018

Related U.S. Application Data

(60) Provisional application No. 62/249,180, filed on Oct. 30, 2015, provisional application No. 62/146,116, filed on Apr. 10, 2015.

(51) Int. Cl.
| | | |
|---|---|---|
| *B01D 15/16* | (2006.01) | |
| *B01J 39/26* | (2006.01) | |
| *B01J 41/20* | (2006.01) | |
| *B01D 15/36* | (2006.01) | |
| *B01D 15/38* | (2006.01) | |
| *C07K 16/00* | (2006.01) | |
| *C07K 1/18* | (2006.01) | |

(52) U.S. Cl.
CPC ............ *C07K 16/00* (2013.01); *B01D 15/166* (2013.01); *B01D 15/168* (2013.01); *B01D 15/36* (2013.01); *B01D 15/362* (2013.01); *B01D 15/363* (2013.01); *B01D 15/3847* (2013.01); *B01J 39/26* (2013.01); *B01J 41/20* (2013.01); *C07K 1/18* (2013.01); *C07K 2317/21* (2013.01); *C07K 2317/31* (2013.01); *C07K 2317/515* (2013.01); *C07K 2317/52* (2013.01)

(58) Field of Classification Search
None
See application file for complete search history.

(56) References Cited

U.S. PATENT DOCUMENTS

| | | |
|---|---|---|
| 5,731,168 A | 3/1998 | Carter et al. |
| 5,807,706 A | 9/1998 | Carter et al. |
| 5,821,333 A | 10/1998 | Carter et al. |
| 7,642,228 B2 | 1/2010 | Carter et al. |
| 7,695,936 B2 | 4/2010 | Carter et al. |
| 2009/0263392 A1 | 10/2009 | Igawa et al. |
| 2009/0311253 A1 | 12/2009 | Ghayur et al. |
| 2010/0047834 A1 | 2/2010 | Ikeda et al. |
| 2011/0287009 A1* | 11/2011 | Scheer ............... C07K 16/244 424/136.1 |
| 2013/0017200 A1 | 1/2013 | Scheer et al. |
| 2014/0303356 A1 | 10/2014 | Gramer et al. |

FOREIGN PATENT DOCUMENTS

| | | |
|---|---|---|
| EP | 1876236 A1 | 1/2008 |
| WO | WO-2006/020258 A2 | 2/2006 |
| WO | WO-2007/114325 A1 | 10/2007 |
| WO | WO-2009/032782 A2 | 3/2009 |
| WO | WO-2013/136186 A2 | 9/2013 |
| WO | WO-2014/078729 A1 | 5/2014 |
| WO | WO-2016/164708 A1 | 10/2016 |

OTHER PUBLICATIONS

Schubert et al. "Comparison of ceramic hydroxy- and fluoroapatite versus Protein A/G-based resins in the isolation of a recombinant human antibody from cell culture supernatant" J. Chromatography A, 1142 (2007) 106-113 (Year: 2007).*
International Search Report for PCT/US2016/026620, 4 pages (dated Jul. 15, 2016).
Written Opinion for PCT/US2016/026620, 8 pages (dated Jul. 15, 2016).
Chames, P. et al., Therapeutic antibodies: successes, limitations and hopes for the future, Br J Pharmacol, 157(2):220-33 (2009).
Gramer, J. et al., Production of stable bispecific IgG1 by controlled Fab-arm exchange: scalability from bench to large-scale manufacturing by application of standard approaches, MAbs, 5(6):962-73 (2013).
Hall, T. et al., Alkaline cation-exchange chromatography for the reduction of aggregate and a mis-formed disulfide variant in a bispecific antibody purification process, Journal of Chromatography, 978:pp. 1-8 (2015).
Hefti, M. et al., A novel purification method for histidine-tagged proteins containing a thrombin cleavage site, Anal Biochem, 295(2):180-5 (2001).

(Continued)

*Primary Examiner* — Daniel E Kolker
*Assistant Examiner* — James L Rogers
(74) *Attorney, Agent, or Firm* — Robin L. Teskin; Baker, Donelson, Bearman, Caldwell & Berkowitz PC

(57) ABSTRACT

Methods for purifying multispecific antibodies on interest (MAIs) that co-engage at least two different antigens or epitopes (also referred to as targets, used interchangeably throughout), from compositions comprising the MAI and parental homodimeric antibody species are provided, as well as reagents which may be used to practice such methods.

22 Claims, 45 Drawing Sheets

Specification includes a Sequence Listing.

(56) References Cited

OTHER PUBLICATIONS

Lu, D. et al., A fully human recombinant IgG-like bispecific antibody to both the epidermal growth factor receptor and the insulin-like growth factor receptor for enhanced antitumor activity, J Biol Chem, 280(20):19665-72 (2005).
Michaelson, J. et al., Anti-tumor activity of stability-engineered IgG-like bispecific antibodies targeting TRAIL-R2 and LTβR, MAbs, 1(2):128-41 (2009).
Shen, J. et al., Single variable domain-IgG fusion. A novel recombinant approach to Fc domain-containing bispecific antibodies, J Biol Chem, 281(16):10706-14 (2006).
Wu, C. et al., Simultaneous targeting of multiple disease mediators by a dual-variable-domain immunoglobulin, Nat Biotechnol, 25(11):1290-7 (2007).
Zuo, Z. et al., an efficient route to the production of an IgG-like bispecific antibody, Protein Eng, 13(5):361-7 (2000).

\* cited by examiner

| Buffering Agent (or salt) | pKa | Final Concentration of eluant component (mM) |
|---|---|---|
| CAPS | 10.50 | 15.6 |
| CHES | 9.39 | 9.4 |
| TAPS | 8.44 | 4.6 |
| HEPPSO | 8.04 | 9.9 |
| MOPSO | 6.90 | 8.7 |
| MES | 6.10 | 11.0 |
| Acetate (acetic acid) | 4.76 | 13.0 |
| Formate (formic acid) | 3.75 | 9.9 |
| NaCl (salt) | - | 10.0 |

FIG. 1A

| Buffering Agent (or salt) | pKa1 | pKa2 | Final Concentration of eluant component (mM) |
|---|---|---|---|
| methylamine | 10.75 | - | 9.8 |
| 1,2-ethanediamine | 9.93 | 6.99 | 9.1 |
| 1-methylpiperazine | 9.16 | 4.78 | 6.4 |
| 1,4-dimethylpiperazine | 8.15 | 4.04 | 13.7 |
| bis-tris | 6.22 | - | 5.8 |
| hydroxylamine | 5.67 | | 7.7 |
| Sodium Chloride | | | 10 mM |

FIG. 1B

| Resin | Type | Matrix | Particle Size, um | Functional Group | 1mL CV Geometry (ID X H), mm | Process Scale |
|---|---|---|---|---|---|---|
| Mono S<br>GE Healthcare Life Sciences<br>17-5168-01 | Strong Cation Exchanger | polystyrene / divinyl benzene | 10 | methyl sulfonate | 5 X 50 | N |
| Mono Q<br>GE Healthcare Life Sciences<br>17-5166-01 | Strong Anion Exchanger | polystyrene / divinyl benzene | 10 | quaternary ammonium | 5 X 50 | N |
| Capto S<br>GE Healthcare Life Sciences<br>28-9343-88 (sampler pack) | Strong Cation Exchanger | highly cross-linked agarose with dextran surface extender | 90 | sulfonate group | 7 X 25 | Y |
| Capto MMC<br>GE Healthcare Life Sciences<br>28-9343-88 (sampler pack) | Multimodal Weak Cation Exchanger | highly cross-linked agarose | 75 | multimodal ligand | 7 X 25 | Y |
| SP Sepharose FF<br>GE Healthcare Life Sciences<br>17-5054-01 | Strong Cation Exchanger | 6% cross-linked agarose | 90 | sulfopropyl ligand | 7 X 25 | Y |
| UNOsphere S<br>Bio-Rad<br>732-4650 (sampler pack) | Strong Cation Exchanger | UNOsphere (polymeric beads) | 80 | sulfonic acid ligand | 5.6 X 40 | Y |
| Macro-Prep High S<br>Bio-Rad<br>732-4650 (sampler pack) | Strong Cation Exchanger | methacrylate copolymer bead | 50 | sulfonic acid ligand | 5.6 X 40 | Y |
| Poros GoPure XS<br>Life Technologies<br>4481317 | Strong Cation Exchanger | polystyrene / divinyl benzene | 50 | sulfopropyl | 5 X 50 | Y |
| Poros GoPure HS<br>Life Technologies<br>4481316 | Strong Cation Exchanger | polystyrene / divinyl benzene | 50 | sulfopropyl | 5 X 50 | Y |

FIG. 26A

| Resin | Type | Matrix | Particle Size, um | Functional Group | 1mL CV Geometry (ID X H), mm | Process Scale |
|---|---|---|---|---|---|---|
| Capto SP ImpRes GE Healthcare Life Sciences 17-5468-51 | Strong Cation Exchanger | high flow agarose | 40 | sulfonate | 7 X 25 | Y |
| SP Sepharose HP GE Healthcare Life Sciences 17-1151-01 | Strong Cation Exchanger | 6% highly cross linked spherical agarose | 34 | sulfopropyl | 7 X 2.5 | Y |
| SOURCE 30S GE Healthcare Life Sciences 17-1273-01 | Strong Cation Exchanger | polystyrene / divinyl benzene | 30 | sulfonate | 5 X 50 | Y |
| Poros XQ Life Technologies A25812 | Strong Anion Exchanger | crosslinked poly[styrene divinylbenzene] | 50 | proprietary quaternary amine | 5 X 50 | Y |
| Poros HQ Life Technologies 4481315 | Strong Anion Exchanger | crosslinked poly[styrene divinylbenzene] | 50 | quaternized polyethyleneimine | 5 X 50 | Y |
| Capto Q ImpRes GE Healthcare Life Sciences 17-5470-51 | Strong Anion Exchanger | high flow agarose | 40 | quaternary amine | 7 X 25 | Y |
| Q HP GE Healthcare Life Sciences 17-1153-01 | Strong Anion Exchanger | cross linked agarose | 34 | quaternary amine | 7 X 25 | Y |
| SOURCE 30Q GE Healthcare Life Sciences 17-1275-01 | Strong Anion Exchanger | polystyrene / divinyl benzene | 30 | quaternary ammonium | 5 X 50 | Y |

FIG. 26B

METHODS FOR PURIFYING HETERODIMERIC MULTISPECIFIC ANTIBODIES FROM PARENTAL HOMODIMERIC ANTIBODY SPECIES

CROSS REFERENCE TO RELATED APPLICATIONS

The present application is the National Stage of International Application No. PCT/US16/26620, filed Apr. 8, 2016, which claims the benefit of U.S. Provisional Patent Application Ser. No. 62/146,116, filed Apr. 10, 2015, and U.S. Provisional Patent Application Ser. No. 62/249,180, filed Oct. 30, 2015, the entire contents of which are incorporated herein by reference.

SEQUENCE LISTING

The instant application contains a Sequence Listing which has been submitted electronically in ASCII format and is hereby incorporated by reference in its entirety. The ASCII copy, created on Apr. 7, 2016, is named "2009186_0170_SL.TXT" and is 145,072 bytes in size.

FIELD OF THE INVENTION

The present invention relates, inter alia, methods of separating and purifying multispecific antibodies from homodimeric species, such as parental homodimeric species, and reagents useful for carrying out the methods.

BACKGROUND OF THE INVENTION

All references cited herein, including patents, patent applications, and non-patent publications referenced throughout are hereby expressly incorporated by reference in their entireties for all purposes.

Antibodies and antibody-based molecules represent attractive candidates as diagnostic tools and therapeutics. To date more than 30 therapeutic monoclonal antibodies have been approved for and successfully applied in diverse indication areas including cancer, organ transplantation, autoimmune and inflammatory disorders, infectious disease, and cardiovascular disease.

However, the majority of these antibodies are monospecific antibodies, which recognize a single epitope and can be selected to either activate or repress the activity of a target molecule through this single epitope. Many physiological responses, however, require crosslinking, "cross-talk" or co-engagement of or between two or more different proteins or protein subunits to be triggered. An important example is the activation of heteromeric, cell-surface receptor complexes. For these receptor complexes, activation is normally achieved through ligand interaction with multiple domains on different proteins resulting in proximity-associated activation of one or both receptor components.

Multispecific antibodies, such as bispecific antibodies, represent attractive molecules as a means to address and therapeutically exploit some of these more complex physiological processes, and disease states associated therewith, as they can co-engage multiple epitopes or antigens.

One approach to generating bispecific antibodies has to use antibody fragments to make bispecifics. Because the considerable diversity of the antibody variable region (Fv) makes it possible to produce an Fv that recognizes virtually any antigen or epitope, the typical approach to fragment-based multispecifics generation is the introduction of new variable regions, in the context of, e.g., single-chain variable fragments (scFvs), tandem scFvs, Fabs, diabodies, chain diabodies, $Fab_2$ bispecifics and the like; see, e.g., Chames et al., Br. J. Pharmacol, Vol. 157(2):220-233 (2009)), or non-native formats including such fragments. Because such fragments lack the complex quaternary structure of a full length antibody, variable light and heavy chains can be linked in single genetic constructs. While these formats can often be expressed at high levels in bacteria and may have favorable penetration benefits due to their small size, they clear rapidly in vivo and can present manufacturing obstacles related to their production and stability. A principal cause of these drawbacks is that antibody fragments typically lack the constant region of the antibody with its associated functional properties, including larger size, high stability, and binding to various Fc receptors and ligands that maintain long half-life in serum (i.e. the neonatal Fc receptor FcRn) or serve as binding sites for purification (i.e. protein A and protein G).

More recent work has attempted to address the shortcomings of fragment-based bispecifics by engineering dual binding into full length antibody-like formats (Wu et al., 2007, Nature Biotechnology 25[11]:1290-1297; U.S. Ser. No. 12/477,711 (published as US 2009/0311253); Michaelson et al., 2009, mAbs 1[2]:128-141; PCT/US2008/074693 (published as WO 2009/032782); Zuo et al., 2000, Protein Engineering 13[5]:361-367; U.S. Ser. No. 09/865,198; Shen et al., 2006, J Biol Chem 281[16]:10706-10714; Lu et al., 2005, J Biol Chem 280[20]:19665-19672; PCT/US2005/025472 (published as WO 2006/020258).

Still others have attempted to generate bispecific antibodies that are in the native IgG format (i.e., contain two heavy chains and two light chains that interact in the same orientation as found in native (i.e., "wild-type") IgGs. However, the most straightforward way of producing a bispecific antibody (expressing two antibodies in a single cell) gives rise to multiple species in addition to the species of interest, because the respective heavy chains form both homo- and heterodimers, and the two respective light chains can pair with either heavy chain.

Significant effort has been devoted to addressing this heterogeneity issue, either by engineering mutations into either one or more of the immunoglobulin chains in order to drive the desired heterodimerization between chains, or to enable purification schemes that facilitate separation of the desired heterodimeric antibody from other undesired antibody species.

U.S. Pat. Nos. 5,731,168, 5,807,706, 5,821,333, 7,642,228, and 7,695,936, and other equivalents describe the generation of heteromultimeric antibodies comprising two different heavy chains having different antigen specificities and a common light chain, wherein each heavy chain has been modified to order to engineer heterodimer interaction interfaces into the Fc regions. The modifications comprise engineering targeted mutations into the CH3 domain of each heavy chain, wherein in one heavy chain a cavity is generated and in the other heavy chain a complementary protuberance is generated, such that the protuberance engages and inserts within the cavity, thus driving heterodimerization of the two heavy chains.

WO2013/136186 describes the generation of heteromultimeric antibodies comprising two different heavy chains having different antigen specificities, wherein at least one heavy chain has been modified in order reduce or eliminate binding of the CH1 region of the at least one heavy chain to the CaptureSelect® IgG-CH1 affinity reagent. However, the end result of this approach is the generation of antibodies containing non-native amino acid sequences, thus greatly increasing the likelihood of generating antibodies possessing a heightened risk of increased immunogenicity, undesirably altered Fc effector function, and other untoward liabilities, relative to antibodies that do not contain such non-native amino acid sequences.

WO 2007/114325 and corresponding application publication No. US 2009/0263392 teach the purification of certain bispecific antibodies comprising common light chains that have been modified by engineering specific amino acid mutations in each heavy chain constant region of the antibodies for the purpose of increasing the difference in the isoelectric point (pI) between each heavy chain. The engineered heterodimeric bispecific antibodies are then subjected to ion exchange chromatography and separated from homodimeric parental species on the basis of the enhancement in the pI difference resultant from the engineered, pI difference-increasing mutations in the two heavy chains in the heterodimeric species. However, as with the methods disclosed in WO 2013/136186, as the methods disclosed in WO 2007/114325 and US 2009/0263392 require the introduction of non-native amino acid sequence into the Fc region, the end result being the generation of antibodies possessing a heightened risk of increased immunogenicity, undesirably altered Fc effector function, and other untoward liabilities, relative to antibodies that do not contain such non-native amino acid sequences.

WO 2014/078729 teaches that proteins, such as monoclonal antibodies have mostly charged and polar amino acids at the surface in aqueous environments, and that the surface residues can undergo multiple chemical and enzymatic modifications, leading to heterogeneous mixtures of protein variant contaminants characterized by differences on their electrostatic surface. The reference further teaches methods of analyzing single antibody species for the presence of such contaminating variants of the species, such as charge variants, degradation products, etc., by using pH and ionic strength gradients in ion exchange chromatography procedures (see Examples therein). The elution buffers used in the exemplified methods include piperazine, Tris, and imidazole. The reference does not demonstrate the purification of a multispecific heavy chain-heterodimeric antibody of interest (MAI) from a composition comprising the MAI and each of the two parental heavy chain-homodimeric antibody species from which the heavy chains of the MAI are derived. Additionally, Hefti et al., Anal Biochem., Vol. 295(2), pages 180-185 (2001) teach that the presence of imidazole in protein compositions often results in the generation of protein aggregates, and thus potentially complicating any chromatographic process in which imidazole is included in either a loading or an elution buffer when trying to separate or purify individual antibody species from a composition comprising multiple antibody species.

Gramer et al., (*mAbs*, Vol. 5(6), pages 962-973 (2013)) report the production of stable bispecific antibodies in the IgG1 format by controlled Fab-arm exchange. The method involves introduction of mutations into the CH3 regions of parental heavy chains, which drive heterodimerization of the two different heavy chains after reduction of the two parental species (described below); expression of the mutated parental homodimeric monospecific antibodies; purification of the parental homodimeric antibodies; subjecting the expressed parental homodimeric antibody samples to appropriate reducing conditions, such that inter-heavy chain disulfide bonds are reduced while maintaining disulfide linkage between heavy chains and light chains; subjecting the reduced antibodies to (re)-oxidizing conditions in order to facilitate disulfide linkage formation between the two different parental heavy chains; separation of the heterodimeric antibody species from residual parental homodimeric species (and other impurities). Gramer also teach that "because the nature of any homodimeric pair may vary quite significantly, cationic exchange chromatography is not likely to be generally applicable" to the separation or purification of a desired heterodimeric species from parental homodimeric species.

There remains, therefore, a need for the provision of methods for preparing and/or purifying multispecific antibodies of interest (MAIs) from compositions comprising an MAI and parental homodimeric antibody species), which do not require engineering the MAI (or the parental antibodies) in order to facilitate either the formation of the purification of the heterodimeric antibodies of interest from the parental homodimeric species. This need is particularly great for cases in which the multispecific antibodies of interest are to be in native (i.e., "wild-type") format, such as a native IgG isotype format (e.g., IgG1, IgG2, IgG3, IgG4, and hybrids thereof).

SUMMARY OF THE INVENTION

The present invention provides, inter alia, methods of purifying multispecific antibodies of interest (MAIs) (referred to interchangeably throughout as "multispecific antibodies", "heavy chain-heterodimeric antibodies", "multispecific antibodies of interest", "multispecific antibody analogs", "analogs", or "antibody analogs"), which advantageously co-engage at least two different antigens or epitopes (also referred to "targets", used interchangeably throughout) comprising a heterodimer comprising a first polypeptide comprising a first heavy chain (HC) variable region and a second polypeptide comprising a second HC variable region, from compositions comprising the MAI and at least two corresponding parental homodimeric antibody species. In some embodiments a first such parental homodimeric antibody species comprises one copy of the first polypeptide comprising the first HC variable region and a second such parental homodimeric antibody species comprises one copy of the second polypeptide comprising the second HC variable region. In some embodiments, a first such parental homodimeric antibody species comprises two copies of the first polypeptide comprising the first HC variable region and a second such parental homodimeric antibody species comprises two copies of the second polypeptide comprising the second HC variable region. In some embodiments, a first such parental homodimeric antibody species comprises more than two copies (i.e., three or more copies) of the first polypeptide comprising the first HC variable region and a second such parental homodimeric antibody species comprises more than two copies (i.e., three or more copies) of the second polypeptide comprising the second HC variable region.

In certain embodiments which may be used alone or in combination with any other embodiments disclosed herein, the composition comprising the MAI and the at least two corresponding homodimeric species is expressed by a population of host cells, such as prokaryotic host cells or eukaryotic host cells; bacterial host cells; yeast host cells; mammalian host cells; insect host cells; *Pichia* yeast cells; *Saccharomyces cerevisiae* yeast host cells; and the like. In certain embodiments which may be used alone or in combination with any other embodiments disclosed herein, the composition comprising the MAI and the at least two corresponding homodimeric species is expressed by a population of host cells comprising such host cells that have been transformed with nucleic acid encoding the at least two homodimeric species.

In certain embodiments which may be used alone or in combination with any other embodiments disclosed herein, the MAI comprises an antibody. In certain embodiments which may be used alone or in combination with any other embodiments disclosed herein, the MAI comprises an immunoglobulin. In certain embodiments which may be used alone or in combination with any other embodiments disclosed herein, the MAI comprises an IgG. In certain embodiments which may be used alone or in combination with any other embodiments disclosed herein, the MAI comprises an Ig isotype hybrid. In certain embodiments which may be used alone or in combination with any other embodiments disclosed herein, the MAI comprises an IgG1/IgG2 hybrid, and IgG1/IgG3 hybrid, or an IgG1/IgG4 hybrid. In certain embodiments which may be used alone or in combination with any other embodiments disclosed herein, the MAI comprises an IgG1/IgG4 hybrid.

In certain embodiments which may be used alone or in combination with any other embodiments disclosed herein, the invention provides a method of purifying a multispecific antibody of interest (MAI), wherein the MAI comprises a heterodimer comprising a first heavy chain polypeptide comprising a first heavy chain (HC) variable region and a second heavy chain polypeptide comprising a second HC variable region, wherein the first and the second variable regions have different antigen specificities and different isoelectric points, the method comprising:

i) obtaining a composition comprising the MAI, a first parental homodimeric antibody species comprising either at least one copy of the first heavy chain polypeptide or at least two copies of the first heavy chain polypeptide, and a second parental homodimeric antibody species comprising either at least one copy of the second heavy chain polypeptide or at least two copies of the second heavy chain polypeptide; and ii) performing chromatography whereby the MAI is separated from the first and the second parental homodimeric antibody species;

thereby purifying the MAI. In certain embodiments, which may be used alone or in combination with any other embodiments disclosed herein, the performing step ii) comprises:

contacting the composition with a chromatographic material forming a composition-chromatographic material complex; and performing an elution step wherein the chromatographic material-composition complex is contacted with an sample of eluant that is capable of eluting the MAI and parental homodimeric antibody species in a pH-dependent manner. In certain embodiments, the different isoelectric points are actual isoelectric points. In certain other embodiments, the different isoelectric points are calculated isoelectric points.

In certain embodiments, which may be used alone or in combination with any other embodiments disclosed herein, the eluant comprises at least two buffering agents that each has a different negative log acid dissociation constant (pKa).

In certain embodiments, which may be used alone or in combination with any other embodiments disclosed herein, the inventive methods further comprise preparing or equilibrating either:

the composition; or the composition-chromatographic material complex;

in a first sample of the eluant at a desired starting pH prior performing the elution step.

In certain embodiments, which may be used alone or in combination with any other embodiments disclosed herein, the inventive methods further comprise flowing a volume of a second sample of the eluant that is prepared at a desired ending pH through the chromatographic material-composition complex.

In certain embodiments, which may be used alone or in combination with any other embodiments disclosed herein, a pH gradient is generated as the eluant flows through the chromatographic material-composition complex.

In certain embodiments, which may be used alone or in combination with any other embodiments disclosed herein, the inventive methods comprise a pH gradient that is generated as the eluant flows through the chromatographic material-composition complex, wherein the pH gradient comprises a step pH gradient phase.

In certain embodiments, which may be used alone or in combination with any other embodiments disclosed herein, a pH gradient is generated as the eluant flows through the chromatographic material-composition complex, wherein the pH gradient comprises a linear pH gradient phase.

In certain embodiments, which may be used alone or in combination with any other embodiments disclosed herein, a pH gradient is generated as the eluant flows through the chromatographic material-composition complex, wherein the pH gradient comprises a step pH gradient phase and linear pH gradient phase.

In certain embodiments, which may be used alone or in combination with any other embodiments disclosed herein, a pH gradient is generated as the eluant flows through the chromatographic material-composition complex, wherein the pH gradient each comprises two or more step pH gradient phases and a linear pH gradient phase.

In certain embodiments, which may be used alone or in combination with any other embodiments disclosed herein, the pH gradient comprises a step pH gradient phase prior to a linear pH gradient phase.

In certain embodiments, which may be used alone or in combination with any other embodiments disclosed herein, the pH gradient comprises a step pH gradient phase subsequent to a linear pH gradient phase.

In certain embodiments, which may be used alone or in combination with any other embodiments disclosed herein, the pH gradient comprises an essentially linear pH gradient phase.

In certain embodiments, which may be used alone or in combination with any other embodiments disclosed herein, the pH gradient is an essentially linear pH gradient phase.

In certain embodiments, which may be used alone or in combination with any other embodiments disclosed herein, the MAI, the first parental homodimeric antibody species, and the second parental homodimeric antibody species each elute from the chromatographic material in essentially distinguishable elution volumes.

In certain embodiments, which may be used alone or in combination with any other embodiments disclosed herein, the MAI, the first parental homodimeric antibody species, and the second parental homodimeric antibody species each elute from the chromatographic material in a pH-dependent manner.

In certain embodiments, which may be used alone or in combination with any other embodiments disclosed herein, the eluant comprises either:

at least two;
at least three;
at least four;
at least five;

at least six;
at least seven; or
eight;
of the following buffering agents: Ncyclohexyl-3-aminopropanesulfonic acid (CAPS), N-Cyclohexyl-2-aminoethanesulfonic acid (CHES), N-Tris(hydroxymethyl)methyl-3-aminopropanesulfonic acid (TAPS), N-(2-Hydroxyethyl)piperazine-N'-(2-hydroxypropanesulfonic acid) (HEPPSO), 3-morpholino-2-hydroxypropanesulfonic acid sodium salt, 3-(N-morpholinyl)-2-hydroxypropanesulfonic acid (MOPSO), 2-(N-morpholino)ethanesulfonic acid (MES), acetic acid, and formic acid; or
at least two;
at least three;
at least four;
at least five; or
at least six; of the following buffering agents: methylamine, 1,2-ethanediamine, 1-methylpiperazine, 1,4-dimethylpiperazine, 2-[Bis(2-hydroxyethyl)amino]-2-(hydroxymethyl)propane-1,3-diol (bis-tris), and hydroxylamine.

In certain embodiments, which may be used alone or in combination with any other embodiments disclosed herein, the eluant comprises either:
(i) CAPS, CHES, TAPS, HEPPSO, MOPSO, MES, acetic acid, formic acid, and a salt; or
(ii) methylamine, 1,2-ethanediamine, 1-methylpiperazine, 1,4-dimethylpiperazine, 2-[Bis(2-hydroxyethyl)amino]-2-(hydroxymethyl)propane-1,3-diol (bis-tris), and hydroxylamine and optionally at least one salt.

In certain embodiments, which may be used alone or in combination with any other embodiments disclosed herein, the eluant comprises:
at least two;
at least three;
at least four;
at least five;
at least six;
at least seven; or
eight;
of the following buffering agents: Ncyclohexyl-3-aminopropanesulfonic acid (CAPS), N-Cyclohexyl-2-aminoethanesulfonic acid (CHES), N-Tris(hydroxymethyl)methyl-3-aminopropanesulfonic acid (TAPS), N-(2-Hydroxyethyl)piperazine-N'-(2-hydroxypropanesulfonic acid) (HEPPSO), 3-morpholino-2-hydroxypropanesulfonic acid sodium salt, 3-(N-morpholinyl)-2-hydroxypropanesulfonic acid (MOPSO), 2-(N-morpholino)ethanesulfonic acid (MES), acetic acid, and formic acid;
with the proviso that the eluant does not include any of the following: imidazole; piperazine, tris(hydroxymethyl)aminomethane (TRIS).

In certain embodiments, which may be used alone or in combination with any other embodiments disclosed herein, the eluant consists essentially of either: (i) CAPS; CHES; TAPS; HEPPSO; MOPSO; MES; acetic acid; and formic acid; and optionally at least one salt. or
(ii) methylamine, 1,2-ethanediamine, 1-methylpiperazine, 1,4-dimethylpiperazine, 2-[Bis(2-hydroxyethyl)amino]-2-(hydroxymethyl)propane-1,3-diol (bis-tris), and hydroxylamine and optionally at least one salt.

In certain embodiments, which may be used alone or in combination with any other embodiments disclosed herein, the eluant consists of either:
(i) CAPS, CHES, TAPS, HEPPSO, MOPSO, MES, acetic acid, formic acid, and a salt; or
(ii) methylamine, 1,2-ethanediamine, 1-methylpiperazine, 1,4-dimethylpiperazine, 2-[Bis(2-hydroxyethyl)amino]-2-(hydroxymethyl)propane-1,3-diol (bis-tris), and hydroxylamine and optionally at least one salt.

In certain embodiments, which may be used alone or in combination with any other embodiments disclosed herein, the eluant comprises at least one salt selected from the group consisting of: NaCl, KCl, and $Na_2SO_4$.

In certain embodiments, which may be used alone or in combination with any other embodiments disclosed herein, each sample of the eluant comprises at least one salt at a concentration range selected from the group consisting of: 0 mM to about 100 mM; 0 mM to about 60 mM; 0 mM to about 50 mM; 0 mM to about 40 mM; 0 mM to about 30 mM; 0 mM to about 20 mM; 0 mM to about 10 mM; 0 mM to about 5 mM; about 10 mM to about 200 mM; about 10 mM to about 100 mM; about 10 mM to about 50 mM; about 10 mM to about 40 mM; about 10 mM to about 30 mM; about 10 mM to about 20 mM; about 20 mM to about 200 mM; about 20 mM to about 100 mM; about 20 mM to about 50 mM; about 20 mM to about 30 mM; about 30 mM to about 200 mM; about 30 mM to about 100 mM; and about 30 mM to about 50 mM; and about 5 mM to about 15 mM.

In certain embodiments, which may be used alone or in combination with any other embodiments disclosed herein, each sample of the eluant comprises at least one salt at a concentration of about 10 mM.

In certain embodiments, which may be used alone or in combination with any other embodiments disclosed herein, each sample of the eluant comprises NaCl at a concentration of about 10 mM.

In certain embodiments, which may be used alone or in combination with any other embodiments disclosed herein, the difference between the actual isoelectric point of a first heavy chain polypeptide derived from a first heavy chain parental homodimeric antibody species and the actual isoelectric point of the second polypeptide derived from a second heavy chain parental homodimeric antibody species is less than 7.0 pH units; less than 6.5 pH units; less than 6.0 pH units; less than 5.5 pH units; less than 5.0 pH units; less than 4.5 pH units; less than 4.0 units; less than 3.5 pH units; less than 2.5 pH units; less than 2.4 pH units; less than 2.3 pH units; less than 2.2 pH units; less than 2.1 pH units; less than 2.0 pH units; less than 1.9 pH units; less than 1.8 pH units; less than 1.7 pH units; less than 1.6 pH units; less than 1.5 pH units; less than 1.4 pH units; less than 1.3 pH units, less than 1.2 pH units; less than 1.1 pH units; less than 1.0 pH unit; less than 0.95 pH unit; less than 0.90 pH unit; less than 0.85 pH unit; less than 0.80 pH unit; less than 0.75 pH unit; less than 0.70 pH unit; less than 0.65 pH unit; less than 0.60 pH unit; less than 0.55 pH unit; less than 0.50 pH unit; less than 0.45 pH unit; less than 0.40 pH unit; less than 0.35 pH unit; less than 0.30 pH unit; less than 0.25 pH unit; less than 0.20 pH unit; less than 0.15 pH unit; less than 0.14 pH unit; less than 0.13 pH unit; less than 0.12 pH unit; less than 0.11 pH unit; less than 0.10 pH unit; less than 0.09 pH unit; less than 0.08 pH unit; less than 0.07 pH unit; less than 0.06 pH unit less than 0.04 pH unit; less than 0.03 pH unit; less than 0.025 pH unit; less than 0.02 pH unit; or pH values that are between any of the preceding values.

In certain embodiments, the difference between: the actual isoelectric point of a first antibody, such as a first immunoglobulin, first IgG, or first parental homodimeric antibody species; and the actual isoelectric point of a second antibody, such as a second immunoglobulin, second IgG, or second parental homodimeric antibody species; is less than 7.0 pH units; less than 6.5 pH units; less than 6.0 pH units;

less than 5.5 pH units; less than 5.0 pH units; less than 4.5 pH units; less than 4.0 units; less than 3.5 pH units; less than 2.5 pH units; less than 2.4 pH units; less than 2.3 pH units; less than 2.2 pH units; less than 2.1 pH units; less than 2.0 pH units; less than 1.9 pH units; less than 1.8 pH units; less than 1.7 pH units; less than 1.6 pH units; less than 1.5 pH units; less than 1.4 pH units; less than 1.3 pH units, less than 1.2 pH units; less than 1.1 pH units; less than 1.0 pH unit; less than 0.95 pH unit; less than 0.90 pH unit; less than 0.85 pH unit; less than 0.80 pH unit; less than 0.75 pH unit; less than 0.70 pH unit; less than 0.65 pH unit; less than 0.60 pH unit; less than 0.55 pH unit; less than 0.50 pH unit; less than 0.45 pH unit; less than 0.40 pH unit; less than 0.35 pH unit; less than 0.30 pH unit; less than 0.25 pH unit; less than 0.20 pH unit; less than 0.15 pH unit; less than 0.14 pH unit; less than 0.13 pH unit; less than 0.12 pH unit; less than 0.11 pH unit; less than 0.10 pH unit; less than 0.09 pH unit; less than 0.08 pH unit; less than 0.07 pH unit; less than 0.06 pH unit less than 0.04 pH unit; less than 0.03 pH unit; less than 0.025 pH unit; less than 0.02 pH unit; or pH values that are between any of the preceding values.

In certain embodiments, the difference between the actual isoelectric point of a first parental homodimeric antibody species and the actual isoelectric point of a second parental homodimeric antibody species is less than 7.0 pH units; less than 6.5 pH units; less than 6.0 pH units; less than 5.5 pH units; less than 5.0 pH units; less than 4.5 pH units; less than 4.0 units; less than 3.5 pH units; less than 2.5 pH units; less than 2.4 pH units; less than 2.3 pH units; less than 2.2 pH units; less than 2.1 pH units; less than 2.0 pH units; less than 1.9 pH units; less than 1.8 pH units; less than 1.7 pH units; less than 1.6 pH units; less than 1.5 pH units; less than 1.4 pH units; less than 1.3 pH units, less than 1.2 pH units; less than 1.1 pH units; less than 1.0 pH unit; less than 0.95 pH unit; less than 0.90 pH unit; less than 0.85 pH unit; less than 0.80 pH unit; less than 0.75 pH unit; less than 0.70 pH unit; less than 0.65 pH unit; less than 0.60 pH unit; less than 0.55 pH unit; less than 0.50 pH unit; less than 0.45 pH unit; less than 0.40 pH unit; less than 0.35 pH unit; less than 0.30 pH unit; less than 0.25 pH unit; less than 0.20 pH unit; less than 0.15 pH unit; less than 0.14 pH unit; less than 0.13 pH unit; less than 0.12 pH unit; less than 0.11 pH unit; less than 0.10 pH unit; less than 0.09 pH unit; less than 0.08 pH unit; less than 0.07 pH unit; less than 0.06 pH unit less than 0.04 pH unit; less than 0.03 pH unit; less than 0.025 pH unit; less than 0.02 pH unit; or pH values that are between any of the preceding values.

In certain embodiments, which may be used alone or in combination with any other embodiments disclosed herein, the difference between the calculated isoelectric point of a first heavy chain polypeptide derived from a first heavy chain parental homodimeric antibody species and the calculated isoelectric point of the second polypeptide derived from a second heavy chain parental homodimeric antibody species is less than 7.0 pH units; less than 6.5 pH units; less than 6.0 pH units; less than 5.5 pH units; less than 5.0 pH units; less than 4.5 pH units; less than 4.0 units; less than 3.5 pH units; less than 2.5 pH units; less than 2.4 pH units; less than 2.3 pH units; less than 2.2 pH units; less than 2.1 pH units; less than 2.0 pH units; less than 1.9 pH units; less than 1.8 pH units; less than 1.7 pH units; less than 1.6 pH units; less than 1.5 pH units; less than 1.4 pH units; less than 1.3 pH units, less than 1.2 pH units; less than 1.1 pH units; less than 1.0 pH unit; less than 0.95 pH unit; less than 0.90 pH unit; less than 0.85 pH unit; less than 0.80 pH unit; less than 0.75 pH unit; 0.70 pH unit; less than 0.65 pH unit; less than 0.60 pH unit; less than 0.55 pH unit; less than 0.50 pH unit; less than 0.45 pH unit; less than 0.40 pH unit; less than 0.35 pH unit; less than 0.30 pH unit; less than 0.25 pH unit; less than 0.20 pH unit; less than 0.15 pH unit; less than 0.14 pH unit; less than 0.13 pH unit; less than 0.12 pH unit; less than 0.11 pH unit; less than 0.10 pH unit; less than 0.09 pH unit; less than 0.08 pH unit; less than 0.07 pH unit; less than 0.06 pH unit less than 0.04 pH unit; less than 0.03 pH unit; less than 0.025 pH unit; less than 0.02 pH unit; or pH values that are between any of the preceding values.

In certain embodiments, the difference between: the calculated isoelectric point of a first antibody, such as a first immunoglobulin, first IgG, or first parental homodimeric antibody species; and the calculated isoelectric point of a second antibody, such as a second immunoglobulin, second IgG, or second parental homodimeric antibody species; is less than 7.0 pH units; less than 6.5 pH units; less than 6.0 pH units; less than 5.5 pH units; less than 5.0 pH units; less than 4.5 pH units; less than 4.0 units; less than 3.5 pH units; less than 2.5 pH units; less than 2.4 pH units; less than 2.3 pH units; less than 2.2 pH units; less than 2.1 pH units; less than 2.0 pH units; less than 1.9 pH units; less than 1.8 pH units; less than 1.7 pH units; less than 1.6 pH units; less than 1.5 pH units; less than 1.4 pH units; less than 1.3 pH units, less than 1.2 pH units; less than 1.1 pH units; less than 1.0 pH unit; less than 0.95 pH unit; less than 0.90 pH unit; less than 0.85 pH unit; less than 0.80 pH unit; less than 0.75 pH unit; less than 0.70 pH unit; less than 0.65 pH unit; less than 0.60 pH unit; less than 0.55 pH unit; less than 0.50 pH unit; less than 0.45 pH unit; less than 0.40 pH unit; less than 0.35 pH unit; less than 0.30 pH unit; less than 0.25 pH unit; less than 0.20 pH unit; less than 0.15 pH unit; less than 0.14 pH unit; less than 0.13 pH unit; less than 0.12 pH unit; less than 0.11 pH unit; less than 0.10 pH unit; less than 0.09 pH unit; less than 0.08 pH unit; less than 0.07 pH unit; less than 0.06 pH unit less than 0.04 pH unit; less than 0.03 pH unit; less than 0.025 pH unit; less than 0.02 pH unit; or pH values that are between any of the preceding values.

In certain embodiments, the difference between the calculated isoelectric point of a first parental homodimeric antibody species and the calculated isoelectric point of a second parental homodimeric antibody species is less than 7.0 pH units; less than 6.5 pH units; less than 6.0 pH units; less than 5.5 pH units; less than 5.0 pH units; less than 4.5 pH units; less than 4.0 units; less than 3.5 pH units; less than 2.5 pH units; less than 2.4 pH units; less than 2.3 pH units; less than 2.2 pH units; less than 2.1 pH units; less than 2.0 pH units; less than 1.9 pH units; less than 1.8 pH units; less than 1.7 pH units; less than 1.6 pH units; less than 1.5 pH units; less than 1.4 pH units; less than 1.3 pH units, less than 1.2 pH units; less than 1.1 pH units; less than 1.0 pH unit; less than 0.95 pH unit; less than 0.90 pH unit; less than 0.85 pH unit; less than 0.80 pH unit; less than 0.75 pH unit; less than 0.70 pH unit; less than 0.65 pH unit; less than 0.60 pH unit; less than 0.55 pH unit; less than 0.50 pH unit; less than 0.45 pH unit; less than 0.40 pH unit; less than 0.35 pH unit; less than 0.30 pH unit; less than 0.25 pH unit; less than 0.20 pH unit; less than 0.15 pH unit; less than 0.14 pH unit; less than 0.13 pH unit; less than 0.12 pH unit; less than 0.11 pH unit; less than 0.10 pH unit; less than 0.09 pH unit; less than 0.08 pH unit; less than 0.07 pH unit; less than 0.06 pH unit less than 0.04 pH unit; less than 0.03 pH unit; less than 0.025 pH unit; less than 0.02 pH unit; or pH values that are between any of the preceding values.

In certain embodiments, which may be used alone or in combination with any other embodiments disclosed herein, the desired starting pH is less than 9.0; less than 8.5; less than 8.0; less than 7.5; less than 7.0; less than 6.5; less than 6.0; less than 5.5; less than 5.0; less than 4.5; less than 4.0; less than 3.5; or less than 3.0; or a pH values that is between any of the preceding values.

In certain embodiments, which may be used alone or in combination with any other embodiments disclosed herein, the desired ending pH is more than 7.0; more than 7.5; more than 8.0; more than 8.5; more than 9.0; more than 9.5; more than 10.0; more than 10.5; or more than 11.0; more than 11.5; more than 12.0; more than 12.5; more than 13.0; more than 13.5; or a pH values that is between any of the preceding values.

In certain embodiments, which may be used alone or in combination with any other embodiments disclosed herein, the eluant comprises at least two buffering agents and wherein the acid dissociation constant (pKa) of each buffering agent is between about 3 and 11.

In certain embodiments, which may be used alone or in combination with any other embodiments disclosed herein, the eluant comprises at least two buffering agents wherein the acid dissociation constant (pKa) of each buffering agent is in a range selected from the group consisting of: about 3.25 to about 3.85; about 4.5 to about 4.85; about 6.0 to about 6.45; about 6.60 to about 7.0; about 7.5 to about 8.15; about 8.35 to about 8.55; about 9.25 to about 9.65; and about 10.00 to about 11.5.

In certain embodiments, which may be used alone or in combination with any other embodiments disclosed herein, the eluant comprises at least two buffering agents wherein the acid dissociation constant (pKa) of each buffering agent is in a different range that is selected from the group consisting of: about 3.25 to about 3.85; about 4.5 to about 4.85; about 6.0 to about 6.45; about 6.60 to about 7.0; about 7.5 to about 8.15; about 8.35 to about 8.55; about 9.25 to about 9.65; and about 10.00 to about 11.5.

In certain embodiments, which may be used alone or in combination with any other embodiments disclosed herein, the eluant comprises at least two buffering agents wherein the acid dissociation constant (pKa) of each buffering agent is selected from the group consisting of about 3.75; about 4.76; about 6.10; about 6.90; about 8.04; about 8.44; about 9.39; and about 10.50.

In certain embodiments, which may be used alone or in combination with any other embodiments disclosed herein, the MAI further comprises a third polypeptide comprising a first light chain variable region.

In certain embodiments, which may be used alone or in combination with any other embodiments disclosed herein, the MAI further comprises a third polypeptide and a fourth polypeptide, wherein each of the third polypeptide and the fourth polypeptide comprises a second light chain variable region.

In certain embodiments, which may be used alone or in combination with any other embodiments disclosed herein, the first light chain variable region and the second light chain variable region are identical.

In certain embodiments, which may be used alone or in combination with any other embodiments disclosed herein, the third polypeptide and the fourth polypeptide are identical.

In certain embodiments, which may be used alone or in combination with any other embodiments disclosed herein, the first polypeptide and the second polypeptide each further comprise an Fc region.

In certain embodiments, which may be used alone or in combination with any other embodiments disclosed herein, the first polypeptide and the second polypeptide each further comprise a wild-type Fc region.

In certain embodiments, which may be used alone or in combination with any other embodiments disclosed herein, the first polypeptide and the second polypeptide each further comprise an IgG1 isotype Fc region, an IgG3 isotype Fc region, an IgG3 isotype Fc region, or an IgG4 isotype Fc region.

In certain embodiments, which may be used alone or in combination with any other embodiments disclosed herein, the first polypeptide and the second polypeptide each further comprise an IgG1 isotype Fc region.

In certain embodiments, which may be used alone or in combination with any other embodiments disclosed herein, the first polypeptide and the second polypeptide each further comprise an Fc region that has not been engineered in order to alter the pI of the first parental homodimeric antibody species, the second parental homodimeric species, or the MAI.

In certain embodiments, which may be used alone or in combination with any other embodiments disclosed herein, the first polypeptide and the second polypeptide each further comprise an IgG1 isotype Fc region that has not been engineered in order to alter the pI of the first parental homodimeric antibody species, the second parental homodimeric species, or the MAI.

In certain embodiments, which may be used alone or in combination with any other embodiments disclosed herein, either: the MAI is in a native antibody format; at least the first parental homodimeric antibody species is in a native format; at least the second parental homodimeric antibody species is in a native format; the first parental homodimeric antibody species is in a native format and the second parental homodimeric antibody species is in a native format; or the MAI is in a native antibody format, the first parental homodimeric antibody species is in a native format, and the second parental homodimeric antibody species is in a native format.

In certain embodiments, which may be used alone or in combination with any other embodiments disclosed herein, wherein either: the MAI; the first parental homodimeric antibody species; the second parental homodimeric antibody species; the first parental homodimeric antibody species and the second parental homodimeric antibody species; or the MAI, the first parental homodimeric antibody species and the second parental homodimeric antibody species; is in an IgG1 format, and IgG2 format, and IgG3 format, or an IgG4 format, or a hybrid format.

In certain embodiments, which may be used alone or in combination with any other embodiments disclosed herein, the chromatography performed at essentially the same ionic strength.

In certain embodiments, which may be used alone or in combination with any other embodiments disclosed herein, the ionic strength of the eluant remains essentially the same throughout the elution step.

In certain embodiments, which may be used alone or in combination with any other embodiments disclosed herein, the first sample of the eluant and the second sample of the eluant each have essentially the same ionic strength.

In certain embodiments, which may be used alone or in combination with any other embodiments disclosed herein, the chromatography is ion exchange chromatography.

In certain embodiments, which may be used alone or in combination with any other embodiments disclosed herein, the chromatography is selected from the group consisting of: cation exchange chromatography; anion exchange chromatography; multimodal chromatography; and mixed-mode chromatography.

In certain embodiments, which may be used alone or in combination with any other embodiments disclosed herein, the chromatographic material is selected from the group consisting of: an anion exchanger and a cation exchanger.

In certain embodiments, which may be used alone or in combination with any other embodiments disclosed herein, the chromatographic material is selected from the group consisting of: a strong cation exchanger; a strong anion exchanger; a multimodal exchanger; and a mixed-mode exchanger.

In certain embodiments, which may be used alone or in combination with any other embodiments disclosed herein, the chromatographic material is selected from the group consisting of a strong cation exchanger and a strong anion exchanger. In certain embodiments, which may be used alone or in combination with any other embodiments disclosed herein, the chromatography further comprises using a chromatographic material selected from the group consisting Mustang S, Sartobind S, S03 Monolith, S Ceramic HyperD, Poros XS, Poros HS50, Poros HS20, HS20, SPSFF, Porors GoPure HS, Poros GoPure XS, SP-Sepharose XL (SPXL), CM Sepharose Fast Flow, Capto Q ImpRes, Capto SP ImpRes, Capto S, Capto MMC, Fractogel Se HiCap, Fractogel S03, Fractogel COO, Poros HQ 50, Poros PI 50, Poros D, Mustang Q, Q Sepharose FF, SP Sepharose FF, UNOshere S, Macro-Prep High S, DEAE, Mono S, Mono S 5/50 GL, Mono Q, Mono Q 5/50 GL, Mono S 10/100 GL, SP Sepharose HP, Source 30S, Poros XQ, Poros HQ, Q HP, and Source 30Q.

In certain embodiments, which may be used alone or in combination with any other embodiments disclosed herein, the chromatography further comprises using a chromatographic material selected from Mono S, Mono S 5/50 GL, Mono Q, Mono Q 5/50 GL, SP Sepharose HP, Source 30S, Poros XQ, Poros HQ, Q HP, and Source 30Q, and Mono S 10/100 GL.

In certain embodiments, which may be used alone or in combination with any other embodiments disclosed herein, the chromatographic material is an ion exchange chromatographic material.

In certain embodiments, which may be used alone or in combination with any other embodiments disclosed herein, the chromatographic material is selected from the group consisting of: a cation exchange chromatographic material; an anion exchange chromatographic material; a multimodal chromatographic material; and a mixed-mode chromatographic material.

In certain embodiments, which may be used alone or in combination with any other embodiments disclosed herein, the ion exchange chromatographic material is selected from the group consisting of Mustang S, Sartobind S, S03 Monolith, S Ceramic HyperD, Poros XS, Poros HS50, Poros HS20, HS20, SPSFF, Porors GoPure HS, Poros GoPure XS, SP-Sepharose XL (SPXL), CM Sepharose Fast Flow, Capto Q ImpRes, Capto SP ImpRes, Capto S, Capto MMC, Fractogel Se HiCap, Fractogel S03, Fractogel COO, Poros HQ 50, Poros PI 50, Poros D, Mustang Q, Q Sepharose FF, SP Sepharose FF, UNOshere S, Macro-Prep High S, DEAE, Mono S, Mono S 5/50 GL, Mono Q, Mono Q 5/50 GL, Mono S 10/100 GL, SP Sepharose HP, Source 30S, Poros XQ, Poros HQ, Q HP, and Source 30Q.

In certain embodiments, which may be used alone or in combination with any other embodiments disclosed herein, the ion exchange chromatographic material selected from Mono S, Mono S 5/50 GL, Mono Q, Mono Q 5/50 GL, SP Sepharose HP, Source 30S, Poros XQ, Poros HQ, Q HP, and Source 30Q, and Mono S 10/100 GL.

In certain embodiments, which may be used alone or in combination with any other embodiments disclosed herein, either the first heavy chain variable region or the second heavy chain variable region is obtained by performing a first selection against a first antigen from a first library comprising unique heavy chain variable regions.

In certain embodiments, which may be used alone or in combination with any other embodiments disclosed herein, the first heavy chain variable region and the second heavy chain variable region is obtained by performing a first selection against a first antigen from a first library comprising unique heavy chain variable regions.

In certain embodiments, which may be used alone or in combination with any other embodiments disclosed herein, the first heavy chain variable region is obtained by performing a first selection against a first antigen from a first library comprising unique heavy chain variable regions and the second heavy chain variable region is obtained by performing a second selection against a second antigen from a second library comprising unique heavy chain variable regions.

In certain embodiments, which may be used alone or in combination with any other embodiments disclosed herein, the first heavy chain variable region is obtained by performing a first selection against a first antigen from a first library comprising unique heavy chain variable regions and the second heavy chain variable region is obtained by performing a second selection against a second antigen from a second library comprising unique heavy chain variable regions.

In certain embodiments, which may be used alone or in combination with any other embodiments disclosed herein, at least one of the libraries further comprises at least one light chain.

In certain embodiments, which may be used alone or in combination with any other embodiments disclosed herein, the composition is expressed by prokaryotic host cells or eukaryotic host cells, into which nucleic acid sequences encoding the first polypeptide and the second polypeptide have each been introduced.

In certain embodiments, which may be used alone or in combination with any other embodiments disclosed herein, the composition is expressed by prokaryotic host cells or eukaryotic host cells into which nucleic acid sequences encoding the first polypeptide and the second polypeptide have each been introduced.

In certain embodiments, which may be used alone or in combination with any other embodiments disclosed herein, the composition is expressed by prokaryotic host cells or eukaryotic host cells into which nucleic acid sequences encoding the first polypeptide, the second polypeptide, the third polypeptide, and the fourth polypeptide have each been introduced.

In certain embodiments, which may be used alone or in combination with any other embodiments disclosed herein, each encoded polypeptide is expressed by the host cells.

In certain embodiments, which may be used alone or in combination with any other embodiments disclosed herein, the composition is expressed by the host cells.

In certain embodiments, which may be used alone or in combination with any other embodiments disclosed herein, essentially each host cell has been transformed or transfected with the first polypeptide, the second polypeptide, the third polypeptide, and the fourth polypeptide.

In certain embodiments, which may be used alone or in combination with any other embodiments disclosed herein, essentially each host cell expresses the MAI, the first parental antibody species, and the second parental antibody species.

In certain embodiments, which may be used alone or in combination with any other embodiments disclosed herein, the host cells are selected from the group consisting of: eukaryotic cells; fungal cells; yeast cells; insect cells; mammalian cells; *Saccharomyces cerevisiae* cells; *Pichia pastoris* cells; mammalian cells; COS cells; human embryonic kidney (HEK) cells; and CHO cells.

In certain embodiments, which may be used alone or in combination with any other embodiments disclosed herein, the ion exchange eluant comprises a cation exchange eluant or an anion exchange eluant for use in separating an MAI from parental homodimeric species.

In certain embodiments, which may be used alone or in combination with any other embodiments disclosed herein, the invention provides an ion exchange eluant comprising CAPS, CHES, TAPS, HEPPSO, MOPSO, MES, acetic acid, formic acid, and a salt for use in separating an MAI from parental homodimeric species.

In certain embodiments, which may be used alone or in combination with any other embodiments disclosed herein, the invention provides an ion exchange eluant comprising CAPS, CHES, TAPS, HEPPSO, MOPSO, MES, acetic acid, formic acid, and NaCl for use in separating an MAI from parental homodimeric species.

In certain embodiments, which may be used alone or in combination with any other embodiments disclosed herein, the invention provides an ion exchange eluant comprising an anion exchange eluant for use in separating an MAI from parental homodimeric species.

In certain embodiments, which may be used alone or in combination with any other embodiments disclosed herein, the invention provides an anion exchange eluant comprising methylamine, 1,2-ethanediamine, 1-methylpiperazine, 1,4-dimethylpiperazine, 2-[Bis(2-hydroxyethyl)amino]-2-(hydroxymethyl)propane-1,3-diol (bis-tris), and hydroxylamine and optionally at least one salt for use in separating an MAI from parental homodimeric species.

In certain embodiments, which may be used alone or in combination with any other embodiments disclosed herein, the invention provides a cation exchange eluant comprising CAPS, CHES, TAPS, HEPPSO, MOPSO, MES, acetic acid, formic acid, and NaCl for use in separating an MAI from parental homodimeric species.

In certain embodiments, which may be used alone or in combination with any other embodiments disclosed herein, the invention provides an ion exchange eluant comprising an anion exchange eluant for use in separating an MAI from parental homodimeric species.

In certain embodiments, which may be used alone or in combination with any other embodiments disclosed herein, the cation exchange eluant does not include TRIS, piperazine, or imidazole.

In certain embodiments, which may be used alone or in combination with any other embodiments disclosed herein, the invention provides an ion exchange eluant consisting essentially of CAPS, CHES, TAPS, HEPPSO, MOPSO, MES, acetic acid, formic acid, and a salt.

In certain embodiments, which may be used alone or in combination with any other embodiments disclosed herein, the invention provides an ion exchange eluant consisting of CAPS, CHES, TAPS, HEPPSO, MOPSO, MES, acetic acid, formic acid, and a salt.

In certain embodiments, which may be used alone or in combination with any other embodiments disclosed herein, the salt is selected from the group consisting of NaCl, KCl, or $Na_2SO_4$.

In certain embodiments, which may be used alone or in combination with any other embodiments disclosed herein, the invention provides the ion exchange eluant according to any one of above, wherein the eluant is used for purifying an MAI from a composition comprising the MAI and parental homodimeric antibody species.

In certain embodiments, which may be used alone or in combination with any other embodiments disclosed herein, the eluant comprises at least one salt at a concentration range selected from the group consisting of: 0 mM to about 100 mM; 0 mM to about 60 mM; 0 mM to about 50 mM; 0 mM to about 40 mM; 0 mM to about 30 mM; 0 mM to about 20 mM; 0 mM to about 10 mM; 0 mM to about 5 mM; about 10 mM to about 200 mM; about 10 mM to about 100 mM; about 10 mM to about 50 mM; about 10 mM to about 40 mM; about 10 mM to about 30 mM; about 10 mM to about 20 mM; about 20 mM to about 200 mM; about 20 mM to about 100 mM; about 20 mM to about 50 mM; about 20 mM to about 30 mM; about 30 mM to about 200 mM; about 30 mM to about 100 mM; and about 30 mM to about 50 mM; and about 5 mM to about 15 mM.

In certain embodiments, which may be used alone or in combination with any other embodiments disclosed herein, each sample of the eluant comprises at least one salt at a concentration of about 10 mM.

In certain embodiments, which may be used alone or in combination with any other embodiments disclosed herein, the salt is NaCl.

In certain embodiments, which may be used alone or in combination with any other embodiments disclosed herein, each sample of the eluant comprises NaCl at a concentration of about 10 mM.

As the artisan will understand, any and all of the embodiments disclosed above and throughout may be practiced in any combination and, accordingly, all such combinations are contemplated, and are hereby disclosed and encompassed within the scope of the invention.

BRIEF DESCRIPTION OF THE FIGURES

FIGS. 1A and 1B provide the composition of exemplary eluants (buffering agents and salt) as described in the Examples. The final concentration of each listed component (buffering agent and salt) in the exemplary eluant is provided, as well as the acid dissociation constant (pKa) of each listed buffering agent. FIG. 1A provides an exemplary eluant composition designed for cation exchange procedures (but as described in the Examples, was also used for certain anion exchanged procedures. FIG. 1B provides an exemplary anion exchange eluant composition as used in some of the Examples.

FIG. 4A depicts the separation of 0.228 milligram (mg) of total protein material over a linear gradient across the indicated pH range (approximately pH 6.6-pH 8.2; see y axis). FIG. 4B depicts the separation of 1.57 mg of total protein material over a linear gradient across the indicated pH range (approximately pH 6.9-pH 7.9; see y axis). FIG. 4C depicts the separation of 8.88 mg of total protein material over a linear gradient across the indicated pH range (approximately pH 6.9-pH 7.9; see y axis). All antibodies (MAI and parental homodimeric antibody species) were in the native IgG1 format.

FIG. 5A depicts the separation of heterodimeric and parental; species in which the difference in calculated pI between the two heavy chains is 0.68 pH units; the calculated isoelectric points (pIs) of the two corresponding parental homodimeric antibody species differed by 1.33 pH units. FIG. 5B depicts the separation of heterodimeric and parental species in which the difference in calculated pI between the two heavy chains is 0.43 pH units; the calculated isoelectric points (pIs) of the two corresponding parental homodimeric antibody species differed by 0.48 pH units. FIG. 5C depicts the separation of heterodimeric and parental species in which the difference in calculated pI between the two heavy chains is 0.25 pH units; the calculated isoelectric points (pIs) of the two corresponding parental homodimeric antibody species differed by 0.59 pH units. FIG. 5D depicts the separation of heterodimeric and parental species in which the difference in calculated pI between the two heavy chains is 0.24; the calculated isoelectric points (pIs) of the two corresponding parental homodimeric antibody species differed by 0.26 pH units. FIG. 5E depicts the separation of heterodimeric and parental species in which the difference in calculated pI between the two heavy chains is 0.21; the calculated isoelectric points (pIs) of the two corresponding parental homodimeric antibody species differed by 0.38 pH units. A280=absorbance units measured at a wavelength of 280 nm; ΔpI=difference in calculated isoelectric point between the two different heavy chains; run duration=elution volume in milliliters (mL). All antibodies (MAI and parental homodimeric antibody species) were in the native IgG1 format.

FIG. 8A depicts the separation of heterodimeric and parental species in which the exchanger used was Mono S 5/50 GL (column volume was 1 mL), and the pH gradient was run from pH 4.0 to pH 11.0 (pH gradient range=7.0 pH units). FIG. 8B depicts the separation of heterodimeric and parental species in which the exchanger used was Mono S 10/100 GL (column volume was 8 mL), and the pH gradient was run from pH 6.65 to 7.65 (pH gradient range=1.0 pH units). FIG. 8C depicts the separation of heterodimeric and parental species in which the exchanger used was Mono S 10/100 GL (column volume was 8 mL), and the pH gradient was run from pH 6.87 to 7.27 (pH gradient range=0.4 pH unit).

FIGS. 26A and 26B collectively provide a list of exemplary chromatographic materials ("resin" and "matrix") amenable for use in accordance with the disclosed and claimed methods and certain of their characteristics.

DETAILED DESCRIPTION OF THE INVENTION

Figure 2:
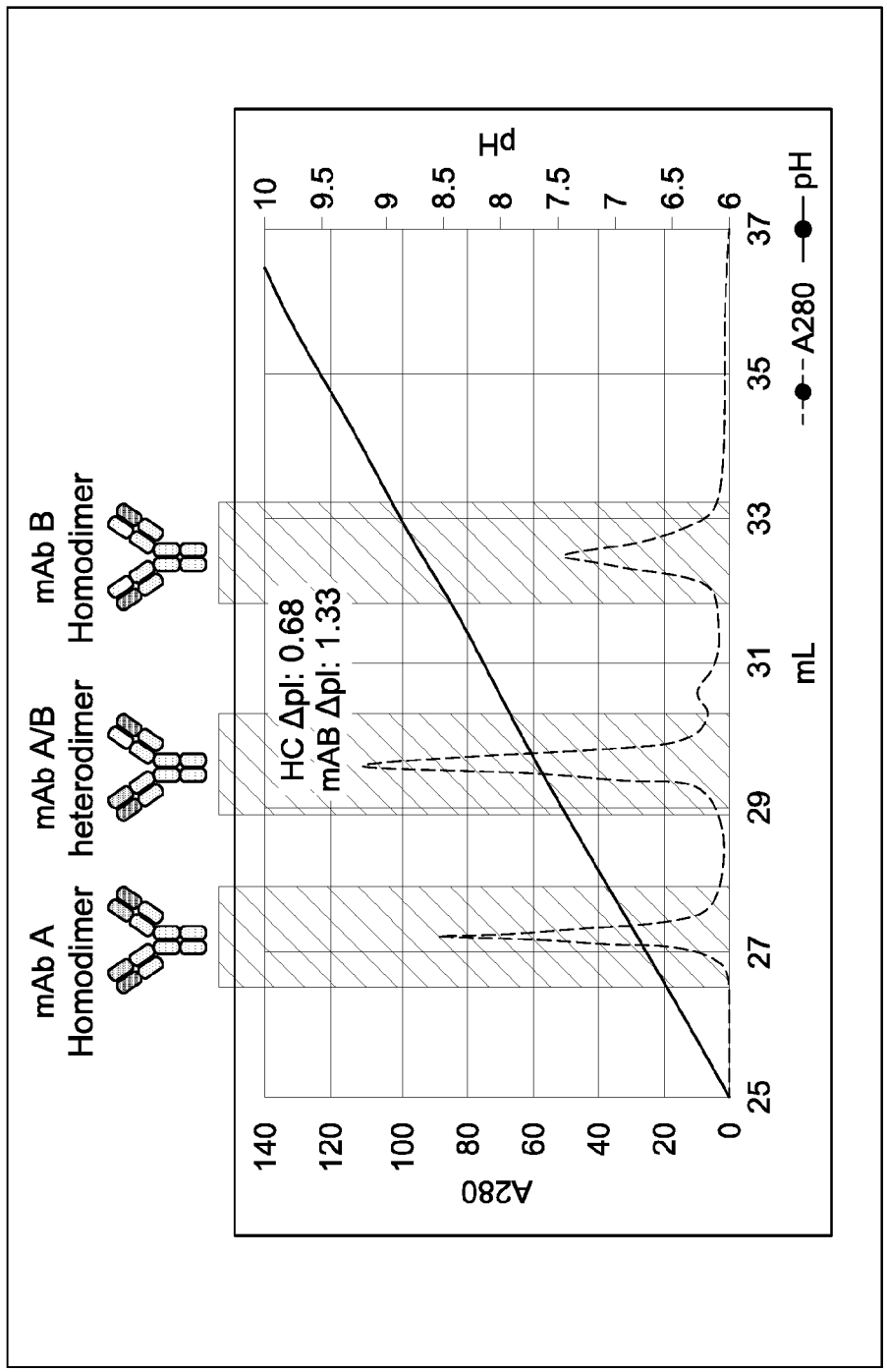
FIG. 2 provides a schematic representation of a cation exchange chromatography experiment as described in Example 1, in which a Mono S 5/50 GL column was used to separate a multispecific antibody of interest comprising a two different heavy chain polypeptides (heavy chain "A" and heavy chain "B") from the two corresponding heavy chain homodimeric antibody species and two copies of an identical light chain (i.e., a "common light chain"). The calculated isoelectric points (pIs) of the two different heavy chains differed by 0.68 pH units ("HC ΔpI: 0.68"). The calculated isoelectric points (pIs) of the two corresponding parental homodimeric antibody species ("mAb A homodimer" and "mAb B homodimer", respectively) differ by 1.33 pH units ("mAB ΔpI: 1.33"). A280=absorbance units measured at a wavelength of 280 nm; ΔpI=difference in calculated isoelectric point between the two different heavy chains; mL=elution volume in milliliters. All antibodies (MAI and parental homodimeric species) were in the IgG1 format.

The invention provides, inter alia, methods for separating, resolving, and purifying multispecific antibodies of interest (MAIs) (referred to interchangeably herein and throughout as "heterodimeric antibody species" or "heavy chain-heterodimeric antibodies", alternative singular and plural forms of such terms, and the like) from at least two different parental homodimeric antibody species (referred to interchangeably herein and throughout as "parental antibody species", "homodimeric parental antibody species", "heavy chain-homodimeric parental antibody species", "heavy chain-homodimeric parental species, and the like). Advantageously, the disclosed methods do not require the engineering or introduction of mutations into any of the homodimeric parental antibody species for the purpose of enhancing the separation, resolution, or purification of the MAI from such parental antibody species.

The methods comprise, inter alia, obtaining a composition comprising each of the aforementioned species and performing chromatography, for example, ion exchange chromatography, with the composition, whereby the MAI is separated from each of a first parental antibody species and a second parental antibody species. In certain embodiments, the MAI comprises a first polypeptide comprising a first heavy chain (HC) variable region and a second heavy chain variable region, wherein the first and the second variable regions have different antigen specificities and different isoelectric points (pIs). In certain embodiments, the different isoelectric points are different actual isoelectric points. In certain other embodiments, the different isoelectric points are different calculated isoelectric points. In certain other embodiments, the MAI further comprises a third polypeptide comprising a first light chain variable region. In certain other embodiments, the MAI further comprises a third polypeptide and a fourth polypeptide, wherein each of the third polypeptide and the fourth polypeptide comprises a second light chain variable region. In certain other embodiments, the first light chain variable region and the second light chain variable region are identical. In certain other embodiments, the third polypeptide and the fourth polypeptide are identical (i.e., they constitute a "common light chain").

As will be understood by the artisan and as disclosed throughout, "specificity" refers to the property of an antibody which enables to react with one or more antigenic determinants, such as one or more epitopes, of an antigen of interest, and not with other epitopes of the antigen of interest or with other antigens of interest. As understood in the art, antibody specificity is dependent on chemical composition, physical forces, energetic favorability, steric hindrance, and molecular structure or topology of the binding site of the epitope and/or the antibody.

As will be understood by the artisan and as disclosed throughout, "affinity" refers to the strength, or stability of an antibody-epitope interaction. Antibodies with better affinity for an epitope bind relatively tightly and/or stably with the epitope, whereas antibodies with poorer affinity for an epitope bind relatively weakly and or less stably.

As will be understood by the artisan and as disclosed throughout, "collecting" or "collected" antibodies having specificity for (an) epitope(s) of an antigen of interest refers to distinguishing (or distinguished) antibodies that have such specificity from those antibodies that do not have such specificity. Collecting antibodies or collected antibodies having specificity for (an) epitope(s) of an antigen of interest need not require physical separation of antibodies from those antibodies that do not have such specificity in order for them to be distinguished. However, in certain embodiments, collecting antibodies having specificity for (an) epitope(s) of an antigen of interest comprises physically separating such antibodies from those antibodies that do not have such specificity. Exemplary methods and means for collecting antibodies are known in the art, and include, for example, flow cytometry, florescence activated cell sorting (FACS), magnetic activated cell sorting (MACS), enzyme-linked immunosorbent assay (ELISA), and the like, and combinations thereof.

Any means for determining such specificity in the art may be employed for determining such specificity in accordance with the methods disclosed throughout, and include, for example, labelling such antibodies with a detectable label; detecting a detectable label; detecting a functional consequence of antibody binding to (an) epitope of an antigen, such as competition with another antibody known to have specificity for such epitope(s); modulation of protein-protein or protein-ligand interaction between the antigen of interest and a known protein interaction partner or ligand.

As used herein and throughout, a "common light chain" comprises polypeptide comprising a light chain variable region that is able to stably pair independently with at least two different heavy chain polypeptides and thereby generate, in each independent case, an antigen binding domain comprising the heavy chain variable region of each heavy chain polypeptide and the light chain variable region. Accordingly, each of two copies of a common light chain is able to stably pair with a first heavy chain polypeptide and a second heavy chain polypeptide, such that a multispecific (e.g., a bispecific) heterodimeric antibody MAI in the native format, such as an IgG isotype format, such as an IgG1 format, and IgG2 format, an IgG3 format, and/or an IgG4 format, wherein the MAI has specificity for two different antigens.

As used herein and throughout, "stable pair" means that a native or native-like interaction between a heavy chain polypeptide and a light chain polypeptide, such as a common light chain, is generated, wherein an MAI in a chemically and functionally relevant and stable manner.

As used herein and throughout, "stable" means relatively fixed and or permanent. Accordingly, a "stable" MAI or a "stable" pair of associated polypeptides, for example, is one that may be collected and/or isolated in the stable form such that that form is essentially preserved such that the chemical and/or functional properties of the stable form can be observed.

As used herein and throughout, "native", "wild-type", describe structures or entities, such as molecules, polypeptides, antibodies, formats, immunoglobulins, immunoglobulin constant regions, Fc regions, heavy chains, light chains, IgGs, IgMs, IgAs, IgDs, IgEs, IgG1, IgG2s, IgG3s, IgG4s, MAIs, parental homodimeric antibody species, heavy chains from parental homodimeric antibody species, and the like that are in a format that exists in a natural setting, such as in an animal or animal species, such as a human or a human species. Such "native" or "wild-type" structures or entities do not possess or contain mutations that have been engineered into such structure or entities for the purpose, for example, of increasing or enhancing the ability to resolve, separate, or purify such engineered structures or entities from non-engineered structures or entities. For example, "native" or "wild-type" MAIs, parental homodimeric antibody species, heavy chains from parental homodimeric antibody species, and the like, have not been engineered to possess mutations that increase or enhance the difference in either the actual isoelectric point or the calculated isoelectric point between different forms of such MAIs, parental homodimeric antibody species, heavy chains from parental homodimeric antibody species, in order to increase or enhance the ability of such different forms to be separated, resolved, or purified by performing chromatography in accordance with the methods disclosed herein and throughout.

As used herein and throughout, "native-like" describes structures or entities that possess a substantially large amount of properties of a native form of such a structure or entity, or is designed to physically and/or functionally resemble or mimic a corresponding native structure or entity to a substantial degree.

In certain embodiments is provided a method of purifying a multispecific antibody of interest (MAI), wherein the MAI comprises a heterodimer comprising a first polypeptide comprising a first heavy chain (HC) variable region and a second polypeptide comprising a second HC variable region, wherein the first and the second variable regions have different antigen specificities and different isoelectric points, the method comprising: i) obtaining a composition comprising the MAI, a first parental antibody species comprising one copy of the first polypeptide, and a second parental antibody species comprising one copy of the second polypeptide; and ii) performing chromatography whereby the MAI is separated from the first and the second parental antibody species; thereby purifying the MAI. In certain embodiments, the different isoelectric points are different actual isoelectric points. In certain other embodiments, the different isoelectric points are different calculated isoelectric points. In certain embodiments, the performing step ii) comprises a. contacting the composition with a chromatographic material forming a composition-chromatographic material complex; and b. performing an elution step wherein the chromatographic material-composition complex is contacted with an sample of eluant that is capable of eluting the MAI and parental antibody species in a pH-dependent manner.

In certain embodiments is provided a method of purifying a multispecific antibody of interest (MAI), wherein the MAI comprises a heterodimer comprising a first polypeptide comprising a first heavy chain (HC) variable region and a second polypeptide comprising a second HC variable region, wherein the first and the second variable regions have different antigen specificities and different isoelectric points, the method comprising: i) obtaining a composition comprising the MAI, a first parental antibody species comprising two copies of the first polypeptide, and a second parental antibody species comprising two copies of the second polypeptide; and ii) performing chromatography whereby the MAI is separated from the first and the second parental antibody species; thereby purifying the MAI. In certain embodiments, the different isoelectric points are different actual isoelectric points. In certain other embodiments, the different isoelectric points are different calculated isoelectric points. In certain embodiments, the performing step ii) comprises a. contacting the composition with a chromatographic material forming a composition-chromatographic material complex; and b. performing an elution step wherein the chromatographic material-composition complex is contacted with an sample of eluant that is capable of eluting the MAI and parental antibody species in a pH-dependent manner.

In connection with the development of the inventive methods, Applicants have surprisingly discovered that, contrary to many prior methods, the successful practice of the inventive methods does not require that the Fc region (or any other portion, for that matter) of the MAI (or parental antibody species) to be engineered, mutagenized, substituted, or otherwise altered in a manner that is designed or purposed for enhancing either affinity- or ion exchange-mediated resolution, separation, or purification of heterodimeric MAI from corresponding parental homodimeric antibody species. The disclosed and claimed methods thus advantageously afford the preparation and purification of MAIs that do not carry with them many of the immunogenicity, PK, and other liabilities associated with MAIs into which such non-native mutations have been engineered.

Accordingly, in certain embodiments is provided a method of purifying a multispecific antibody of interest (MAI), wherein the MAI comprises a heterodimer comprising a first polypeptide comprising a first heavy chain (HC) variable region and a second polypeptide comprising a second HC variable region, wherein the first and the second variable regions have different antigen specificities and different isoelectric points, the method comprising: i) obtaining a composition comprising the MAI, a first parental antibody species comprising one copy of the first polypeptide, and a second parental antibody species comprising one copy of the second polypeptide; and ii) performing chromatography whereby the MAI is separated from the first and the second parental antibody species; thereby purifying the MAI, wherein at least one of the first polypeptide and the second polypeptide are in a native format, such as a native IgG format, such as a native IgG1 format, native IgG2 format, a native IgG3 format, a native IgG4 format, a native IgG1/IgG2 hybrid format, a native IgG1/IgG3 hybrid format, or a native IgG1/IgG4 hybrid format. In certain embodiments, the different isoelectric points are different actual isoelectric points. In certain other embodiments, the different isoelectric points are different calculated isoelectric points. In certain embodiments, the performing step ii) comprises a. contacting the composition with a chromatographic material forming a composition-chromatographic material complex; and b. performing an elution step wherein the chromatographic material-composition complex is contacted with an sample of eluant that is capable of eluting the MAI and parental antibody species in a pH-dependent manner.

Accordingly, in certain embodiments is provided a method of purifying a multispecific antibody of interest (MAI), wherein the MAI comprises a heterodimer comprising a first polypeptide comprising a first heavy chain (HC) variable region and a second polypeptide comprising a second HC variable region, wherein the first and the second variable regions have different antigen specificities and different isoelectric points, the method comprising: i) obtaining a composition comprising the MAI, a first parental antibody species comprising two copies of the first polypeptide, and a second parental antibody species comprising two copies of the second polypeptide; and ii) performing chromatography whereby the MAI is separated from the first and the second parental antibody species; thereby purifying the MAI, wherein at least one of the first polypeptide and the second polypeptide are in a native format, such as a native IgG format, such as a native IgG1 format, native IgG2 format, a native IgG3 format, a native IgG4 format, a native IgG1/IgG2 hybrid format, a native IgG1/IgG3 hybrid format, or a native IgG1/IgG4 hybrid format. In certain embodiments, the different isoelectric points are different actual isoelectric points. In certain other embodiments, the different isoelectric points are different calculated isoelectric points. In certain embodiments, the performing step ii) comprises a. contacting the composition with a chromatographic material forming a composition-chromatographic material complex; and b. performing an elution step wherein the chromatographic material-composition complex is contacted with an sample of eluant that is capable of eluting the MAI and parental antibody species in a pH-dependent manner.

As used herein and throughout, "purifying" means separating one species, such as a heterodimeric MAI, from other species, such as one or more parental homodimeric species, such that an essentially homogenous sample is generated with regard to the MAI from a heterogeneous composition comprising the MAI and the one or more parental homodimeric species.

As used herein and throughout, "obtaining" means discovering, receiving, or otherwise coming into the possession of a material, such as an MAI, a parental homodimeric antibody species, a heavy chain variable region, an light chain variable region, a heavy chain polypeptide comprising a heavy chain variable region, a light chain polypeptide comprising a light chain variable region, an MAI comprising any of the aforementioned, a parental homodimeric antibody species comprising any of the aforementioned, a composition comprising any of the aforementioned, and/or a chromatographic material-composition complex comprising any of the aforementioned. Furthermore, obtaining may refer to discovering such materials by interrogating a library comprising variants of such materials through the use of an antigen in order to identify such materials having specificity for the antigen. Obtaining may also or alternatively comprise receiving such a material from another source or person, such as another previously identified or characterized antibody or antibody sequence.

As used herein and throughout, a "composition" means a fluid, such as a liquid, containing a collection of species, such as a heterodimeric MAI and the two corresponding parental homodimeric antibody species. Such compositions are generated by expressing the first and second polypeptides, and optionally the third and fourth polypeptides (which may comprise identical light chain variable regions).

A heterodimeric multimeric antibody of interest (used interchangeably throughout with "hetero MAI" or "MAI") means an antibody species of interest that comprises a first polypeptide comprising a first heavy chain (HC) variable region and a second polypeptide comprising a second HC variable region, wherein the first and the second heavy chain variable regions are different in amino acid sequence and have different antigen specificities. The first and second polypeptides are, in some embodiments, contained in and/or derived from the heavy chain polypeptides of two different parental homodimeric antibody species. In certain embodiments, the MAI further comprises a third polypeptide comprising a first light chain variable region. In further embodiments, the MAI further comprises a fourth polypeptide comprising a second light chain variable region. In certain embodiments, the first and second light chain variable regions are identical. In yet further embodiments, the third and fourth polypeptides are identical (i.e., they constitute a "common light chain").

A "parental homodimeric antibody species" (used interchangeably throughout with "homodimeric parental antibody species", "parental antibody species", "homodimeric parental species", "homodimeric antibody species", and the like) means an antibody species that comprises: at least one copy of a heavy chain having one of two antigen specificities from which the specificities of the MAI are obtained or derived, and from which the MAI is generated; are at least two copies copy of a heavy chain having one of two antigen specificities from which the specificities of the MAI are obtained or derived, and from which the MAI is generated. In certain embodiments, the polypeptides of each parental homodimeric antibody species that comprise the first and the second heavy chain variable regions are expressed in host cells along with a third and fourth polypeptide comprising a first and a second light chain variable region. In some embodiments, the first and second light chain variable regions are identical in amino acid sequence. In certain embodiments the third and fourth polypeptides are identical in amino acid sequence (i.e., the third and fourth polypeptides constitute a "common light chain"). In certain embodiments a parental homodimeric species comprises two copies copy of a heavy chain having one of two antigen specificities from which the specificities of the MAI are obtained or derived, and from which the MAI is generated.

As used herein and throughout, "chromatography" means, in its broadest sense, the set of laboratory available in the art for the separation or purification of species of interest from compositions comprising the species of interest as well as other species. The composition is contacted with the chromatographic material, such that the various constituents of the composition may adsorb onto the chromatographic material thus forming the chromatographic material-composition complex. Subsequently, an eluant is contacted with the chromatographic material-composition complex, and differential removal, or "elution", of adsorbed species occurs as a function of differences in affinity for each species for the chromatographic material in the presence of the eluant.

Chromatography may be preparative or analytical. The purpose of preparative chromatography is to separate the components of a mixture for more advanced use (and is thus a form of purification). Analytical chromatography is done normally with smaller amounts of material and is for measuring the relative proportions of analytes in a mixture. The two are not mutually exclusive.

As used herein and throughout, "contacting" means physically interacting, such as by covalent or non-covalent interactions. Non-covalent interactions include, hydrophobic, hydrophilic, ionic, cationic anionic, polar, dipolar, van der Waals forces, and the like. Materials that have or have been "contacted" have physically touched each other. In certain embodiments, contacting a material, such as a chromatographic material, with a composition comprising antibody species, such as an MAI and corresponding homodimeric parental antibody species, etc. results in the generation of a chromatographic material-composition complex, wherein at least two, perhaps three or perhaps more, of all of the antibody species in the composition physically interact with and remain attached to the chromatographic material.

A "chromatographic material-composition complex" means a multi-component material that is generated a physical interaction between two materials or more materials that have not previously come into contact or interacted. The physical interaction can be a physiochemical interaction, such as a covalent or non-covalent interaction between two types of molecular entities, and/or between certain functional groups or moieties found on each of the respective interacting materials. A chromatographic material-composition complex may comprise one or more antibody species of a composition, which are adsorbed onto/into a chromatographic material upon or subsequent to contacting the composition with the chromatographic material, such adsorption resulting from attractive physiochemical forces or interactions between functional groups on the chromatographic material and certain regions or portions of the antibody species.

In some embodiments of any of the methods described herein, the chromatographic material is a cation exchange material. In some embodiments, the cation exchange material is a solid phase that is negatively charged and has free cations for exchange with cations in an aqueous solution passed over or through the solid phase. In some embodiments of any of the methods described herein, the cation exchange material may be a membrane, a monolith, or resin. In some embodiments, the cation exchange material may be a resin. The cation exchange material may comprise a carboxylic acid functional group or a sulfonic acid functional group such as, but not limited to, sulfonate, carboxylic, carboxymethyl sulfonic acid, sulfoisobutyl, sulfoethyl, carboxyl, sulphopropyl, sulphonyl, sulphoxyethyl, or orthophosphate. In some embodiments of the above, the cation exchange chromatographic material is a cation exchange chromatography column.

In some embodiments of any of the methods described herein, the chromatographic material is an anion exchange material. In some embodiments, the anion exchange chromatographic material is a solid phase that is positively charged and has free anions for exchange with anions in an aqueous solution passed over or through the solid phase. In some embodiments of any of the methods described herein, the anion exchange material may be a membrane, a monolith, or resin. In an embodiment, the anion exchange material may be a resin. In some embodiments, the anion exchange material may comprise a primary amine, a secondary amine, a tertiary amine or a quaternary ammonium ion functional group, a polyamine functional group, or a diethylaminoethyl functional group. In some embodiments of the above, the anion exchange chromatographic material is an anion exchange chromatography column.

In some embodiments of any of the methods described herein, the ion exchange material may utilize a conventional chromatographic material or a convective chromatographic material. The conventional chromatographic materials include, for example, perfusive materials (e.g., poly(styrene-divinylbenzene) resin) and diffusive materials (e.g., cross-linked agarose resin). In some embodiments, the poly(styrene-divinylbenzene) resin can be Poros resin. In some embodiments, the cross-linked agarose resin may be sulphopropyl-Sepharose Fast Flow ("SPSFF") resin. The convective chromatographic material may be a membrane (e.g., polyethersulfone) or monolith material (e.g. cross-linked polymer). The polyethersulfone membrane may be Mustang. The cross-linked polymer monolith material may be cross-linked poly(glycidyl methacrylate-co-ethylene dimethacrylate).

In some embodiments of any of the methods of the invention, the chromatographic material is in a chromatography column; for example a cation exchange chromatography column or an anion exchange chromatography column. In some embodiments, the chromatography column is used for liquid chromatography. In some embodiments, the chromatography column is used for high performance liquid chromatography (HPLC). In some embodiments, the chromatography column is an HPLC chromatography column; for example, a cation exchange HPLC column or an anion exchange HPLC column.

Examples of cation exchange chromatographic materials are known in the art and include, but are not limited to, Mono S, Poros HS, Source 30S, Mustang S, Sartobind S, S03 Monolith, S Ceramic HyperD, Poros XS, Poros HS50, Poros HS20, Poros GoPure XS, Poros GoPure HS, SP Sepharose FF, SP Sepharose HP, SP-Sepharose XL (SPXL), CM Sepharose Fast Flow, Capto S, UNOsphere S, Macro-prep High S, Capto SP ImpRes, Fractogel Se HiCap, Fractogel S03, Fractogel COO, ProPac WCX-10 and ProPac WCX-10HT. In some embodiments of any of the methods described herein, the cation exchange material is Poros HS50. In some embodiments of any of the methods described herein, the Poros HS resin may be Poros HS 50 µm or Poros HS 20 µm particles. In some embodiments of any of the methods described herein, the cation exchange chromatographic material is selected from the group consisting of Mono S, SP Sepharose FF, Macro-prep High S, Poros GoPure XS, Poros GoPure HS, Capto SP ImpRes, SP Sepharose HP, and Sourse 30S. In some embodiments of any of the methods described herein, the cation exchange chromatographic material is selected from the group consisting of Mono S, Poros HS, SP Sepharose HP, and Source 30S. In some embodiments of any of the methods described herein, the cation exchange chromatographic material is selected from the group consisting of Mono S, SP Sepharose HP, and Source 30S. In some embodiments of any of the methods described herein, the cation exchange chromatographic material is selected from the group consisting of Mono S, Poros HS, and Source 30S.

Examples of anion exchange chromatographic materials are known in the art and include, but are not limited to, Mono Q, Poros HQ 50, Poros PI 50, Poros D, Poros XQ, Poros HQ, Capto Q ImpRes, Q HP, Source 30Q, Mustang Q, Q Sepharose FF, Dionex ProPac 10 SAX and Tosoh GSKgel Q STAT 7 µM WAX and DEAE Sepharose. In some embodiments of any of the methods described herein, the anion exchange chromatographic material is selected from the group consisting of Mono Q, Poros XQ, Poros HQ, Capto Q ImpRes, Q HP, and Source 30Q. In some embodiments of any of the methods described herein, the anion exchange chromatographic material is selected from the group consisting of Mono Q, Sourse 30Q, and Q HP. An example of a multimodal ion exchange chromatographic material is Capto MMC.

As used herein and throughout, an "eluant" (used interchangeably with "eluent") comprises a fluid, such as a liquid solution that is used to remove a species that has adsorbed onto a chromatographic material. An eluant for use in accordance with the disclosed and claimed methods comprises at least two, at least three, at least four, at least five, at least six, at least seven, or at least eight different buffering agents. The choice of the number and chemical identity may be made based on the desired pH range through which the artisan desires to generate the essentially linear pH gradient. The choice of this pH range may, in turn, as disclosed herein and throughout, be made based on a determination of the difference in the actual isoelectric points or the calculated, or theoretical, isoelectric points ("ΔpI") of the first heavy chain polypeptide and the second heavy chain polypeptide. Alternatively, if desired, the artisan may, in turn, as disclosed herein and throughout, choose based on a determination of the difference in the actual isoelectric points or the calculated, or theoretical, isoelectric points ("ΔpI") of a first parental homodimeric antibody species and a second parental homodimeric antibody species. Accordingly, the artisan may choose to select buffering agents that have pKas that sufficiently cover the pH range that is associated with the pIs of the polypeptides (as well as the difference in their pIs).

As used herein and throughout, an "isoelectric point" (also referred to herein and throughout as "pI") is the pH at which a polypeptide or protein, such as a heavy chain polypeptide, a parental homodimeric antibody species, an MAI, an antibody, an immunoglobulin, an IgG, or the like, possesses no net electrical charge, and is generally expressed as a pH value. An isoelectric point may be a "calculated (or theoretical) isoelectric point" or an "actual" (empirically determined) isoelectric point.

As used herein and throughout, a "calculated isoelectric point" (or "theoretical isoelectric point") is an isoelectric point value that is reported or determined by subjecting the primary sequence of the polypeptide or protein to an algorithm, program, code, etc. that is designed to provide a predictive or theoretical pI value based on certain defined parameters of assumptions concerning the chemical and physical properties of the polypeptide or protein (or its constituent amino acids) and/or the solvent components or other chemical species to which it may be exposed; predicted secondary structural features and topology; predicted solvent exposure of certain ionizable groups; and the like. Non-limiting examples of tools and methods for calculating pI include those disclosed in: Bas et al, Protein, Vol. 72(3), pp. 765-783 (2008); Stothard P, Biotechniques, Vol. 28(6), pp. 1102-1104 (2000); and the Sequence Manipulation Site (SMS), for example, on the world wide web at hypertext protocol transfer bioinformatics.org/sms2/. In any case, without wishing to be bound by any theory and as the artisan will understand, when calculating pI for a heavy chain polypeptide, a parental homodimeric antibody species, MAI, an antibody, an immunoglobulin, an IgG, or the like, it may be preferable to, for instance consider certain cysteine residues, such as those that may participate in disulfide bridges, as non-ionizable, and/or to consider suspected N-terminal glycosylation sites as non-ionizable.

As used herein and throughout, an "actual isoelectric point" (or "actual isoelectric point") is an isoelectric point value that is reported or determined by measuring the pI of a physical sample of a polypeptide or protein, such as a heavy chain polypeptide, a parental homodimeric antibody species, an MAI, an antibody, an immunoglobulin, an IgG, or the like (or a composition, such as a solution, containing such sample), using methods and tool that are available in the art.

As used herein and throughout, a "buffering agent" is an acid or base, usually a weak acid or weak base, which is used to maintain the acidity (pH) of a solution, such as an eluant near a chosen value after the addition of another acid or base. That is, the function of a buffering agent is to prevent a rapid change in pH when acids or bases are added to the solution. Buffering agents have variable properties—some are more soluble than others; some are acidic while others are basic. The effective pH around which a given buffering agent is best able to buffer a solution is approximately around the negative log of the acid dissociation constant ("pKa") of that buffering agent. The (negative log of an) acid association constant is a quantitative measure of the strength of an acid in solution. Each acid has a different pKa. It is the equilibrium constant for a chemical reaction known as dissociation in the context of acid-base reactions. The larger the Ka value, the more dissociation of the molecules in solution and thus the stronger the acid. Thus, a strong acid tends to deprotonate more readily than a weak acid.

In certain embodiments, the eluant comprises at least two buffering agents wherein the pKa of each buffering agent is between about 3 and about 11.

In certain embodiments, the eluant comprises at least two buffering agents wherein the pKa of each buffering agent is in a range selected from the group consisting of: about 3.25 to about 3.85; about 4.5 to about 4.85; about 6.0 to about 6.45; about 6.60 to about 7.0; about 7.5 to about 8.15; about 8.35 to about 8.55; about 9.25 to about 9.65; and about 10.00 to about 11.5.

In certain embodiments, the eluant comprises at least two buffering agents, wherein the acid dissociation constant (pKa) of each buffering agent is selected from the group consisting of about 3.75; about 4.76; about 6.10; about 6.90; about 8.04; about 8.44; about 9.39; and about 10.50.

As used herein and throughout, "pH-dependent manner" means behaving in a way that varies with a change in pH. For example, species with different pIs will elute from a column in different and distinguishable times and volumes of eluant if that eluant is capable of generating a pH gradient. Such pH gradients are generated, in certain embodiments, by preparing a sample of the eluant at a desired starting pH and preparing another sample of the eluant at a desired ending pH. In certain embodiments, the desired starting pH is less than 7.0; less than 6.5; less than 6.0; less than 5.5; less than 5.0; less than 4.5; less than 4.0; less than 3.5; or less than 3.0; or a pH values that is between any of the preceding values. In certain embodiments, the desired ending pH is more than 7.0; more than 7.5; more than 8.0; more than 8.5; more than 9.0; more than 9.5; more than 10.0; more than 10.5; or more than 11.0; more than 11.5; more than 12.0; or a pH values that is between any of the preceding values.

In certain embodiments, difference between the calculated isoelectric point of the first polypeptide and the calculated isoelectric point of the second polypeptide of an MAI is a less than 7.0 pH units; less than 6.5 pH units; less than 6.0 pH units; less than 5.5 pH units; less than 5.0 pH units; less than 4.5 pH units; less than 4.0 units; less than 3.5 pH units; less than 2.5 pH units; less than 2.0 pH units; less than 1.0 pH unit; less than 0.95 pH unit; less than 0.90 pH unit; less than 0.85 pH unit; less than 0.80 pH unit; less than 0.75 pH unit; less than 0.70 pH unit; less than 0.65 pH unit; less than 0.60 pH unit; less than 0.55 pH unit; less than 0.50 pH unit; less than 0.45 pH unit; less than 0.40 pH unit; less than 0.35 pH unit; less than 0.30 pH unit; less than 0.25 pH unit; less than 0.20 pH unit; less than 0.15 pH unit; less than 0.10 pH unit; 0.05 pH unit; less than 0.025 pH unit; or pH values that are between any of the preceding values.

In certain embodiments, difference between: the calculated isoelectric point of a first antibody, such as a first immunoglobulin, first IgG, or first parental homodimeric antibody species; and the calculated isoelectric point of a second antibody, such as a second immunoglobulin, second IgG, or second homodimeric antibody species; is less than 7.0 pH units; less than 6.5 pH units; less than 6.0 pH units; less than 5.5 pH units; less than 5.0 pH units; less than 4.5 pH units; less than 4.0 units; less than 3.5 pH units; less than 2.5 pH units; less than 2.0 pH units; less than 1.0 pH unit; less than 0.95 pH unit; less than 0.90 pH unit; less than 0.85 pH unit; less than 0.80 pH unit; less than 0.75 pH unit; less than 0.70 pH unit; less than 0.65 pH unit; less than 0.60 pH unit; less than 0.55 pH unit; less than 0.50 pH unit; less than 0.45 pH unit; less than 0.40 pH unit; less than 0.35 pH unit; less than 0.30 pH unit; less than 0.25 pH unit; less than 0.20 pH unit; less than 0.15 pH unit; less than 0.10 pH unit; 0.05 pH unit; less than 0.025 pH unit; or pH values that are between any of the preceding values.

In accordance with the herein disclosed and claimed methods, the eluant is flowed through the chromatographic material-composition complex in order to elute the MAI and/or parental homodimeric antibody species from the chromatographic material. In certain embodiments, the eluted species are eluted as individual solutions of essentially homogeneous samples, wherein each sample contains one species, such as an MAI, and is essentially devoid of appreciable amounts of the other species, such as a parental homodimeric antibody species. In other embodiments the species are eluted from the chromatographic material such that one species, such as an MAI, is eluted in a series of solution volumes, some of which comprise essentially homogeneous samples of an MAI, and some of which comprise as the major species the MAI, along with varying minor amounts of one or more parental homodimeric antibody species. In such embodiments, the artisan may routinely select to retain those volumes that comprise the essentially homogeneous sample of the MAI and discard other volumes.

Accordingly, as the artisan will understand, the inventive methods allow for the MAI and parental homodimeric antibody species to elute from chromatographic material such that these species are essentially distinguishable from one another. As used herein and throughout, "essentially distinguishable" means that such species are sufficiently separated chromatographically such that samples of each species may be collected essentially free from other species. Such separation may be visualized in chromatographic traces which allow for visualization of other means of monitoring, for example, the concentration of proteinaceous material that elutes from a column as a function of time, eluant volume, and the like. Such distinguishable separation may comprise elutions in which essentially all of each species are separated from one another, or elutions in which a certain amount of overlap between two or more species elution volumes occurs. In embodiments in which some overlap occurs, as the artisan will understand, as described above, one may collect eluant volumes that are observed to comprise no or essentially no overlap, and thus achieve separation in accordance with the claimed methods.

As used herein and throughout, "flowing" (and alternatively, "flowed") means applying and/or passing a sufficient amount of an eluant through a chromatographic material and/or chromatographic material-composition complex, such that the material and/or complex is contacted with eluant. As the art may understand, one may flow several or multiple column volumes' worth of such a fluid/solution in order to equilibrate the material or matrix prior to the elution step, as well as multiple volumes' worth when performing the elution step. This can be varied in order to increase or decrease the slope of the pH gradient and thus the total elution volume required to elute the various species adsorbed onto the column.

Advantageously, however, it has additionally been discovered that one may prepare eluants comprising a large number of buffering agents at appropriate concentrations as disclosed herein, such that the eluant may be used to prepare pH gradients comprising: a linear pH gradient phase; at least one step pH gradient phase prior to a linear pH gradient phase; at least one step pH gradient phase subsequent to a linear pH gradient phase; a linear pH gradient phase only; an essentially linear pH gradient phase; and the like, throughout the majority of the pH scale as the artisan may desire and as described herein and throughout, such that a majority of MAIs may be purified from compositions comprising such MAIs and parental homodimeric antibody species without regard to the pI of the heavy chain polypeptides or the pI difference. For example, one exemplary eluant that has been found to elute certain model proteins in single-protein mixtures (see Kroner et al, J. Chromatog., Vol. 1285, pages 78-87 (2013)), effectively buffers from approximately pH 3 through approximately pH 11, such that an essentially linear pH gradient may be generated throughout this range, contains Ncyclohexyl-3-aminopropanesulfonic acid (CAPS), N-Cyclohexyl-2-aminoethanesulfonic acid (CHES), N-Tris (hydroxymethyl)methyl-3-aminopropanesulfonic acid (TAPS), N-(2-Hydroxyethyl)piperazine-N'-(2-hydroxypropanesulfonic acid) (HEPPSO), 3-morpholino-2-hydroxypropanesulfonic acid sodium salt, 3-(N-morpholinyl)-2-hydroxypropanesulfonic acid (MOPSO), 2-(N-morpholino)ethanesulfonic acid (MES), acetic acid, formic acid, and NaCl. An additional eluant that has been surprisingly discovered to be particularly amenable to certain embodiments of the disclosed and claimed methods comprises methylamine, 1,2-ethanediamine, 1-methylpiperazine, 1,4-dimethylpiperazine, 2-[Bis(2-hydroxyethyl)amino]-2-(hydroxymethyl)propane-1,3-diol (bis-tris), and hydroxylamine and optionally at least one salt. It has been discovered, as disclosed herein and throughout, that these eluants are also effective in purifying a variety of MAIs from compositions comprising the MAI and parental homodimeric antibody species as provided in the disclosed and claimed methods throughout. As these eluants are effective at generating essentially linear pH gradients through a pH range of approximately 3 through approximately 11, the invention provides in certain embodiments, methods for purifying an MAI from a composition comprising the MAI and parental homodimeric antibody species compositions without regard, or prior knowledge of, the pI of the first and second heavy chain polypeptides of the MAI (and thus of the heavy chains in the corresponding parental homodimeric antibody species).

As used herein and throughout, a "linear pH gradient phase", or a "linear pH gradient", used interchangeably throughout, means a pH gradient that exhibits a largely, or essentially, a smooth, constant rate of change per unit volume of eluate that flows or is flowed through a chromatographic material and/or chromatographic material-composition complex over a relatively large eluant volume or a relatively large number of contiguous column eluant fractions.

As used herein and throughout, a "step pH gradient phase", or a "step pH gradient", used interchangeably throughout, means a pH gradient that exhibits an relatively abrupt change pH such that a large pH change in the eluant occurs as it flows or is flowed through a chromatographic material and/or chromatographic material-composition complex over in a relatively small volume of the eluant or a relatively small number of contiguous column eluant fractions. Although such step pH gradient phases, as a practical matter, do exhibit an observable rate of change per unit eluant volume, such step pH gradient phases are nonetheless distinguishable from linear pH gradient phases as used herein and throughout. In certain embodiments, such step pH gradient phases are considered to exhibit essentially instantaneous rates of change of pH per unit eluant volume relative to linear pH gradient phases.

Additionally, however, it has been surprisingly discovered that step pH gradient phases may also be employed using the eluants described herein and throughout in circumstances in which such step pH gradient phases may be desirable and useful for inclusion in a chromatographic procedure aimed at separating certain MAIs from MAI-parental homodimeric parental species mixtures.

In certain embodiments, the eluant does not include the following agents: imidazole; piperazine, tris(hydroxymethyl)aminomethane (TRIS).

In certain embodiments, the eluant consists essentially of: CAPS; CHES; TAPS; HEPPSO; MOPSO; MES; acetic acid; and formic acid; and optionally at least one salt.

In other embodiments, the eluant consists of CAPS; CHES; TAPS; HEPPSO; MOPSO; MES; acetic acid; and formic acid; and at least one salt.

The inventive methods afford the ability to modify or manipulate the ionic strength of the eluant as may be desired by selecting a variety of salt concentrations. Accordingly, in certain embodiments, a salt concentration may be selected from the group consisting of: 0 mM to about 100 mM; 0 mM to about 60 mM; 0 mM to about 50 mM; 0 mM to about 40 mM; 0 mM to about 30 mM; 0 mM to about 20 mM; 0 mM to about 10 mM; 0 mM to about 5 mM; about 10 mM to about 200 mM; about 10 mM to about 100 mM; about 10 mM to about 50 mM; about 10 mM to about 40 mM; about 10 mM to about 30 mM; about 10 mM to about 20 mM; about 20 mM to about 200 mM; about 20 mM to about 100 mM; about 20 mM to about 50 mM; about 20 mM to about 30 mM; about 30 mM to about 200 mM; about 30 mM to about 100 mM; and about 30 mM to about 50 mM; and about 5 mM to about 15 mM.

In certain embodiments, the eluant comprises at least one salt selected from the group consisting of: NaCl, KCl, and $Na_2SO_4$.

In certain embodiments, the eluant NaCl at a concentration of approximately 10 mM.

In accordance with the inventive methods disclosed and claimed herein and throughout, Applicants have further discovered both loading buffer and eluant compositions that facilitate the facile purification of MAIs from such compositions, and have further discovered that one may conveniently employ the same buffer composition (herein and throughout termed an "eluant") as both a loading buffer and an elution buffer—one need only to prepare a first sample of the buffer composition at a first pH (the "loading pH") and a second sample of the buffer composition at a second pH (the "eluting pH"), in which the loading pH and eluting pH are chosen by the artisan order to generate an essentially linear pH gradient through the elution step of the inventive methods. The determination of the desired pH range through which the essentially liner pH gradient should be applied may be arrived at based on, for example, a calculation of the expected pIs of each heavy chain to be included in the MAI. Similarly, the determination of the slope of the gradient to be applied may be informed by determining the difference in pI units ($\Delta$pI) between each heavy chain to be included in the MAI.

As disclosed herein and throughout, the inventive methods afford the purification of MAIs, and reagents, such as buffering agents, eluants, and the like, for performing the methods.

The term "antibody" is used herein in the broadest sense and specifically encompasses at least monoclonal antibodies, polyclonal antibodies, multi-specific antibodies (e.g., bispecific antibodies), chimeric antibodies, humanized antibodies, human antibodies, and antibody fragments. An antibody is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes.

An "antibody" also refers to an immunoglobulin molecule, a fragment of an immunoglobulin molecule, or a derivative thereof, which has the ability to specifically bind to an antigen, which may be, for example: a protein; a polypeptide; peptide; a hormone; a cytokine; a chemokine; a growth factor; a neurotransmitter; a carbohydrate-containing biological molecule; a lipid or fatty acid-containing biological molecule; or other biological molecule; via an epitope present on such antigen.

"Antibodies" as used herein and throughout also refer to polypeptides comprising one or more variable regions or variable domains of an antibody, wherein such variable regions(s) or variable domain(s) are capable of engaging and binding to one or more epitopes of one or more antigens.

By "polypeptide" or "protein as used herein is meant at least two covalently attached amino acids, which includes proteins, polypeptides, oligopeptides and peptides. The protein may be made up of naturally occurring amino acids and peptide bonds, or synthetic peptidomimetic structures, i.e. "analogs", such as peptides.

Antibodies (used interchangeably with "immunoglobulins", or "immunoglobulin molecules") can be monomeric, dimeric, trimeric, tetrameric, pentameric, etc., and may comprise a class of structurally related proteins consisting of two pairs of polypeptide chains: one pair of light chains (LC) and one pair of heavy chains (HC), all of which are inter-connected by disulfide bonds. The structure of immunoglobulins has been well characterized. See for instance Fundamental Immunology Ch. 7 (Paul, W., ed., 2nd ed. Raven Press, N.Y. (1989)).

Traditional natural antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. IgA has several subclasses, including but not limited to IgA1 and IgA2. Thus, "isotype" as used herein is meant any of the classes and subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE. The distinguishing features between these antibody classes are their constant regions, although subtler differences may exist in the variable region.

Each of the light and heavy chains is made up of two distinct regions, referred to as the variable and constant regions. The IgG heavy chain is composed of four immunoglobulin domains linked from N- to C-terminus in the order VH-CH1-CH2-CH3, referring to the "variable heavy domain" (also referred to as a "heavy chain variable domain", used interchangeably throughout), heavy chain constant domain 1, heavy chain constant domain 2, and heavy chain constant domain 3 respectively (also referred to as VH-Cγ1-Cγ2-Cγ3, referring to the variable heavy domain, constant gamma 1 domain, constant gamma 2 domain, and constant gamma 3 domain respectively). The IgG light chain is composed of two immunoglobulin domains linked from N- to C-terminus in the order VL-CL, referring to the "variable light domain" (also referred to as a "light chain variable domain", used interchangeably throughout) and the light chain constant domain respectively. The constant regions show less sequence diversity, and are responsible for binding a number of natural proteins to elicit important biochemical events. The structure that constitutes the natural biological form of an antibody, including the variable and constant regions, is referred to herein as a "full length antibody". In most mammals, including humans and mice, the full length antibody of the IgG isotype is a tetramer and consists of two identical pairs of two immunoglobulin chains, each pair having one light chain and one heavy chain, each light chain comprising a VL and a CL, and each heavy chain comprising a VH, CH1, a CH2, and a CH3. In some mammals, for example in camels and llamas, IgG antibodies may consist of only two heavy chains, each heavy chain comprising a variable domain attached to the Fc region.

The heavy chain constant region typically is comprised of three domains, CH1, CH2, and CH3, and the CH1 and CH2 domains are connected by a hinge region. Each light chain typically is comprised of a light chain variable domain (abbreviated herein as "$V_L$" or "VL") and a light chain constant domain. The $V_H$ and $V_L$ domains may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4. Typically, the numbering of amino acid residues in this region is performed by the method described in Kabat (see, e.g., Kabat et al, in "Sequences of Proteins of Immunological Interest," 5$^{th}$ Edition, U.S. Department of Health and Human Services, 1992). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of $V_H$ CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "variable", "variable domain", or "variable region" each interchangeably refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable" regions or "complementarity determining regions" (CDRs). The more conserved (i.e., non-hypervariable) portions of the variable domains are called the "framework" regions (FRM). The variable domains of naturally occurring heavy and light chains each comprise four FRM regions, largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding site (see Kabat et al. Sequences of Proteins of Immunological Interest, 5th Ed. Public Health Service, National Institutes of Health, Bethesda, Md., 1991, incorporated by reference in its entirety). The constant domains are not directly involved in antigen binding, but exhibit various effector functions, such as, for example, antibody-dependent, cell-mediated cytotoxicity and complement activation.

The term "framework region" refers to the art-recognized portions of an antibody variable region that exist between the more divergent (i.e., hypervariable) CDRs. Such framework regions are typically referred to as frameworks 1 through 4 (FRM1, FRM2, FRM3, and FRM4) and provide a scaffold for the presentation of the six CDRs (three from the heavy chain and three from the light chain) in three dimensional space, to form an antigen-binding surface. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. Mol. Biol., 1987, 196: 901; Chothia et al, Nature, 1989, 342: 877; Martin and Thornton, J. Mol. Biol, 1996, 263: 800. Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

By "position" as used herein is meant a location in the sequence of a protein or nucleic acid. Protein positions may be numbered sequentially, or according to an established format, for example the Kabat index for antibody variable regions or the EU index for antibody constant regions. For example, position 297 is a position in the human antibody IgG1. Corresponding positions are determined as outlined above, generally through alignment with other parent sequences.

By "residue" as used herein is meant a position in a protein and its associated amino acid identity. For example, Asparagine 297 (also referred to as Asn297, also referred to as N297) is a residue in the human antibody IgG1. In some embodiments it can also refer to nucleic acid bases.

The term "canonical structure" may also include considerations as to the linear sequence of the antibody, for example, as catalogued by Kabat (Kabat et al, in "Sequences of Proteins of Immunological Interest," $5^{th}$ Edition, U.S. Department of Health and Human Services, 1992). The Kabat numbering scheme is a widely adopted standard for numbering the amino acid residues of an antibody variable domain in a consistent manner. Additional structural considerations can also be used to determine the canonical structure of an antibody. For example, those differences not fully reflected by Kabat numbering can be described by the numbering system of Chothia et al and/or revealed by other techniques, for example, crystallography and two or three-dimensional computational modeling. Accordingly, a given antibody sequence may be placed into a canonical class which allows for, among other things, identifying appropriate chassis sequences (e.g., based on a desire to include a variety of canonical structures in a library). Kabat numbering of antibody amino acid sequences and structural considerations as described by Chothia et al., and their implications for construing canonical aspects of antibody structure, are described in the literature.

By "Fc" or "Fc region", as used herein is meant the polypeptide comprising the constant region of an antibody excluding the first constant region immunoglobulin domain. Thus "Fc region" refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Accordingly, and without departing from the above, "Fc region" may also be defined as comprising a "CH2 domain or a variant thereof" and a "CH3 domain or a variant thereof". Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, for example an antibody. By "Fc polypeptide" as used herein is meant a polypeptide that comprises all or part of an Fc region. Fc polypeptides include antibodies, Fc fusions, isolated Fcs, and Fc fragments.

A variable light chain (VL) and corresponding variable heavy domain (VH) of the inventive multivalent antibody analogs comprise a binding domain, also referred to interchangeably throughout as an "antigen binding site" that interacts with an antigen. Thus, a "first variable light domain" and a "first variable heavy domain" of the inventive multivalent antibody analogs together form a "first antigen binding site". Similarly, a "second variable light domain" and a "second variable heavy domain" of the inventive multivalent antibody analogs together form a "second antigen binding site". A "third variable light domain" and a "third variable heavy domain" of the inventive multivalent antibody analogs together form a "third antigen binding site", and so on.

The antigen binding sites for use in accordance with the invention, including the VHs, VLs, and/or CDRs that comprise such, may be obtained or derived from any source of such, as will be understood by the artisan. Accordingly, such antigen binding sites, VHs, VLs, and/or CDRs may be obtained or derived from hybridoma cells that express antibodies against a target recognized by such; from B cells from immunized donors, which express antibodies against a target recognized by such; from B-cells that have been stimulated to express antibodies against a target recognized by such; and or from identification of antibodies or antibody fragments that have been identified by screening a library comprising a plurality of polynucleotides or polypeptides for antigen binding antibodies (or antigen binding fragments thereof).

"Antibody fragments" comprise a portion of an intact antibody, for example, one or more portions of the antigen-binding region thereof. Examples of antibody fragments include Fab, Fab', F(ab')2, and Fv fragments, scFvs, diabodies, linear antibodies, single-chain antibodies, and multispecific antibodies formed from intact antibodies and antibody fragments.

By "scFv" as used herein is meant a polypeptide consisting of two variable regions connected by a linker sequence; e.g., "Linkers" (also referred to a "linker moieties", used interchangeably throughout), are described in more detail below.

By "Fab" or "Fab region" as used herein is meant the polypeptides that comprise the VH, CH1, VL, and CL immunoglobulin domains. Typically, the VH and CH1 domains comprise one polypeptide and the VL and CL domains comprise another polypeptide, wherein the two polypeptides are linked to one another via at least one inter-polypeptide disulfide bond. Fab may refer to this region in isolation, or this region in the context of a full length antibody or antibody fragment.

"Humanized antibodies" generally refer to non-human antibodies that have had the variable-domain framework regions swapped for sequences found in human antibodies. Generally in a humanized antibody the entire antibody, except the CDRs, is encoded by a polynucleotide of human origin or is identical to such an antibody except within its CDRs. The CDRs, one, some, or all of which are encoded by nucleic acids originating in a non-human organism, are grafted into the framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239: 1534-1536. "Back mutation" of selected acceptor framework residues to the corresponding donor residues is often required to regain affinity that is lost in the initial grafted construct (see, e.g., U.S. Pat. No. 5,693,762). The humanized antibody optimally also will comprise at least a portion of an immunoglobulin constant region, typically that of a human immunoglobulin, and thus will typically comprise a human Fc region. A variety of techniques and methods for humanizing, reshaping, and resurfacing non-human antibodies are well known in the art (See Tsurushita & Vasquez, 2004, Humanization of Monoclonal Antibodies, Molecular Biology of B Cells, 533-545, Elsevier Science (USA), and references cited therein). In certain variations, the immunogenicity of the antibody is reduced using a method described in Lazar et al., 2007, Mol Immunol 44:1986-1998 and U.S.

Ser. No. 11/004,590, entitled "Methods of Generating Variant Proteins with Increased Host String Content and Compositions Thereof", filed on Dec. 3, 2004.

An "intact antibody" is one comprising full-length heavy- and light-chains and an Fc region. An intact antibody is also referred to as a "full-length, heterodimeric" antibody or immunoglobulin.

The term "variable" refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable" regions or "complementarity determining regions" (CDRs). The more conserved (i.e., non-hypervariable) portions of the variable domains are called the "framework" regions (FRM). The variable domains of naturally occurring heavy and light chains each comprise four FRM regions, largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding site (see Kabat et al. Sequences of Proteins of Immunological Interest, 5th Ed. Public Health Service, National Institutes of Health, Bethesda, Md., 1991, incorporated by reference in its entirety). The constant domains are not directly involved in antigen binding, but exhibit various effector functions, such as, for example, antibody-dependent, cell-mediated cytotoxicity and complement activation.

The "chassis" of the invention represent a portion of the antibody heavy chain variable (IGHV) or light chain variable (IGLV) domains that are not part of CDRH3 or CDRL3, respectively. The chassis of the invention is defined as the portion of the variable region of an antibody beginning with the first amino acid of FRM1 and ending with the last amino acid of FRM3. In the case of the heavy chain, the chassis includes the amino acids including from about Kabat position 1 to about Kabat position 94. In the case of the light chains (kappa and lambda), the chassis are defined as including from about Kabat position 1 to about Kabat position 88. The chassis of the invention may contain certain modifications relative to the corresponding germline variable domain sequences presented herein or available in public databases. These modifications may be engineered (e.g., to remove N-linked glycosylation sites) or naturally occurring (e.g., to account for allelic variation). For example, it is known in the art that the immunoglobulin gene repertoire is polymorphic (Wang et al., Immunol. Cell. Biol, 2008, 86: 111; Collins et al, Immunogenetics, 2008, DOI 10.1007/s00251-008-0325-z, published online, each incorporated by reference in its entirety); chassis, CDRs (e.g., CDRH3) and constant regions representative of these allelic variants are also encompassed by the invention. In some embodiments, the allelic variant(s) used in a particular embodiment of the invention may be selected based on the allelic variation present in different patient populations, for example, to identify antibodies that are non-immunogenic in these patient populations. In certain embodiments, the immunogenicity of an antibody of the invention may depend on allelic variation in the major histocompatibility complex (MHC) genes of a patient population. Such allelic variation may also be considered in the design of libraries of the invention. In certain embodiments of the invention, the chassis and constant regions are contained on a vector, and a CDR3 region is introduced between them via homologous recombination. In some embodiments, one, two or three nucleotides may follow the heavy chain chassis, forming either a partial (if one or two) or a complete (if three) codon. When a full codon is present, these nucleotides encode an amino acid residue that is referred to as the "tail," and occupies position 95.

In certain embodiments, one or more of: the first heavy chain variable region; the second heavy chain variable region; the first light chain variable region; the second light chain variable region; one or more CDRs contained in a variable region; the first polypeptide; the second polypeptide; the third polypeptide; the fourth polypeptide; one or more parental homodimeric antibody species; and/or the MAI are obtained by performing one or more selections against a one or more antigens from one or more libraries comprising unique members of any of the aforementioned antibody components or regions.

In certain embodiments, either the first heavy chain variable region or the second heavy chain variable region of an antibody, such as an MAI, is obtained by performing a first selection against a first antigen from a first library comprising unique heavy chain variable regions.

In certain embodiments, the first heavy chain variable region and the second heavy chain variable region of an antibody, such as an MAI, is obtained by performing a first selection against a first antigen from a first library comprising unique heavy chain variable regions.

In certain embodiments, the first heavy chain variable region of an antibody, such as an MAI, is obtained by performing a first selection against a first antigen from a first library comprising unique heavy chain variable regions and the second heavy chain variable region is obtained by performing a second selection against a second antigen from a second library comprising unique heavy chain variable regions.

In certain embodiments, the first heavy chain variable region of an antibody, such as an MAI, is obtained by performing a first selection against a first antigen from a first library comprising unique heavy chain variable regions and the second heavy chain variable region is obtained by performing a second selection against a second antigen from a second library comprising unique heavy chain variable regions.

In certain embodiments, at least one of the libraries further comprises at least one light chain.

As will be appreciated by the artisan, the terms "library" and "plurality" (and "libraries" and "pluralities") may be readily used interchangeably. However, in the context of the inventions disclosed throughout, whereas a "plurality" of items, such as antibodies, nucleic acid encoding antibodies, or host cells, may comprise many or most members that are essentially identical, a "library" of items, such as antibodies, nucleic acid encoding antibodies, or host cells comprise members many or most members that are unique.

In certain embodiments, one or more naïve libraries are employed in selections in accordance with the claimed methods. A "naïve library" refers to a library of polynucleotides (or polypeptides encoded by such polynucleotides) that has not been interrogated for the presence of antibodies having specificity a particular antigen. A "naïve library" also refers to a library that is not restricted to, or otherwise biased or enriched for, antibody sequences having specificity for any group of antigens, or for a particular antigen. A naïve library is thus distinct from a "restricted library" and "maturation library" (such as, for example, an "affinity maturation library"), both of which are described below.

A naïve library may also comprise a "preimmune" library, which refers to a library that has sequence diversity and length diversity similar to naturally occurring antibody sequences, such as human antibody sequences, before such naturally occurring sequences have undergone negative selection and/or somatic hypermutation. Such preimmune libraries may be designed and prepared so as to reflect or mimic the pre-immune repertoire, and/or may be designed and prepared based on rational design informed by the collection of human V, D, and J genes, and other large databases of human heavy and light chain sequences (e.g., publicly known germline sequences; sequences from Jackson et al, J. Immunol Methods, 2007, 324: 26, incorporated by reference in its entirety; sequences from Lee et al., Immunogenetics, 2006, 57: 917, incorporated by reference in its entirety; and sequences compiled for rearranged VK and Vλ. Additional information may be found, for example, in Scaviner et al., Exp. Clin. Immunogenet., 1999, 16: 234; Tomlinson et al, J. Mol. Biol, 1992, 227: 799; and Matsuda et al, J. Exp. Med., 1998, 188: 2151 each incorporated by reference in its entirety. In certain embodiments of the invention, cassettes representing the possible V, D, and J diversity found in the human repertoire, as well as junctional diversity (i.e., N1 and N2), are synthesized de novo as single or double-stranded DNA oligonucleotides. Exemplary such preimmune libraries, and the design and composition of polynucleotide sequences (and polypeptide sequences encoded by them) comprising them, are further described in, for example, Lee et al. (Immunogenetics, 2006, 57: 917); Martin et al., Proteins, 1996, 25:130; WO 2009/036379; and WO 2012/09568.

In the context of antibodies that are employed in practicing the disclosed inventions, a library (or plurality) of such antibodies will comprise many or most members that each possess a unique primary acid sequence; however, such libraries (or pluralities) may also include members that have identical amino acid sequences. In certain embodiments, the variable regions of such members will comprise many of the differences in amino acid sequence between such members.

In the context of host cells that are employed in practicing the disclosed inventions, a plurality (or library) of such host cells will comprise host cell members, many of which that each express a unique antibody; however, such host cell pluralities (or libraries) may also include members that express identical antibody sequences. In certain embodiments, such host cells will also harbor nucleic acid that collectively encodes the antibody libraries that are collectively expressed by the host cells.

As will be understood by the artisan and as disclosed throughout, "diversity" refers to a variety or a noticeable heterogeneity. The term "sequence diversity" refers to a variety of sequences which are collectively representative of several possibilities of sequences, for example, those found in natural human antibodies. For example, heavy chain CDR3 (CDRH3) sequence diversity may refer to a variety of possibilities of combining the known human DH and H3-JH segments, including the N1 and N2 regions, to form heavy chain CDR3 sequences. The light chain CDR3 (CDRL3) sequence diversity may refer to a variety of possibilities of combining the naturally occurring light chain variable region contributing to CDRL3 (i.e., L3-VL) and joining (i.e., L3-JL) segments, to form light chain CDR3 sequences. As used herein, H3-JH refers to the portion of the IGHJ gene contributing to CDRH3. As used herein, L3-VL and L3-JL refer to the portions of the IGLV and IGLJ genes (kappa or lambda) contributing to CDRL3, respectively.

As used herein, the term "expression" includes any step involved in the production of a polypeptide including, but not limited to, transcription, post-transcriptional modification, translation, post-translational modification, and secretion.

In certain embodiments of the invention, antibody libraries are designed to be small enough to chemically synthesize and physically realize, but large enough to encode antibodies with the potential to recognize any antigen. In certain embodiments, an antibody library comprises about $10^7$ to about $10^{20}$ different antibodies and/or polynucleotide sequences encoding the antibodies of the library. In some embodiments, the libraries are designed to include $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, or $10^{20}$ different antibodies and/or polynucleotide sequences encoding the antibodies. In certain embodiments, the libraries may comprise or encode about $10^3$ to about $10^5$, about $10^5$ to about $10^7$, about $10^7$ to about $10^9$, about $10^9$ to about $10^{11}$, about $10^{11}$ to about $10^{13}$, about $10^{13}$ to about $10^{15}$, about $10^{15}$ to about $10^{17}$, or about $10^{17}$ to about $10^{20}$ different antibodies. In certain embodiments, the diversity of the libraries may be characterized as being greater than or less than one or more of the diversities enumerated above, for example greater than about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, or $10^{20}$ or less than about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, or $10^{20}$. In certain other embodiments of the invention, the probability of an antibody of interest being present in a physical realization of a library with a size as enumerated above is at least about 0.0001%, 0.001%, 0.01%, 0.1%, 1%, 5%, 10%, 20%, 30%, 40%, 50%, 60%, 70%, 80%, 85%, 90%, 95%, 99%, 99.5%, or 99.9% (see Library Sampling, in the Detailed Description, for more information on the probability of a particular sequence being present in a physical realization of a library).

As will be understood by the artisan and as disclosed throughout antibody libraries suitable for use in accordance with the disclosed methods may be designed and prepared by any method available in the art as disclosed, for example, in WO2009036379; WO2012009568; WO2010105256; U.S. Pat. Nos. 8,258,082; 6,300,064; 6,696,248; 6,165,718; 6,500,644; 6,291,158; 6,291,159; 6,096,551; 6,368,805; 6,500,644; and the like.

For instance, libraries may be designed and prepared so as to reflect or mimic the pre-immune repertoire, and/or may be designed and prepared based on rational design informed by the collection of human V, D, and J genes, and other large databases of human heavy and light chain sequences (e.g., publicly known germline sequences; sequences from Jackson et al, J. Immunol Methods, 2007, 324: 26, incorporated by reference in its entirety; sequences from Lee et al., Immunogenetics, 2006, 57: 917, incorporated by reference in its entirety; and sequences compiled for rearranged VK and Vλ—see Appendices A and B filed herewith). Additional information may be found, for example, in Scaviner et al., Exp. Clin. Immunogenet., 1999, 16: 234; Tomlinson et al, J. Mol. Biol, 1992, 227: 799; and Matsuda et al, J. Exp. Med., 1998, 188: 2151 each incorporated by reference in its entirety. In certain embodiments of the invention, cassettes representing the possible V, D, and J diversity found in the human repertoire, as well as junctional diversity (i.e., N1 and N2), are synthesized de novo as single or double-stranded DNA oligonucleotides. In certain embodiments of the invention, oligonucleotide cassettes encoding CDR sequences are introduced into yeast along with one or more acceptor vectors containing heavy or light chain chassis sequences. No primer-based PCR amplification or template-directed cloning steps from mammalian cDNA or mRNA are employed. Through standard homologous recombination, the recipient yeast recombines the cassettes (e.g., CDR3s) with the acceptor vector(s) containing the chassis sequence(s) and constant regions, to create a properly ordered synthetic, full-length human heavy chain and/or light chain immunoglobulin library that can be genetically propagated, expressed, displayed, and screened. One of ordinary skill in the art will readily recognize that the chassis contained in the acceptor vector can be designed so as to produce constructs other than full-length human heavy chains and/or light chains. For example, in certain embodiments of the invention, the chassis may be designed to encode portions of a polypeptide encoding an antibody fragment or subunit of an antibody fragment, so that a sequence encoding an antibody fragment, or subunit thereof, is produced when the oligonucleotide cassette containing the CDR is recombined with the acceptor vector. In certain embodiments, the invention provides a synthetic, preimmune human antibody repertoire comprising about $10^7$ to about $10^{20}$ antibody members, wherein the repertoire comprises:

(a) selected human antibody heavy chain chassis (i.e., amino acids 1 to 94 of the heavy chain variable region, using Kabat's definition); (b) a CDRH3 repertoire, designed based on the human IGHD and IGHJ germline sequences, the CDRH3 repertoire comprising the following:
  (i) optionally, one or more tail regions;
  (ii) one or more N1 regions, comprising about 0 to about 10 amino acids selected from the group consisting of fewer than 20 of the amino acid types preferentially encoded by the action of terminal deoxynucleotidyl transferase (TdT) and functionally expressed by human B cells;
  (iii) one or DH segments, based on one or more selected IGHD segments, and one or more N- or C-terminal truncations thereof;
  (iv) one or more N2 regions, comprising about 0 to about 10 amino acids selected from the group consisting of fewer than 20 of the amino acids preferentially encoded by the activity of TdT and functionally expressed by human B cells; and
  (v) one or more H3-JH segments, based on one or more IGHJ segments, and one or more N-terminal truncations thereof (e.g., down to XXWG); (c) one or more selected human antibody kappa and/or lambda light chain chassis; and
(b) a CDRL3 repertoire designed based on the human IGLV and IGLJ germline sequences, wherein "L" may be a kappa or lambda light chain. The means and methods for preparing such libraries are disclosed, for example, in WO2009036379; WO2012009568; WO2010105256.

As will be understood by the artisan and as disclosed throughout, "specificity" refers to the property of an antibody which enables to react with one or more antigenic determinants, such as one or more epitopes, of an antigen of interest, and not with other epitopes of the antigen of interest or with other antigens of interest. As understood in the art, antibody specificity is dependent on chemical composition, physical forces, energetic favorability, steric hindrance, and molecular structure or topology of the binding site of the epitope and/or the antibody.

As will be understood by the artisan and as disclosed throughout, "affinity" refers to the strength, or stability of an antibody-epitope interaction. Antibodies with better affinity for an epitope bind relatively tightly and/or stably with the epitope, whereas antibodies with poorer affinity for an epitope bind relatively weakly and or less stably.

As will be understood by the artisan and as disclosed throughout, "collecting" or "collected" antibodies having specificity for (an) epitope(s) of an antigen of interest refers to distinguishing (or distinguished) antibodies that have such specificity from those antibodies that do not have such specificity. Collecting antibodies or collected antibodies having specificity for (an) epitope(s) of an antigen of interest need not require physical separation of antibodies from those antibodies that do not have such specificity in order for them to be distinguished. However, in certain embodiments, collecting antibodies having specificity for (an) epitope(s) of an antigen of interest comprises physically separating such antibodies from those antibodies that do not have such specificity. Exemplary methods and means for collecting antibodies are known in the art, and include, for example, flow cytometry, florescence activated cell sorting (FACS), magnetic activated cell sorting (MACS), enzyme-linked immunosorbent assay (ELISA), and the like, and combinations thereof.

Any means for determining such specificity in the art may be employed for determining such specificity in accordance with the methods disclosed throughout, and include, for example, labelling such antibodies with a detectable label; detecting a detectable label; detecting a functional consequence of antibody binding to (an) epitope of an antigen, such as competition with another antibody known to have specificity for such epitope(s); modulation of protein-protein or protein-ligand interaction between the antigen of interest and a known protein interaction partner or ligand.

It is often desirable to include one more maturation library selections as part of an antibody discovery process. Such maturation library selections, such as affinity maturation library selections, may be advantageously incorporated into the methods disclosed herein.

A "maturation library" refers to a library that is designed to enhance or improve at least one characteristic of an antibody sequence that is identified upon interrogation of a library, such as a naïve library or a preimmune library, for the presence of antibody sequences having specificity for the antigen. Such maturation libraries may be generated by incorporating nucleic acid sequences corresponding to: one or more CDRs; one or more antigen binding regions; one or more VH or VL regions; and/or one or more heavy chains or light chains; obtained from or identified in an interrogation of a naïve library (herein referred to as "antibody leads") into libraries designed to further mutagenize in vitro or in vivo to generate libraries with diversity introduced in the context of the initial antibody leads. Such maturation libraries and methods of making them are provided in, for example, WO 2009/036379 (for example, at pages 75 through 77); and WO 2012/09568 (for example pages 69 to 72), and include: maturation libraries in which variegation is performed in which a CDRH3 of interest remains unaltered, and heavy chain framework regions, CHRH1, and/or CHDH2 regions are variegated; libraries in which a CDRL3 of interest remains unaltered, and light chain framework regions, CHRL1, and/or CHDL2 regions are variegated; libraries in which premade, diverse, light chains are combined with one or more heavy chains of interest.

A "restricted library" refers to a library that comprises: one or more unique heavy chains, one or more unique light chains, or one or more unique heavy chains and one or more unique light chains; that have been obtained or identified by performing a selection from, for example, a naive library for antigen binding regions having specificity for one antigen of interest; and is used to obtain or identify antigen binding regions having specificity for another antigen of interest. Such restricted libraries typically comprise a number of either heavy chains or light chains that is in far excess of the number of light chains or heavy chains, respectively. In certain embodiments, the number of unique heavy chains is at least $10^5$, at least $10^6$, at least $10^7$, $10^8$, or at least $10^9$ or greater and the number of unique light chains is one, two, three, four, five, ten, 15, 20, 50, 100, 200, 500, or 1000. In certain embodiments, the number of unique heavy chains is between $10^7$ and 108, and the number of unique light chains is less than 10, preferably approximately 5.

In certain embodiments, the methods disclosed throughout may comprise the use of pluralities of host cells, members of which collectively harbor nucleic acids that collectively encode the libraries of antibodies, wherein such host cells collectively express the libraries of antibodies that are interrogated for binders to the antigen of interest. When such pluralities of host cells are prepared and employed in accordance with the methods disclosed throughout, either: those host cells that express antibodies with specificity toward an antigen of interest are be collected from amongst the plurality of host cells host cells that are interrogated; or the antibodies that are encoded by such host cells may be collected. In certain embodiments, the antibodies are collected after the host cells express and secrete them.

In accordance with the use of host cells in the methods disclosed throughout libraries of polynucleotides generated by any of the techniques described herein, or other suitable techniques, may be introduced into such host cells and thereby expressed and screened to identify antibodies having desired structure and/or activity. Expression of the antibodies can be carried out, for example, using cell-free extracts (and e.g., ribosome display), phage display, prokaryotic host cells (e.g., bacterial display), or eukaryotic host cells (e.g., yeast display, mammalian cell display). In certain embodiments of the invention, the antibody libraries are expressed and/or encoded by yeast. In certain embodiments, the yeast are *Saccharomyces cerevesaie*. In other embodiments, the yeast are *Pichia pastoris*.

In other embodiments, the polynucleotides are engineered to serve as templates that can be expressed in a cell-free extract. Vectors and extracts as described, for example in U.S. Pat. Nos. 5,324,637; 5,492,817; 5,665,563, (each incorporated by reference in its entirety) can be used and many are commercially available. Ribosome display and other cell-free techniques for linking a polynucleotide (i.e., a genotype) to a polypeptide (i.e., a phenotype) can be used, e.g., Profusion™ (see, e.g., U.S. Pat. Nos. 6,348,315; 6,261,804; 6,258,558; and 6,214,553, each incorporated by reference in its entirety).

Alternatively, the polynucleotides of the invention can be expressed in an *E. coli* expression system, such as that described by Pluckthun and Skerra. (Meth. Enzymol., 1989, 178: 476; Biotechnology, 1991, 9: 273, each incorporated by reference in its entirety). The mutant proteins can be expressed for secretion in the medium and/or in the cytoplasm of the bacteria, as described by Better and Horwitz, Meth. Enzymol., 1989, 178: 476, incorporated by reference in its entirety. In some embodiments, the single domains encoding VH and VL are each attached to the 3' end of a sequence encoding a signal sequence, such as the ompA, phoA or pelB signal sequence (Lei et al, J. Bacteriol, 1987, 169: 4379, incorporated by reference in its entirety). These gene fusions are assembled in a dicistronic construct, so that they can be expressed from a single vector, and secreted into the periplasmic space of *E. coli* where they will refold and can be recovered in active form. (Skerra et al, Biotechnology, 1991, 9: 273, incorporated by reference in its entirety). For example, antibody heavy chain genes can be concurrently expressed with antibody light chain genes to produce antibodies or antibody fragments.

In other embodiments of the invention, the antibody sequences are expressed on the membrane surface of a prokaryote, e.g., *E. coli*, using a secretion signal and lipidation moiety as described, e.g., in US20040072740; US20030100023; and US20030036092 (each incorporated by reference in its entirety).

Higher eukaryotic cells, such as mammalian cells, for example myeloma cells (e.g., NS/0 cells), hybridoma cells, Chinese hamster ovary (CHO), and human embryonic kidney (HEK) cells, can also be used for expression of the antibodies of the invention. Typically, antibodies expressed in mammalian cells are designed to be secreted into the culture medium, or expressed on the surface of the cell. The antibody or antibody fragments can be produced, for example, as intact antibody molecules or as individual VH and VL fragments, Fab fragments, single domains, or as single chains (scFv) (Huston et al, PNAS, 1988, 85: 5879, incorporated by reference in its entirety).

Alternatively, antibodies can be expressed and screened by anchored periplasmic expression (APEx 2-hybrid surface display), as described, for example, in Jeong et al, PNAS, 2007, 104: 8247 (incorporated by reference in its entirety) or by other anchoring methods as described, for example, in Mazor et al., Nature Biotechnology, 2007, 25: 563 (incorporated by reference in its entirety).

In other embodiments of the invention, antibodies can be selected using mammalian cell display (Ho et al, PNAS, 2006, 103: 9637, incorporated by reference in its entirety).

The screening of the antibodies derived from the libraries of the invention can be carried out by any appropriate means. For example, binding activity can be evaluated by standard immunoassay and/or affinity chromatography. Screening of the antibodies of the invention for catalytic function, e.g., proteolytic function can be accomplished using a standard assays, e.g., the hemoglobin plaque assay as described in U.S. Pat. No. 5,798,208 (incorporated by reference in its entirety). Determining the ability of candidate antibodies to bind therapeutic targets can be assayed in vitro using, e.g., a BIACORE™ instrument, which measures binding rates of an antibody to a given target or antigen based on surface plasmon resonance. In vivo assays can be conducted using any of a number of animal models and then subsequently tested, as appropriate, in humans. Cell-based biological assays are also contemplated.

As mentioned above, the inventive methods do not require the design or engineering of heterodimerization motifs in order to obtain meaningful quantities and purities of the desired MAI. However, the inventive methods are amenable to the inclusion of such motifs. Interaction between heterodimeric pairs or disclosed multispecific antibody analogs comprising such heterodimeric pairs may be promoted at the heterodimeric pair interface by the formation of protuberance-into-cavity complementary regions at such interfaces; the formation of non-naturally occurring disulfide bonds at such interfaces; leucine zipper at such interfaces; hydrophobic regions at such interfaces; and/or hydrophilic regions at such interfaces. "Protuberances" are constructed by replacing small amino acid side chains from the interface of the first polypeptide with larger side chains (e.g. tyrosine or tryptophan). Compensatory "cavities" of identical or similar size to the protuberances are optionally created on the interface of the second polypeptide by replacing large amino acid side chains with smaller ones (e.g. alanine or threonine). Where a suitably positioned and dimensioned protuberance or cavity exists at the interface of either the first or second polypeptide, it is only necessary to engineer a corresponding cavity or protuberance, respectively, at the adjacent interface. Non-naturally occurring disulfide bonds are constructed by replacing on the first polypeptide a naturally occurring amino acid with a free thiol-containing residue, such as cysteine, such that the free thiol interacts with another free thiol-containing residue on the second polypeptide such that a disulfide bond is formed between the first and second polypeptides Exemplary heterodimerization pairs and methods for making such in accordance with the present invention are available in the art, and are disclosed, for example, in US 2011/0054151; US 2007/0098712; and the like.

In certain embodiments, the heterodimeric pairs are contained within the Fc region of the inventive multispecific antibody analogs. Fc regions that contain such heterodimeric pairs are referred to as "heterodimeric Fc regions".

Accordingly, in certain embodiments, multispecific antibody analogs comprise a CH2 and/or a CH3 domain variant, wherein either: a) the CH2 domain variant and the CH3 domain variant each independently comprises a at least one protuberance in either the CH2 domain or the CH3 domain of the first polypeptide and at least one corresponding cavity in the CH2 domain or the CH3 domain of the second; or the CH2 domain variant and the CH3 domain variant each independently comprises at least one cavity in either the CH2 domain or the CH3 domain of the first polypeptide and at least one corresponding protuberance in the CH2 domain or the CH3 domain of the second polypeptide. In certain other embodiments, the multispecific antibody analogs comprise a CH2 and/or a CH3 domain variant, wherein either: a) the CH2 domain variant and the CH3 domain variant each independently comprises at least one substituted negatively-charged amino acid in either the CH2 domain or the CH3 domain of the first polypeptide and at least one corresponding positively-charged amino acid in either the CH2 domain or the CH3 domain of the second polypeptide; or b) the CH2 domain variant and the CH3 domain variant each independently comprises at least one substituted positively-charged amino acid in either the CH2 domain or the CH3 domain of the first polypeptide and at least one corresponding substituted negatively-charged substituted amino acid in either the CH2 domain or the CH3 domain of the second polypeptide.

With regard to Fc function in "natural" antibodies (i.e., those antibodies generated in vivo via native biological antibody synthesis by native B-cells), the Fc region of an antibody interacts with a number of Fc receptors and ligands, imparting an array of important functional capabilities referred to as effector functions. For IgG the Fc region, Fc comprises Ig domains Cγ2 and Cγ3 and the N-terminal hinge leading into Cγ2. An important family of Fc receptors for the IgG class is the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and 75 T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP).

A particular feature of the Fc region of "natural" antibodies is the conserved N-linked glycosylation that occurs at N297. This carbohydrate, or oligosaccharide as it is sometimes referred, plays a critical structural and functional role for the antibody, and is one of the principle reasons that antibodies must be produced using mammalian expression systems. Efficient Fc binding to FcγR and C1q requires this modification, and alterations in the composition of the N297 carbohydrate or its elimination affect binding to these proteins In some embodiments, the inventive multispecific antibody analogs disclosed herein comprise an Fc variant. An Fc variant comprises one or more amino acid modifications relative to a parent Fc polypeptide, wherein the amino acid modification(s) provide one or more optimized properties. Fc variants further comprise either a CH2 domain variant, a CH3 domain variant, or both a CH2 domain variant and a CH3 domain variant. By "modification" herein is meant an alteration in the physical, chemical, or sequence properties of a protein, polypeptide, antibody, inventive multispecific antibody analog, or immunoglobulin. An amino acid modification can be an amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution Y349T refers to a variant polypeptide, in this case a constant heavy chain variant, in which the tyrosine at position 349 is replaced with threonine. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence.

An Fc variant disclosed herein differs in amino acid sequence from its parent by virtue of at least one amino acid modification. The inventive multispecific antibody analogs disclosed herein may have more than one amino acid modification as compared to the parent, for example from about one to fifty amino acid modifications, e.g., from about one to ten amino acid modifications, from about one to about five amino acid modifications, etc. compared to the parent. Thus the sequences of the Fc variants and those of the parent Fc polypeptide are substantially homologous. For example, the variant Fc variant sequences herein will possess about 80% homology with the parent Fc variant sequence, e.g., at least about 90% homology, at least about 95% homology, at least about 98% homology, at least about 99% homology, etc. Modifications disclosed herein also include glycoform modifications. Modifications may be made genetically using molecular biology, or may be made enzymatically or chemically.

Fc variants disclosed herein are defined according to the amino acid modifications that compose them. Thus, for example, the substitution Y349T refers to a variant polypeptide, in this case a constant heavy chain variant, in which the tyrosine at position 349 is replaced with threonine. Likewise, Y349T/T394F defines an Fc variant with the substitutions Y349T and T394F relative to the parent Fc polypeptide. The identity of the WT amino acid may be unspecified, in which case the aforementioned variant is referred to as 349T/394F. It is noted that the order in which substitutions are provided is arbitrary, that is to say that, for example, 349T/394F is the same Fc variant as 394F/349T. Unless otherwise noted, constant region and Fc positions discussed herein are numbered according to the EU index or EU numbering scheme (Kabat et al., 1991, Sequences of Proteins of Immunological Interest, 5th Ed., United States Public Health Service, National Institutes of Health, Bethesda). The EU index or EU index as in Kabat or EU numbering scheme refers to the numbering of the EU antibody (Edelman et al., 1969, Proc Natl Acad Sci USA 63:78-85).

In certain embodiments, the Fc variants disclosed herein are based on human IgG sequences, and thus human IgG sequences are used as the "base" sequences against which other sequences are compared, including but not limited to sequences from other organisms, for example rodent and primate sequences. Immunoglobulins may also comprise sequences from other immunoglobulin classes such as IgA, IgE, IgD, IgM, and the like. It is contemplated that, although the Fc variants disclosed herein are engineered in the context of one parent IgG, the variants may be engineered in or "transferred" to the context of another, second parent IgG. This is done by determining the "equivalent" or "corresponding" residues and substitutions between the first and second IgG, typically based on sequence or structural homology between the sequences of the first and second IgGs. In order to establish homology, the amino acid sequence of a first IgG outlined herein is directly compared to the sequence of a second IgG. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first immunoglobulin are defined. Alignment of conserved residues may conserve 100% of such residues. However, alignment of greater than 75% or as little as 50% of conserved residues is also adequate to define equivalent residues. Equivalent residues may also be defined by determining structural homology between a first and second IgG that is at the level of tertiary structure for IgGs whose structures have been determined. In this case, equivalent residues are defined as those for which the atomic coordinates of two or more of the main chain atoms of a particular amino acid residue of the parent or precursor (N on N, CA on CA, C on C and O on O) are within about 0.13 nm, after alignment. In another embodiment, equivalent residues are within about 0.1 nm after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the parent IgG in which the IgGs are made, what is meant to be conveyed is that the Fc variants discovered as disclosed herein may be engineered into any second parent IgG that has significant sequence or structural homology with the Fc variant. Thus for example, if a variant antibody is generated wherein the parent antibody is human IgG1, by using the methods described above or other methods for determining equivalent residues, the variant antibody may be engineered in another IgG1 parent antibody that binds a different antigen, a human IgG2 parent antibody, a human IgA parent antibody, a mouse IgG2a or IgG2b parent antibody, and the like. Again, as described above, the context of the parent Fc variant does not affect the ability to transfer the Fc variants disclosed herein to other parent IgGs.

Fc variants that comprise or are CH3 domain variants as described above may comprise at least one substitution at a position in a CH3 domain selected from the group consisting of 349, 351, 354, 356, 357, 364, 366, 368, 370, 392, 394, 395, 396, 397, 399, 401, 405, 407, 409, 411, and 439, wherein numbering is according to the EU index as in Kabat. In a preferred embodiment, CH3 domain variants comprise at least one CH3 domain substitution per heavy chain selected from the group consisting of 349A, 349C, 349E, 349I, 349K, 349S, 349T, 349W, 351 E, 351K, 354C, 356K, 357K, 364C, 364D, 364E, 364F, 364G, 364H, 364R, 364T, 364Y, 366D, 366K, 366S, 366W, 366Y, 368A, 368E, 368K, 368S, 370C, 370D, 370E, 370G, 370R, 370S, 370V, 392D, 392E, 394F, 394S, 394W, 394Y, 395T, 395V, 396T, 397E, 397S, 397T, 399K, 401 K, 405A, 405S, 407T, 407V, 409D, 409E, 411D, 411 E, 411K, and 439D. Each of these variants can be used individually or in any combination for each heavy chain Fc region. As will be appreciated by those in the art, each heavy chain can comprise different numbers of substitutions. For example, both heavy chains that make up the Fc region may comprise a single substitution, one chain may comprise a single substitution and the other two substitutions, both can contain two substitutions (although each chain will contain different substitutions), etc.

In some embodiments, the CH2 and/or CH3 domain variants are made in combinations, that is, two or more variants per heavy chain Fc domain, selected from the group outlined above.

Other CH2 and/or CH3 domain variants that favor heterodimerization that may be employed in the design and preparation of the inventive multispecific antibody analogs of the invention are provided in, for example, Ridgeway et al., 1996, Protein Engineering 9[7]:617-621; U.S. Pat. No. 5,731,168; Xie et al., 2005, J Immunol Methods 296:95-101; Davis et al., 2010, Protein Engineering, Design & Selection 23[4]:195-202; Gunasekaran et al., 2010, J Biol Chem 285[25]:1937-19646; and PCT/US2009/000071 (published as WO 2009/089004).

The Fc variants disclosed herein may be optimized for improved or reduced binding to Fc receptors or Fc ligands.

By "Fc receptor" or "Fc ligand" as used herein is meant a molecule, preferably a polypeptide, from any organism that binds to the Fc region of an antibody to form an Fc-ligand complex. Fc ligands include but are not limited to FcγRs, (as described above, including but not limited to FcγRIIIa, FcγRIIa, FcγRIIb, FcγRI and FcRn), C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs. Fc ligands may include undiscovered molecules that bind Fc.

The inventive multispecific antibody analogs may be designed to optimize properties, including but are not limited to enhanced or reduced affinity for an Fc receptor. By "greater affinity" or "improved affinity" or "enhanced affinity" or "better affinity" than a parent Fc polypeptide, as used herein, is meant that an Fc variant binds to an Fc receptor with a significantly higher equilibrium constant of association (KA or $K_a$) or lower equilibrium constant of dissociation (KD or $K_d$) than the parent Fc polypeptide when the amounts of variant and parent polypeptide in the binding assay are essentially the same. For example, the Fc variant with improved Fc receptor binding affinity may display from about 5 fold to about 1000 fold, e.g. from about 10 fold to about 500 fold improvement in Fc receptor binding affinity compared to the parent Fc polypeptide, where Fc receptor binding affinity is determined, for example, by the binding methods disclosed herein, including but not limited to Biacore, by one skilled in the art. Accordingly, by "reduced affinity" as compared to a parent Fc polypeptide as used herein is meant that an Fc variant binds an Fc receptor with significantly lower KA or higher KD than the parent Fc polypeptide. Greater or reduced affinity can also be defined relative to an absolute level of affinity.

As would be understood by those of ordinary skill in the art, the term "antibody" is used herein in the broadest sense and specifically encompasses at least monoclonal antibodies, polyclonal antibodies, multi-specific antibodies (e.g., bispecific antibodies), chimeric antibodies, humanized antibodies, human antibodies, antibody fragments, and derivatives thereof. An antibody is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. An "antibody" also refers to an immunoglobulin molecule, a fragment of an immunoglobulin molecule, or a derivative thereof, which has the ability to specifically bind to an antigen, which may be, for example: a protein; a polypeptide; peptide; a hormone; a cytokine; a chemokine; a growth factor; a neurotransmitter; a carbohydrate-containing biological molecule; a lipid or fatty acid-containing biological molecule; or other biological molecule; via an epitope present on such antigen.

Antibodies (used interchangeably with "immunoglobulins", or "immunoglobulin molecules") can be monomeric, dimeric, trimeric, tetrameric, pentameric, etc., and comprise a class of structurally related proteins consisting of two pairs of polypeptide chains: one pair of light chains (LC) and one pair of heavy chains (HC), all of which are inter-connected by disulfide bonds. The structure of immunoglobulins has been well characterized. See for instance Fundamental Immunology Ch. 7 (Paul, W., ed., 2nd ed. Raven Press, N.Y. (1989)).

Traditional natural antibody structural formats typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. IgA has several subclasses, including but not limited to IgA1 and IgA2. Thus, "isotype" as used herein is meant any of the classes and subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE. The distinguishing features between these antibody classes are their constant regions, although subtler differences may exist in the variable region.

Each of the light and heavy chains is made up of two distinct regions, referred to as the variable and constant regions. The IgG heavy chain is composed of four immunoglobulin domains linked from N- to C-terminus in the order VH-CH1-CH2-CH3, referring to the "variable heavy domain" (also referred to as a "heavy chain variable domain", used interchangeably throughout), heavy chain constant domain 1, heavy chain constant domain 2, and heavy chain constant domain 3 respectively (also referred to as VH-Cγ1-Cγ2-Cγ3, referring to the variable heavy domain, constant gamma 1 domain, constant gamma 2 domain, and constant gamma 3 domain respectively). The IgG light chain is composed of two immunoglobulin domains linked from N- to C-terminus in the order VL-CL, referring to the "variable light domain" (also referred to as a "light chain variable domain", used interchangeably throughout) and the light chain constant domain respectively. The constant regions show less sequence diversity, and are responsible for binding a number of natural proteins to elicit important biochemical events. The structure that constitutes the natural biological form of an antibody, including the variable and constant regions, is referred to herein as a "full length antibody". In most mammals, including humans and mice, the full length antibody of the IgG isotype is a tetramer and consists of two identical pairs of two immunoglobulin chains, each pair having one light chain and one heavy chain, each light chain comprising a VL and a CL, and each heavy chain comprising a VH, CH1, a CH2, and a CH3. In some mammals, for example in camels and llamas, IgG antibodies may consist of only two heavy chains, each heavy chain comprising a variable domain attached to the Fc region.

The heavy chain constant region typically is comprised of three domains, CH1, CH2, and CH3, and the CH1 and CH2 domains are connected by a hinge region. Each light chain typically is comprised of a light chain variable domain (abbreviated herein as "$V_L$" or "VL") and a light chain constant domain. The $V_H$ and $V_L$ domains may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and VL is typically composed of three CDRs and four FRs, arranged from amino-terminus to carboxy-terminus in the following order: FR1, CDR1, FR2, CDR2, FR3, CDR3, FR4. Typically, the numbering of amino acid residues in this region is performed by the method described in Kabat (see, e.g., Kabat et al, in "Sequences of Proteins of Immunological Interest," 5$^{th}$ Edition, U.S. Department of Health and Human Services, 1992). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of $V_H$ CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "variable", "variable domain", or "variable region" each interchangeably refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable" regions or "complementarity determining regions" (CDRs). The more conserved (i.e., non-hypervariable) portions of the variable domains are called the "framework" regions (FRM). The variable domains of naturally occurring heavy and light chains each comprise four FRM regions, largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding site (see Kabat et al. Sequences of Proteins of Immunological Interest, 5th Ed. Public Health Service, National Institutes of Health, Bethesda, Md., 1991, incorporated by reference in its entirety). The constant domains are not directly involved in antigen binding, but exhibit various effector functions, such as, for example, antibody-dependent, cell-mediated cytotoxicity and complement activation.

The term "framework region" refers to the art-recognized portions of an antibody variable region that exist between the more divergent (i.e., hypervariable) CDRs. Such framework regions are typically referred to as frameworks 1 through 4 (FRM1, FRM2, FRM3, and FRM4) and provide a scaffold for the presentation of the six CDRs (three from the heavy chain and three from the light chain) in three dimensional space, to form an antigen-binding surface. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. Mol. Biol., 1987, 196: 901; Chothia et al, Nature, 1989, 342: 877; Martin and Thornton, J. Mol. Biol, 1996, 263: 800. Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

The term "canonical structure" may also include considerations as to the linear sequence of the antibody, for example, as catalogued by Kabat (Kabat et al, in "Sequences of Proteins of Immunological Interest," 5$^{th}$ Edition, U.S. Department of Health and Human Services, 1992). The Kabat numbering scheme is a widely adopted standard for numbering the amino acid residues of an antibody variable domain in a consistent manner. Additional structural considerations can also be used to determine the canonical structure of an antibody. For example, those differences not fully reflected by Kabat numbering can be described by the numbering system of Chothia et al and/or revealed by other techniques, for example, crystallography and two or three-dimensional computational modeling. Accordingly, a given antibody sequence may be placed into a canonical class which allows for, among other things, identifying appropriate chassis sequences (e.g., based on a desire to include a variety of canonical structures in a library). Kabat numbering of antibody amino acid sequences and structural considerations as described by Chothia et al., and their implications for construing canonical aspects of antibody structure, are described in the literature.

By "Fc" or "Fc region", as used herein is meant the polypeptide comprising the constant region of an antibody excluding the first constant region immunoglobulin domain. Thus "Fc region" refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Accordingly, and without departing from the above, "Fc region" may also be defined as comprising a "CH2 domain or a variant thereof" and a "CH3 domain or a variant thereof". Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, for example an antibody. By "Fc polypeptide" as used herein is meant a polypeptide that comprises all or part of an Fc region. Fc polypeptides include antibodies, Fc fusions, isolated Fcs, and Fc fragments.

A variable light chain (VL) and corresponding variable heavy domain (VH) of the inventive multispecific antibodies of interest comprise a binding domain, also referred to interchangeably throughout as an "antigen binding site" that interacts with an antigen. Thus, a "first variable light domain" and a "first variable heavy domain" of the inventive multispecific antibody of interest together form a "first antigen binding site". Similarly, a "second variable light domain" and a "second variable heavy domain" of the inventive multispecific antibody of interest together form a "second antigen binding site". A "third variable light domain" and a "third variable heavy domain" of the inventive multispecific antibody of interest together form a "third antigen binding site", and so on.

The antigen binding sites for use in accordance with the invention, including the VHs, VLs, and/or CDRs that comprise such, may be obtained or derived from any source of such, as will be understood by the artisan. Accordingly, such antigen binding sites, VHs, VLs, and/or CDRs may be obtained or derived from hybridoma cells that express antibodies against a target recognized by such; from B cells from immunized donors, which express antibodies against a target recognized by such; from B-cells that have been stimulated to express antibodies against a target recognized by such; and or from identification of antibodies or antibody fragments that have been identified by screening a library comprising a plurality of polynucleotides or polypeptides for antigen binding antibodies (or antigen binding fragments thereof). With regard to the design, preparation, display, and implementation of such libraries for use in identifying and obtaining antigen binding sites for use in accordance with the invention, see, e.g., WO 2009/036379; WO2012009568; WO2010105256; U.S. Pat. Nos. 8,258,082; 6,300,064; 6,696,248; 6,165,718; 6,500,644; 6,291,158; 6,291,159; 6,096,551; 6,368,805; 6,500,644; and the like.

Any one or more of the antigen binding sites, VHs, VLs, or CDRs, and combinations thereof, of the inventive multispecific antibodies of interest, may comprise sequences from a variety of species. In some embodiments, such antigen binding sites, VHs, VLs, or CDRs, and combinations thereof may be obtained from a nonhuman source, including but not limited to mice, rats, rabbits, camels, llamas, and monkeys. In some embodiments, the scaffold and/or framework regions can be a mixture from different species. As such, a multispecific antibody of interest in accordance with the invention may comprise a chimeric antibody and/or a humanized antibody. In general, both "chimeric antibodies" and "humanized antibodies" refer to antibodies in which regions from more than one species have been combined. For example, "chimeric antibodies" traditionally comprise variable region(s) from a mouse or other nonhuman species and the constant region(s) from a human.

"Humanized antibodies" generally refer to non-human antibodies that have had the variable-domain framework regions swapped for sequences found in human antibodies. Generally in a humanized antibody the entire antibody, except the CDRs, is encoded by a polynucleotide of human origin or is identical to such an antibody except within its CDRs. The CDRs, one, some, or all of which are encoded by nucleic acids originating in a non-human organism, are grafted into the framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239: 1534-1536. "Backmutation" of selected acceptor framework residues to the corresponding donor residues is often required to regain affinity that is lost in the initial grafted construct (see, e.g., U.S. Pat. No. 5,693,762). The humanized antibody optimally also will comprise at least a portion of an immunoglobulin constant region, typically that of a human immunoglobulin, and thus will typically comprise a human Fc region. A variety of techniques and methods for humanizing, reshaping, and resurfacing non-human antibodies are well known in the art (See Tsurushita & Vasquez, 2004, Humanization of Monoclonal Antibodies, Molecular Biology of B Cells, 533-545, Elsevier Science (USA), and references cited therein). In certain variations, the immunogenicity of the antibody is reduced using a method described in Lazar et al., 2007, Mol Immunol 44:1986-1998 and U.S. Ser. No. 11/004,590, entitled "Methods of Generating Variant Proteins with Increased Host String Content and Compositions Thereof", filed on Dec. 3, 2004.

Accordingly, any one or more of the antigen binding sites, or one or more VHs, VLs, CDRs, or combinations thereof, which comprise the inventive multispecific antibodies of interest disclosed herein may be derived from a non-human species and/or result from humanization of a non-human antibody or antibody fragment. Such VHs, VLs, and/or CDRs obtained or derived from non-human species, when included in the inventive multispecific analogs disclosed herein, are referred to as "humanized" such regions and/or domains.

The inventive antibody analogs disclosed herein preferably comprise first and second polypeptides that each comprise a hinge region, wherein each hinge region comprises at least one thiol group that is capable of participating in an intermolecular disulfide bond such that the first and the second polypeptide are covalently linked as a result of formation of the disulfide bond. As is understood in the art, chemical modification may be introduced into (or onto) certain residues within such hinge regions which effect the introduction of such thiol groups for disulfide bond formation. Alternatively, the thiol groups may be provided by a cysteine residue that is present within the hinge region. Such cysteines may be provided by native hinge polypeptide sequence, or may be introduced by mutagenesis into nucleic acid encoding the hinge region. As used herein, whereas a "hinge" or a "hinge region" of the inventive antibody analogs may comprise or constitute a natural or native hinge region as found in, for example, immunoglobulins such as IgGs, IgMs, IgAs, IgEs, and the like, such a hinge or hinge region may also comprise or constitute a substitutes form thereof. Further, such a hinge or hinge region may, in certain embodiments comprise or constitute a "linker moiety" as disclosed throughout. In other embodiments, a hinge or hinge region may comprise both a natural or native hinge region as disclosed above and a linker moiety as disclosed throughout.

In certain embodiments, the inventive antibody analogs disclosed herein comprise one or more linkers or linker moieties. Such linkers or linker moieties may comprise a peptidic linker moiety or a non-peptidic linker moiety. The terms "linker" and "linker moiety" and the like, means a divalent species (-L-) covalently bonded in turn to a polypeptide having a valency available for bonding and to an amino acid that comprises the inventive multispecific antibody of interest, which amino acid has a valency available for bonding. The available bonding site may conveniently comprise a side chain of an amino acid (e.g., a lysine, cysteine, or aspartic acid side chain, and homologs thereof). In some embodiments, the available bonding site in the analog is the side chain of a lysine or a cysteine residue. In some embodiments, the available bonding site in the analog is the N-terminal amine of a polypeptide comprising the analog. In some embodiments, the available bonding site in the analog is the C-terminal carboxyl of a polypeptide comprising the analog. In some embodiments, the available bonding site in the analog is a backbone atom (e.g., a c-alpha carbon atom) of a polypeptide comprising the analog.

Preferably, a linker moiety is employed to covalently attach a VH or a VL to the C-terminus of a CH3 domain of an antibody analog. A linker moiety may also be employed to covalently attach a first VH or a first VL to a second VH or a second VL, respectively. A linker moiety may also be employed to covalently attach a first VH or a first VL to a second VL or a second VH, respectively. A linker moiety may also be employed to covalently attach a VH of a single chain antigen binding site, such as an scFv, to the VL of such a single chain antigen binding site, and vice versa. A linker moiety may also be employed to attach the VH or the VL of such a single chain antigen binding site, such as an scFv, to a C-terminus of a CH3 domain or variant thereof. A linker moiety may also be employed to attach a VH to the N-terminus of a CL domain or to the N-terminus of a CH2. A linker moiety may also be employed to attach a VL to the N-terminus of a CL domain or to the N-terminus of a CH2 domain. As will be appreciated, combinations and/or multiples of the foregoing may be employed in order to prepare any of the multispecific antibodies of interest disclosed herein, such that a plurality of antigen binding sites may be included in such analogs, optionally with a multiple of specificities. Accordingly, a multispecific antibody of interest may be generated by employing one or more linkers to covalently attach one, two, three, four, five, six, seven, or more VLs, VHs, and/or single chain antigen binding sites, such as scFvs to the first polypeptide, the second polypeptide, a VH, or a VL attached to the first polypeptide or the second polypeptide, and the like, so as to generate an antibody analog having bi-, tri-, tetra-, pent-, hexa-, hepta-, or octa-valency, and so on, and/or bi-, tri-, tetra-, pent-, hexa-, hepta-, or octa-specificity, and so on.

Accordingly, in certain embodiments, the multispecific antibody of interest comprises a first VL that is covalently attached to the CH3 domain, or variant thereof, of the first heavy chain of the analog via a linker moiety, forming the second antigen binding site. In additional embodiments, the multispecific antibody of interest comprises a first VH that is covalently attached to the CH3 domain, or variant thereof, of the Fc region of the analog via a linker moiety, thereby forming the second antigen binding site.

In further embodiments, the multispecific antibody of interest comprises a third antigen binding site, wherein the third antigen binding site is covalently attached via a linker moiety to either the first VL or the first VH. In still further embodiments, the third antigen binding site comprises a single chain antigen binding site, such single chain variable region (scFv), wherein the scFv comprises a second VL that is covalently attached to a second VH via a linker moiety or wherein the second VL is covalently attached to the second VH via a linker moiety.

In further embodiments, the inventive multispecific antibodies of interest further comprise additional binding sites, such as a fourth antigen binding site, a fifth antigen binding site, a sixth antigen binding site, and so on, wherein one or more of which may comprise a single chain antigen binding site, such as an scFv, which are attached via linker moieties to the other VLs and/or VHs of the multispecific antibody of interest.

In certain embodiments the linker moieties comprise amino acids that are selected from glycine, alanine, proline, asparagine, glutamine, lysine, aspartate, and glutamate. In a further embodiment the linker moiety is made up of a majority of amino acids that are sterically unhindered, such as glycine, alanine and/or serine. In certain embodiments the linker moiety is comprises a sequence selected from the group [Gly-Ser]$_n$ (SEQ ID NO: 1); [Gly-Gly-Ser]$_n$ (SEQ ID NO: 2); [Gly-Gly-Gly-Ser]$_n$ (SEQ ID NO: 3); [Gly-Gly-Gly-Gly-Ser]$_n$ (SEQ ID NO: 4]; [Gly-Gly-Gly-Gly-Ser-Gly-Gly-Gly-Gly]$_n$ (SEQ ID NO: 5); [Gly-Gly-Gly-Gly-Ser-Gly-Gly-Gly-Gly-Ser-Gly-Gly-Gly-Gly]$_n$(SEQ ID NO: 6); [Gly-Gly-Gly-Gly-Ser Gly-Gly-Gly-Gly-Ser-Gly-Gly-Gly-Ser-Gly-Gly-Gly-Gly-Gly]$_n$ (SEQ ID NO: 7); [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Gly]$_n$ (SEQ ID NO: 8); [Gly-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Gly]$_n$ (SEQ ID NO: 9); [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Gly]$_n$ (SEQ ID NO: 10); and combinations thereof; where n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75.

Such linkers may comprise: an acidic linker, a basic linker, and a structural motif, or combinations thereof; a polyglycine, a polyalanine, poly(Gly-Ala), or poly(Gly-Ser); (Gly)3, (Gly)4 (SEQ ID NO: 11), or (Gly)5 (SEQ ID NO: 12); (Gly)$_3$Lys(Gly)$_4$ (SEQ ID NO: 13), (Gly)$_3$AsnGly-Ser(Gly)$_2$ (SEQ ID NO: 14), (Gly)$_3$Cys(Gly)$_4$ (SEQ ID NO: 15), or GlyProAsnGlyGly (SEQ ID NO: 16), [Gly-Ser]$_n$ (SEQ ID NO: 1), [Gly-Gly-Ser]$_n$ (SEQ ID NO: 2), [Gly-Gly-Gly-Ser]$_n$ (SEQ ID NO: 3), [Gly-Gly-Gly-Gly-Ser]$_n$ (SEQ ID NO: 4), [Gly-Gly-Gly-Gly-Ser-Gly-Gly-Gly-Gly]$_n$ (SEQ ID NO: 5), [Gly-Gly-Gly-Gly-Ser-Gly-Gly-Gly-Gly-Ser-Gly-Gly-Gly-Gly-Gly]$_n$ (SEQ ID NO: 6), [Gly-Gly-Gly-Gly-Ser Gly-Gly-Gly-Gly-Ser-Gly-Gly-Gly-Gly-Ser-Gly-Gly-Gly-Gly-Gly]$_n$ (SEQ ID NO: 7), [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Gly]$_n$ (SEQ ID NO: 8), [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Gly]$_n$ (SEQ ID NO: 9), or [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Gly]$_n$ (SEQ ID NO: 10); [Gly-Glu]$_n$ (SEQ ID NO: 17), [Gly-Gly-Glu]$_n$ (SEQ ID NO: 18), [Gly-Gly-Gly-Glu]$_n$ (SEQ ID NO: 19), [Gly-Gly-Gly-Gly-Glu]$_n$ (SEQ ID NO: 20), [Gly-Asp]n (SEQ ID NO: 21); [Gly-Gly-Asp]$_n$ (SEQ ID NO: 22), [Gly-Gly-Gly-Asp]$_n$ (SEQ ID NO: 23), [Gly-Gly-Gly-Gly-Asp]$_n$ (SEQ ID NO: 24); where n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75.

In certain embodiments, charged linker moieties are employed. Such charges linker moieties may contain a significant number of acidic residues (e.g., Asp, Glu, and the like), or may contain a significant number of basis residues (e.g., Lys, Arg, and the like), such that the linker moiety has a pi lower than 7 or greater than 7, respectively. As understood by the artisan, and all other things being equal, the greater the relative amount of acidic or basic residues in a given linker moiety, the lower or higher, respectively, the pI of the linker moiety will be. Such linker moieties may impart advantages to the multispecific antibodies of interest disclosed herein, such as improving solubility and/or stability characteristics of such polypeptides at a particular pH, such as a physiological pH (e.g., between H 7.2 and pH 7.6, inclusive), or a pH of a pharmaceutical composition comprising such analogs, as well as allowing for optimization of characteristics such as rotational and translational flexibility of the domains and/or regions of the analog that are attached via the linker moiety. Such characteristics may advantageously be optimized and tailored for any given multispecific analog by the artisan.

For example, an "acidic linker" is a linker moiety that has a pI of less than 7; between 6 and 7, inclusive; between 5 and 6, inclusive; between 4 and 5, inclusive; between 3 and 4, inclusive; between 2 and 3, inclusive; or between 1 and 2, inclusive. Similarly, a "basic linker" is a linker moiety that has a pi of greater than 7; between 7 and 8, inclusive; between 8 and 9, inclusive; between 9 and 10, inclusive; between 10 and 11, inclusive; between 11 and 12 inclusive, or between 12 and 13, inclusive. In certain embodiments, an acidic linker will contain a sequence that is selected from the group consisting of [Gly-Glu]$_n$ (SEQ ID NO: 17); [Gly-Gly-Glu]$_n$ (SEQ ID NO: 18); [Gly-Gly-Gly-Glu]$_n$ (SEQ ID NO: 19); [Gly-Gly-Gly-Gly-Glu]$_n$ (SEQ ID NO: 20); [Gly-Asp]n (SEQ ID NO: 21); [Gly-Gly-Asp]$_n$ (SEQ ID NO: 22); [Gly-Gly-Gly-Asp]$_n$ (SEQ ID NO: 23); [Gly-Gly-Gly-Gly-Asp]$_n$(SEQ ID NO: 24); and combinations thereof; where n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75. In certain embodiments, a basic linker will contain a sequence that is selected from the group consisting of [Gly-Lys]$_n$ (SEQ ID NO: 25); [Gly-Gly-Lys]$_n$ (SEQ ID NO: 26); [Gly-Gly-Gly-Lys]$_n$ (SEQ ID NO: 27); [Gly-Gly-Gly-Gly-Lys]$_n$ (SEQ ID NO: 28); [Gly-Arg]$_n$ (SEQ ID NO: 29); [Gly-Gly-Arg]$_n$ (SEQ ID NO: 30); [Gly-Gly-Gly-Arg]$_n$ (SEQ ID NO: 31); [Gly-Gly-Gly-Gly-Arg]$_n$ (SEQ ID NO: 32); and combinations thereof; where n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75.

Additionally, linker moieties may be employed which possess certain structural motifs or characteristics, such as an alpha helix. For example, such a linker moiety may contain a sequence that is selected from the group consisting of [Glu-Ala-Ala-Ala-Lys]$_n$ (SEQ ID NO: 33), where n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75: for example, [Glu-Ala-Ala-Ala-Lys]$_3$ (SEQ ID NO: 34), [Glu-Ala-Ala-Ala-Lys]$_4$ (SEQ ID NO: 35), or [Glu-Ala-Ala-Ala-Lys]$_5$ (SEQ ID NO: 36), and so on.

In still further embodiments the each linker moiety employed in the disclosed multispecific antibody of interest independently comprises: polyglycine, polyalanine, poly(Gly-Ala), or poly(Gly-Ser), (Gly)3, (Gly)4 (SEQ ID NO: 11), and (Gly)5 (SEQ ID NO: 12), (Gly)$_3$Lys(Gly)$_4$ (SEQ ID NO: 13), (Gly)$_3$AsnGlySer(Gly)$_2$ (SEQ ID NO: 14), (Gly)$_3$Cys(Gly)$_4$ (SEQ ID NO: 15), and GlyProAsnGlyGly (SEQ ID NO: 16), a combination of Gly and Ala, a combination of Gly and Ser, a combination of, Gly and Glu, a combination of Gly and Asp, a combination of Gly and Lys, or combinations thereof.

In certain embodiments, the inventive multispecific antibody of interest comprises, for example, a CH2 domain variant and/or a CH3 domain variant, wherein such variants each independently comprise at least one different amino acid substitution such that a heterodimeric domain pair is generated such that heterodimerization of the first and second polypeptides of the inventive multispecific antibody of interest is favored over homodimerization.

With regard to a "variant" of a domain or region of a multispecific antibody of interest as used herein throughout, such a variant refers a polypeptide sequence that comprises such a domain or region, and that differs from that of a parent polypeptide sequence by virtue of at least one amino acid modification. The parent polypeptide sequence may be a naturally occurring or wild-type (WT) polypeptide sequence, or may be a modified version of a WT sequence. Preferably, the variant has at least one amino acid modification compared to the parent polypeptide, region, or domain, e.g. from about one to about ten amino acid modifications, and preferably from about one to about five amino acid modifications compared to the parent. The variant polypeptide sequence herein will preferably possess at least about 80% homology with a parent sequence, and most preferably at least about 90% homology, more preferably at least about 95% homology.

By "parent polypeptide", "parent polypeptide sequence", "parent protein", "precursor polypeptide", or "precursor protein" as used herein is meant an unmodified polypeptide or polypeptide sequence that is subsequently modified to generate a variant polypeptide or polypeptide sequence. Said parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it.

By "Fc variant" or "variant Fc" as used herein is meant an Fc sequence that differs from that of a parent Fc sequence by virtue of at least one amino acid modification. An Fc variant may only encompass an Fc region, or may exist in the context of an antibody, Fc fusion, isolated Fc, Fc fragment, or other polypeptide that is substantially encoded by Fc. Fc variant may refer to the Fc polypeptide itself, compositions comprising the Fc variant polypeptide, or the amino acid sequence that encodes it.

By "Fc polypeptide variant" or "variant Fc polypeptide" as used herein is meant an Fc polypeptide that differs from a parent Fc polypeptide by virtue of at least one amino acid modification. By "Fc variant antibody" or "antibody Fc variant" as used herein is meant an antibody that differs from a parent antibody by virtue of at least one amino acid modification in the Fc region.

By "protein variant" or "variant protein" as used herein is meant a protein that differs from a parent protein by virtue of at least one amino acid modification. By "antibody variant" or "variant antibody" as used herein is meant an antibody that differs from a parent antibody by virtue of at least one amino acid modification. By "IgG variant" or "variant IgG" as used herein is meant an antibody that differs from a parent IgG by virtue of at least one amino acid modification. By "immunoglobulin variant" or "variant immunoglobulin" as used herein is meant an immunoglobulin sequence that differs from that of a parent immunoglobulin sequence by virtue of at least one amino acid modification.

Interaction between heterodimeric pairs or disclosed multispecific antibodies of interest comprising such heterodimeric pairs may be promoted at the heterodimeric pair interface by the formation of protuberance-into-cavity complementary regions at such interfaces; the formation of non-naturally occurring disulfide bonds at such interfaces; leucine zipper at such interfaces; hydrophobic regions at such interfaces; and/or hydrophilic regions at such interfaces. "Protuberances" are constructed by replacing small amino acid side chains from the interface of the first polypeptide with larger side chains (e.g. tyrosine or tryptophan). Compensatory "cavities" of identical or similar size to the protuberances are optionally created on the interface of the second polypeptide by replacing large amino acid side chains with smaller ones (e.g. alanine or threonine). Where a suitably positioned and dimensioned protuberance or cavity exists at the interface of either the first or second polypeptide, it is only necessary to engineer a corresponding cavity or protuberance, respectively, at the adjacent interface. Non-naturally occurring disulfide bonds are constructed by replacing on the first polypeptide a naturally occurring amino acid with a free thiol-containing residue, such as cysteine, such that the free thiol interacts with another free thiol-containing residue on the second polypeptide such that a disulfide bond is formed between the first and second polypeptides Exemplary heterodimerization pairs and methods for making such in accordance with the present invention are available in the art, and are disclosed, for example, in US 2011/0054151; US 2007/0098712; and the like.

In certain embodiments, the heterodimeric pairs are contained within the Fc region of the inventive multispecific antibody of interest. Fc regions that contain such heterodimeric pairs are referred to as "heterodimeric Fc regions".

Accordingly, in certain embodiments, multispecific antibodies of interest comprise a CH2 and/or a CH3 domain variant, wherein either: a) the CH2 domain variant and the CH3 domain variant each independently comprises a at least one protuberance in either the CH2 domain or the CH3 domain of the first polypeptide and at least one corresponding cavity in the CH2 domain or the CH3 domain of the second; or the CH2 domain variant and the CH3 domain variant each independently comprises at least one cavity in either the CH2 domain or the CH3 domain of the first polypeptide and at least one corresponding protuberance in the CH2 domain or the CH3 domain of the second polypeptide. In certain other embodiments, the multispecific antibodies of interest comprise a CH2 and/or a CH3 domain variant, wherein either: a) the CH2 domain variant and the CH3 domain variant each independently comprises at least one substituted negatively-charged amino acid in either the CH2 domain or the CH3 domain of the first polypeptide and at least one corresponding positively-charged amino acid in either the CH2 domain or the CH3 domain of the second polypeptide; or b) the CH2 domain variant and the CH3 domain variant each independently comprises at least one substituted positively-charged amino acid in either the CH2 domain or the CH3 domain of the first polypeptide and at least one corresponding substituted negatively-charged substituted amino acid in either the CH2 domain or the CH3 domain of the second polypeptide.

With regard to Fc function in "natural" antibodies (i.e., those antibodies generated in vivo via native biological antibody synthesis by native B-cells), the Fc region of an antibody interacts with a number of Fc receptors and ligands, imparting an array of important functional capabilities referred to as effector functions. For IgG the Fc region, Fc comprises Ig domains Cγ2 and Cγ3 and the N-terminal hinge leading into Cγ2. An important family of Fc receptors for the IgG class is the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and γδ T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP).

The different IgG subclasses have different affinities for the FcγRs, with IgG1 and IgG3 typically binding substantially better to the receptors than IgG2 and IgG4 (Jefferis et al., 2002, Immunol Lett 82:57-65). The FcγRs bind the IgG Fc region with different affinities. The extracellular domains of FcγRIIIa and FcγRIIIb are 96% identical; however FcγRIIIb does not have an intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. Despite these differences in affinities and activities, all FcγRs bind the same region on Fc, at the N-terminal end of the Cγ2 domain and the preceding hinge.

An overlapping but separate site on Fc serves as the interface for the complement protein C1q. In the same way that Fc/FcγR binding mediates ADCC, Fc/C1q binding mediates complement dependent cytotoxicity (CDC). A site on Fc between the Cγ2 and Cγ3 domains mediates interaction with the neonatal receptor FcRn, the binding of which recycles endocytosed antibody from the endosome back to the bloodstream (Raghavan et al., 1996, Annu Rev Cell Dev Biol 12:181-220; Ghetie et al., 2000, Annu Rev Immunol 18:739-76). This process, coupled with preclusion of kidney filtration due to the large size of the full length molecule, results in favorable antibody serum half-lives ranging from one to three weeks. Binding of Fc to FcRn also plays a key role in antibody transport. The binding site for FcRn on Fc is also the site at which the bacterial proteins A and G bind. The tight binding by these proteins is typically exploited as a means to purify antibodies by employing protein A or protein G affinity chromatography during protein purification. The fidelity of these regions, the complement and FcRn/protein A binding regions are important for both the clinical properties of antibodies and their development.

A particular feature of the Fc region of "natural" antibodies is the conserved N-linked glycosylation that occurs at N297. This carbohydrate, or oligosaccharide as it is sometimes referred, plays a critical structural and functional role for the antibody, and is one of the principle reasons that antibodies must be produced using mammalian expression systems. Efficient Fc binding to FcγR and C1q requires this modification, and alterations in the composition of the N297 carbohydrate or its elimination affect binding to these proteins.

In some embodiments, the inventive multispecific antibodies of interest disclosed herein comprise an Fc variant. An Fc variant comprises one or more amino acid modifications relative to a parent Fc polypeptide, wherein the amino acid modification(s) provide one or more optimized properties. Fc variants further comprise either a CH2 domain variant, a CH3 domain variant, or both a CH2 domain variant and a CH3 domain variant. By "modification" herein is meant an alteration in the physical, chemical, or sequence properties of a protein, polypeptide, antibody, inventive multispecific antibody of interest, or immunoglobulin. An amino acid modification can be an amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution Y349T refers to a variant polypeptide, in this case a constant heavy chain variant, in which the tyrosine at position 349 is replaced with threonine. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence.

An Fc variant disclosed herein differs in amino acid sequence from its parent by virtue of at least one amino acid modification. The inventive multispecific antibodies of interest disclosed herein may have more than one amino acid modification as compared to the parent, for example from about one to fifty amino acid modifications, e.g., from about one to ten amino acid modifications, from about one to about five amino acid modifications, etc. compared to the parent. Thus the sequences of the Fc variants and those of the parent Fc polypeptide are substantially homologous. For example, the variant Fc variant sequences herein will possess about 80% homology with the parent Fc variant sequence, e.g., at least about 90% homology, at least about 95% homology, at least about 98% homology, at least about 99% homology, etc. Modifications disclosed herein also include glycoform modifications. Modifications may be made genetically using molecular biology, or may be made enzymatically or chemically.

Fc variants disclosed herein are defined according to the amino acid modifications that compose them. Thus, for example, the substitution Y349T refers to a variant polypeptide, in this case a constant heavy chain variant, in which the tyrosine at position 349 is replaced with threonine. Likewise, Y349T/T394F defines an Fc variant with the substitutions Y349T and T394F relative to the parent Fc polypeptide. The identity of the WT amino acid may be unspecified, in which case the aforementioned variant is referred to as 349T/394F. It is noted that the order in which substitutions are provided is arbitrary, that is to say that, for example, 349T/394F is the same Fc variant as 394F/349T. Unless otherwise noted, constant region and Fc positions discussed herein are numbered according to the EU index or EU numbering scheme (Kabat et al., 1991, Sequences of Proteins of Immunological Interest, 5th Ed., United States Public Health Service, National Institutes of Health, Bethesda). The EU index or EU index as in Kabat or EU numbering scheme refers to the numbering of the EU antibody (Edelman et al., 1969, Proc Natl Acad Sci USA 63:78-85).

In certain embodiments, the Fc variants disclosed herein are based on human IgG sequences, and thus human IgG sequences are used as the "base" sequences against which other sequences are compared, including but not limited to sequences from other organisms, for example rodent and primate sequences. Immunoglobulins may also comprise sequences from other immunoglobulin classes such as IgA, IgE, IgGD, IgGM, and the like. It is contemplated that, although the Fc variants disclosed herein are engineered in the context of one parent IgG, the variants may be engineered in or "transferred" to the context of another, second parent IgG. This is done by determining the "equivalent" or "corresponding" residues and substitutions between the first and second IgG, typically based on sequence or structural homology between the sequences of the first and second IgGs. In order to establish homology, the amino acid sequence of a first IgG outlined herein is directly compared to the sequence of a second IgG. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first immunoglobulin are defined. Alignment of conserved residues may conserve 100% of such residues. However, alignment of greater than 75% or as little as 50% of conserved residues is also adequate to define equivalent residues. Equivalent residues may also be defined by determining structural homology between a first and second IgG that is at the level of tertiary structure for IgGs whose structures have been determined. In this case, equivalent residues are defined as those for which the atomic coordinates of two or more of the main chain atoms of a particular amino acid residue of the parent or precursor (N on N, CA on CA, C on C and O on O) are within about 0.13 nm, after alignment. In another embodiment, equivalent residues are within about 0.1 nm after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the parent IgG in which the IgGs are made, what is meant to be conveyed is that the Fc variants discovered as disclosed herein may be engineered into any second parent IgG that has significant sequence or structural homology with the Fc variant. Thus for example, if a variant antibody is generated wherein the parent antibody is human IgG1, by using the methods described above or other methods for determining equivalent residues, the variant antibody may be engineered in another IgG1 parent antibody that binds a different antigen, a human IgG2 parent antibody, a human IgA parent antibody, a mouse IgG2a or IgG2b parent antibody, and the like. Again, as described above, the context of the parent Fc variant does not affect the ability to transfer the Fc variants disclosed herein to other parent IgGs.

Fc variants that comprise or are CH3 domain variants as described above may comprise at least one substitution at a position in a CH3 domain selected from the group consisting of 349, 351, 354, 356, 357, 364, 366, 368, 370, 392, 394, 395, 396, 397, 399, 401, 405, 407, 409, 411, and 439, wherein numbering is according to the EU index as in Kabat. In a preferred embodiment, CH3 domain variants comprise at least one CH3 domain substitution per heavy chain selected from the group consisting of 349A, 349C, 349E, 349I, 349K, 349S, 349T, 349W, 351 E, 351K, 354C, 356K, 357K, 364C, 364D, 364E, 364F, 364G, 364H, 364R, 364T, 364Y, 366D, 366K, 366S, 366W, 366Y, 368A, 368E, 368K, 368S, 370C, 370D, 370E, 370G, 370R, 370S, 370V, 392D, 392E, 394F, 394S, 394W, 394Y, 395T, 395V, 396T, 397E, 397S, 397T, 399K, 401 K, 405A, 405S, 407T, 407V, 409D, 409E, 411D, 411 E, 411K, and 439D. Each of these variants can be used individually or in any combination for each heavy chain Fc region. As will be appreciated by those in the art, each heavy chain can comprise different numbers of substitutions. For example, both heavy chains that make up the Fc region may comprise a single substitution, one chain may comprise a single substitution and the other two substitutions, both can contain two substitutions (although each chain will contain different substitutions), etc.

In some embodiments, the CH2 and/or CH3 domain variants are made in combinations, that is, two or more variants per heavy chain Fc domain, selected from the group outlined above.

Other CH2 and/or CH3 domain variants that favor heterodimerization that may be employed in the design and preparation of the inventive multispecific antibodies of interest of the invention are provided in, for example, Ridgeway et al., 1996, Protein Engineering 9[7]:617-621; U.S. Pat. No. 5,731,168; Xie et al., 2005, J Immunol Methods 296:95-101; Davis et al., 2010, Protein Engineering, Design & Selection 23[4]:195-202; Gunasekaran et al., 2010, J Biol Chem 285[25]:1937-19646; and PCT/US2009/000071 (published as WO 2009/089004).

The Fc variants disclosed herein may be optimized for improved or reduced binding to Fc receptors or Fc ligands. By "Fc receptor" or "Fc ligand" as used herein is meant a molecule, preferably a polypeptide, from any organism that binds to the Fc region of an antibody to form an Fc-ligand complex. Fc ligands include but are not limited to FcγRs, (as described above, including but not limited to FcγRIIIa, FcγRIIa, FcγRIIb, FcγRI and FcRn), C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs. Fc ligands may include undiscovered molecules that bind Fc.

The inventive multispecific antibodies of interest may be designed to optimize properties, including but are not limited to enhanced or reduced affinity for an Fc receptor. By "greater affinity" or "improved affinity" or "enhanced affinity" or "better affinity" than a parent Fc polypeptide, as used herein, is meant that an Fc variant binds to an Fc receptor with a significantly higher equilibrium constant of association (KA or $K_a$) or lower equilibrium constant of dissociation (KD or $K_d$) than the parent Fc polypeptide when the amounts of variant and parent polypeptide in the binding assay are essentially the same. For example, the Fc variant with improved Fc receptor binding affinity may display from about 5 fold to about 1000 fold, e.g. from about 10 fold to about 500 fold improvement in Fc receptor binding affinity compared to the parent Fc polypeptide, where Fc receptor binding affinity is determined, for example, by the binding methods disclosed herein, including but not limited to Biacore, by one skilled in the art. Accordingly, by "reduced affinity" as compared to a parent Fc polypeptide as used herein is meant that an Fc variant binds an Fc receptor with significantly lower KA or higher KD than the parent Fc polypeptide. Greater or reduced affinity can also be defined relative to an absolute level of affinity.

In one embodiment, particularly useful Fc modifications for the present invention are variants that reduce or ablate binding to one or more FcγRs and/or complement proteins, thereby reducing or ablating Fc-mediated effector functions such as ADCC, ADCP, and CDC. Such variants are also referred to herein as "knockout variants" or "KO variants". Variants that reduce binding to FcγRs and complement are useful for reducing unwanted interactions mediated by the Fc region and for tuning the selectivity of the inventive multispecific antibody of interest. Preferred knockout variants are described in U.S. Ser. No. 11/981,606, filed Oct. 31, 2007, entitled "Fc Variants with Optimized Properties". Preferred modifications include but are not limited substitutions, insertions, and deletions at positions 234, 235, 236, 237, 267, 269, 325, and 328, wherein numbering is according to the EU index. Preferred substitutions include but are not limited to 234G, 235G, 236R, 237K, 267R, 269R, 325L, and 328R, wherein numbering is according to the EU index. A preferred variant comprises 236R/328R. Variants may be used in the context of any IgG isotype or IgG isotype Fc region, including but not limited to human IgG1, IgG2, IgG3, and/or IgG4 and combinations thereof. Preferred IgG Fc regions for reducing FcγR and complement binding and reducing Fc-mediated effector functions are IgG2 and IgG4 Fc regions. Hybrid isotypes may also be useful, for example hybrid IgG1/IgG2 isotypes as described in US 2006-0134105. Other modifications for reducing FcγR and complement interactions include but are not limited to substitutions 297A, 234A, 235A, 237A, 318A, 228P, 236E, 268Q, 309L, 330S, 331S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, 2009, Current Opinion in Biotechnology 20:685-691.

Fc modifications that improve binding to FcγRs and/or complement are also amenable to incorporation in the design and preparation of the inventive multispecific antibodies of interest disclosed herein. Such Fc variants may enhance Fc-mediated effector functions such as ADCC, ADCP, and/or CDC. Preferred modifications for improving FcγR and complement binding are described in, e.g., U.S. Pat. No. 8,188,231 and US 2006-0235208. Preferred modifications comprise a substitution at a position selected from the group consisting of 236, 239, 268, 324, and 332, wherein numbering is according to the EU index. Preferred substitutions include but are not limited to 236A, 239D, 239E, 268D, 267E, 268E, 268F, 324T, 332D, and 332E. Preferred variants include but are not limited to 239D/332E, 236A/332E, 236A/239D/332E, 268F/324T, 267E/268F, 267E/324T, and 267E/268F/324T. Other modifications for enhancing FcγR and complement interactions include but are not limited to substitutions 298A, 333A, 334A, 326A, 247I, 339D, 339Q, 280H, 290S, 298D, 298V, 243L, 292P, 300L, 396L, 305I, and 396L. These and other modifications are reviewed in Strohl, 2009, ibid.

In one embodiment, the inventive multispecific antibodies of interest disclosed herein may incorporate Fc variants that enhance affinity for an inhibitory receptor FcγRIIb. Such variants may provide the inventive multispecific antibodies of interest herein with immunomodulatory activities related to FcγRIIb$^+$ cells, including for example B cells and monocytes. In one embodiment, the Fc variants provide selectively enhanced affinity to FcγRIIb relative to one or more activating receptors. Modifications for altering binding to FcγRIIb are described in U.S. Pat. No. 8,063,187, filed May 30, 2008, entitled "Methods and Compositions for Inhibiting CD32b Expressing Cells". In particular, Fc variants that improve binding to FcγRIIb may include one or more modifications at a position selected from the group consisting of 234, 235, 236, 237, 239, 266, 267, 268, 325, 326, 327, 328, and 332, according to the EU index. Preferable substitutions for enhancing FcγRIIb affinity include but are not limited to 234D, 234E, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. More preferably, substitutions include but are not limited to 235Y, 236D, 239D, 266M, 267E, 268D, 268E, 328F, 328W, and 328Y. Preferred Fc variants for enhancing binding to FcγRIIb include but are not limited to 235Y/267E, 236D/267E, 239D/268D, 239D/267E, 267E/268D, 267E/268E, and 267E/328F.

In some embodiments, the inventive multispecific antibodies of interest disclosed herein may incorporate Fc variants that improve FcRn binding. Such variants may enhance the in vivo pharmacokinetic properties of the inventive multispecific antibodies of interest. Preferred variants that increase binding to FcRn and/or improve pharmacokinetic properties include but are not limited to substitutions at positions 259, 308, 428, and 434, including but not limited to for example 259I, 308F, 428L, 428M, 434S, 434H, 434F, 434Y, 434M, 428L/434S, 259I/308F and 259I/308F/428L (and others described in U.S. Ser. No. 12/341,769, filed Dec. 22, 2008, entitled "Fc Variants with Altered Binding to FcRn"). Other variants that increase Fc binding to FcRn include but are not limited to: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 286A, 305A, 307A, 307Q, 311A, 312A, 376A, 378Q, 380A, 382A, 434A (Shields et al, Journal of Biological Chemistry, 2001, 276(9):6591-6604), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/256E, 433K/434F/436H, 308T/309P/311S (Dall'Acqua et al. Journal of Immunology, 2002, 169:5171-5180, Dall'Acqua et al., 2006, Journal of Biological Chemistry 281:23514-23524). Other modifications for modulating FcRn binding are described in Yeung et al., 2010, J Immunol, 182:7663-7671.

The inventive multispecific antibodies of interest disclosed herein can incorporate Fc modifications in the context of any IgG isotype or IgG isotype Fc region, including but not limited to human IgG1, IgG2, IgG3, and/or IgG4. The IgG isotype may be selected such as to alter FcγR- and/or complement-mediated effector function(s). Hybrid IgG isotypes may also be useful. For example, US Patent Publication No. 2006-0134105 describes a number of hybrid IgG1/IgG2 constant regions that may find use in the particular invention. In some embodiments of the invention, inventive multispecific antibodies of interest may comprise means for isotypic modifications, that is, modifications in a parent IgG to the amino acid type in an alternate IgG. For example, an IgG1/IgG3 hybrid variant may be constructed by a substitutional means for substituting IgG1 positions in the CH2 and/or CH3 region with the amino acids from IgG3 at positions where the two isotypes differ. Thus a hybrid variant IgG antibody may be constructed that comprises one or more substitutional means, e.g., 274Q, 276K, 300F, 339T, 356E, 358M, 384S, 392N, 397M, 422I, 435R, and 436F. In other embodiments of the invention, an IgG1/IgG2 hybrid variant may be constructed by a substitutional means for substituting IgG2 positions in the CH2 and/or CH3 region with amino acids from IgG1 at positions where the two isotypes differ. Thus a hybrid variant IgG antibody may be constructed that comprises one or more substitutional means, e.g., one or more of the following amino acid substations: 233E, 234L, 235L, -236G (referring to an insertion of a glycine at position 236), and 327A.

All antibodies contain carbohydrate at conserved positions in the constant regions of the heavy chain. Each antibody isotype has a distinct variety of N-linked carbohydrate structures. Aside from the carbohydrate attached to the heavy chain, up to 30% of human IgGs have a glycosylated Fab region. IgG has a single N-linked biantennary carbohydrate at Asn297 of the CH2 domain. For IgG from either serum or produced ex vivo in hybridomas or engineered cells, the IgG are heterogeneous with respect to the Asn297 linked carbohydrate. For human IgG, the core oligosaccharide normally consists of GlcNAc2Man3GlcNAc, with differing numbers of outer residues.

The inventive multispecific antibodies of interest herein may also comprise carbohydrate moieties, which moieties will be described with reference to commonly used nomenclature for the description of oligosaccharides. A review of carbohydrate chemistry which uses this nomenclature is found in Hubbard et al. 1981, Ann. Rev. Biochem. 50:555-583. This nomenclature includes, for instance, Man, which represents mannose; GlcNAc, which represents 2-N-acetylglucosamine; Gal which represents galactose; Fuc for fucose; and Glc, which represents glucose. Sialic acids are described by the shorthand notation NeuNAc, for 5-N-acetylneuraminic acid, and NeuNGc for 5-glycolylneuraminic.

The term "glycosylation" means the attachment of oligosaccharides (carbohydrates containing two or more simple sugars linked together e.g. from two to about twelve simple sugars linked together) to a glycoprotein. The oligosaccharide side chains are typically linked to the backbone of the glycoprotein through either N- or O-linkages. The oligosaccharides of inventive multispecific antibodies of interest disclosed herein occur generally are attached to a CH2 domain of an Fc region as N-linked oligosaccharides. "N-linked glycosylation" refers to the attachment of the carbohydrate moiety to an asparagine residue in a glycoprotein chain. The skilled artisan will recognize that, for example, each of murine IgG1, IgG2a, IgG2b and IgG3 as well as human IgG1, IgG2, IgG3, IgG4, IgA and IgD CH2 domains have a single site for N-linked glycosylation at residue 297.

For the purposes herein, a "mature core carbohydrate structure" refers to a processed core carbohydrate structure attached to an Fc region which generally consists of the following carbohydrate structure GlcNAc(Fucose)-GlcNAc-Man-(Man-GlcNAc)$_2$ typical of biantennary oligosaccharides. The mature core carbohydrate structure is attached to the Fc region of the glycoprotein, generally via N-linkage to Asn297 of a CH2 domain of the Fc region. A "bisecting GlcNAc" is a GlcNAc residue attached to the α1,4 mannose of the mature core carbohydrate structure. The bisecting GlcNAc can be enzymatically attached to the mature core carbohydrate structure by a α(1,4)-N-acetylglucosaminyltransferase III enzyme (GnTIII). CHO cells do not normally express GnTIII (Stanley et al., 1984, J. Biol. Chem. 261: 13370-13378), but may be engineered to do so (Umana et al., 1999, Nature Biotech. 17:176-180).

Described herein are multispecific antibodies of interest that comprise modified glycoforms or engineered glycoforms. By "modified glycoform" or "engineered glycoform"

as used herein is meant a carbohydrate composition that is covalently attached to a protein, for example an antibody, wherein said carbohydrate composition differs chemically from that of a parent protein. Engineered glycoforms may be useful for a variety of purposes, including but not limited to enhancing or reducing FcγR-mediated effector function. In one embodiment, the inventive multispecific antibodies of interest disclosed herein are modified to control the level of fucosylated and/or bisecting oligosaccharides that are covalently attached to the Fc region.

A variety of methods are well known in the art for generating modified glycoforms (Umana et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; U.S. Ser. No. 12/434,533). These techniques control the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells), by regulating enzymes involved in the glycosylation pathway (for example FUT8 [α-1,6-fucosyltranserase] and/or β1-4-N-acetylglucosaminyltransferase III [GnTIII]), by modifying carbohydrate(s) after the IgG has been expressed, or by expressing antibody in the presence of fucose analogs as enzymatic inhibitors. Other methods for modifying glycoforms of the inventive multispecific antibodies of interest disclosed herein include using glycoengineered strains of yeast (Li et al., 2006, Nature Biotechnology 24(2):210-215), moss (Nechansky et al., 2007, Mol Immunol 44(7):1826-8), and plants (Cox et al., 2006, Nat Biotechnol 24(12):1591-7). The use of a particular method to generate a modified glycoform is not meant to constrain embodiments to that method. Rather, embodiments disclosed herein encompass inventive multispecific antibodies of interest with modified glycoforms irrespective of how they are produced.

In one embodiment, the inventive multispecific antibodies of interest disclosed herein are glycoengineered to alter the level of sialylation. Higher levels of sialylated Fc glycans in immunoglobulin G molecules can adversely impact functionality (Scallon et al., 2007, Mol. Immunol. 44(7): 1524-34), and differences in levels of Fc sialylation can result in modified anti-inflammatory activity (Kaneko et al., 2006, Science 313:670-673). Because antibodies may acquire anti-inflammatory properties upon sialylation of Fc core polysaccharide, it may be advantageous to glycoengineer the inventive multispecific antibodies of interest disclosed herein for greater or reduced Fc sialic acid content.

"Engineered glycoform" typically refers to the different carbohydrate or oligosaccharide; thus for example an immunoglobulin may comprise an engineered glycoform. In one embodiment, a composition disclosed herein comprises a glycosylated inventive multispecific antibody of interest having an Fc region, wherein about 51-100% of the glycosylated antibody, e.g., 80-100%, 90-100%, 95-100%, etc. of the antibody in the composition comprises a mature core carbohydrate structure which lacks fucose. In another embodiment, the antibody in the composition both comprises a mature core carbohydrate structure that lacks fucose and additionally comprises at least one amino acid modification in the Fc region. In an alternative embodiment, a composition comprises a glycosylated inventive multispecific antibody of interest having an Fc region, wherein about 51-100% of the glycosylated antibody, 80-100%, or 90-100%, of the antibody in the composition comprises a mature core carbohydrate structure which lacks sialic acid. In another embodiment, the antibody in the composition both comprises a mature core carbohydrate structure that lacks sialic acid and additionally comprises at least one amino acid modification in the Fc region. In yet another embodiment, a composition comprises a glycosylated inventive multispecific antibody of interest having an Fc region, wherein about 51-100% of the glycosylated antibody, 80-100%, or 90-100%, of the antibody in the composition comprises a mature core carbohydrate structure which contains sialic acid. In another embodiment, the antibody in the composition both comprises a mature core carbohydrate structure that contains sialic acid and additionally comprises at least one amino acid modification in the Fc region. In another embodiment, the combination of engineered glycoform and amino acid modification provides optimal Fc receptor binding properties to the antibody.

The inventive multispecific antibodies of interest disclosed herein may comprise one or more modifications that provide additional optimized properties. Said modifications may be amino acid modifications, or may be modifications that are made enzymatically or chemically. Such modification(s) likely provide some improvement in the inventive multispecific antibody of interest, for example an enhancement in its stability, solubility, function, or clinical use. Disclosed herein are a variety of improvements that may be made by coupling the inventive multispecific antibodies of interest disclosed herein with additional modifications.

In one embodiment, at least one variable region of multispecific antibody of interest disclosed herein may be affinity matured, that is to say that amino acid modifications have been made in the VH and/or VL domains to enhance binding of the antibody to its target antigen. Such types of modifications may improve the association and/or the dissociation kinetics for binding to the target antigen. Other modifications include those that improve selectivity for target antigen vs. alternative targets. These include modifications that improve selectivity for antigen expressed on target vs. non-target cells. Inventive multispecific antibodies of interest disclosed herein may comprise one or more modifications that provide reduced or enhanced internalization of an inventive multispecific antibody of interest.

In other embodiments, modifications are made to improve biophysical properties of the inventive multispecific antibodies of interest disclosed herein, including but not limited to stability, solubility, and oligomeric state. Modifications can include, for example, substitutions that provide more favorable intramolecular interactions in the inventive multispecific antibody of interest such as to provide greater stability, or substitution of exposed nonpolar amino acids with polar amino acids for higher solubility. Other modifications to the inventive multispecific antibodies of interest disclosed herein include those that enable the specific formation or homodimeric or homomultimeric molecules. Such modifications include but are not limited to engineered disulfides, as well as chemical modifications or aggregation methods.

In further embodiments, the inventive multispecific antibodies of interest disclosed herein comprise modifications that remove proteolytic degradation sites. These may include, for example, protease sites that reduce production yields, as well as protease sites that degrade the administered protein in vivo. In one embodiment, additional modifications are made to remove covalent degradation sites such as deamidation (i.e. deamidation of glutaminyl and asparaginyl residues to the corresponding glutamyl and aspartyl residues), oxidation, and proteolytic degradation sites. Deamidation sites that are particular useful to remove are those that have enhance propensity for deamidation, including, but not limited to asparaginyl and glutamyl residues followed by glycines (NG and QG motifs, respectively). In such cases, substitution of either residue can significantly reduce the tendency for deamidation. Common oxidation sites include methionine and cysteine residues. Other covalent modifications, that can either be introduced or removed, include hydroxylation of proline and lysine, phosphorylation of hydroxyl groups of seryl or threonyl residues, methylation of the "-amino groups of lysine, arginine, and histidine side chains, acetylation of the N-terminal amine, and amidation of any C-terminal carboxyl group. Additional modifications also may include but are not limited to posttranslational modifications such as N-linked or O-linked glycosylation and phosphorylation.

Modifications may include those that improve expression and/or purification yields from hosts or host cells commonly used for production of biologics. These include, but are not limited to various mammalian cell lines (e.g. CHO, HEK, COS, NIH LT3, Saos, and the like), yeast cells, bacterial cells, and plant cells. Additional modifications include modifications that remove or reduce the ability of heavy chains to form inter-chain disulfide linkages. Additional modifications include modifications that remove or reduce the ability of heavy chains to form intra-chain disulfide linkages.

The inventive multispecific antibodies of interest disclosed herein may comprise modifications that include the use of unnatural amino acids incorporated using, including but not limited to methods described in Liu & Schultz, 2010, Annu Rev Biochem 79:413-444. In some embodiments, these modifications enable manipulation of various functional, biophysical, immunological, or manufacturing properties discussed above. In additional embodiments, these modifications enable additional chemical modification for other purposes.

Other modifications are contemplated herein. For example, the inventive multispecific antibodies of interest may be linked to one of a variety of nonproteinaceous polymers, e.g., polyethylene glycol (PEG), polypropylene glycol, polyoxyalkylenes, or copolymers of polyethylene glycol and polypropylene glycol. Additional amino acid modifications may be made to enable specific or non-specific chemical or posttranslational modification of the inventive multispecific antibodies of interest. Such modifications, include, but are not limited to PEGylation and glycosylation. Specific substitutions that can be utilized to enable PEGylation include, but are not limited to, introduction of novel cysteine residues or unnatural amino acids such that efficient and specific coupling chemistries can be used to attach a PEG or otherwise polymeric moiety. Introduction of specific glycosylation sites can be achieved by introducing novel N-X-T/S sequences into the inventive multispecific antibodies of interest disclosed herein.

Modifications to reduce immunogenicity may include modifications that reduce binding of processed peptides derived from the parent sequence to MHC proteins. For example, amino acid modifications would be engineered such that there are no or a minimal number of immune epitopes that are predicted to bind, with high affinity, to any prevalent MHC alleles. Several methods of identifying MHC-binding epitopes in protein sequences are known in the art and may be used to score epitopes in an antibody disclosed herein.

Covalent modifications are included within the scope of inventive multispecific antibodies of interest disclosed herein, and are generally, but not always, done post-translationally. For example, several types of covalent modifications can be introduced into the molecule by reacting specific amino acid residues with an organic derivatizing agent that is capable of reacting with selected side chains or the N- or C-terminal residues. In some embodiments, the covalent modification of the inventive multispecific antibodies of interest disclosed herein comprises the addition of one or more labels. The term "labeling group" means any detectable label. In some embodiments, the labeling group is coupled to the inventive multispecific antibody of interest via spacer arms of various lengths to reduce potential steric hindrance. Various methods for labeling proteins are known in the art and may be used in generating inventive multispecific antibodies of interest disclosed herein.

In certain embodiments, the inventive multispecific antibodies of interest disclosed herein comprise "fusion proteins", also referred to herein as "conjugates". The fusion partner or conjugate partner can be proteinaceous or nonproteinaceous; the latter generally being generated using functional groups on the inventive multispecific antibody of interest and on the conjugate partner. Conjugate and fusion partners may be any molecule, including small molecule chemical compounds and polypeptides. For example, a variety of conjugates and methods are described in Trail et al., 1999, Curr. Opin. Immunol. 11:584-588. Possible conjugate partners include but are not limited to cytokines, cytotoxic agents, toxins, radioisotopes, chemotherapeutic agent, anti-angiogenic agents, a tyrosine kinase inhibitors, and other therapeutically active agents. In some embodiments, conjugate partners may be thought of more as payloads, that is to say that the goal of a conjugate is targeted delivery of the conjugate partner to a targeted cell, for example a cancer cell or immune cell, by the multispecific antibodies of interest. Thus, for example, the conjugation of a toxin to a multispecific antibody of interest targets the delivery of said toxin to cells expressing the target antigen. As will be appreciated by one skilled in the art, in reality the concepts and definitions of fusion and conjugate are overlapping. The designation of a fusion or conjugate is not meant to constrain it to any particular embodiment disclosed herein. Rather, these terms are used to convey the broad concept that any multispecific antibody of interest disclosed herein may be linked genetically, chemically, or otherwise, to one or more polypeptides or molecules to provide some desirable property.

Suitable conjugates include, but are not limited to, labels as described below, drugs and cytotoxic agents including, but not limited to, cytotoxic drugs (e.g., chemotherapeutic agents) or toxins or active fragments of such toxins. Suitable toxins and their corresponding fragments include diphtheria A chain, exotoxin A chain, ricin A chain, abrin A chain, curcin, crotin, phenomycin, enomycin and the like. Cytotoxic agents also include radiochemicals made by conjugating radioisotopes to inventive multispecific antibody of interest, or binding of a radionuclide to a chelating agent that has been covalently attached to the inventive multispecific antibody of interest. Additional embodiments utilize calicheamicin, auristatins, geldanamycin, maytansine, and duocarmycins and analogs. Antibody-drug conjugates are described in Alley et al., 2010, Curr Opin Chem Biol 14[4]:529-37.

In certain embodiments, the inventive multispecific antibodies of interest disclosed herein are fused or conjugated to a cytokine. By "cytokine" as used herein is meant a generic term for proteins released by one cell population that act on another cell as intercellular mediators. For example, as described in Penichet et al., 2001, J. Immunol. Methods 248:91-101, cytokines may be fused to an inventive multispecific antibody of interest to provide an array of desirable properties. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; C5a; and other polypeptide factors including LIF and kit ligand (KL). As used herein, the term cytokine includes proteins from natural sources or from recombinant cell culture, and biologically active equivalents of the native sequence cytokines.

In further embodiments, the inventive multispecific antibodies of interest disclosed herein may be conjugated to a "receptor" (such streptavidin) for utilization in tumor pretargeting wherein the analog-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the inventive multispecific antibody of interest is conjugated or operably linked to an enzyme in order to employ Antibody Dependent Enzyme Mediated Prodrug Therapy (ADEPT). ADEPT may be used by conjugating or operably linking the inventive multispecific antibody of interest to a prodrug-activating enzyme that converts a prodrug (e.g. a peptidyl chemotherapeutic agent.

Also disclosed herein are methods for producing and experimentally testing the inventive multispecific antibodies of interest. The disclosed methods are not meant to constrain embodiments to any particular application or theory of operation. Rather, the provided methods are meant to illustrate generally that one or more multispecific antibodies of interest of the invention may be produced and experimentally tested to obtain inventive multispecific antibodies of interest. General methods for antibody molecular biology, expression, purification, and screening are described in Antibody Engineering, edited by Kontermann & Dubel, Springer, Heidelberg, 2001; and Hayhurst & Georgiou, 2001, Curr Opin Chem Biol 5:683-689; Maynard & Georgiou, 2000, Annu Rev Biomed Eng 2:339-76.

In one embodiment disclosed herein, nucleic acids are created that encode the inventive multispecific antibodies of interest, and that may then be cloned into host cells, such as yeast cells or mammalian cells, expressed and assayed, if desired. Thus, nucleic acids, and particularly DNA, may be made that encode each protein sequence. These practices are carried out using well-known procedures. For example, a variety of methods that may find use in generating inventive multispecific antibodies of interest disclosed herein are described in Molecular Cloning—A Laboratory Manual, 3rd Ed. (Maniatis, Cold Spring Harbor Laboratory Press, New York, 2001), and Current Protocols in Molecular Biology (John Wiley & Sons). There are a variety of techniques that may be used to efficiently generate DNA encoding inventive multispecific antibodies of interest disclosed herein. Such methods include but are not limited to gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in for generating nucleic acids that encode inventive multispecific antibodies of interest.

The inventive multispecific antibodies of interest disclosed herein may be produced by culturing a host cell transformed with nucleic acid, e.g., expression vectors containing nucleic acid encoding the first and second polypeptides of inventive multispecific antibodies of interest, under the appropriate conditions to induce or cause expression of the polypeptides. The conditions appropriate for expression will vary with the choice of the expression vector and the host cell, and will be easily ascertained by one skilled in the art through routine experimentation. A wide variety of appropriate host cells may be used, including but not limited to mammalian cells, bacteria, insect cells, yeast cells, and plant cells. For example, a variety of cell lines that may find use in generating inventive multispecific antibodies of interest disclosed herein are described in the ATCC® cell line catalog, available from the American Type Culture Collection.

In certain embodiments, the inventive multispecific antibodies of interest are expressed in mammalian expression systems, including systems in which the expression constructs are introduced into the mammalian cells using virus such as retrovirus or adenovirus. Any mammalian cells may be used, e.g., human, mouse, rat, hamster, and primate cells. Suitable cells also include known research cells, including but not limited to Jurkat T cells, NIH3T3, CHO, BHK, COS, HEK293, PER C.6, HeLa, Sp2/0, NS0 cells and variants thereof. In an alternative embodiment, library proteins are expressed in bacterial cells. Bacterial expression systems are well known in the art, and include Escherichia coli (E. coli), Bacillus subtilis, Streptococcus cremoris, and Streptococcus lividans. In alternate embodiments, inventive multispecific antibodies of interest are produced in insect cells (e.g. Sf21/Sf9, Trichoplusia ni Bti-Tn5b1-4) or yeast cells (e.g. S. cerevisiae, Pichia, etc.). In an alternate embodiment, inventive multispecific antibodies of interest are expressed in vitro using cell free translation systems. In vitro translation systems derived from both prokaryotic (e.g. E. coli) and eukaryotic (e.g. wheat germ, rabbit reticulocytes) cells are available and may be chosen based on the expression levels and functional properties of the protein of interest. For example, as appreciated by those skilled in the art, in vitro translation is required for some display technologies, for example ribosome display. In addition, the inventive multispecific antibodies of interest may be produced by chemical synthesis methods. Also transgenic expression systems both animal (e.g. cow, sheep or goat milk, embryonated hen's eggs, whole insect larvae, etc.) and plant (e.g. corn, tobacco, duckweed, etc.)

The nucleic acids that encode the first and second polypeptides of inventive multispecific antibodies of interest disclosed herein may be incorporated into one or more expression vectors, as appropriate, in order to express the encoded polypeptides. A variety of expression vectors may be utilized for protein expression. Expression vectors may comprise self-replicating extra-chromosomal vectors or vectors which integrate into a host genome. Expression vectors are constructed to be compatible with the host cell type. Thus expression vectors which find use in generating inventive multispecific antibodies of interest disclosed herein include but are not limited to those which enable protein expression in mammalian cells, bacteria, insect cells, yeast cells, and in vitro systems. As is known in the art, a variety of expression vectors are available, commercially or otherwise, that may find use for expressing inventive multispecific antibodies of interest disclosed herein.

Expression vectors typically comprise a protein or polypeptide to be expressed, which is operably linked with control or regulatory sequences, selectable markers, any fusion partners, and/or additional elements. By "operably linked" herein is meant that the nucleic acid is placed into a functional relationship with another nucleic acid sequence. Generally, these expression vectors include transcriptional and translational regulatory nucleic acid operably linked to the nucleic acid encoding the inventive multispecific antibody of interest, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used.

The first and second polypeptides of the invention may each be independently operably linked to a fusion partner to enable targeting of the expressed polypeptide and/or multispecific antibody of interest, purification, screening, display, and the like. Fusion partners may be linked to the inventive multispecific antibody of interest sequence via a linker sequences. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence GGGGS (SEQ ID NO: 37). A fusion partner may be a targeting or signal sequence that directs inventive multispecific antibody of interest and any associated fusion partners to a desired cellular location or to the extracellular media. As is known in the art, certain signaling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example H6 (SEQ ID NO: 38) and H10 (SEQ ID NO: 39) or other tags for use with Immobilized Metal Affinity Chromatography (IMAC) systems (e.g. Ni+2 affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both. For example, an inventive multispecific antibody of interest may be purified using a His-tag by immobilizing it to a Ni+2 affinity column, and then after purification the same His-tag may be used to immobilize the antibody to a Ni+2 coated plate to perform an ELISA or other binding assay (as described below). A fusion partner may enable the use of a selection method to screen inventive multispecific antibodies of interest (see below). Fusion partners that enable a variety of selection methods are well-known in the art.

For example, by fusing the members of an inventive multispecific antibody of interest library to the gene III protein, phage display can be employed. Fusion partners may enable inventive multispecific antibodies of interest to be labeled. Alternatively, a fusion partner may bind to a specific sequence on the expression vector, enabling the fusion partner and associated inventive multispecific antibody of interest to be linked covalently or noncovalently with the nucleic acid that encodes them. The methods of introducing exogenous nucleic acid into host cells are well known in the art, and will vary with the host cell used. Techniques include but are not limited to dextran-mediated transfection, calcium phosphate precipitation, calcium chloride treatment, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

Additional non-limiting, exemplary embodiments are as follows:

Embodiment 1

A method of purifying a multispecific antibody of interest (MAI), wherein the MAI comprises a heterodimer comprising a first heavy chain polypeptide comprising a first heavy chain (HC) variable region and a second heavy chain polypeptide comprising a second HC variable region, wherein the first and the second variable regions have different antigen specificities and different isoelectric points, the method comprising:

i) obtaining a composition comprising the MAI, a first parental homodimeric antibody species comprising either at least one copy of the first heavy chain polypeptide or at least two copies of the first heavy chain polypeptide, and a second parental homodimeric antibody species comprising either at least one copy of the second heavy chain polypeptide or at least two copies of the second heavy chain polypeptide; and ii) performing chromatography whereby the MAI is separated from the first and the second parental homodimeric antibody species;

thereby purifying the MAI.

Embodiment 2

The method of Embodiment 1, wherein the performing step ii) comprises:
contacting the composition with a chromatographic material forming a composition-chromatographic material complex; and
performing an elution step wherein the chromatographic material-composition complex is contacted with a sample of eluant that is capable of eluting the MAI and parental homodimeric antibody species in a pH-dependent manner.

Embodiment 3

The method of Embodiment 2, wherein the eluant comprises at least two buffering agents that each have a different negative log acid dissociation constant (pKa).

Embodiment 4

The method according to Embodiment 2 or Embodiment 3, further comprising preparing or equilibrating either:
the composition; or
the composition-chromatographic material complex;
in a first sample of the eluant at a desired starting pH prior performing the elution step.

Embodiment 5

The method according to any one of Embodiments 2 through 4, further comprising flowing a volume of a second sample of the eluant that is prepared at a desired ending pH through the chromatographic material-composition complex.

Embodiment 6

The method according to any one of Embodiments 2 through 5, wherein a pH gradient is generated as the eluant flows through the chromatographic material-composition complex.

Embodiment 7

The method according to any one of Embodiments 2 through 6, wherein a pH gradient is generated as the eluant flows through the chromatographic material-composition complex, and wherein the pH gradient comprises:
(i) a step pH gradient phase prior to a linear pH gradient phase;
(ii) a step pH gradient subsequent to a linear gradient phase;
(iii) a linear pH gradient phase with no step pH gradient phase.at least one linear pH gradient phase; or
(iv) an essentially linear pH gradient phase.

Embodiment 8

The method according to any one of Embodiments 2 through 7, wherein the MAI, the first parental homodimeric antibody species, and the second parental homodimeric antibody species elute from the chromatographic material in essentially distinguishable elution volumes.

Embodiment 9

The method according to any one of Embodiments 2 through 8, wherein the eluant comprises either:
at least two;
at least three;
at least four;
at least five;
at least six;
at least seven; or
eight;
of the following buffering agents: Ncyclohexyl-3-aminopropanesulfonic acid (CAPS), N-Cyclohexyl-2-aminoethanesulfonic acid (CHES), N-Tris(hydroxymethyl)methyl-3-aminopropanesulfonic acid (TAPS), N-(2-Hydroxyethyl)piperazine-N'-(2-hydroxypropanesulfonic acid) (HEPPSO), 3-morpholino-2-hydroxypropanesulfonic acid sodium salt, 3-(N-morpholinyl)-2-hydroxypropanesulfonic acid (MOPSO), 2-(N-morpholino)ethanesulfonic acid (MES), acetic acid, and formic acid; or
at least two;
at least three;
at least four;
at least five; or
at least six; of the following buffering agents: methylamine, 1,2-ethanediamine, 1-methylpiperazine, 1,4-dimethylpiperazine, 2-[Bis(2-hydroxyethyl)amino]-2-(hydroxymethyl)propane-1,3-diol (bis-tris), and hydroxylamine.

Embodiment 10

The method according to any one of Embodiments 2 through 9, wherein the eluant comprises either:
(i) CAPS, CHES, TAPS, HEPPSO, MOPSO, MES, acetic acid, and formic acid; or
(ii) methylamine, 1,2-ethanediamine, 1-methylpiperazine, 1,4-dimethylpiperazine, 2-[Bis(2-hydroxyethyl)amino]-2-(hydroxymethyl)propane-1,3-diol (bis-tris), and hydroxylamine.

Embodiment 11

The method according to any one of Embodiments 2 through 10, wherein the eluant comprises:
at least two;
at least three;
at least four;
at least five;
at least six;
at least seven; or
eight;
of the following buffering agents: Ncyclohexyl-3-aminopropanesulfonic acid (CAPS), N-Cyclohexyl-2-aminoethanesulfonic acid (CHES), N-Tris(hydroxymethyl)methyl-3-aminopropanesulfonic acid (TAPS), N-(2-Hydroxyethyl)piperazine-N'-(2-hydroxypropanesulfonic acid) (HEPPSO), 3-morpholino-2-hydroxypropanesulfonic acid sodium salt, 3-(N-morpholinyl)-2-hydroxypropanesulfonic acid (MOPSO), 2-(N-morpholino)ethanesulfonic acid (MES), acetic acid, and formic acid;
with the proviso that the eluant does not include any of the following: imidazole; piperazine, tris(hydroxymethyl)aminomethane (TRIS).

Embodiment 12

The method according to any one of Embodiments 2 through 11, wherein the eluant consists essentially of:
(i) CAPS; CHES; TAPS; HEPPSO; MOPSO; MES; acetic acid; and formic acid; and optionally at least one salt; or
(ii) methylamine, 1,2-ethanediamine, 1-methylpiperazine, 1,4-dimethylpiperazine, 2-[Bis(2-hydroxyethyl)amino]-2-(hydroxymethyl)propane-1,3-diol (bis-tris), and hydroxylamine and optionally at least one salt.

Embodiment 13

The method according to any one of Embodiments 2 through 12, wherein the eluant consists of:
(i) CAPS; CHES; TAPS; HEPPSO; MOPSO; MES; acetic acid; and formic acid; and at least one salt; or (ii) methylamine, 1,2-ethanediamine, 1-methylpiperazine, 1,4-dimethylpiperazine, 2-[Bis(2-hydroxyethyl)amino]-2-(hydroxymethyl)propane-1,3-diol (bis-tris), and hydroxylamine and optionally at least one salt and optionally at least one salt.

Embodiment 14

The method according to any one of Embodiments 2 through 13, wherein the eluant comprises at least one salt selected from the group consisting of: NaCl, KCl, and Na$_2$SO$_4$.

Embodiment 15

The method according to any one of Embodiments 2 through 14, wherein each sample of the eluant comprises at least one salt at a concentration range selected from the group consisting of: 0 mM to about 100 mM; 0 mM to about 60 mM; 0 mM to about 50 mM; 0 mM to about 40 mM; 0 mM to about 30 mM; 0 mM to about 20 mM; 0 mM to about 10 mM; 0 mM to about 5 mM; about 10 mM to about 200 mM; about 10 mM to about 100 mM; about 10 mM to about 50 mM; about 10 mM to about 40 mM; about 10 mM to about 30 mM; about 10 mM to about 20 mM; about 20 mM to about 200 mM; about 20 mM to about 100 mM; about 20 mM to about 50 mM; about 20 mM to about 30 mM; about 30 mM to about 200 mM; about 30 mM to about 100 mM; and about 30 mM to about 50 mM; and about 5 mM to about 15 mM.

Embodiment 16

The method according to any one of Embodiments 2 through 15, wherein each sample of the eluant comprises at least one salt at a concentration of about 10 mM.

Embodiment 17

The method according to any one of Embodiments 2 through 16, wherein each sample of the eluant comprises NaCl at a concentration of about 10 mM.

Embodiment 18

The method according to any one of Embodiments 1 through 17, wherein either:
a. the difference in the actual isoelectric point of the first heavy chain polypeptide and the actual isoelectric point of the second heavy chain polypeptide is less than 7.0 pH units; less than 6.5 pH units; less than 6.0 pH units; less than 5.5 pH units; less than 5.0 pH units; less than 4.5 pH units; less than 4.0 units; less than 3.5 pH units; less than 2.5 pH units; less than 2.4 pH units; less than 2.3 pH units; less than 2.2 pH units; less than 2.1 pH units; less than 2.0 pH units; less than 1.9 pH units; less than 1.8 pH units; less than 1.7 pH units; less than 1.6 pH units; less than 1.5 pH units; less than 1.4 pH units; less than 1.3 pH units, less than 1.2 pH units; less than 1.1 pH units; less than 1.0 pH unit; less than 0.95 pH unit; less than 0.90 pH unit; less than 0.85 pH unit; less than 0.80 pH unit; less than 0.75 pH unit; less than 0.70 pH unit; less than 0.65 pH unit; less than 0.60 pH unit; less than 0.55 pH unit; less than 0.50 pH unit; less than 0.45 pH unit; less than 0.40 pH unit; less than 0.35 pH unit; less than 0.30 pH unit; less than 0.25 pH unit; less than 0.20 pH unit; less than 0.15 pH unit; less than 0.14 pH unit; less than 0.13 pH unit; less than 0.12 pH unit; less than 0.11 pH unit; less than 0.10 pH unit; less than 0.09 pH unit; less than 0.08 pH unit; less than 0.07 pH unit; less than 0.06 pH unit less than 0.04 pH unit; less than 0.03 pH unit; less than 0.025 pH unit; less than 0.02 pH unit; or pH values that are between any of the preceding values;
b. the difference in the actual isoelectric point of the first parental homodimeric species and the actual isoelectric point of the second parental homodimeric species is less than 7.0 pH units; less than 6.5 pH units; less than 6.0 pH units; less than 5.5 pH units; less than 5.0 pH units; less than 4.5 pH units; less than 4.0 units; less than 3.5 pH units; less than 2.5 pH units; less than 2.4 pH units; less than 2.3 pH units; less than 2.2 pH units; less than 2.1 pH units; less than 2.0 pH units; less than 1.9 pH units; less than 1.8 pH units; less than 1.7 pH units; less than 1.6 pH units; less than 1.5 pH units; less than 1.4 pH units; less than 1.3 pH units, less than 1.2 pH units; less than 1.1 pH units; less than 1.0 pH unit; less than 0.95 pH unit; less than 0.90 pH unit; less than 0.85 pH unit; less than 0.80 pH unit; less than 0.75 pH unit; less than 0.70 pH unit; less than 0.65 pH unit; less than 0.60 pH unit; less than 0.55 pH unit; less than 0.50 pH unit; less than 0.45 pH unit; less than 0.40 pH unit; less than 0.35 pH unit; less than 0.30 pH unit; less than 0.25 pH unit; less than 0.20 pH unit; less than 0.15 pH unit; less than 0.14 pH unit; less than 0.13 pH unit; less than 0.12 pH unit; less than 0.11 pH unit; less than 0.10 pH unit; less than 0.09 pH unit; less than 0.08 pH unit; less than 0.07 pH unit; less than 0.06 pH unit less than 0.04 pH unit; less than 0.03 pH unit; less than 0.025 pH unit; less than 0.02 pH unit; or pH values that are between any of the preceding values;
c. the difference in the calculated isoelectric point of the first heavy chain polypeptide and the calculated isoelectric point of the second heavy chain polypeptide is less than 7.0 pH units; less than 6.5 pH units; less than 6.0 pH units; less than 5.5 pH units; less than 5.0 pH units; less than 4.5 pH units; less than 4.0 units; less than 3.5 pH units; less than 2.5 pH units; less than 2.4 pH units; less than 2.3 pH units; less than 2.2 pH units; less than 2.1 pH units; less than 2.0 pH units; less than 1.9 pH units; less than 1.8 pH units; less than 1.7 pH units; less than 1.6 pH units; less than 1.5 pH units; less than 1.4 pH units; less than 1.3 pH units, less than 1.2 pH units; less than 1.1 pH units; less than 1.0 pH unit; less than 0.95 pH unit; less than 0.90 pH unit; less than 0.85 pH unit; less than 0.80 pH unit; less than 0.75 pH unit; less than 0.70 pH unit; less than 0.65 pH unit; less than 0.60 pH unit; less than 0.55 pH unit; less than 0.50 pH unit; less than 0.45 pH unit; less than 0.40 pH unit; less than 0.35 pH unit; less than 0.30 pH unit; less than 0.25 pH unit; less than 0.20 pH unit; less than 0.15 pH unit; less than 0.14 pH unit; less than 0.13 pH unit; less than 0.12 pH unit; less than 0.11 pH unit; less than 0.10 pH unit; less than 0.09 pH unit; less than 0.08 pH unit; less than 0.07 pH unit; less than 0.06 pH unit less than 0.04 pH unit; less than 0.03 pH unit; less than 0.025 pH unit; less than 0.02 pH unit; or pH values that are between any of the preceding values; or
d. the difference in the calculated isoelectric point of the first parental homodimeric species and the calculated isoelectric point of the second parental homodimeric species is less than 7.0 pH units; less than 6.5 pH units; less than 6.0 pH units; less than 5.5 pH units; less than 5.0 pH units; less than 4.5 pH units; less than 4.0 units; less than 3.5 pH units; less than 2.5 pH units; less than 2.4 pH units; less than 2.3 pH units; less than 2.2 pH units; less than 2.1 pH units; less than 2.0 pH units; less than 1.9 pH units; less than 1.8 pH units; less than 1.7 pH units; less than 1.6 pH units; less than 1.5 pH units; less than 1.4 pH units; less than 1.3 pH units, less than 1.2 pH units; less than 1.1 pH units; less than 1.0 pH unit; less than 0.95 pH unit; less than 0.90 pH unit; less than 0.85 pH unit; less than 0.80 pH unit; less than 0.75 pH unit; less than 0.70 pH unit; less than 0.65 pH unit; less than 0.60 pH unit; less than 0.55 pH unit; less than 0.50 pH unit; less than 0.45 pH unit; less than 0.40 pH unit; less than 0.35 pH unit; less than 0.30 pH unit; less than 0.25 pH unit; less than 0.20 pH unit; less than 0.15 pH unit; less than 0.14 pH unit; less than 0.13 pH unit; less than 0.12 pH unit; less than 0.11 pH unit; less than 0.10 pH unit; less than 0.09 pH unit; less than 0.08 pH unit; less than 0.07 pH unit; less than 0.06 pH unit less than 0.04 pH unit; less than 0.03 pH unit; less than 0.025 pH unit; less than 0.02 pH unit; or pH values that are between any of the preceding values.

Embodiment 19

The method according to any one of Embodiments 4 through 18, wherein the desired starting pH is less than 9.0; less than 8.5; less than 8.0; less than 7.5; less than 7.0; less than 6.5; less than 6.0; less than 5.5; less than 5.0; less than 4.5; less than 4.0; less than 3.5; or less than 3.0; or a pH values that is between any of the preceding values.

Embodiment 20

The method according to any one of Embodiments 5 through 19, wherein the desired ending pH is more than 7.0; more than 7.5; more than 8.0; more than 8.5; more than 9.0; more than 9.5; more than 10.0; more than 10.5; or more than 11.0; more than 11.5; more than 12.0; more than 12.5; more than 13.0; more than 13.5; or a pH values that is between any of the preceding values.

Embodiment 21

The method according to any one of Embodiments 2 through 20, wherein the eluant comprises at least two buffering agents and wherein the acid dissociation constant (pKa) of each buffering agent is between about 3 and 11.

Embodiment 22

The method according to any one of Embodiments 2 through 21, wherein the eluant comprises at least two buffering agents wherein the acid dissociation constant (pKa) of each buffering agent is in a range selected from the group consisting of: about 3.25 to about 3.85; about 4.5 to about 4.85; about 6.0 to about 6.45; about 6.60 to about 7.0; about 7.5 to about 8.15; about 8.35 to about 8.55; about 9.25 to about 9.65; and about 10.00 to about 11.5.

Embodiment 23

The method according to any one of Embodiments 2 through 22, wherein the eluant comprises at least two buffering agents wherein the acid dissociation constant (pKa) of each buffering agent is in a different range that is selected from the group consisting of: about 3.25 to about 3.85; about 4.5 to about 4.85; about 6.0 to about 6.45; about 6.60 to about 7.0; about 7.5 to about 8.15; about 8.35 to about 8.55; about 9.25 to about 9.65; and about 10.00 to about 11.5.

Embodiment 24

The method according to any one of Embodiments 2 through 23, wherein the eluant comprises at least two buffering agents wherein the acid dissociation constant (pKa) of each buffering agent is selected from the group consisting of about 3.75; about 4.76; about 6.10; about 6.90; about 8.04; about 8.44; about 9.39; and about 10.50.

Embodiment 25

The method according to any one of Embodiments 1 through 24, wherein the MAI further comprises a third polypeptide comprising a first light chain variable region.

Embodiment 26

The method according to any one of Embodiments 1 through 25, wherein the MAI further comprises a third polypeptide and a fourth polypeptide, wherein each of the third polypeptide and the fourth polypeptide comprises a second light chain variable region.

Embodiment 27

The method according to Embodiment 26, wherein the first light chain variable region and the second light chain variable region are identical.

Embodiment 28

The method according to Embodiment 26 or Embodiment 27, wherein the third polypeptide and the fourth polypeptide are identical.

Embodiment 29

The method according to any one of Embodiments 1 through 28, wherein the first polypeptide and the second polypeptide each further comprise an Fc region.

Embodiment 30

The method according to any one of Embodiments 1 through 29, wherein the first polypeptide and the second polypeptide each further comprise a wild-type Fc region.

Embodiment 31

The method according to any one of Embodiments 1 through 30, wherein the first polypeptide and the second polypeptide each further comprise an IgG1 isotype Fc region, an IgG3 isotype Fc region, an IgG3 isotype Fc region, or an IgG4 isotype Fc region.

Embodiment 32

The method according to any one of Embodiments 1 through 31, wherein the first polypeptide and the second polypeptide each further comprise an IgG1 isotype Fc region.

Embodiment 33

The method according to any one of Embodiments 1 through 32, wherein the first polypeptide and the second polypeptide each further comprise an Fc region that has not been engineered in order to alter the pI of the first parental homodimeric antibody species, the second parental homodimeric species, or the MAI.

Embodiment 34

The method according to any one of Embodiments 1 through 33, wherein the first polypeptide and the second polypeptide each further comprise an IgG1 isotype Fc region that has not been engineered in order to alter the pI of the first parental homodimeric antibody species, the second parental homodimeric species, or the MAI.

Embodiment 35

The method according to any one of Embodiments 1 through 34, wherein either: MAI is in a native antibody format; at least the first parental homodimeric antibody species is in a native format; at least the second parental homodimeric antibody species is in a native format; the first parental homodimeric antibody species is in a native format and the second parental homodimeric antibody species is in a native format; or the MAI is in a native antibody format, the first parental homodimeric antibody species is in a native format, and the second parental homodimeric antibody species is in a native format.

Embodiment 36

The method according to any one of Embodiments 1 through 35, wherein either: the MAI; the first parental homodimeric antibody species; the second parental homodimeric antibody species; the first parental homodimeric antibody species and the second parental homodimeric antibody species; or the MAI, the first parental homodimeric antibody species and the second parental homodimeric antibody species; is in an IgG1 format, and IgG2 format, and IgG3 format, or an IgG4 format, or a hybrid format.

Embodiment 37

The method according to any one of Embodiments 1 through 36, wherein the chromatography performed at essentially the same ionic strength.

Embodiment 38

The method according to any one of Embodiments 2 through 37, wherein the ionic strength of the eluant remains essentially the same throughout the elution step.

Embodiment 39

The method according to any one of Embodiments 4 through 38, wherein first sample of the eluant and the second sample of the eluant each have essentially the same ionic strength.

Embodiment 40

The method according to any one of Embodiments 1 through 39, wherein the chromatography is ion exchange chromatography.

Embodiment 41

The method according to any one of Embodiments 1 through 40, wherein the chromatography is selected from the group consisting of: cation exchange chromatography; anion exchange chromatography; multimodal chromatography; and mixed-mode chromatography.

Embodiment 42

The method according to any one of Embodiments 1 through 41, wherein the chromatography further comprises using a chromatographic material selected from the group consisting of Mustang S, Sartobind S, S03 Monolith, S Ceramic HyperD, Poros XS, Poros HS50, Poros HS20, HS20, SPSFF, Porors GoPure HS, Poros GoPure XS, SP-Sepharose XL (SPXL), CM Sepharose Fast Flow, Capto Q ImpRes, Capto SP ImpRes, Capto S, Capto MMC, Fractogel Se HiCap, Fractogel S03, Fractogel COO, Poros HQ 50, Poros PI 50, Poros D, Mustang Q, Q Sepharose FF, SP Sepharose FF, UNOshere S, Macro-Prep High S, DEAE, Mono S, Mono S 5/50 GL, Mono Q, Mono Q 5/50 GL, Mono S 10/100 GL, SP Sepharose HP, Source 30S, Poros XQ, Poros HQ, Q HP, and Source 30Q.

Embodiment 43

The method according to any one of Embodiments 1 through 42, wherein the chromatography further comprises using a chromatographic material selected from the group consisting of Mono S, Mono S 5/50 GL, Mono Q, Mono Q 5/50 GL, SP Sepharose HP, Source 30S, Poros XQ, Poros HQ, Q HP, and Source 30Q, and Mono S 10/100 GL.

Embodiment 44

The method according to any one of Embodiments 2 through 43, wherein the chromatographic material is an ion exchange chromatographic material.

Embodiment 45

The method according to any one of Embodiments 2 through 44, wherein the chromatographic material is selected from the group consisting of: a cation exchange chromatographic material; an anion exchange chromatographic material; a multimodal chromatographic material; and a mixed-mode chromatographic material.

Embodiment 46

The method according to any one of Embodiments 2 through 45, wherein the ion exchange chromatographic material is selected from the group consisting of Mustang S, Sartobind S, S03 Monolith, S Ceramic HyperD, Poros XS, Poros HS50, Poros HS20, HS20, SPSFF, Porors GoPure HS, Poros GoPure XS, SP-Sepharose XL (SPXL), CM Sepharose Fast Flow, Capto Q ImpRes, Capto SP ImpRes, Capto S, Capto MMC, Fractogel Se HiCap, Fractogel S03, Fractogel COO, Poros HQ 50, Poros PI 50, Poros D, Mustang Q, Q Sepharose FF, SP Sepharose FF, UNOshere S, Macro-Prep High S, DEAE, Mono S, Mono S 5/50 GL, Mono Q, Mono Q 5/50 GL, Mono S 10/100 GL, SP Sepharose HP, Source 30S, Poros XQ, Poros HQ, Q HP, and Source 30Q; or is selected from the group consisting of Mono S, Mono S 5/50 GL, Mono Q, Mono Q 5/50 GL, SP Sepharose HP, Source 30S, Poros XQ, Poros HQ, Q HP, and Source 30Q, and Mono S 10/100 GL.

Embodiment 47

The method according to any one of Embodiments 1 through 46, wherein either the first heavy chain variable region or the second heavy chain variable region is obtained by performing a first selection against a first antigen from a first library comprising unique heavy chain variable regions.

Embodiment 48

The method according to any one of Embodiments 1 through 47, wherein the first heavy chain variable region and

83 the second heavy chain variable region is obtained by performing a first selection against a first antigen from a first library comprising unique heavy chain variable regions.

Embodiment 49

The method according to any one of Embodiments 1 through 48, wherein the first heavy chain variable region is obtained by performing a first selection against a first antigen from a first library comprising unique heavy chain variable regions and the second heavy chain variable region is obtained by performing a second selection against a second antigen from a second library comprising unique heavy chain variable regions.

Embodiment 50

The method according to any one of Embodiments 1 through 49, wherein the first heavy chain variable region is obtained by performing a first selection against a first antigen from a first library comprising unique heavy chain variable regions and the second heavy chain variable region is obtained by performing a second selection against a second antigen from a second library comprising unique heavy chain variable regions.

Embodiment 51

The method according to any one of Embodiments 1 through 50, wherein at least one of the libraries further comprises at least one light chain.

Embodiment 52

The method according to any one of Embodiments 1 through 51, the composition is expressed by prokaryotic host cells or eukaryotic host cells, into which nucleic acid sequences encoding the first polypeptide and the second polypeptide have each been introduced.

Embodiment 53

The method according to any one of Embodiments 25 through 23, the composition is expressed by prokaryotic host cells or eukaryotic host cells into which nucleic acid sequences encoding the first polypeptide and the second polypeptide have each been introduced.

Embodiment 54

The method according to any one of Embodiments 26 through 53, the composition is expressed by prokaryotic host cells or eukaryotic host cells into which nucleic acid sequences encoding the first polypeptide, the second polypeptide, the third polypeptide, and the fourth polypeptide have each been introduced.

Embodiment 55

The method according to any one of Embodiments 52 through 54, wherein each encoded polypeptide is expressed by the host cells.

84

Embodiment 56

The method according to any one of Embodiments 52 through 55, wherein the composition is expressed by the host cells.

Embodiment 57

The method according to any one of Embodiments 52 through 56, wherein essentially each host cell has been transformed or transfected with the first polypeptide, the second polypeptide, the third polypeptide, and the fourth polypeptide.

Embodiment 58

The method according to any one of Embodiments 52 through 57, wherein essentially each host cell expresses the MAI, the first parental antibody species, and the second parental antibody species.

Embodiment 59

The method to any one of Embodiments 52 through 58, wherein the host cells are selected from the group consisting of: eukaryotic cells; fungal cells; yeast cells; insect cells; mammalian cells; *Saccharomyces cerevisiae* cells; *Pichia pastoris* cells; mammalian cells; COS cells; human embryonic kidney (HEK) cells; and CHO cells.

Embodiment 60

An ion exchange eluant comprising either:
(i) CAPS, CHES, TAPS, HEPPSO, MOPSO, MES, acetic acid, formic acid, and a salt; or
(ii) methylamine, 1,2-ethanediamine, 1-methylpiperazine, 1,4-dimethylpiperazine, 2-[Bis(2-hydroxyethyl)amino]-2-(hydroxymethyl)propane-1,3-diol (bis-tris), and hydroxylamine and optionally at least one salt.

Embodiment 61

An ion exchange eluant comprising CAPS, CHES, TAPS, HEPPSO, MOPSO, MES, acetic acid, formic acid, and NaCl.

Embodiment 62

The ion exchange eluant according to Embodiment 60 or Embodiment 61, with the proviso that the eluant does not include TRIS, piperazine, or imidazole.

Embodiment 63

An ion exchange eluant consisting essentially of either:
(i) CAPS, CHES, TAPS, HEPPSO, MOPSO, MES, acetic acid, formic acid, and a salt; or
(ii) methylamine, 1,2-ethanediamine, 1-methylpiperazine, 1,4-dimethylpiperazine, 2-[Bis(2-hydroxyethyl)amino]-2-(hydroxymethyl)propane-1,3-diol (bis-tris), and hydroxylamine and optionally at least one salt.

Embodiment 64

An ion exchange eluant consisting of either:
(i) CAPS, CHES, TAPS, HEPPSO, MOPSO, MES, acetic acid, formic acid, and a salt; or (ii) methylamine, 1,2-ethanediamine, 1-methylpiperazine, 1,4-dimethylpiperazine, 2-[Bis(2-hydroxyethyl)amino]-2-(hydroxymethyl)propane-1,3-diol (bis-tris), and hydroxylamine and optionally at least one salt.

Embodiment 65

The ion exchange eluant according to any one of Embodiments 61 through 64, wherein the salt is selected from the group consisting of NaCl, KCl, or $Na_2SO_4$.

Embodiment 66

The ion exchange eluant according to any one of Embodiments 60 through 65, wherein the eluant is used for purifying an MAI from a composition comprising the MAI and parental homodimeric antibody species.

Embodiment 67

The ion exchange eluant according to any one of Embodiments 61 through 66, wherein the eluant comprises at least one salt at a concentration range selected from the group consisting of: 0 mM to about 100 mM; 0 mM to about 60 mM; 0 mM to about 50 mM; 0 mM to about 40 mM; 0 mM to about 30 mM; 0 mM to about 20 mM; 0 mM to about 10 mM; 0 mM to about 5 mM; about 10 mM to about 200 mM; about 10 mM to about 100 mM; about 10 mM to about 50 mM; about 10 mM to about 40 mM; about 10 mM to about 30 mM; about 10 mM to about 20 mM; about 20 mM to about 200 mM; about 20 mM to about 100 mM; about 20 mM to about 50 mM; about 20 mM to about 30 mM; about 30 mM to about 200 mM; about 30 mM to about 100 mM; and about 30 mM to about 50 mM; and about 5 mM to about 15 mM.

Embodiment 68

The ion exchange eluant according to any one of Embodiments 61 through 67, wherein each sample of the eluant comprises at least one salt at a concentration of about 10 mM.

Embodiment 69

The ion exchange eluant according to any one of Embodiments 61 through 68, wherein the salt is NaCl.

Embodiment 70

The ionic exchange eluant according to any one of Embodiments 61 through 69, wherein each sample of the eluant comprises NaCl at a concentration of about 10 mM.

EXAMPLES

Materials and Methods

All chromatographic separations presented in the Examples were carried out on a computer controlled ÄKTA avant 150 preparative chromatography system (GE Healthcare Life Sciences) equipped with an integrated pH electrode, enabling in-line pH monitoring during each chromatography experiment. The Mono S 5/50 GL, Mono Q 5/50 GL, and Mono S 10/100 GL columns were purchased each from GE Healthcare Life Sciences. All other columns were purchased from the providers as listed in the column titled "Resin" each of in FIGS. 26A and 26B. Acetic acid and sodium chloride were from VWR, CAPS, MOPSO, and TAPS were from Sigma, CHES and formic acid were from EMD, HEPPSO was from MP Biomedicals, and MES was from Calbiochem. Methylamine (40% in $H_2O$), 1,2-ethanediamine, 1-methylpiperazine, 1,4-dimethylpiperazine, and hydroxylamine (50% in $H_2O$) were purchased from Sigma, bis-tris was purchased from Affymetrix, and sodium chloride was purchased from VWR. The pH gradient-forming solutions were freshly prepared before each experiment by dissolving the buffering agents in water and dividing the solution into two equal parts. Unless otherwise noted, the eluant composition was as listed in FIG. 1. One half was then adjusted to pH 4 (buffer A) using sodium hydroxide, while the other half was adjusted to pH 11 (buffer B) also using sodium hydroxide.

Unless otherwise indicated, the following procedure was used to perform all purifications described in the Examples. Approximately 0.2 mg to 2 mg (for the Mono S 5/50 GL, Mono Q 5/50 GL, and all other similarly sized columns utilized in the Examples below) or approximately 5 mg to 10 mg (for the Mono S 10/100 column and all other similarly sized columns utilized in the Examples below) of the MAI-parental homodimeric antibody species composition to be separated were buffer exchanged into the starting pH buffer and filtered through a 0.2 μm filter. Before each separation, the column was equilibrated with 10 column volumes of starting buffer (either buffer A, buffer B, or the appropriate mixture of buffer A and buffer B). The protein composition was then loaded onto the column via a capillary loop, and the column was washed with another 10 column volumes of starting buffer to remove the unbound material. Subsequently a linear pH gradient of 20 column volumes made up of the appropriate mixtures of buffer A and buffer B was used for separation of the common light chain bispecific antibody mixture. Alternatively, 15 column volumes of a step elution were performed before a shallower gradient of buffers A and B was used to elute.

Common-light-chain antibodies (i.e., parental homodimeric antibody species) were isolated from a full-length human IgG antibody library using an in vitro yeast selection system and associated methods (see, e.g., WO 2009/036379; WO 2010/105256; and WO 2012/009568). Target-binding mAbs were enriched by incubating biotin labeled antigens with antibody expressing yeast cells at different concentrations followed by magnetic bead selection (Miltenyi, Biotec) and fluorescence-activated cell sorting on a FACSAria II cell sorter (BD Biosciences) employing streptavidin secondary reagents in several successive selection rounds. After the last round of enrichment, yeast cells were sorted and plated onto agar plates, clones were analyzed by DNA sequencing and used for IgG production. Optimization of antibodies for higher affinity was performed in successive cycles of selection rounds using lower concentrations of antigen baits with sub-libraries generated by light chain shuffling, targeted mutagenesis of CDR1 and CDR2 of heavy chains and ePCR of the variable region of the heavy or light chain. For Examples in which an IgG isotype format other than the IgG1 isotype format was employed, the variable domains isolated from the libraries as described above were reformatted into the indicated alternative IgG isotype format (e.g., IgG4, etc.).

The compositions comprising each antibody (heavy chain-heterodimeric MAI and two parental heavy-chain homodimeric species) described and tested in each the Examples were obtained from mammalian host cells (HEK cells) harboring and transiently expressing nucleic acid sequences encoding each of a first heavy chain polypeptide, a second heavy chain polypeptide, and a third light chain polypeptide. The transfected cells were cultured under standard conditions known in the art, and the supernatants comprising the antibodies were collected and subjected to Protein A-based affinity purification in order to obtain compositions comprising all antibody species present in the supernatant. Depending on the isotype format of the antibodies encoded by the nucleic acid for each Example as described below, such antibody species (MAI and/or parental homodimeric antibodies) were either in the IgG1 format (described in, e.g., Examples 1 through 9 and Examples 14 and 15), IgG4 format (described in, e.g., Examples 10 through 13) or a hybrid IgG1/IgG4 isotype format (described in, e.g., Example 11).

Compositions and Formats Tested in the Examples

The compositions tested in Examples 1 through 9 and Example 14 comprised the following antibody species:

Scheme A:

an MAI in the native human IgG1 isotype format, comprising a first heavy chain polypeptide in the IgG1 isotype format, a second heavy chain polypeptide in the IgG1 isotype format, and two copies of a light chain polypeptide that were identical in amino acid sequence, wherein the variable regions of the first heavy chain polypeptide and the second heavy chain polypeptide had different amino acid sequences and different antigen specificities (and thus the antigen binding regions formed by each pairing of each of the first and the second heavy chain polypeptide variable regions with one of the two copies of the light chain polypeptide (i.e., "common light chain") had two different antigen specificities);

a first parental heavy chain-homodimeric antibody species in the native human IgG1 isotype format, comprising two copies of the first heavy chain polypeptide and two copies of the light chain polypeptide as in 1) above, wherein the antigen binding regions formed by pairing of one copy of the first heavy chain polypeptide and one copy of the light chain polypeptide has a single antigen specificity (and thus the antigen binding regions formed by pairing of each copy of the heavy chain polypeptide with each copy of the light chain polypeptide each had the same single antigen specificity); and a second parental heavy chain-homodimeric antibody species in the native human IgG1 isotype format, comprising two copies of the second heavy chain polypeptide and two copies of the light chain polypeptide as in 1) above, wherein the antigen binding regions formed by pairing of one copy of the second heavy chain polypeptide and one copy of the light chain polypeptide has a single antigen specificity (and thus the antigen binding regions formed by pairing of each copy of the second heavy chain polypeptide with each copy of the light chain polypeptide each had the same single antigen specificity).

The compositions tested in Example 10 comprised the following antibody species:

Scheme B:

an MAI in the native human IgG4 isotype format, comprising a first heavy chain polypeptide in the IgG4 isotype format, a second heavy chain polypeptide in the IgG4 isotype format, and two copies of a light chain polypeptide that were identical in amino acid sequence, wherein the variable regions of the first heavy chain polypeptide and the second heavy chain polypeptide had different amino acid sequences and different antigen specificities (and thus the antigen binding regions formed by each pairing of each of the first and the second heavy chain polypeptide variable regions with one of the two copies of the light chain polypeptide (i.e., "common light chain") had two different antigen specificities);

a first parental heavy chain-homodimeric antibody species in the native human IgG4 isotype format, comprising two copies of the first heavy chain polypeptide and two copies of the light chain polypeptide as in 1) above, wherein the antigen binding regions formed by pairing of one copy of the first heavy chain polypeptide and one copy of the light chain polypeptide has a single antigen specificity (and thus the antigen binding regions formed by pairing of each copy of the heavy chain polypeptide with each copy of the light chain polypeptide each had the same single antigen specificity); and a second parental heavy chain-homodimeric antibody species in the native human IgG4 isotype format, comprising two copies of the second heavy chain polypeptide and two copies of the light chain polypeptide as in 1) above, wherein the antigen binding regions formed by pairing of one copy of the second heavy chain polypeptide and one copy of the light chain polypeptide has a single antigen specificity (and thus the antigen binding regions formed by pairing of each copy of the second heavy chain polypeptide with each copy of the light chain polypeptide each had the same single antigen specificity).

The compositions tested in Example 11 comprised the following antibody species:

Scheme C:

an MAI in the hybrid IgG1/IgG4 isotype format (native human IgG1 isotype format/human native IgG4 isotype format), comprising a first heavy chain polypeptide in the IgG1 isotype format, a second heavy chain polypeptide in the IgG4 isotype format, and two copies of a light chain polypeptide that were identical in amino acid sequence, wherein the variable regions of the first heavy chain polypeptide and the second heavy chain polypeptide had different amino acid sequences and different antigen specificities (and thus the antigen binding regions formed by each pairing of each of the first and the second heavy chain polypeptide heavy chain variable regions with one of the two copies of the light chain polypeptide (i.e., "common light chain") had two different antigen specificities);

a first parental heavy chain-homodimeric antibody species in the native human IgG1 isotype format, comprising two copies of the first heavy chain polypeptide and two copies of the light chain polypeptide as in 1) above, wherein the antigen binding regions formed by pairing of one copy of the first heavy chain polypeptide and one copy of the light chain polypeptide has a single antigen specificity (and thus the antigen binding regions formed by pairing of each copy of the heavy chain polypeptide with each copy of the light chain polypeptide each had the same single antigen specificity); and a second parental heavy chain-homodimeric antibody species in the native human IgG4 isotype format, comprising two copies of the second heavy chain polypeptide and two copies of the light chain polypeptide as in 1) above, wherein the antigen binding regions formed by pairing of one copy of the second heavy chain polypeptide and one copy of the light chain polypeptide has a single antigen specificity (and thus the antigen binding regions formed by pairing of each copy of the second heavy chain polypeptide with each copy of the light chain polypeptide each had the same single antigen specificity).

The compositions tested in Example 12 and Example 13 comprised the following antibody species:

Scheme D:

an MAI in the native human IgG4 isotype format, comprising a first heavy chain polypeptide in the IgG4 isotype format, a second heavy chain polypeptide in the IgG4 isotype format, one copy of a first light chain polypeptide amino acid sequence in which a first engineered heterodimerization motif was introduced in order to help favor preferential dimerization with the first heavy chain polypeptide relative to dimerization with the second heavy chain polypeptide, and one copy of a second light chain polypeptide amino acid sequence in which a second engineered heterodimerization motif was introduced in order to help favor preferential dimerization with the second heavy chain polypeptide relative to dimerization with the first heavy chain polypeptide, wherein the variable regions of the first heavy polypeptide and the second heavy polypeptide had different amino acid sequences and different antigen specificities (and thus the antigen binding region formed by each pairing of the first heavy chain polypeptide heavy chain variable region with the first light chain polypeptide had a different specificity than the antigen binding region formed by the pairing of the second heavy chain polypeptide heavy chain variable region with the second light chain polypeptide;

a first parental heavy chain-homodimeric antibody species in the native human IgG4 isotype format, comprising two copies of the first heavy chain polypeptide and two copies of the light chain polypeptide as in 1) above, wherein the antigen binding regions formed by pairing of one copy of the heavy chain polypeptide and one copy of the light chain polypeptide has a single antigen specificity (and thus the antigen binding regions formed by pairing of each copy of the heavy chain polypeptide with each copy of the light chain polypeptide each had the same single antigen specificity); and a second parental heavy chain-homodimeric antibody species in the native human IgG4 isotype format, comprising two copies of the second heavy chain polypeptide and two copies of the light chain polypeptide as in 1) above, wherein the antigen binding regions formed by pairing of one copy of the second heavy chain polypeptide and one copy of the light chain polypeptide has a single antigen specificity (and thus the antigen binding regions formed by pairing of each copy of the second heavy chain polypeptide with each copy of the light chain polypeptide each had the same single antigen specificity).

Example 1

Linear pH gradient separation of a composition comprising common-light-chain IgG1 bispecific heterodimer (the "MAI") and each of two different parental homodimeric antibody species (formats as described in Scheme A of Compositions and Formats tested in the Examples, above) with a calculated difference in heavy chain pI of 0.68 pH unit (the calculated pI of HC1=9.73; calculated pI of HC2=9.05; the calculated isoelectric points (pIs) of the two corresponding parental homodimeric antibody species differed by 1.33 pH unit) using a linear pH gradient on a strong cation exchanger Mono S 5/50 GL column. Starting buffer A: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH4.0. Final buffer B: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH11.0 Flow rate 1 ml/min, length of linear gradient formation from 0% B to 100% B 20 column volumes.

The results depicted in FIG. 2 demonstrate that despite the relatively steep pH gradient and the small scale column, the difference in pI of the two heavy chains (as well as the difference in pI of the two corresponding parental homodimeric species from which the two different heavy chains of the MAI were derived) is sufficient to yield baseline resolution between the two homodimer species and the desired heterodimer, and thus purification of the heterodimer (the MAI) (FIG. 2).

Example 2

Figure 4A:
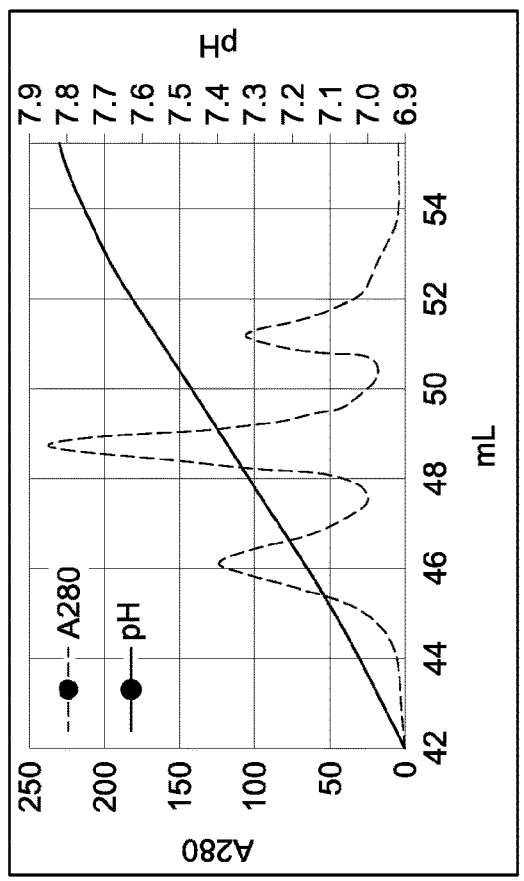
FIGS. 4A through 4C provide schematic representations of independent cation exchange chromatography experiments as described in Example 2, in which either a Mono S 5/50 GL column (FIG. 4A and FIG. 4B) or a Mono S 10/100 GL column (FIG. 4C) was used to separate a multispecific antibody comprising a two different heavy chain polypeptides (heavy chain "A" and heavy chain "B") and two copies of an identical light chain (i.e., a "common light chain") from the two corresponding heavy chain parental homodimeric species. The calculated pIs of the two different heavy chains differed by 0.25 pH units; the calculated pIs the two corresponding parental homodimeric species differed by 0.59 pH units. A280=absorbance units measured at a wavelength of 280 nm; ΔpI=difference in calculated isoelectric point (pI) between the two different heavy chains; mL=elution volume in milliliters.
Figure 4B:
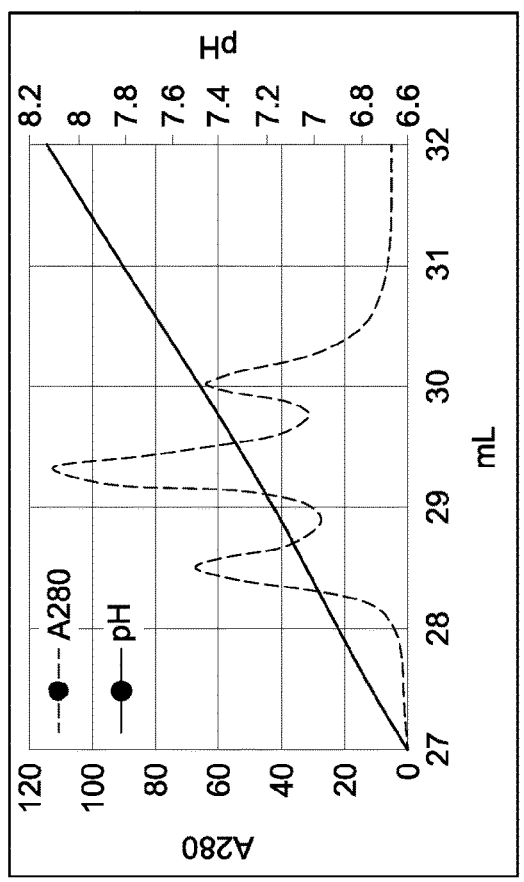
Figure 4C:
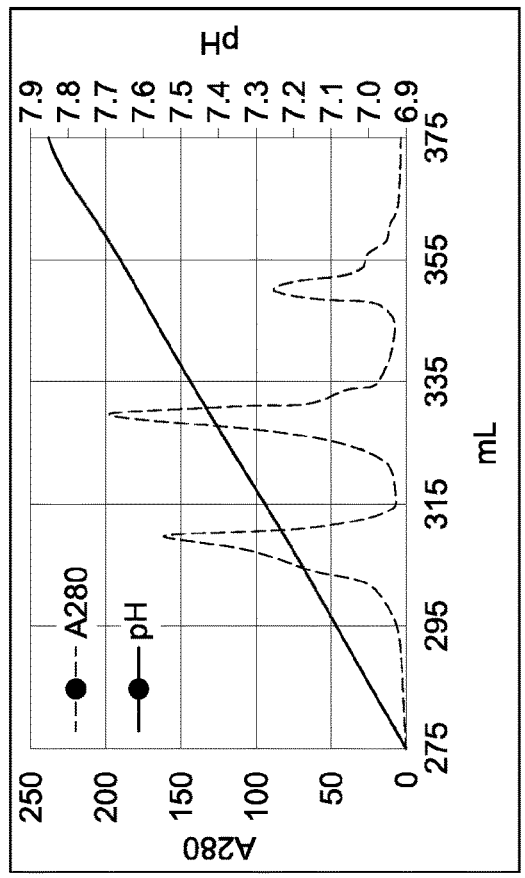

Linear pH gradient separation of a composition comprising common-light-chain IgG1 bispecific heterodimer (the "MAI") and each of two different parental homodimeric antibody species (formats as described in Scheme A of Compositions and Formats tested in the Examples, above) with a calculated difference in heavy chain pI of 0.25 pH unit (calculated pI of HC1=9.46; calculated pI of HC2=9.21; the calculated isoelectric points (pIs) of the two corresponding parental homodimeric antibody species differed by 0.59 pH unit) using various linear pH gradients on a strong cation exchanger Mono S 5/50 GL column or a strong cation exchanger Mono S 10/100 GL column. FIG. 4A: separation of 0.228 mg of total material on a Mono S 5/50 GL column (column volume: 1 mL): Starting buffer A: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH4.0. Final buffer: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH11.0. Flow rate 1 ml/min, length of linear gradient formation from 0% B to 100% B 20 column volumes. FIG. 4B: separation of 1.57 mg of total material on a Mono S 5/50 GL column (column size: 1 mL): Starting buffer A: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH4.0. Final buffer: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH11.0. Flow rate 1 ml/min, length of linear gradient formation from 32.5% B to 55% B 20 column volumes. FIG. 4C: separation of 8.88 mg of total material on a Mono S 10/100 GL column (column size: 8 ml): Starting buffer A: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH4.0. Final buffer: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH11.0. Flow rate 1 ml/min, length of linear gradient formation from 32.5% B to 55% B 20 column volumes.

The elution diagrams in FIGS. 4A through 4C demonstrate that both making the linear gradient shallower (i.e., generating a pH gradient range that encompasses a narrower pH range as illustrated in FIGS. 4B and 4C) relative to that generated as illustrated in FIG. 4A, as well as increasing the sample material mount (mass) and with it the residence time of the sample on the column, lead to increased resolution. Furthermore, the sample that showed only partial resolution on the 1 ml Mono S 5/50 GL column with the full gradient from 0% B to 100% B over 20 column volumes was resolved by increasing the column volume to 8 ml for the Mono S 10/100 GL column and making the gradient shallower (32.5% B to 55% B over 20 column volumes). Accordingly, the results demonstrate that MAIs were purified from two different parental homodimeric antibody species for which the calculated pI difference was approximately 0.59 pH unit. Additionally, the results demonstrate that MAIs were purified from two different parental homodimeric antibody species for which the calculated pI difference of the heavy chains of such parental homodimeric species was approximately 0.25 pH unit.

Example 3

Figure 5A:
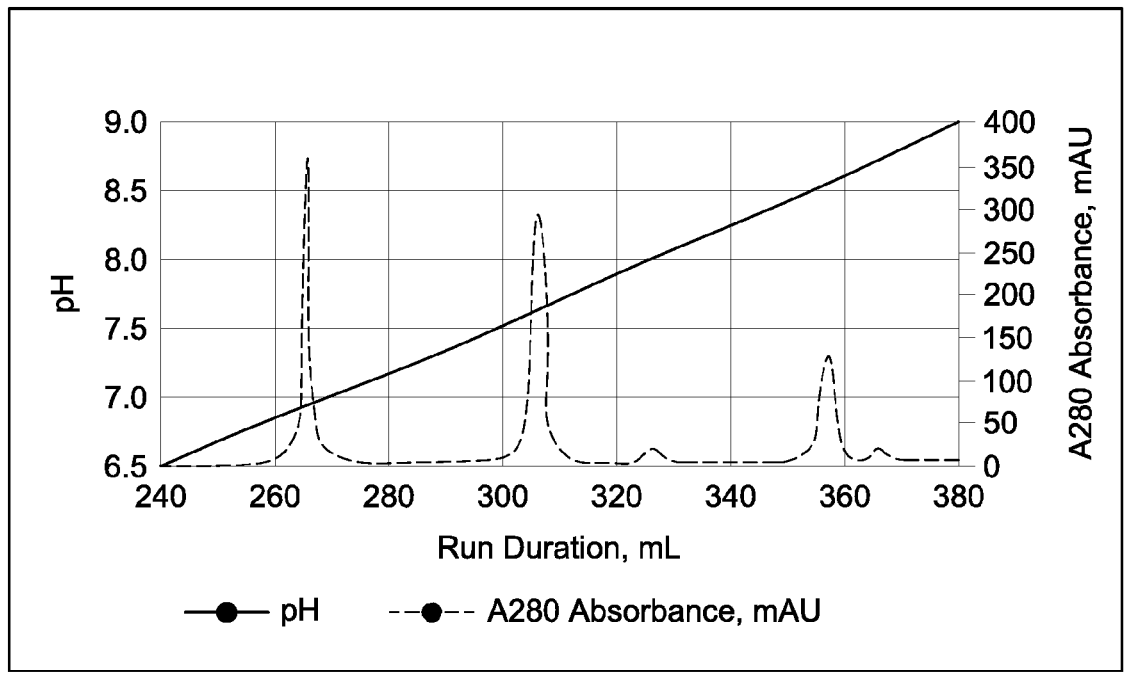
FIGS. 5A through 5E provide schematic representations of independent cation exchange chromatography experiments as described in Example 3, in which a Mono S 10/100 column was used to separate a multispecific antibody comprising a two different heavy chain polypeptides (heavy chain "A" and heavy chain "B") and two copies of an identical light chain (i.e., a "common light chain") from the two corresponding heavy chain homodimeric species.
Figure 5B:
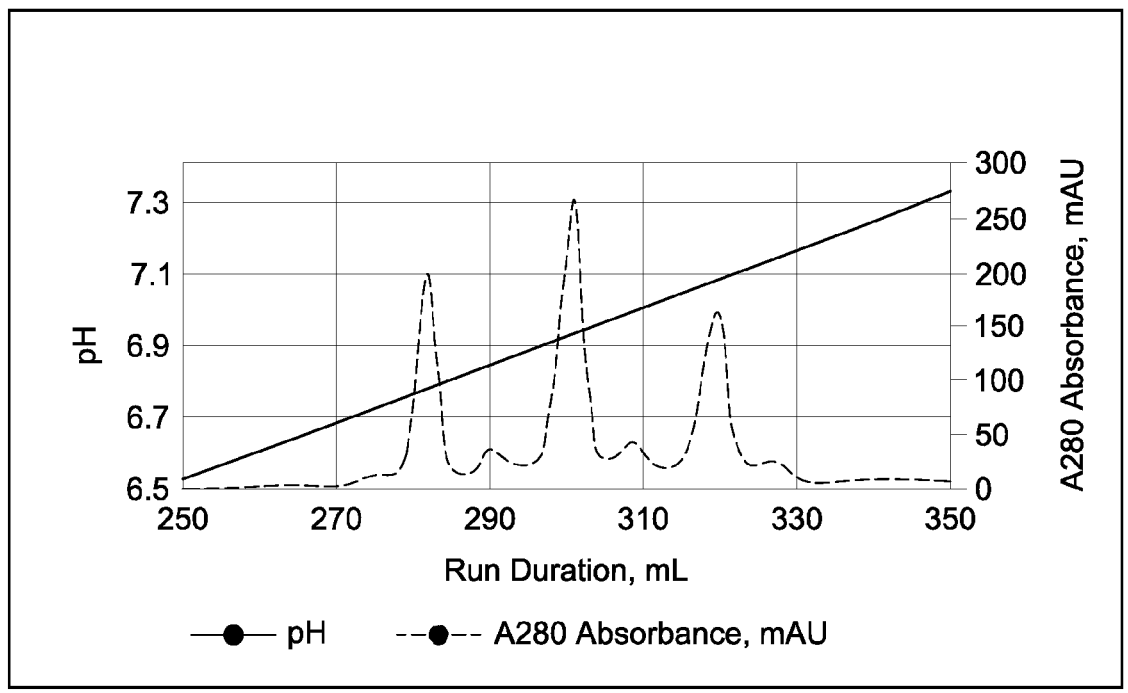
Figure 5C:
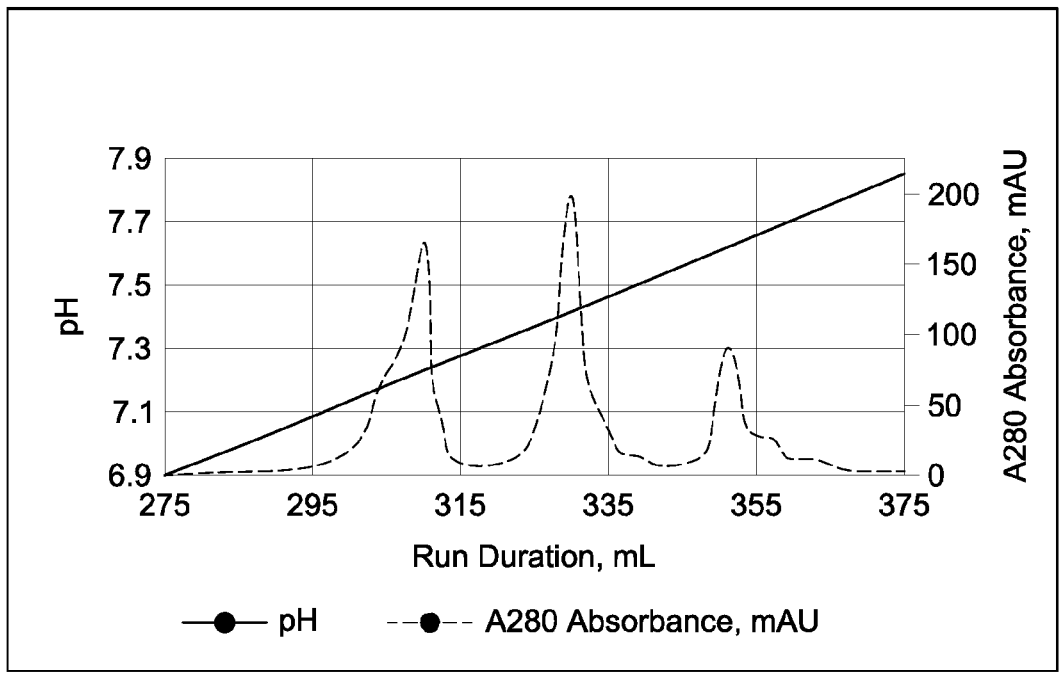
Figure 5D:
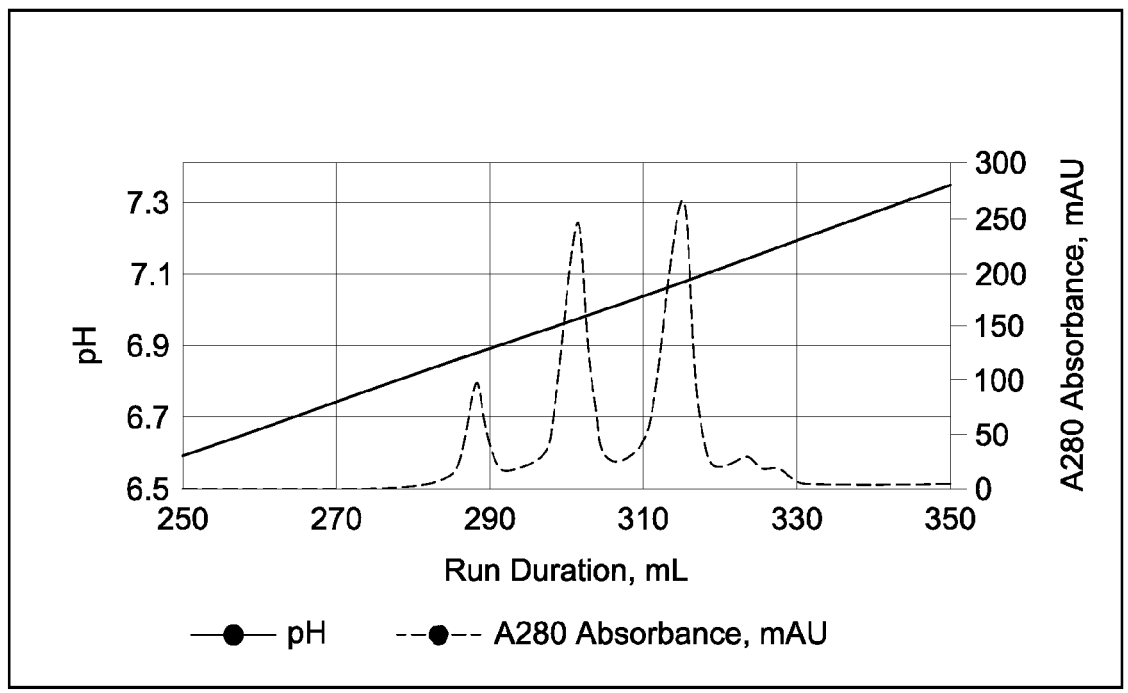
Figure 5E:
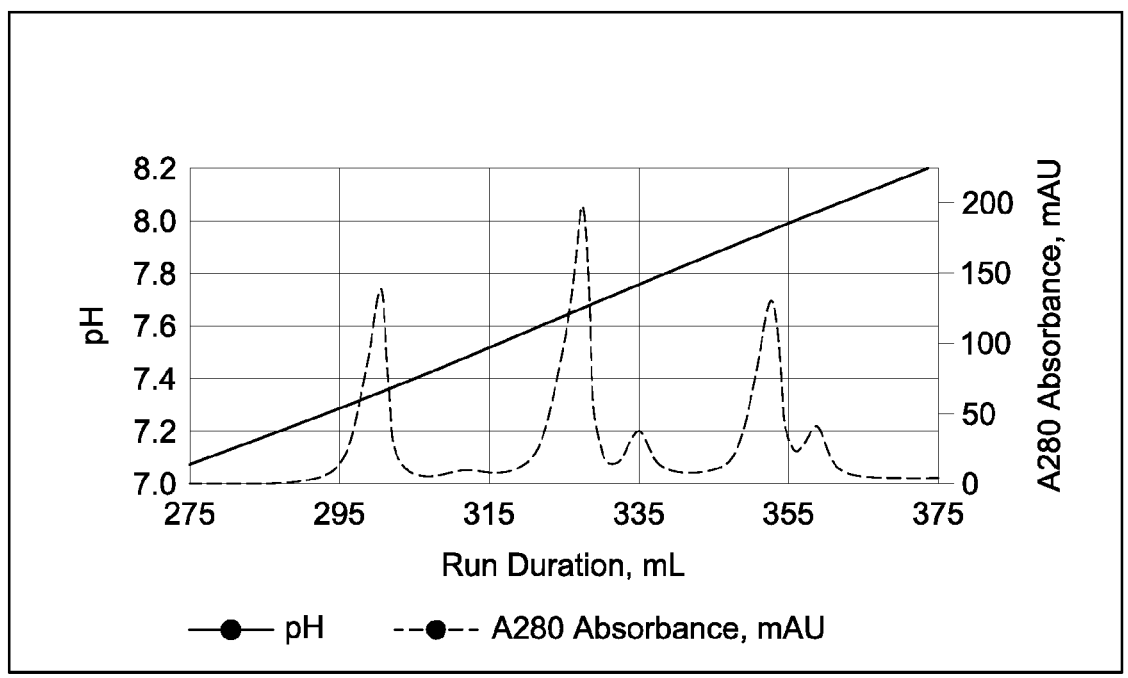

Linear pH gradient separation of a composition comprising common-light-chain IgG1 bispecific heterodimer (the "MAI") and each of two different parental homodimeric antibody species (formats as described in Scheme A of Compositions and Formats tested in the Examples, above) with varying calculated differences in heavy chain pI using a strong cation exchanger Mono S 10/100 GL column and a linear pH gradient with starting buffer A: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH4.0 and final buffer: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH11.0. Flow rate 1 ml/min, length of linear gradient formation from 32.5% B to 55% B 20 column volumes. FIG. 5A: common-light-chain bispecific homodimers and heterodimer with calculated differences in heavy chain pI of 0.68 unit (calculated pI of HC1=9.73; calculated pI of HC2=9.05; the calculated isoelectric points (pIs) of the two corresponding parental homodimeric antibody species differed by 1.33 pH unit). FIG. 5B: common-light-chain bispecific homodimers and heterodimer with calculated differences in heavy chain pI of 0.43 pH unit (calculated pI of HC1=9.43; calculated pI of HC2=9.00; the calculated isoelectric points (pIs) of the two corresponding parental homodimeric antibody species differed by 1.33 pH unit). FIG. 5C: common-light-chain bispecific homodimers and heterodimer with calculated differences in heavy chain pI of 0.25 unit (calculated 1 pI of HC1=9.46; calculated t pI of HC2=9.21; the calculated isoelectric points (pIs) of the two corresponding parental homodimeric antibody species differed by 0.59 pH unit). FIG. 5D: common-light-chain bispecific homodimers and heterodimer with calculated differences in heavy chain pI of 0.24 (calculated pI of HC1=9.43; calculated theoretical pI of HC2=9.18; the calculated isoelectric points (pIs) of the two corresponding parental homodimeric antibody species differed by 0.26 pH unit). FIG. 5E: common-light-chain bispecific homodimers and heterodimer with calculated theoretical differences in heavy chain pI of 0.21 (calculated pI of HC1=9.54; calculated pI of HC2=9.33; the calculated isoelectric points (pIs) of the two corresponding parental homodimeric antibody species differed by 0.38 pH unit). Baseline resolution on the strong cation exchanger Mono S 10/100 GL column and a relatively shallow linear pH gradient is achieved for mixtures of common-light-chain bispecific homodimers and heterodimer with differences the calculated isoelectric points (pIs) of the two corresponding parental homodimeric antibody species differed by 0.26 pH unit Accordingly, the results demonstrate that MAIs were purified from two different parental homodimeric antibody species for which the calculated pI difference was approximately 1.33 to as small as approximately 0.26 pH unit. Additionally the results demonstrate that MAIs were purified from two different parental homodimeric antibody species for which the calculated pI difference of the heavy chains of such parental homodimeric species was from approximately 0.7 pH unit to as low as approximately 0.26 pH unit.

Example 4

Figure 8A:
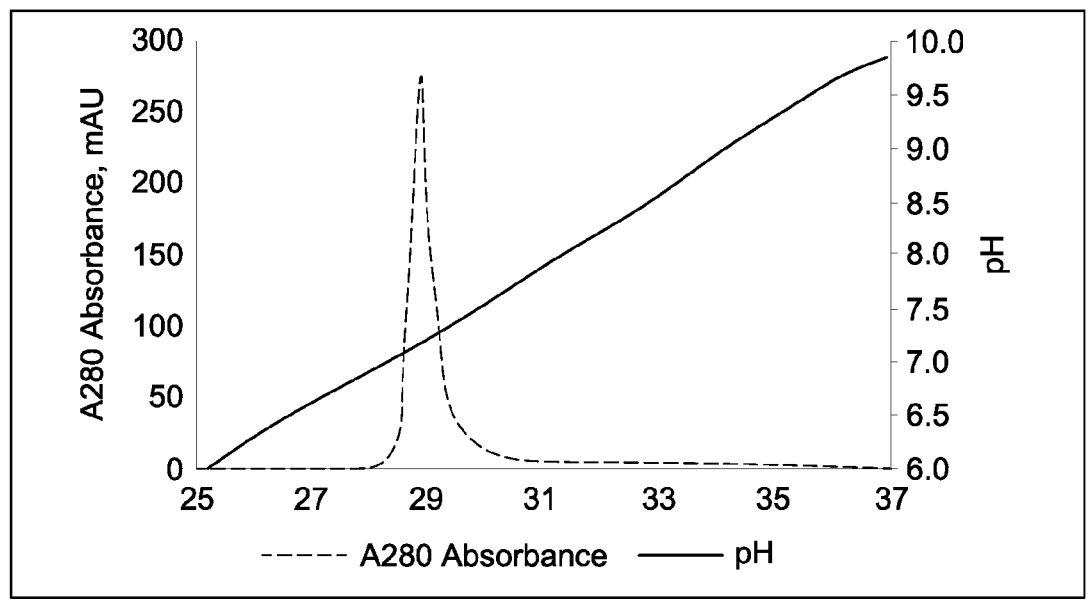
FIGS. 8A through 8C provide schematic representations of independent cation exchange chromatography experiments as described in Example 4, in which the degrees of purification of antibody species in the IgG1 format with heavy chain calculated pI difference of 0.09 (calculated isoelectric point (pIs) of the two corresponding parental homodimeric antibody species differed by 0.10 pH units) using each of the strong cationic exchangers Mono S 5/50 GL or Mono S 10/100 GL were compared. Chromatography conditions were as described in Example 4. All antibodies (MAI and parental homodimeric antibody species) were in the native IgG1 format.
Figure 8B:
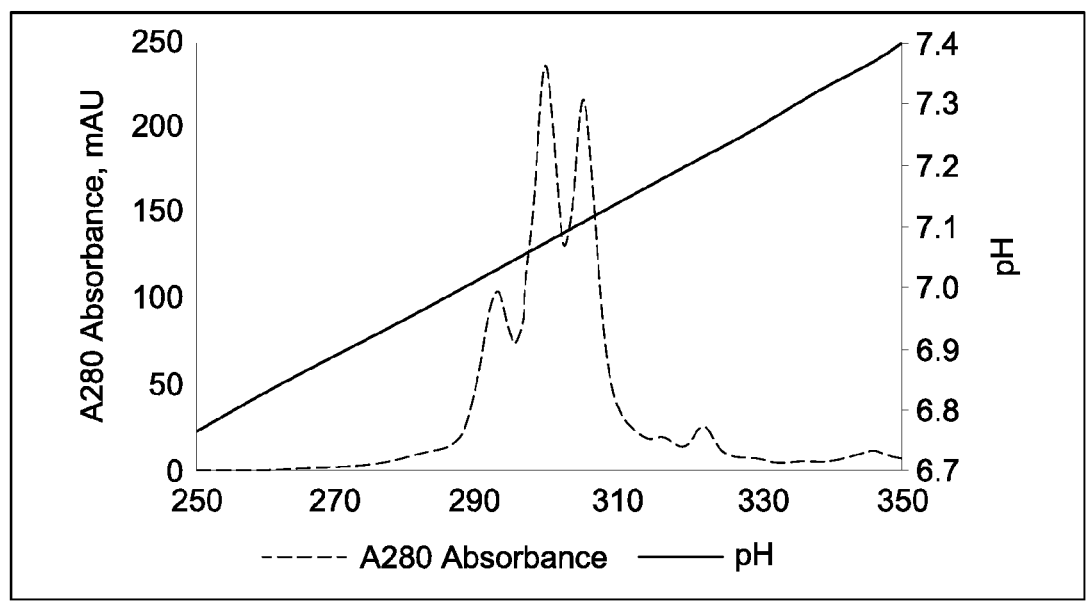
Figure 8C:
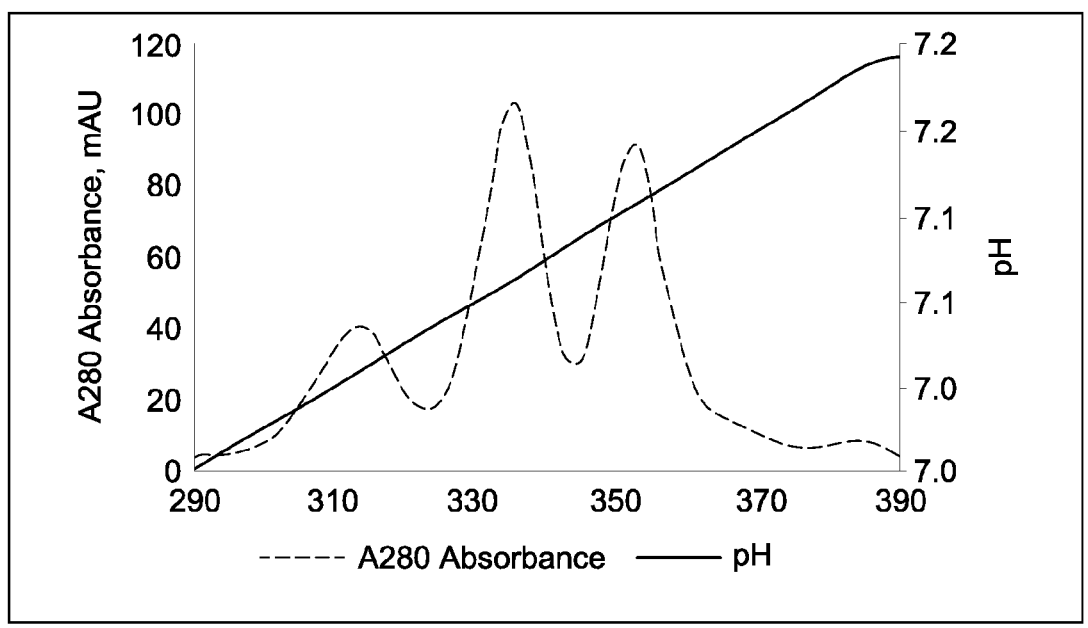

Linear pH gradient separation of a composition comprising common-light-chain IgG1 bispecific heterodimer (the "MAI") and each of two different parental homodimeric antibody species (formats as described in Scheme A of Compositions and Formats tested in the Examples, above) with a calculated difference in heavy chain pI of 0.09 (calculated pI of HC1=9.43; calculated 1 pI of HC2=9.33; calculated isoelectric point(pIs) of the two corresponding parental homodimeric antibody species differed by 0.10 pH unit); using various linear pH gradients on a strong cation exchanger Mono S 5/50 GL column or a strong cation exchanger Mono S 10/100 GL column. FIG. 8A: separation of 0.421 mg of total material on a Mono S 5/50 GL column: Starting buffer A: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH4.0. Final buffer: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH1.0. Flow rate 1 ml/min, length of linear gradient formation from 0% B to 100% B 20 column volumes. FIG. 8B: separation of 7.57 mg of total material on a Mono S 10/100 GL column: Starting buffer A: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH4.0. Final buffer: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH11.0. Flow rate 1 ml/min, length of linear gradient formation from 35% B to 53% B 20 column volumes. FIG. 8C: separation of 6.69 mg of total material on a Mono S 10/100 GL column: Starting buffer A: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH4.0. Final buffer: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl. pH11.0. Flow rate 1 ml/min, length of linear gradient formation from 37% B to 43% B 20 column volumes. The recovery of MAI recovery observed in the experiment illustrated in FIG. 8C was 64% increased relative to the recovery observed in FIG. 8B.

The results demonstrate that MAIs were purified from two different parental homodimeric antibody species for which the calculated pI differences as low as approximately 0.10 pH unit to an acceptable degree (i.e., such that fraction volumes can be selected such that the MAI is purified essentially to homogeneity, albeit with modest loss of yield). Additionally the results demonstrate that MAIs were purified from two different parental homodimeric antibody species for which the calculated pI difference of the heavy chains of such parental homodimeric species was approximately 0.9 pH unit. Furthermore, the results demonstrate that employing a shallower pH gradient (ii., narrowing the pH range of the pH gradient) as well as increasing the column volume (and hence, the residence time of the protein composition that is applied to the column) can increase both the degree of separation of the MAI from the parental homodimeric species and increase the percent recovery of the MAI.

Example 5

Figure 3:
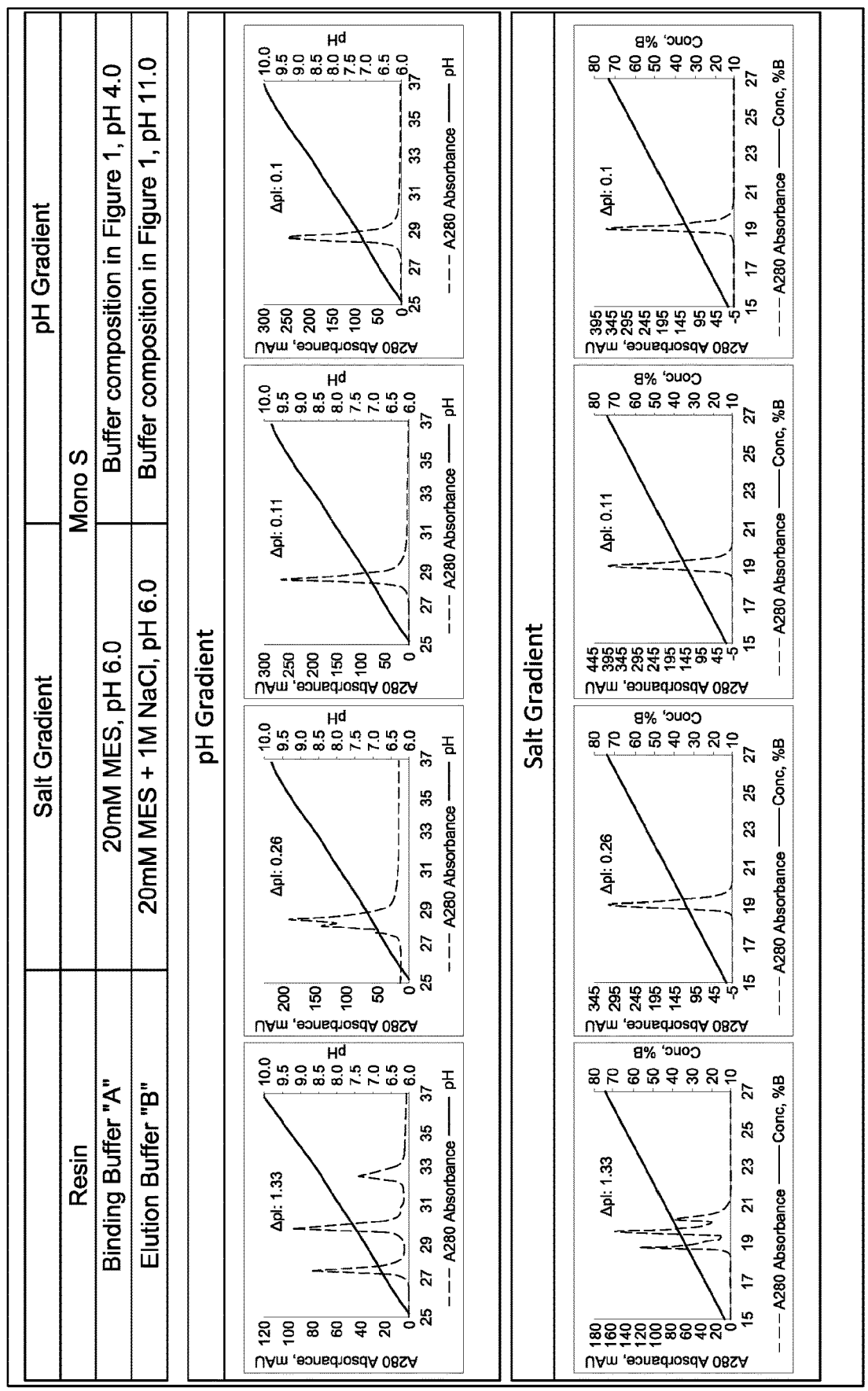
FIG. 3 provides a comparison of the ability of salt gradient (i.e., ionic strength gradient) cation exchange chromatography and pH gradient cationic exchange chromatography to separate four different multispecific antibodies of interest (MAIs), each MAI comprising: two different heavy chain polypeptides from one of four sets of two corresponding parental homodimeric antibody species; and two copies of an identical light chain (i.e., a "common light chain"). The calculated isoelectric points (pIs) of the two corresponding parental homodimeric antibody species differed by 1.33, 0.26, 0.11, and 0.1 pH units, respectively as indicated in the Figure and as described in Example 5. The resin and buffer compositions employed in the experiments are provided in the top table of FIG. 3.

Linear pH gradient separations of compositions comprising common-light-chain IgG1 bispecific heterodimers (the "MAIs") and each of two different parental homodimeric antibody species (formats as described in Scheme A of Compositions and Formats tested in the Examples, above) were compared to separations of the same compositions using linear salt gradients, using the Mono S 10/100 GL strong cation exchanger resin and the buffer compositions as outlined in the table in the top portion of FIG. 3. Briefly, starting buffer A: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH4.0. Final buffer B: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH 11.0 Flow rate 1 ml/min, length of linear gradient formation from 0% B to 100% B 20 column volumes.

For both pH gradient experiments and salt gradient experiments, common-light-chain bispecific homodimers and heterodimer with the following calculated differences were compared: calculated differences in heavy chain pI of 0.68 unit (calculated pI of HC1=9.73; calculated pI of HC2=9.05; the calculated isoelectric points (pIs) of the two corresponding parental homodimeric antibody species differed by 1.33 pH unit); calculated differences in heavy chain pI of 0.24 unit (calculated pI of HC1=9.43; calculated pI of HC2=9.18; the calculated isoelectric points (pIs) of the two corresponding parental homodimeric antibody species differed by 0.26 pH unit); the calculated differences in heavy chain pI of 0.11 (calculated pI of HC1=9.43; calculated pI of HC2=9.32; the calculated isoelectric points (pIs) of the two corresponding parental homodimeric antibody species differed by 0.11 pH unit); and the calculated differences in heavy chain pI of 0.09 (calculated pI of HC1=9.43; calculated pI of HC2=9.34; the calculated isoelectric points (pIs) of the two corresponding parental homodimeric antibody species differed by 0.1 pH unit).

The results demonstrate that the MAIs were better separated from the corresponding parental homodimeric antibody species tested compositions when subjected to pH gradient elution when compared to salt gradient elution.

Example 6

It was desirable to further explore the extent to which differences in calculated pI of different parental homodimeric antibody species affected the ability to separate MAIs from compositions comprising the MAIs and the two different parental homodimeric antibody species.

Linear pH gradient separation of a composition comprising common-light-chain IgG bispecific heterodimer (the "MAI") and each of two different parental homodimeric antibody species (formats as described in Scheme A of Compositions and Formats tested in the Examples, above) with varying calculated differences in heavy chain pI using a strong cation exchanger Mono S 5/50 GL column and a linear pH gradient with starting buffer A: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH4.0 and final buffer: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH11.0. Flow rate 1 ml/min, length of linear gradient formation from 0% B to 100% B 20 column volumes.

Figure 6A:
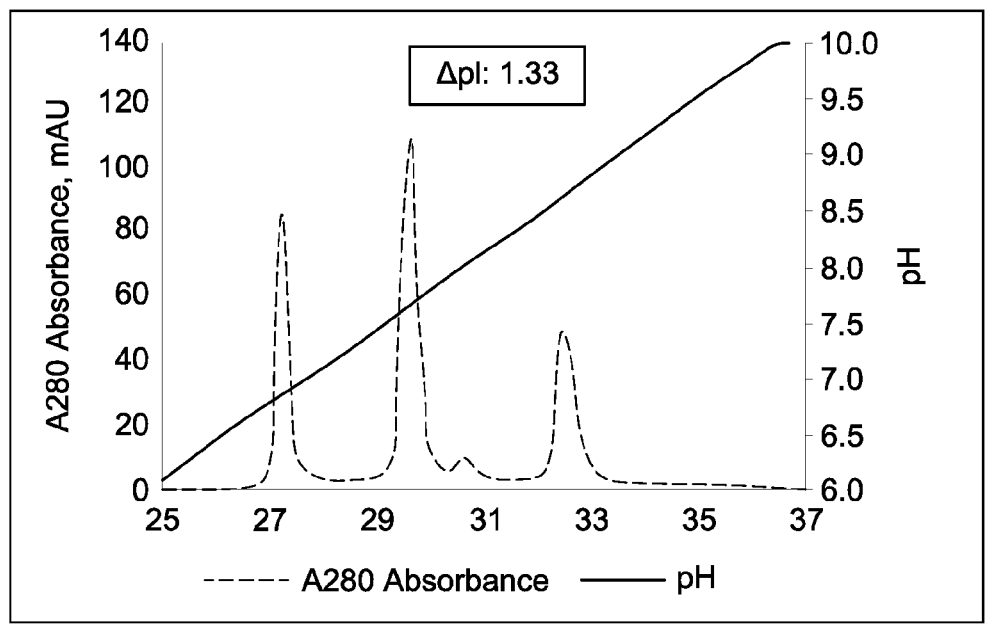
FIGS. 6A through 6G provide schematic representations of independent cation exchange chromatography experiments (FIGS. 6A through 6G) as described in Example 6. A280=absorbance units measured at a wavelength of 280 nm; ΔpI=difference in calculated isoelectric point between the two different heavy chains; run duration=elution volume in milliliters (mL). All antibodies (MAI and parental homodimeric antibody species) were in the native IgG1 format. Sequences disclosed as SEQ ID NOS 40-43, respectively, in order of appearance.
Figure 6B:
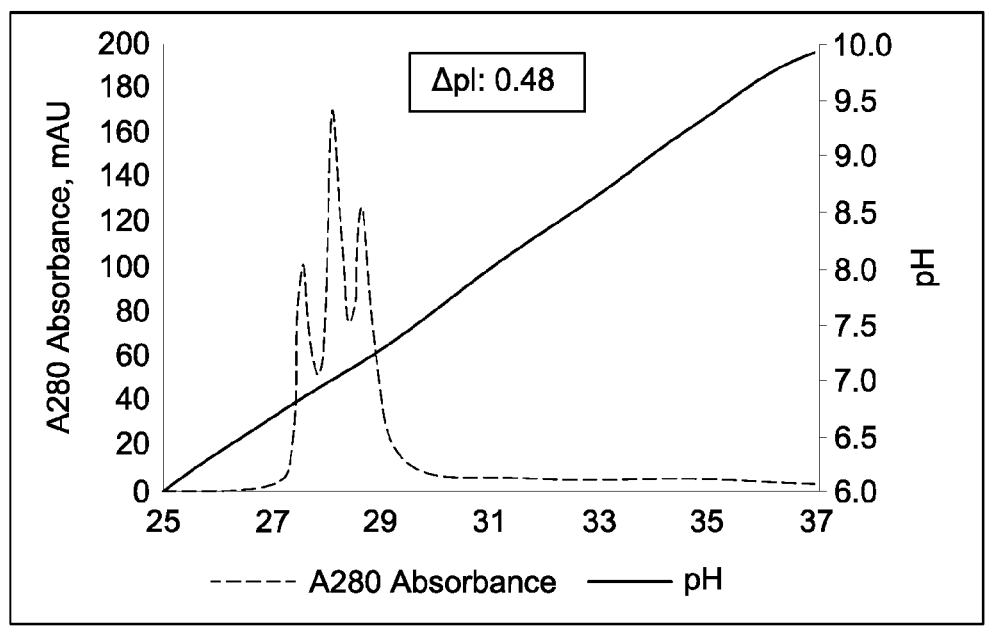
Figure 6C:
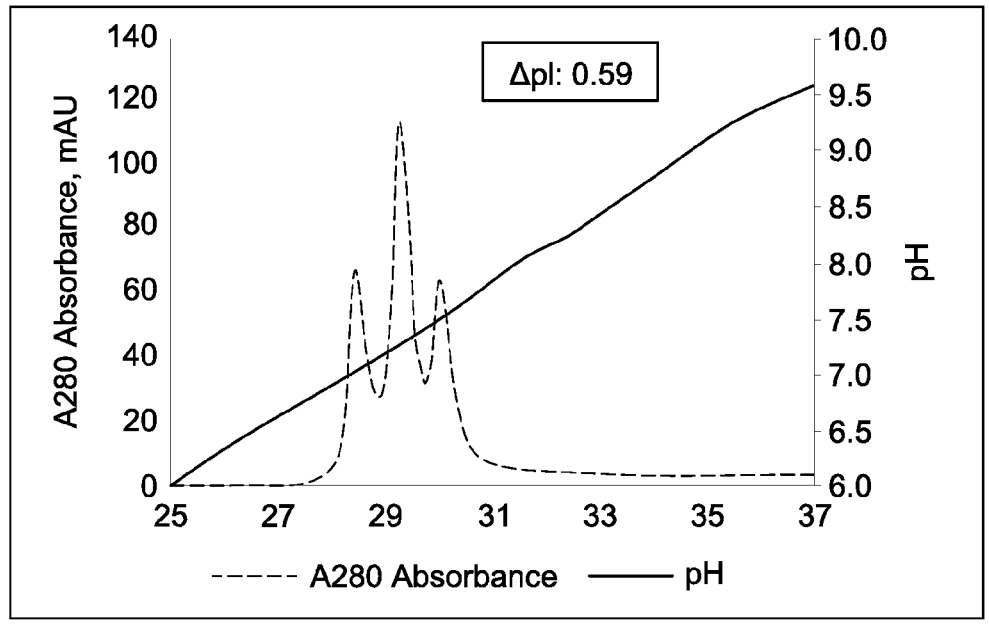
Figure 6D:
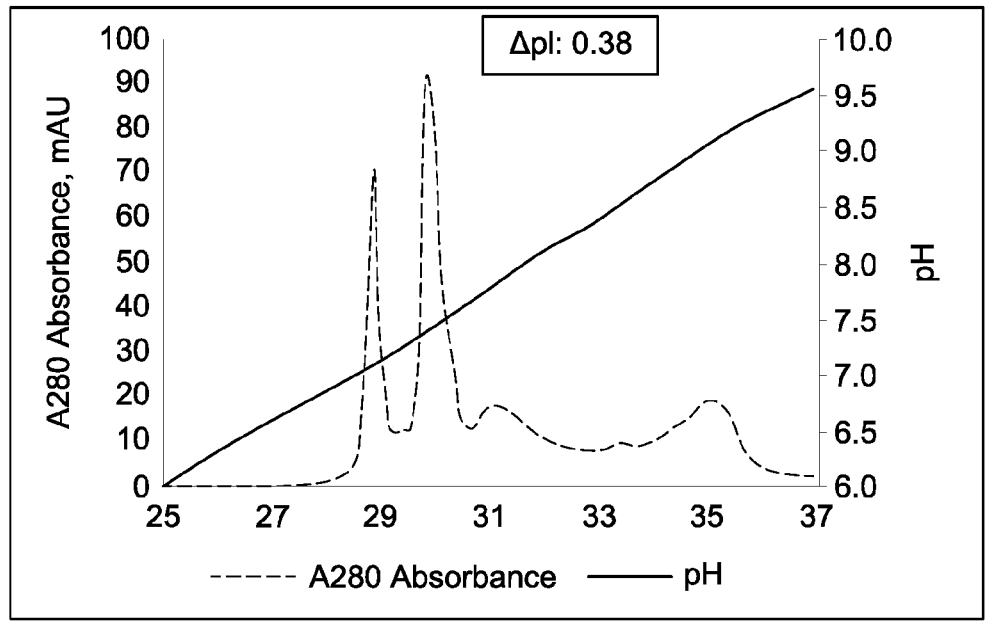
Figure 6E:
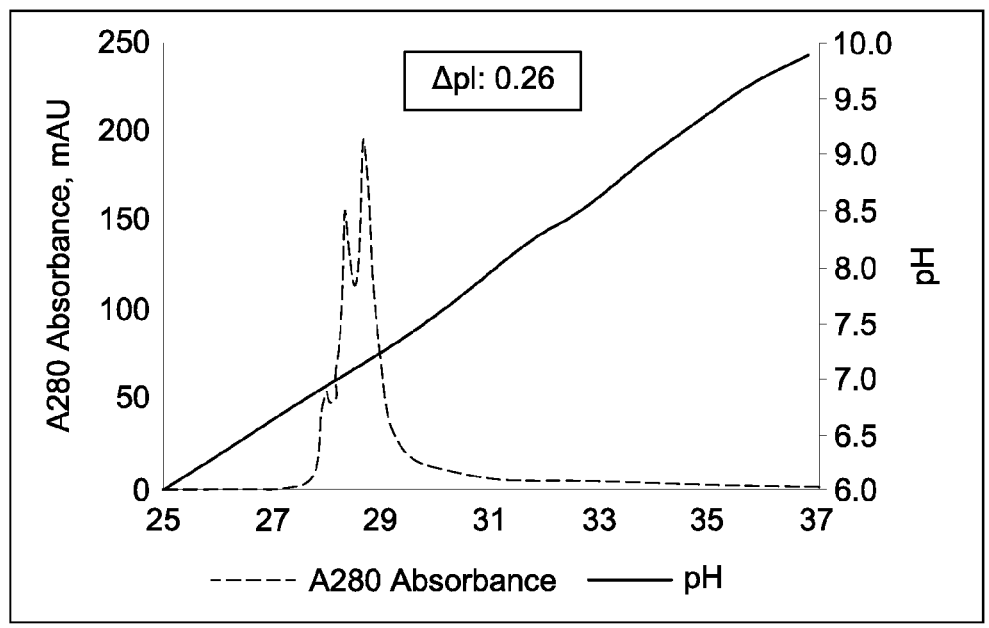
Figure 6F:
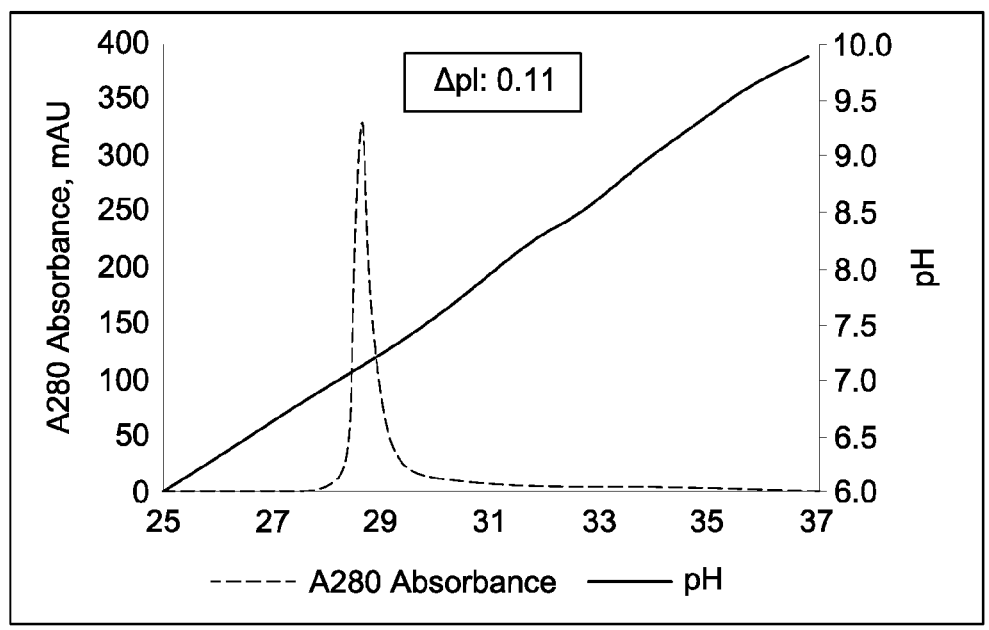
Figure 6G:
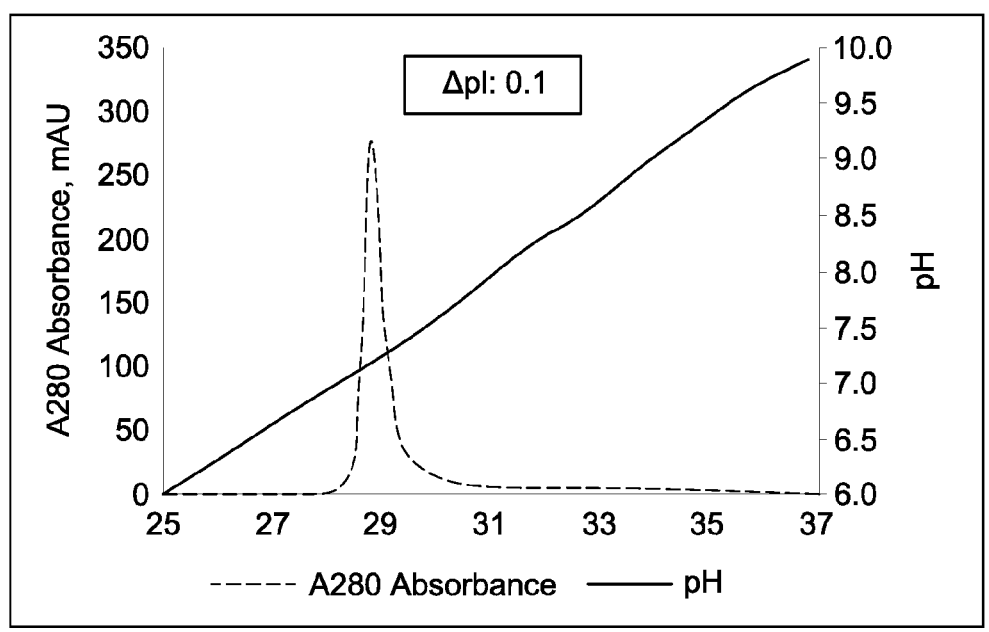

FIG. 6A: common-light-chain bispecific homodimers and heterodimer with calculated differences in heavy chain pI of 0.68 unit (calculated pI of HC1=9.73; calculated pI of HC2=9.05; the calculated isoelectric points (pIs) of the two corresponding parental homodimeric antibody species differed by 1.33 pH unit). FIG. 6B: common-light-chain bispecific homodimers and heterodimer with calculated differences in heavy chain pI of 0.43 pH unit (calculated pI of HC1=9.43; calculated pI of HC2=9.00; the calculated isoelectric points (pIs) of the two corresponding parental homodimeric antibody species differed by 0.48 pH unit). FIG. 6C: common-light-chain bispecific homodimers and heterodimer with calculated differences in heavy chain pI of 0.25 unit (calculated pI of HC1=9.46; calculated pI of HC2=9.21; the calculated isoelectric points (pIs) of the two corresponding parental homodimeric antibody species differed by 0.59 pH unit). FIG. 6D: common-light-chain bispecific homodimers and heterodimer with calculated differences in heavy chain pI of 0.21 (calculated pI of HC1=9.54; calculated theoretical pI of HC2=9.33; the calculated isoelectric points (pIs) of the two corresponding parental homodimeric antibody species differed by 0.38 pH unit). FIG. 6E: common-light-chain bispecific homodimers and heterodimer with calculated theoretical differences in heavy chain pI of 0.24 (calculated pI of HC1=9.43; calculated pI of HC2=9.18: the calculated isoelectric points (pIs) of the two corresponding parental homodimeric antibody species differed by 0.26 pH unit). FIG. 6F: common-light-chain bispecific homodimers and heterodimer with calculated theoretical differences in heavy chain pI of 0.11 (calculated pI of HC1=9.43; calculated pI of HC2=9.32; the calculated isoelectric points (pIs) of the two corresponding parental homodimeric antibody species differed by 0.11 pH unit). FIG. 6G: common-light-chain bispecific homodimers and heterodimer with calculated theoretical differences in heavy chain pI of 0.09 (calculated pI of HC1=9.43; calculated pI of HC2=9.33; the calculated isoelectric points (pIs) of the two corresponding parental homodimeric antibody species differed by 0.10 pH unit).

The results indicate that successful separation of each of the MAIs contained in compositions comprising the MAI and its parental homodimeric antibody species correlates well with calculated difference in pI of the such parental homodimeric antibody species, and correlates fairly well with calculated difference in pI of the heavy chain polypeptides contained in the parental homodimeric antibody species from which the heavy chain polypeptides of the MAI are derived.

Figure 7:
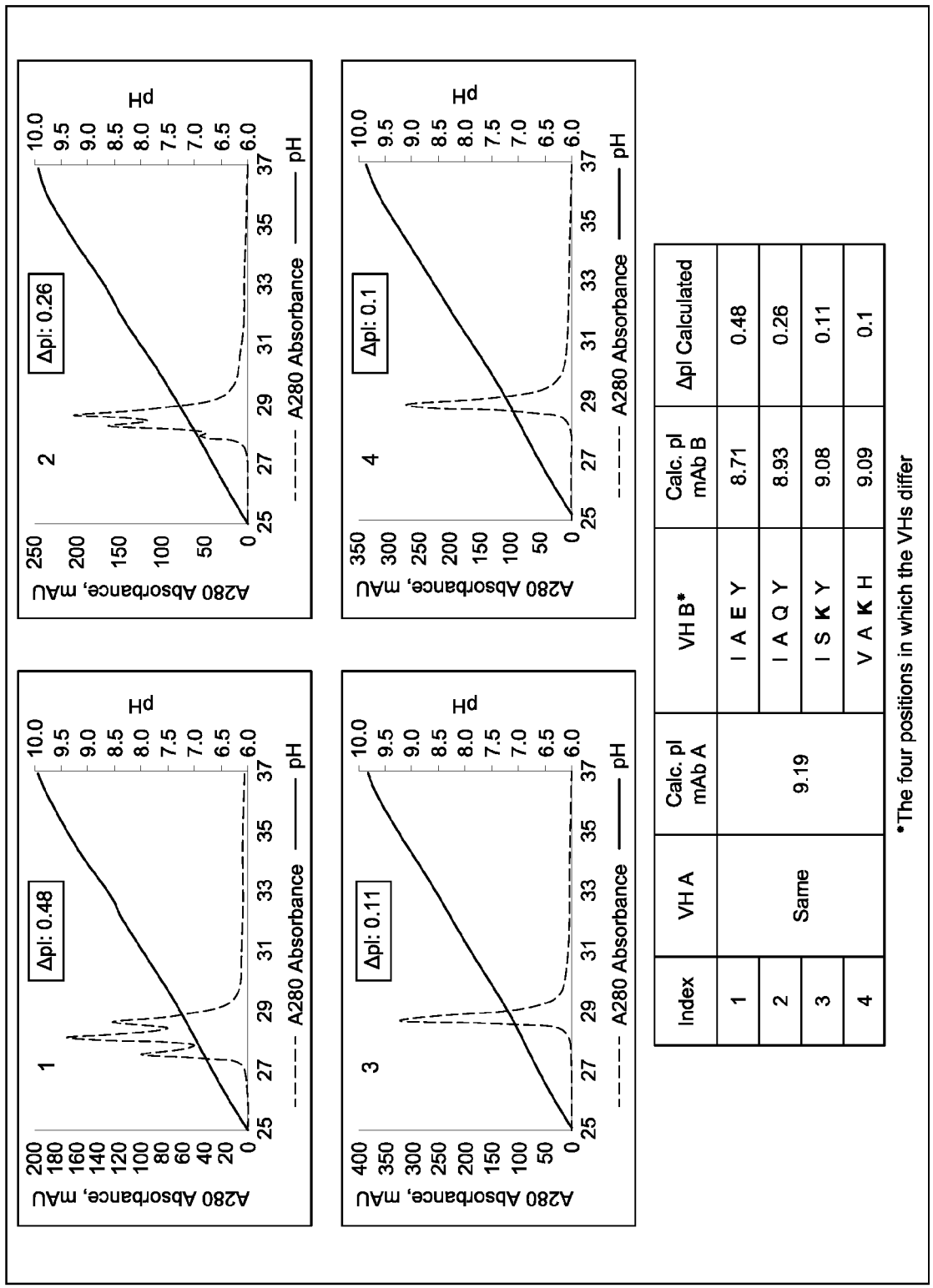
FIG. 7 illustrates that the methods disclosed herein provide the ability to separate MAIs from compositions comprising the MAI and its parental homodimeric antibody species when such species differ in their heavy chains VH regions by as little as one amino acid. IAEY is SEQ ID NO: 40; IAQY is SEQ ID NO: 41; ISKY is SEQ ID NO: 42; VAKH is SEQ ID NO: 43.

The results also demonstrate, as illustrated in FIG. 7, that the methods performed herein are suitable to separate MAIs from corresponding parental homodimeric antibody species at an acceptable degree when the heavy chain sequences of the different parental homodimeric species differ from one another by as little as one amino acid.

Example 7

It was desirable to explore the ability of anion exchange resins to effect separation of MAIs from compositions comprising the MAIs and the two different parental homodimeric antibody species. Accordingly, separations were performed as described below, in which the performance of an exemplary cation exchange resin was compared with the performance of an exemplary anion exchange resin.

Figure 9A:
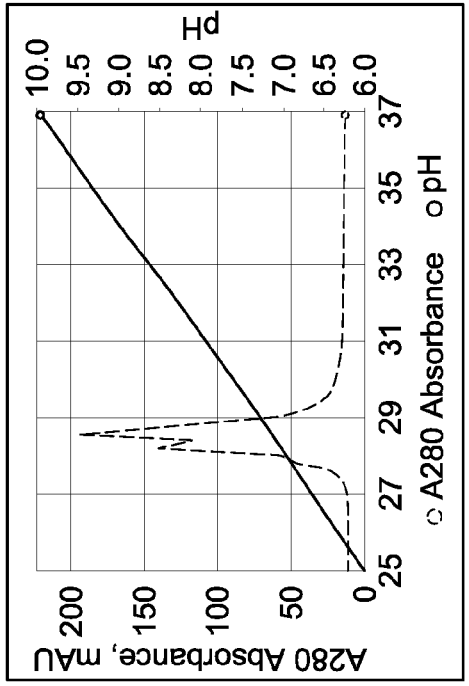
FIGS. 9A through 9F depict the results of the experiments described in Example 7.
Figure 9B:
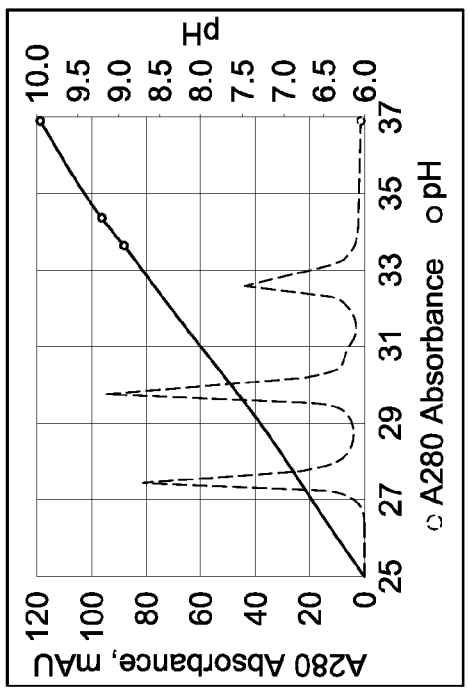
Figure 9C:
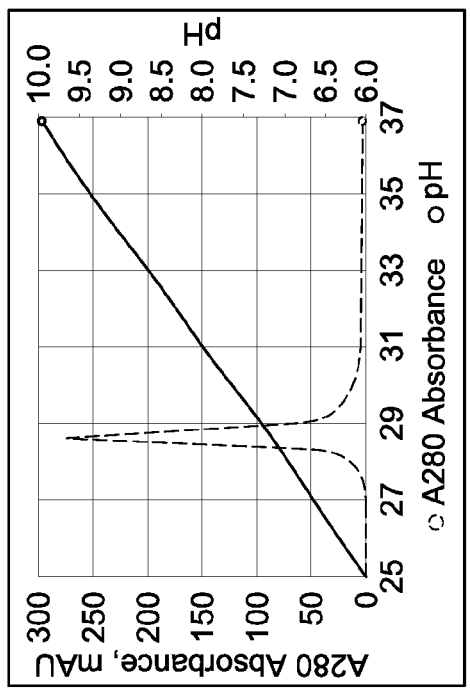
Figure 9E:
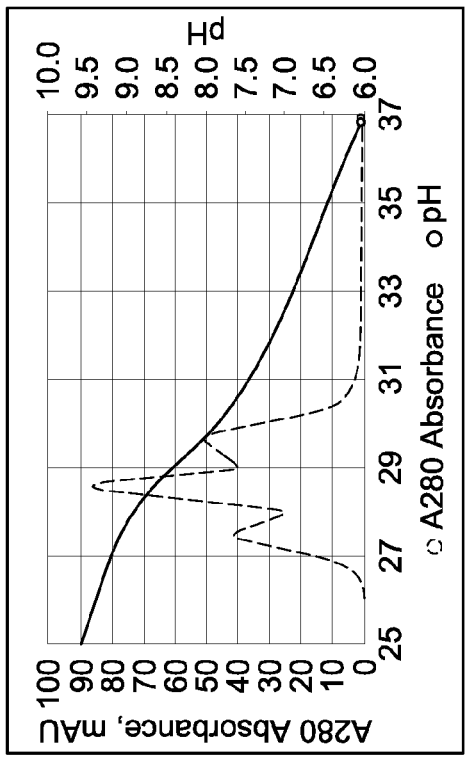
Figure 9D:
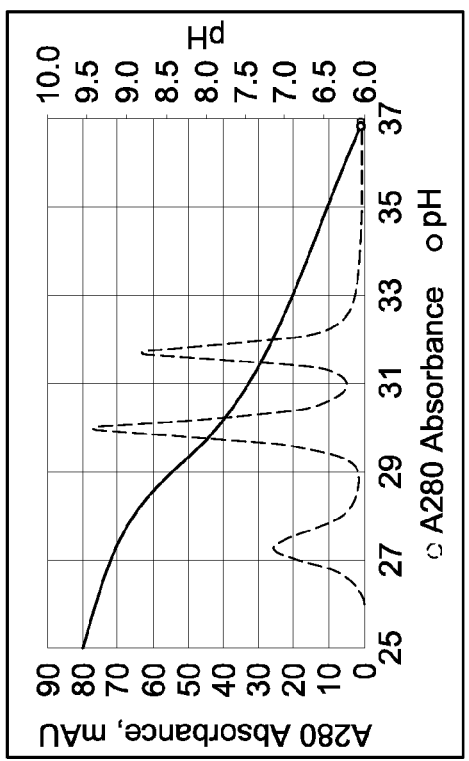
Figure 9F:
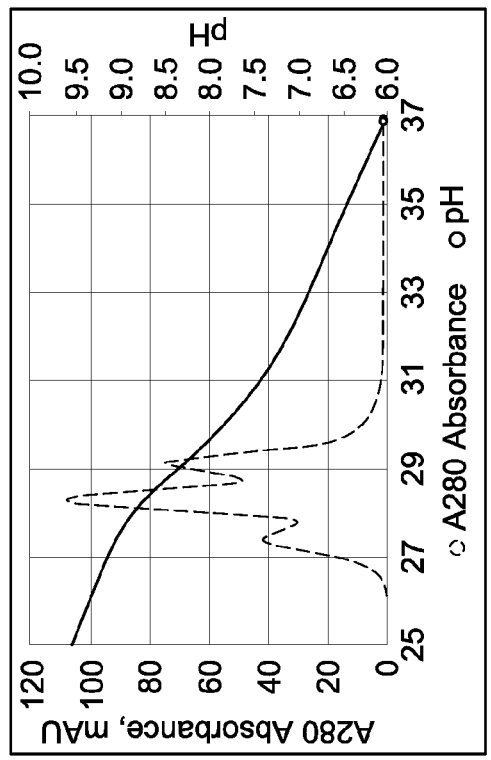

Linear pH gradient separation of a composition comprising common-light-chain IgG1 bispecific heterodimer (the "MAI") and each of two different parental homodimeric antibody species (formats as described in Scheme A of Compositions and Formats tested in the Examples, above) with varying calculated differences in heavy chain pI using a strong cation exchanger Mono S 5/50 GL column and a linear pH gradient with starting buffer A: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH4.0 and final buffer: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH11.0, or using a strong anion exchanger Mono Q 5/50 GL column and a linear pH gradient with starting buffer B: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH11.0 and final buffer: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH4.0. FIG. 9A: common-light-chain bispecific homodimers and heterodimer with calculated differences in heavy chain pI of 0.68 (calculated pI of HC1=9.73; calculated theoretical pI of HC2=9.05; the calculated isoelectric points (pIs) of the two corresponding parental homodimeric antibody species differed by 1.33 pH unit) separated on MONO S 5/50 GL. FIG. 9B: common-light-chain bispecific homodimers and heterodimer with calculated theoretical differences in heavy chain pI of 0.24 (calculated pI of HC1=9.43; calculated pI of HC2=9.18; the calculated isoelectric points (pIs) of the two corresponding parental homodimeric antibody species differed by 0.26 pH unit) separated on MONO S 5/50 GL. FIG. 9C: common-light-chain bispecific homodimers and heterodimer with calculated theoretical differences in heavy chain pI of 0.11 (calculated pI of HC1=9.43; calculated pI of HC2=9.32; the calculated isoelectric points (pIs) of the two corresponding parental homodimeric antibody species differed by 0.11 pH unit) separated on MONO S 5/50 GL. FIG. 9D: common-light-chain bispecific homodimers and heterodimer with calculated differences in heavy chain pI of 0.68 (calculated theoretical pI of HC1=9.73; calculated pI of HC2=9.05; the calculated isoelectric points (pIs) of the two corresponding parental homodimeric antibody species differed by 1.33 pH unit) separated on MONO Q 5/50 GL. FIG. 9E: common-light-chain bispecific homodimers and heterodimer with calculated differences in heavy chain pI of 0.24 (calculated theoretical pI of HC1=9.43; calculated pI of HC2=9.18; the calculated isoelectric points (pIs) of the two corresponding parental homodimeric antibody species differed by 0.26 pH unit) separated on MONO Q 5/50 GL. FIG. 9F: common-light-chain bispecific homodimers and heterodimer with calculated differences in heavy chain pI of 0.11 (calculated pI of HC1=9.43; calculated pI of HC2=9.32; the calculated isoelectric points (pIs) of the two corresponding parental homodimeric antibody species differed by 0.11 pH unit) separated on MONO Q 5/50 GL.

The results demonstrate that the strong anion exchanger Mono Q 5/50 GL column was able to purify MAI from parental homodimeric antibody species to an acceptable level (i.e., such that fraction volumes can be selected such that the MAI is purified essentially to homogeneity, albeit with modest loss of yield) in instances in which the similarly sized strong cation exchanger Mono S 5/50 GL column provided no resolution.

Example 8

Figure 10A:
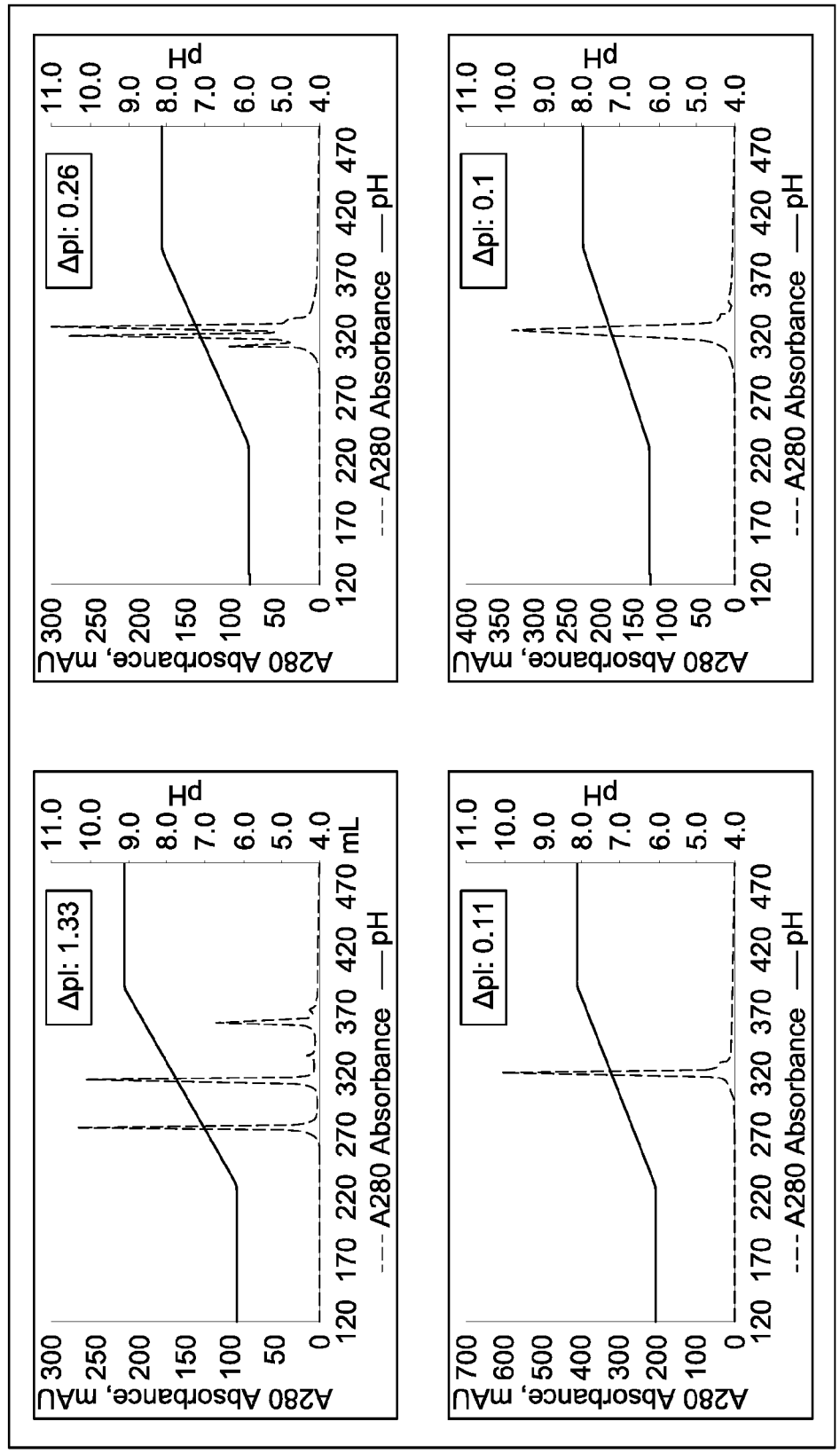
FIGS. 10A and 10B depict the results of the experiments described in Example 8.
Figure 10B:
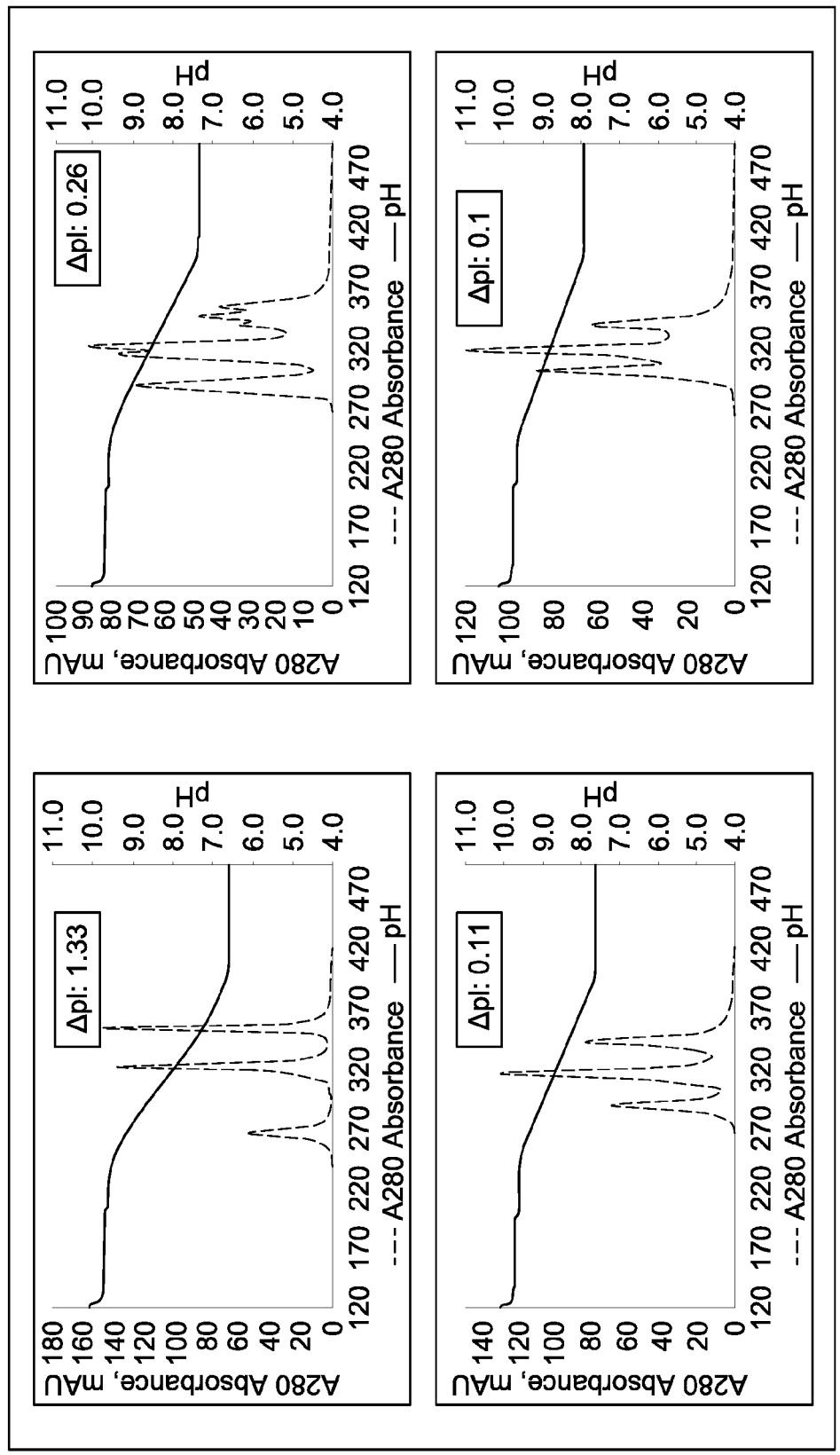

It was desirable to further compare the performance of cation exchange resins with anion exchange resins in the ability to separate MAIs from compositions comprising a given MAI and its parental homodimeric antibody species with a larger sample of differences in calculated pI of the parental homodimeric antibody species. In this case, however, the pH gradients were prepared as described in the above examples, but were generated so as to be more shallow (span a narrower pH range), as indicated in FIG. 10A and FIG. 10 B. Accordingly, 8 mL Mono S columns were used in FIG. 10A and 8 mL Mono Q columns were used in FIG. 10B, and the MAI-parental homodimeric antibody species compositions in which the difference in calculate pI of the parental homodimeric antibody species was 1.33, 0.26, 0.11, and 0.1, respectively, prepared and characterized as described in Example 6, were each tested using the two resins.

The results, depicted in FIGS. 10A and 10B, demonstrate that the MonoQ anion exchange resin effected the separation of each MAI from its corresponding parental homodimeric antibody species to a greater degree than the cation Mono S exchange resin for all compositions tested.

Example 9

It was desirable to determine whether the disclosed methods could be applied with process scale resins. Accordingly, in a first phase experiment, a series of small scale (1 mL column) scouting experiments were conducted in which a series of cation and anion exchange resins were tested for their ability to effect separation of compositions in which the difference in calculate pI of the parental homodimeric antibody species was 1.33 and 0.26, using a full pH gradient (i.e., pH 4 to pH 11) respectively, prepared and characterized as described in Example 6. In a second phase of experiments, the three best performing anion exchange resins and cation exchange resins from the first phase were then employed using larger columns (8 mL and shallower gradients to assess the ability of these best-performing resins to separate compositions in which the difference in calculate pI of the parental homodimeric antibody species was as low as approximately 0.1 pH unit.

Figure 11A:
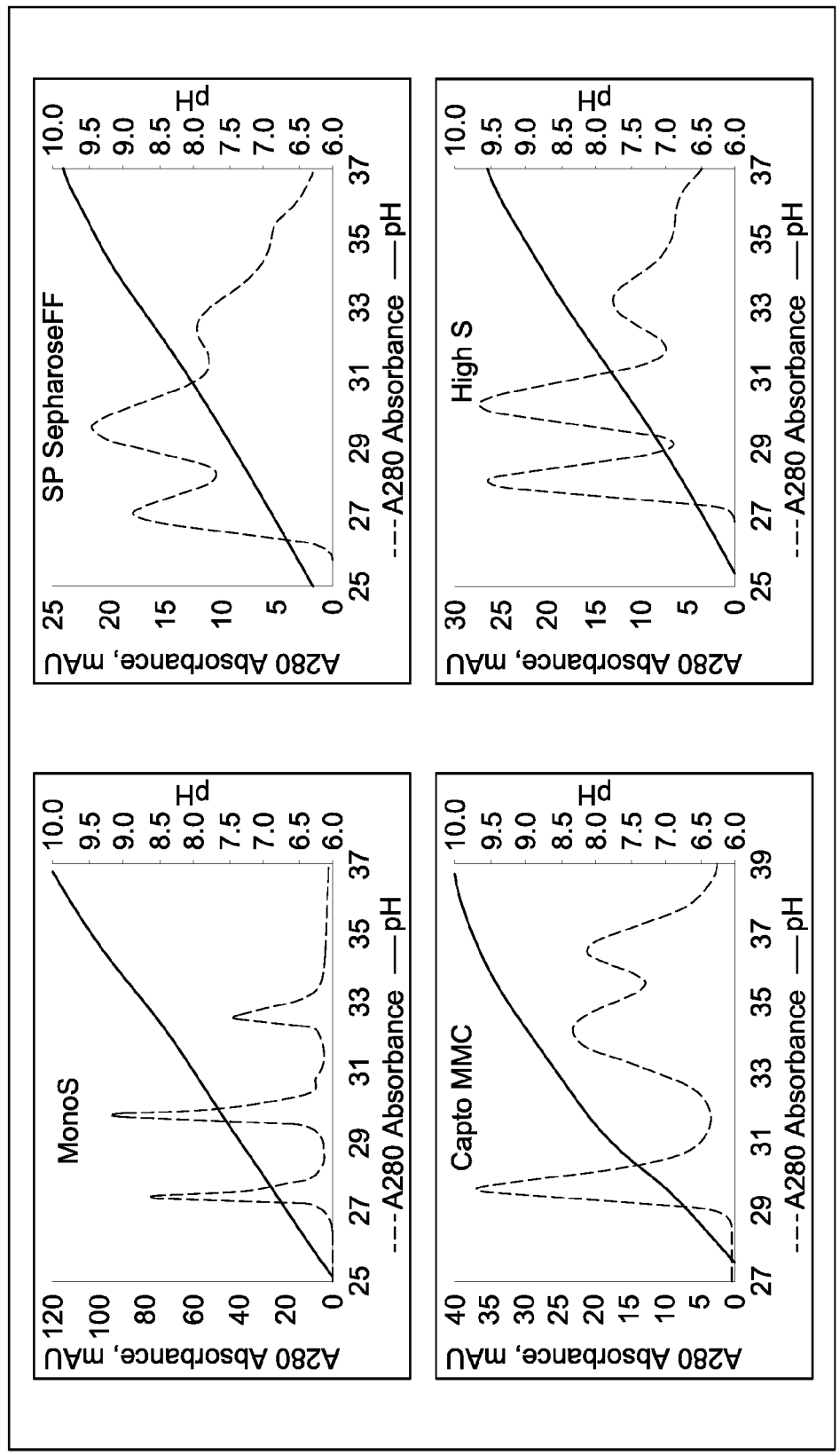
FIGS. 11A and 11B, 12A and 12B, 13A and 13B, 14A and 14B, 15A and 15B, 16A and 16B, and 17A and 17B depict the results of the experiments described in Example 9.
Figure 11B:
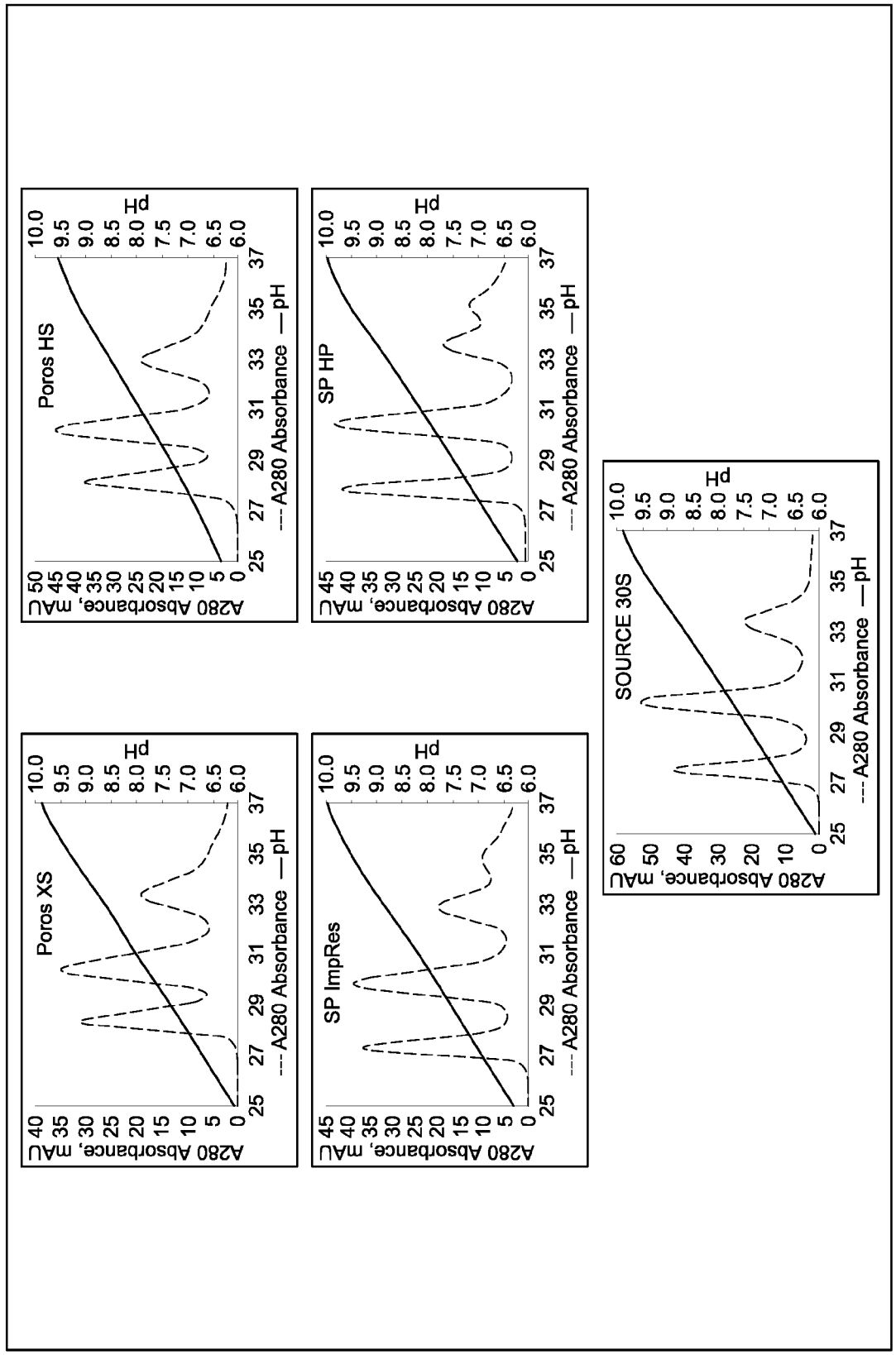
Figure 12A:
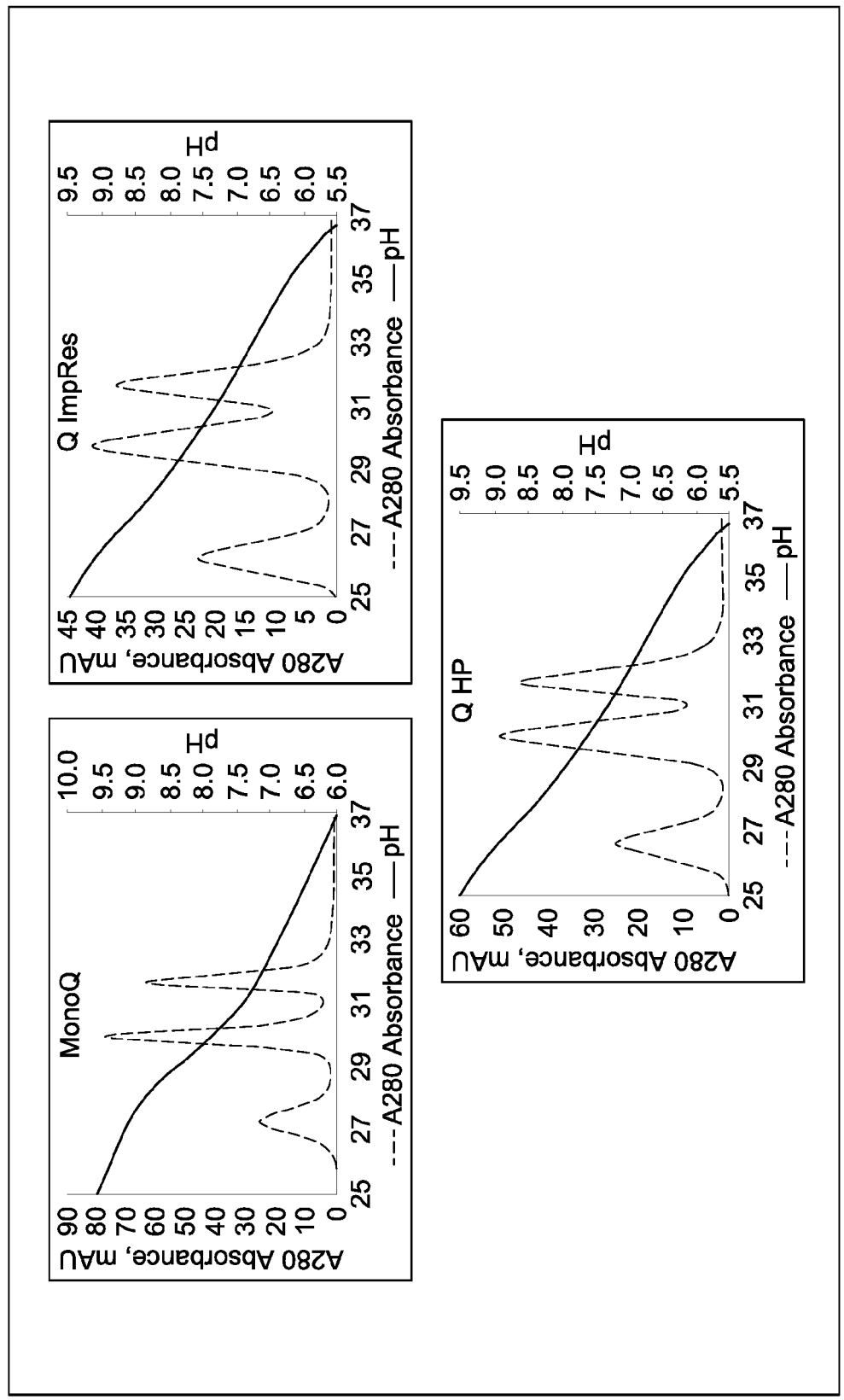
Figure 12B:
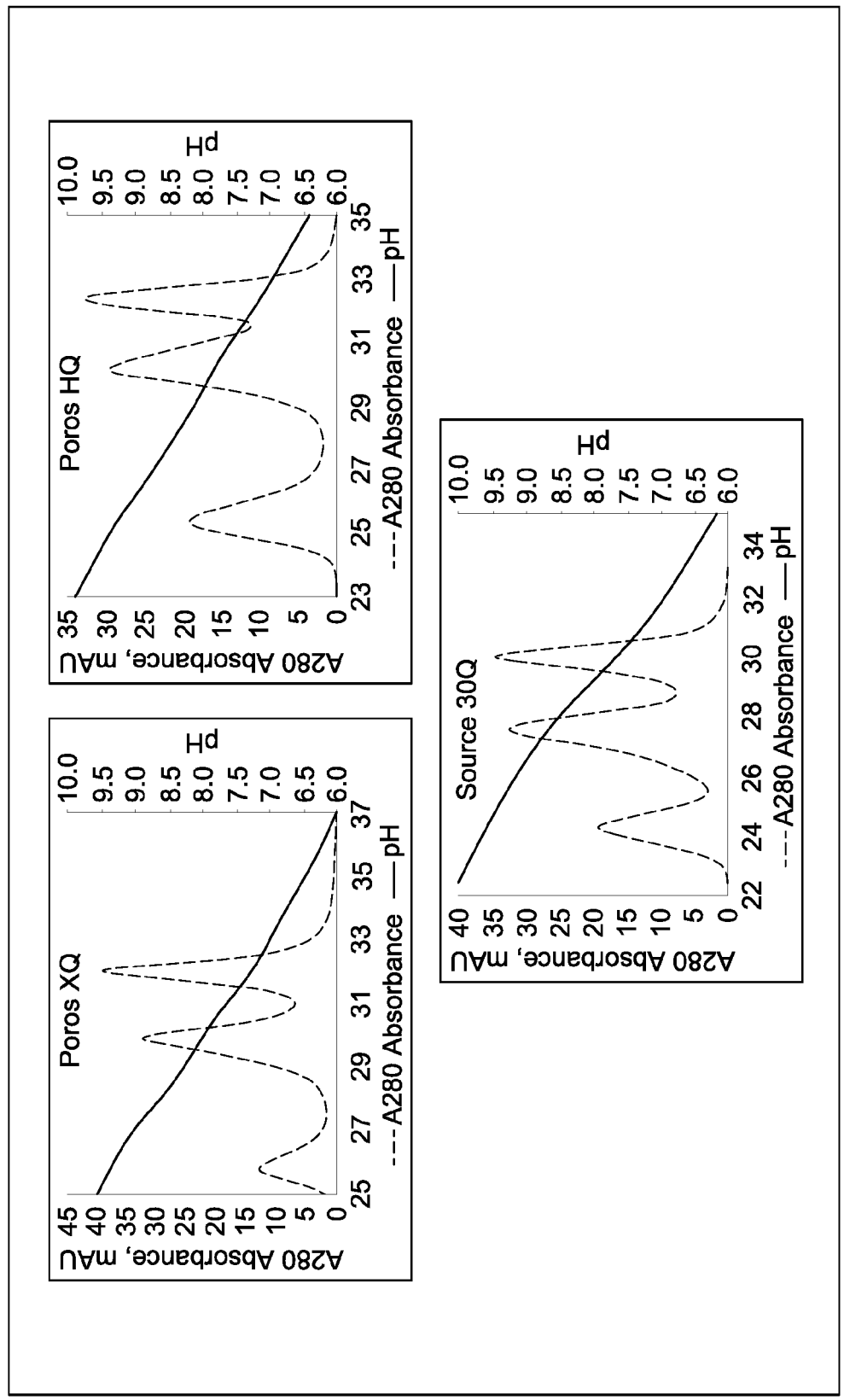
Figure 13A:
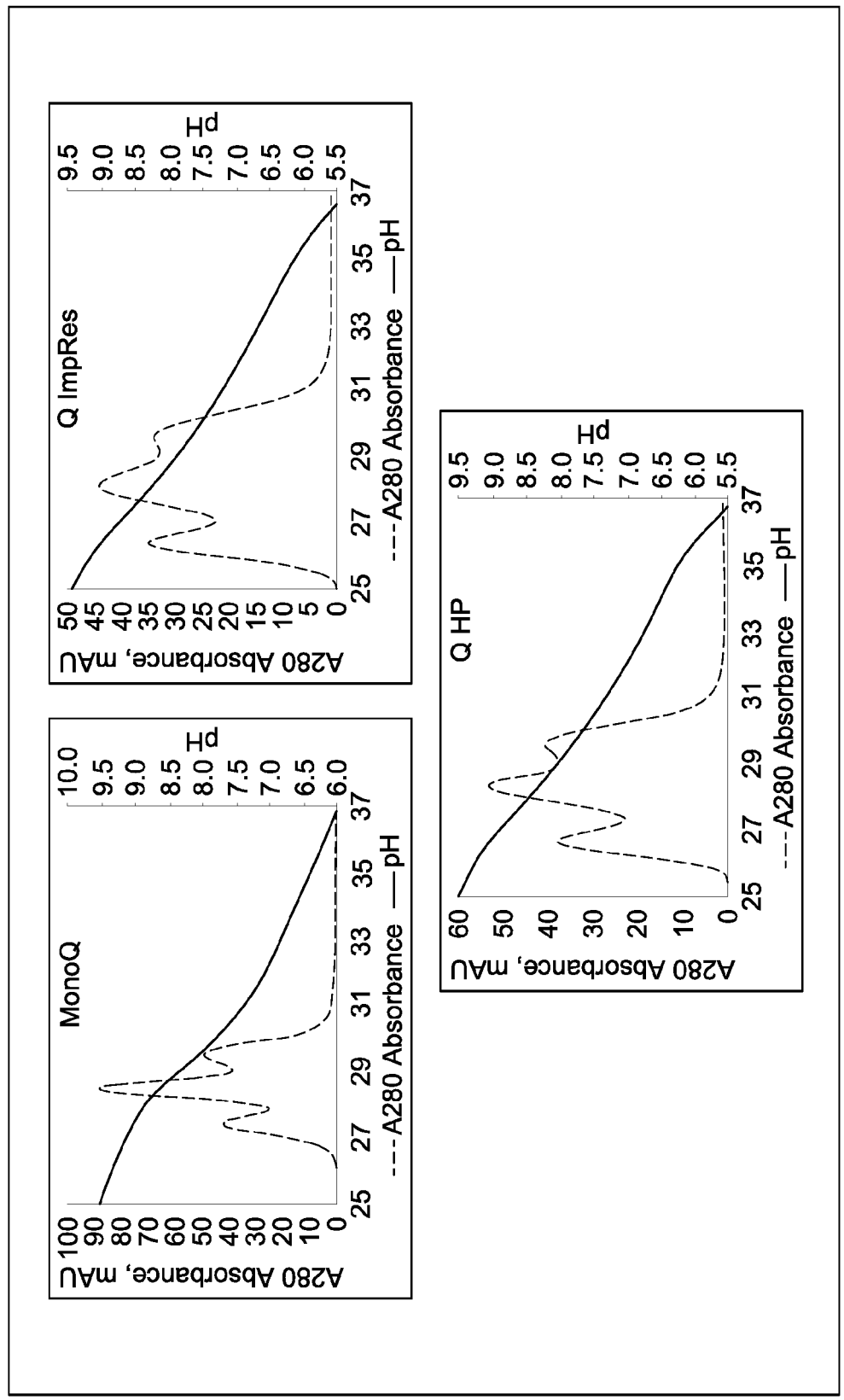
Figure 13B:
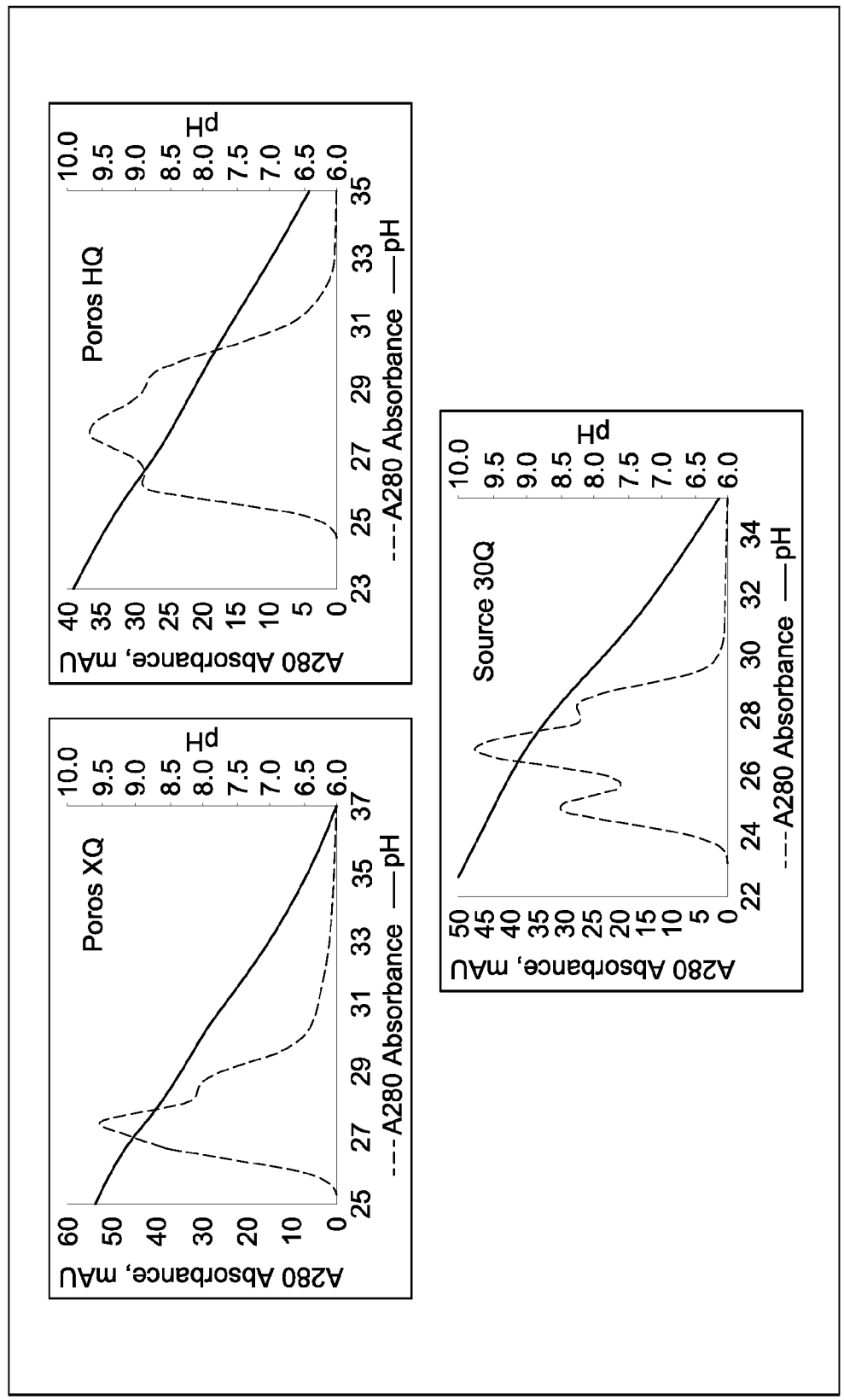
Figure 14A:
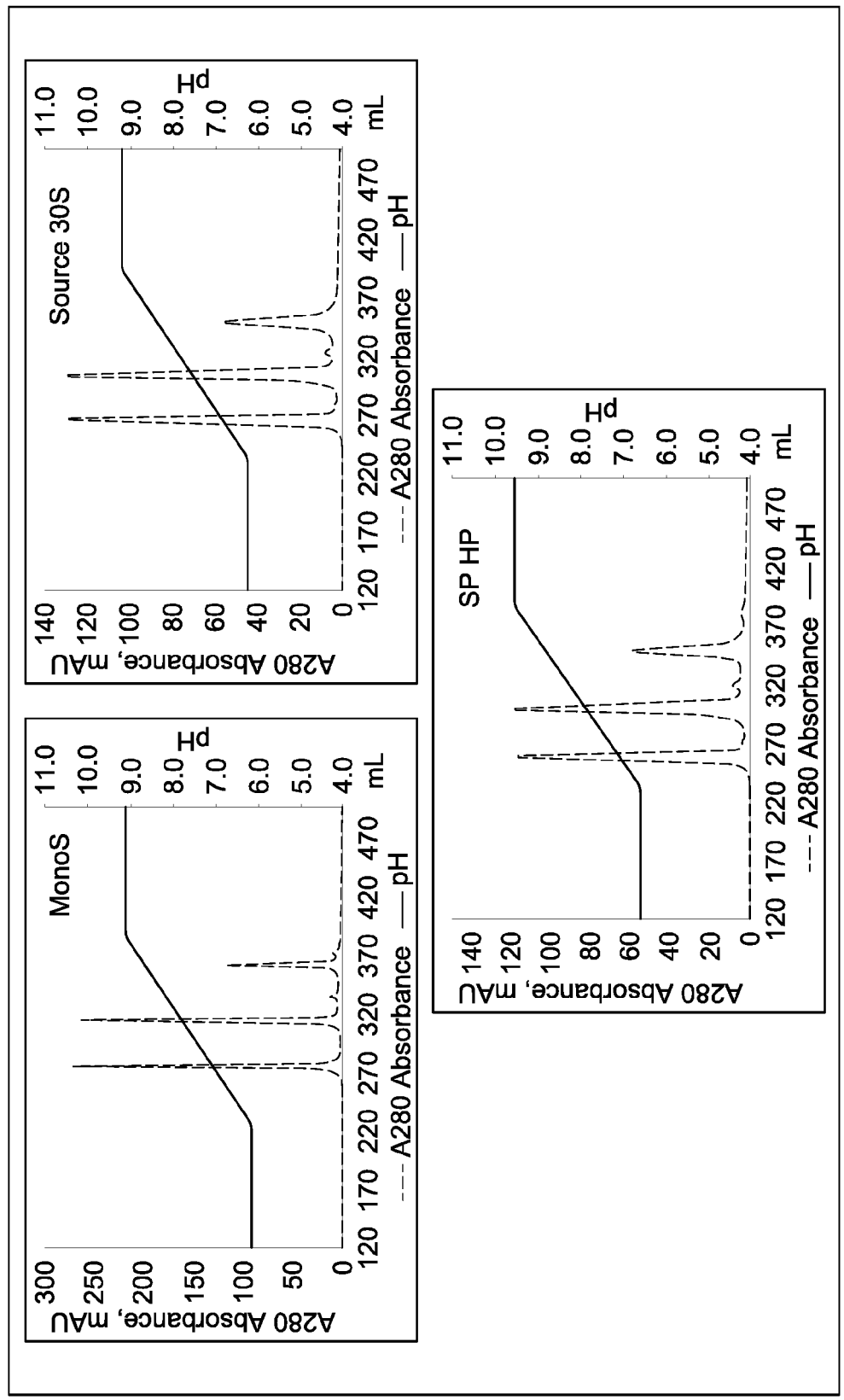
Figure 14B:
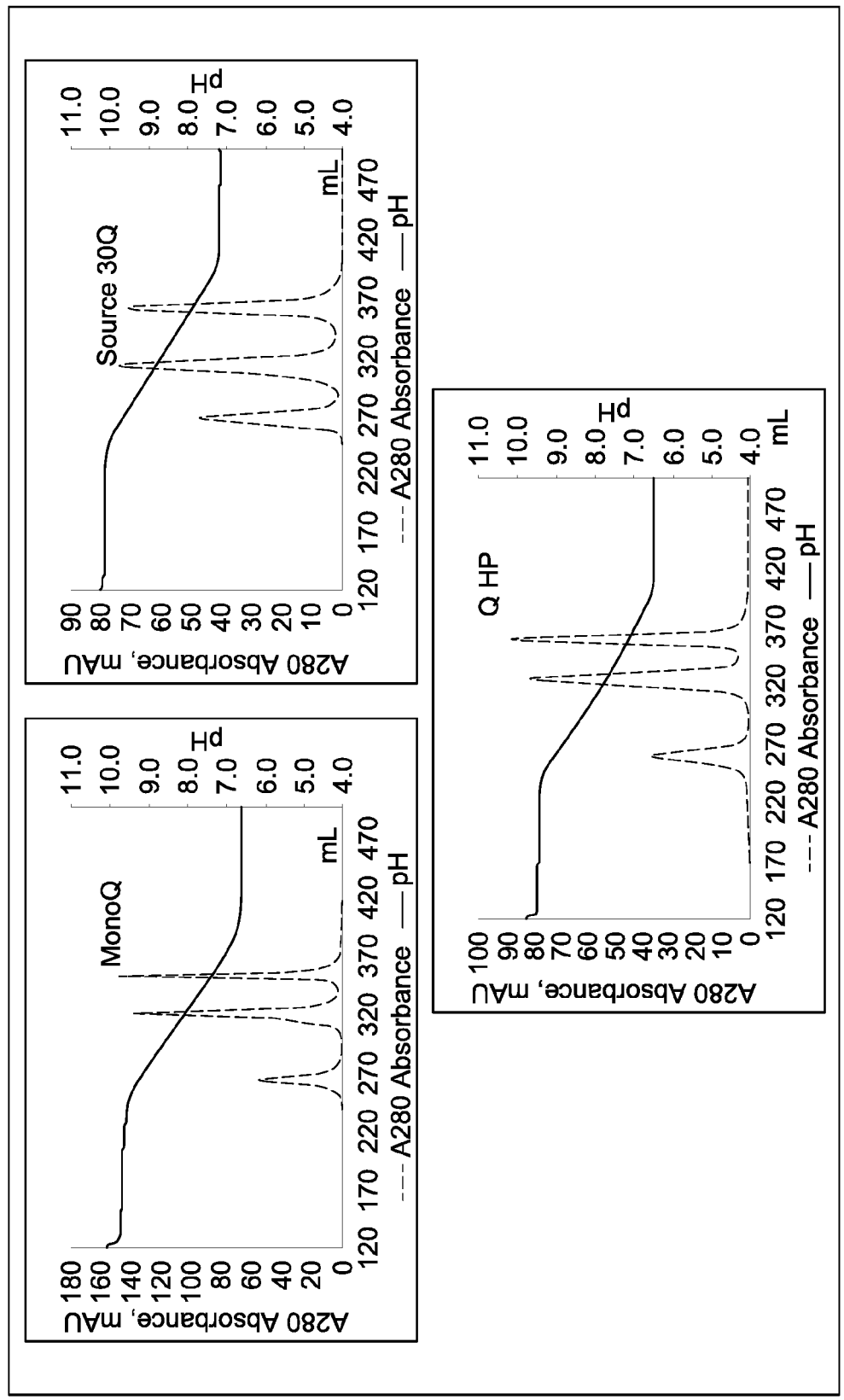

The results of the first phase cation exchange experiments for the compositions containing the 1.33 pH unit pI difference between parental homodimeric antibody species, depicted in FIGS. 11A and 11B, indicated that the Mono S, Source 30S, and SP HP cation exchange resins effected the best separation of the tested composition (i.e., the "1.33" composition). The results of the first phase anion exchange experiments for the compositions containing the 1.33 pH unit pI difference and the 0.26 pH unit difference, respectively, between parental homodimeric antibody species, depicted in FIGS. 12A, 12B, 13A, and 13B indicated that the Mono Q, Source 30Q, and Q HP anion exchange resins effected the best separation of the tested compositions (i.e., the "1.33" composition and the "0.26" composition). However, in order to achieve better resolution using each of the best performing cation resins and anion resins, a series of further scouting experiments were performed, but using shallower pH gradients (i.e., narrower pH range). As depicted in FIGS. 14A and 14B, the cation resins and anion resins, respectively, were tested in small columns (1 mL) with the depicted shallower gradients, for their ability to separate MAIs from compositions containing the 1.33 pH unit pI difference between parental homodimeric antibody species.

Figure 15A:
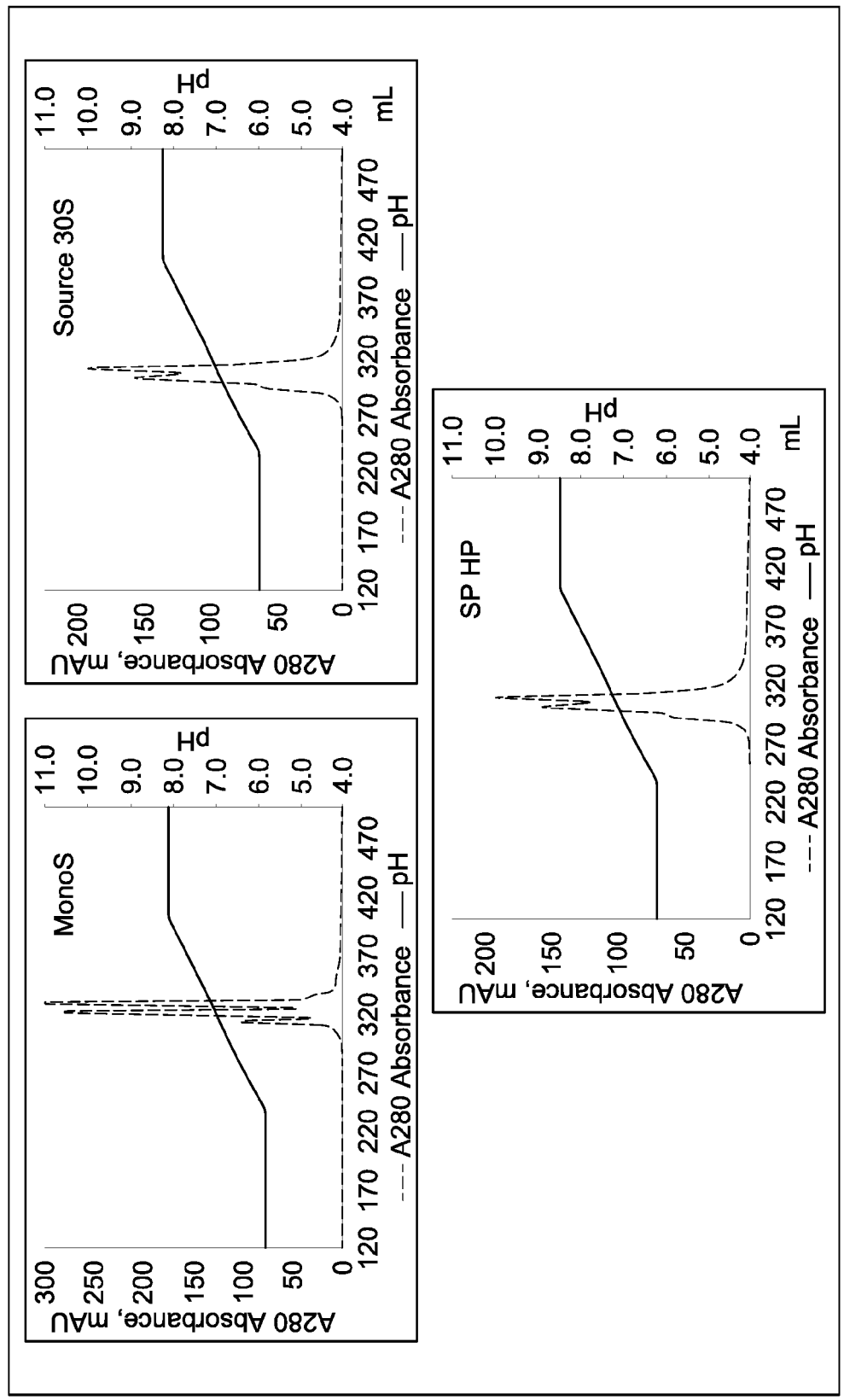
Figure 15B:
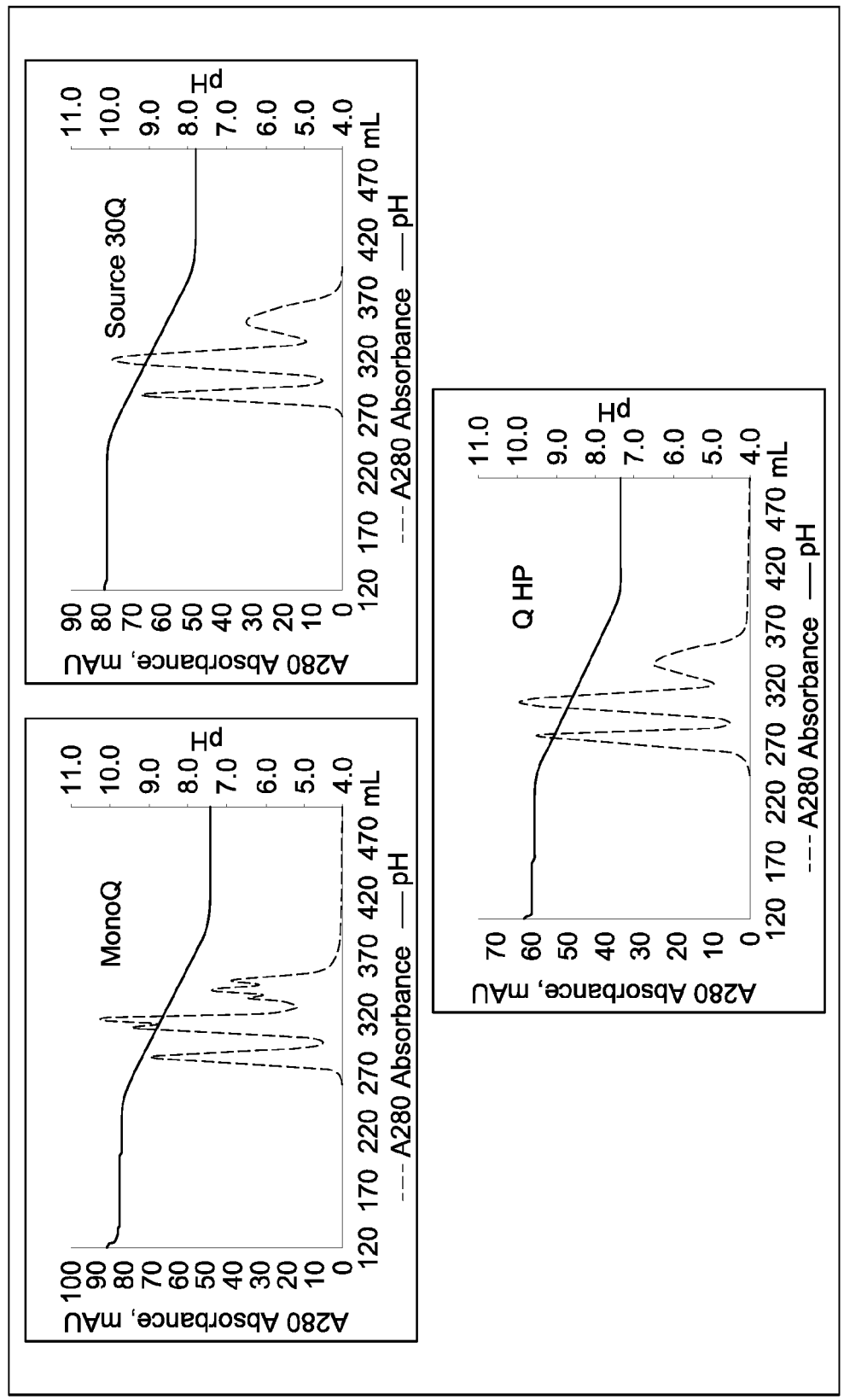
Figure 16A:
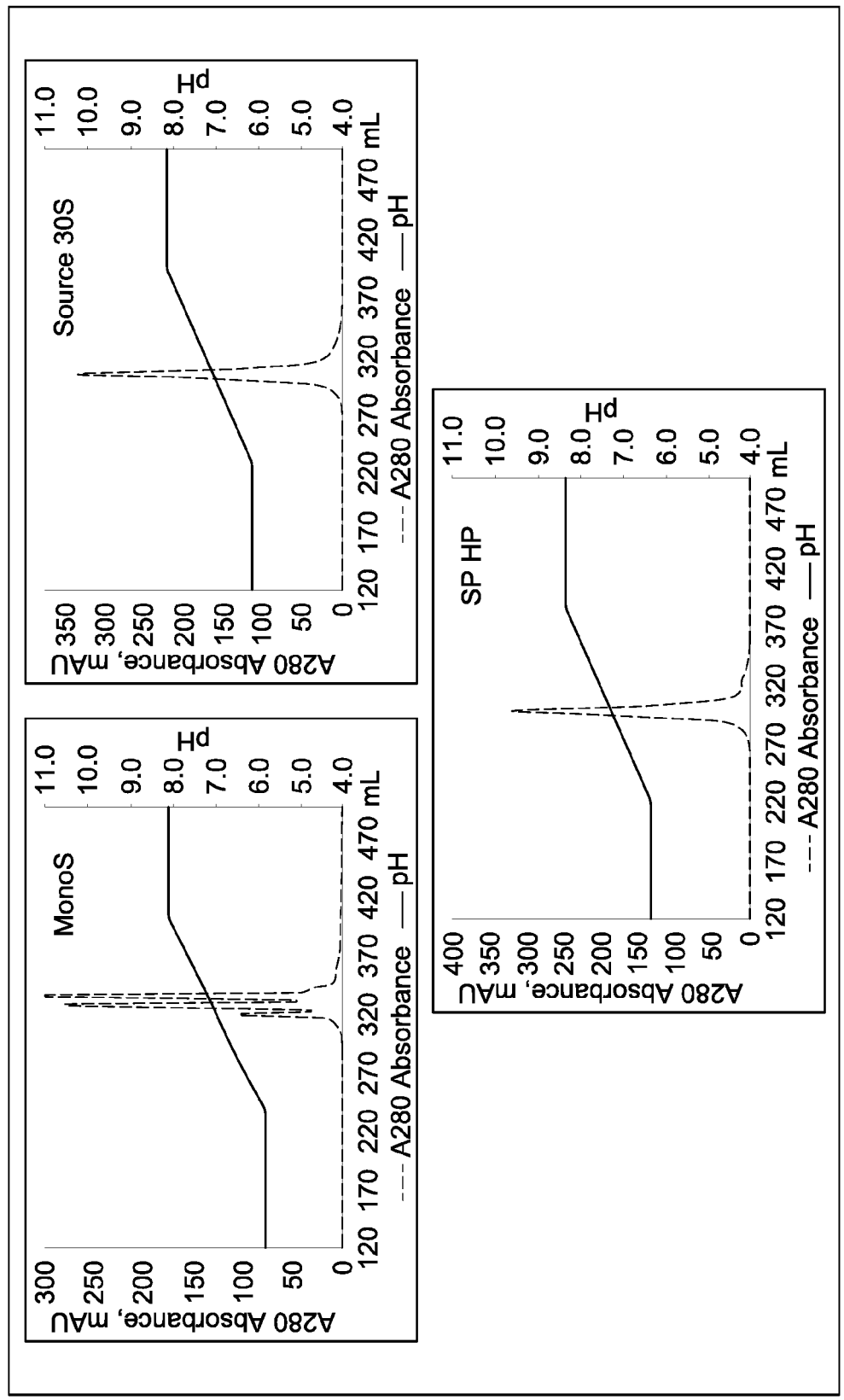
Figure 16B:
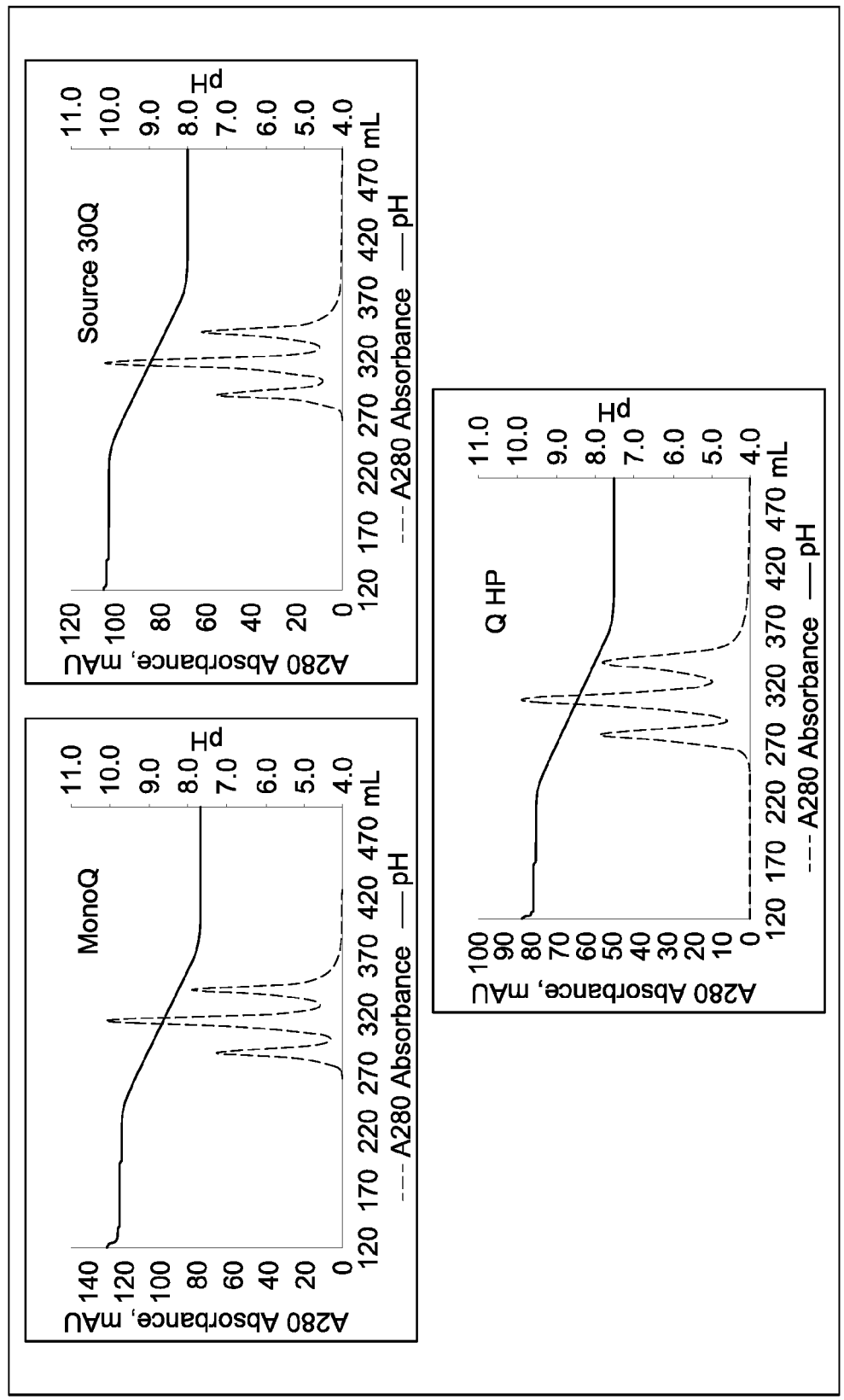
Figure 17A:
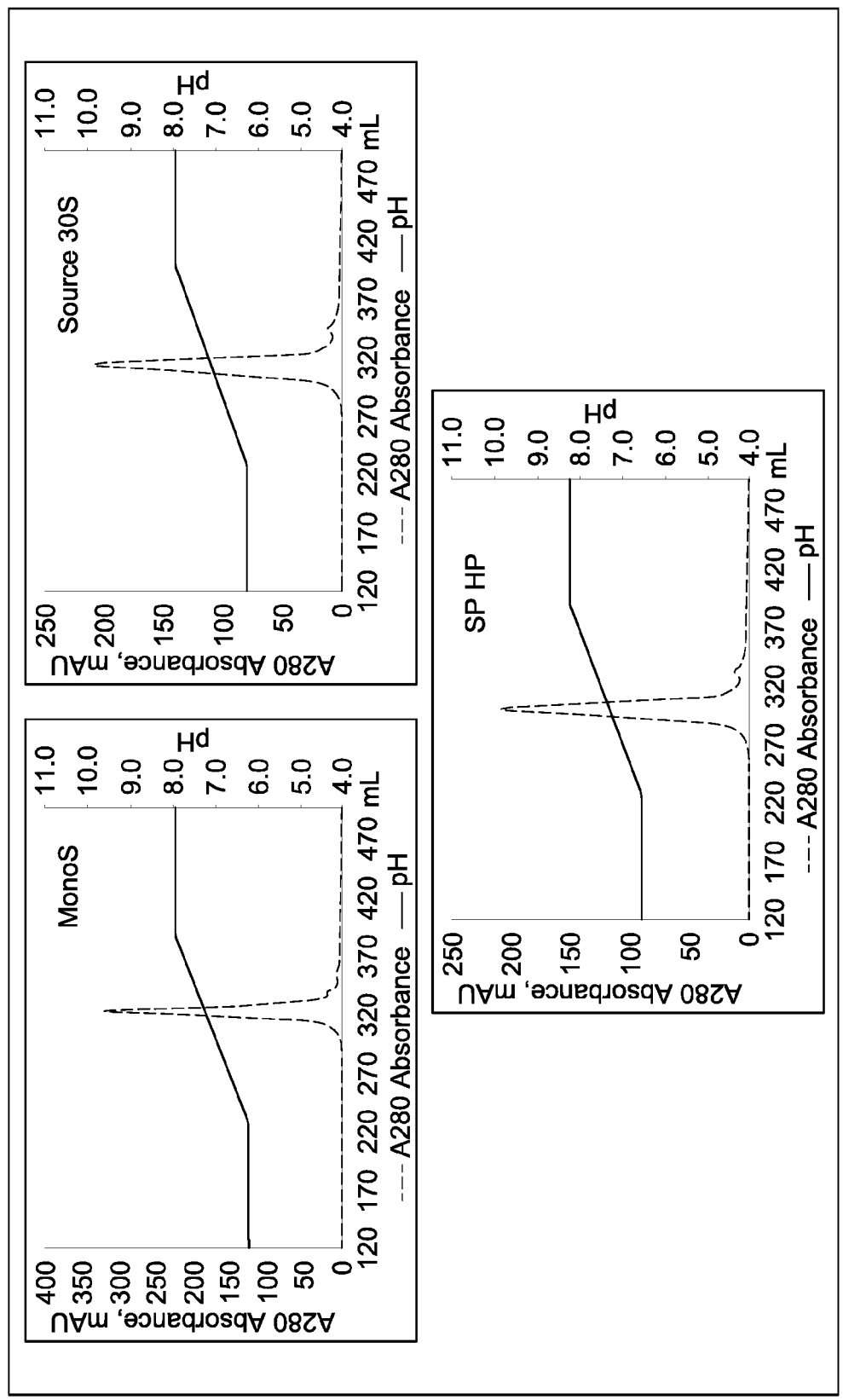
Figure 17B:
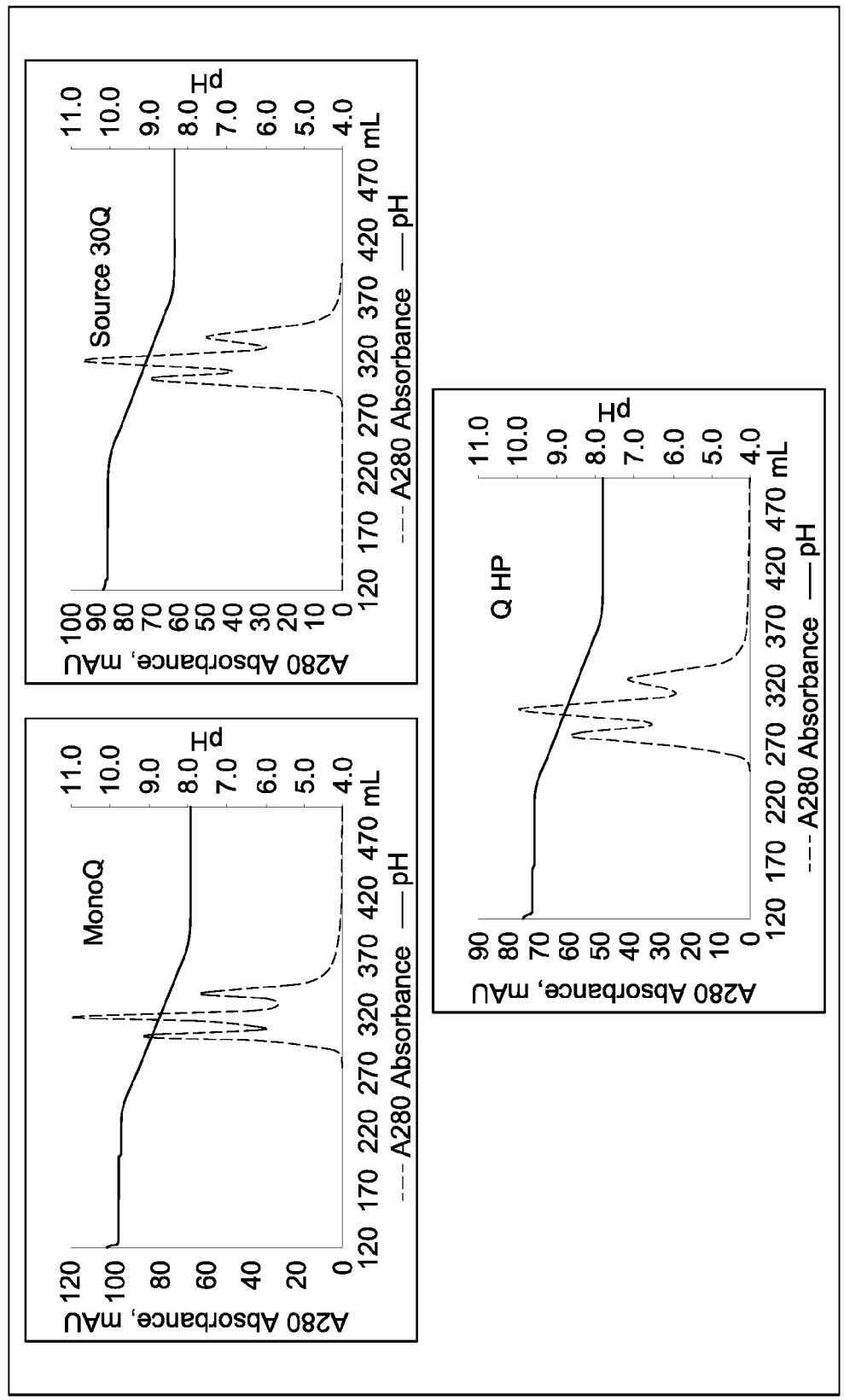

Thus, for the second phase of experiments, shallower gradients were used with large columns (8 mL) and tested for their ability to separate MAIs from compositions in which the difference in calculated pI of the parental homodimeric antibody species was 0.26, 0.11, and 0.10 pH unit, respectively. As depicted in FIGS. 15A and 15B, the cation resins and anion resins, respectively, were tested in large columns (8 mL) with the depicted shallower gradients, for their ability to separate MAIs from compositions containing the 0.26 pH unit pI difference between parental homodimeric antibody species. As depicted in FIGS. 16A and 16B, the cation resins and anion resins, respectively, were tested in large columns (8 mL) with the depicted shallower gradients, for their ability to separate MAIs from compositions containing the 0.11 pH unit pI difference between parental homodimeric antibody species. As depicted in FIGS. 17A and 17B, the cation resins and anion resins, respectively, were tested in large columns (8 mL) with the depicted shallower gradients, for their ability to separate MAIs from compositions containing the 0.1 pH unit pI difference between parental homodimeric antibody species.

The results demonstrate that both sets of the best-performing cation and anion resins separate most of the compositions to adequate to exceptional degrees, with better separations occurring with greater parental homodimeric antibody species pI differences. Generally, the anion exchange resins achieved MAI separation that was better than that achieved by the cation resins.

Example 10

Figure 18A:
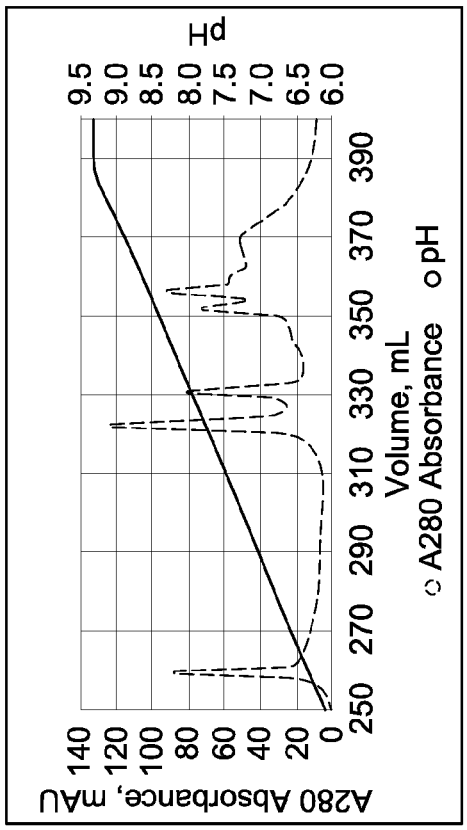
FIGS. 18A through 18D provide schematic representations of independent cation exchange chromatography experiments as described in Example 10. A280=absorbance units measured at a wavelength of 280 nm; ΔpI=difference in calculated isoelectric point between the two different heavy chains; run duration=elution volume in milliliters (mL). All antibodies (MAI and parental homodimeric antibody species) were in the native IgG4 format.
Figure 18B:
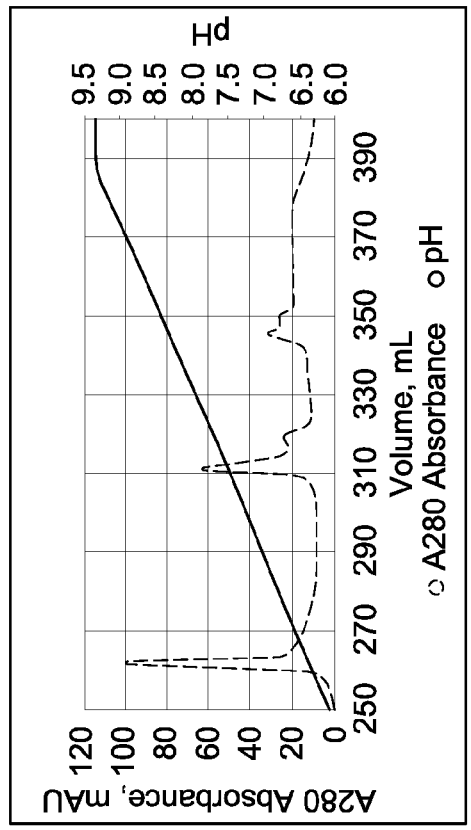
Figure 18C:
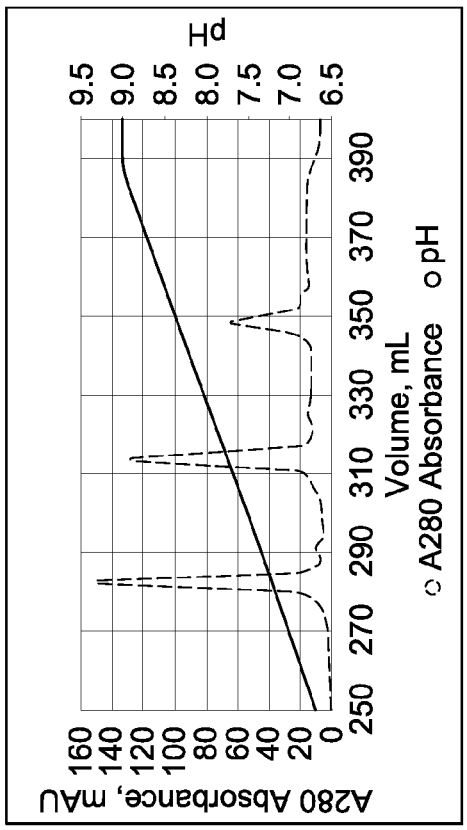
Figure 18D:
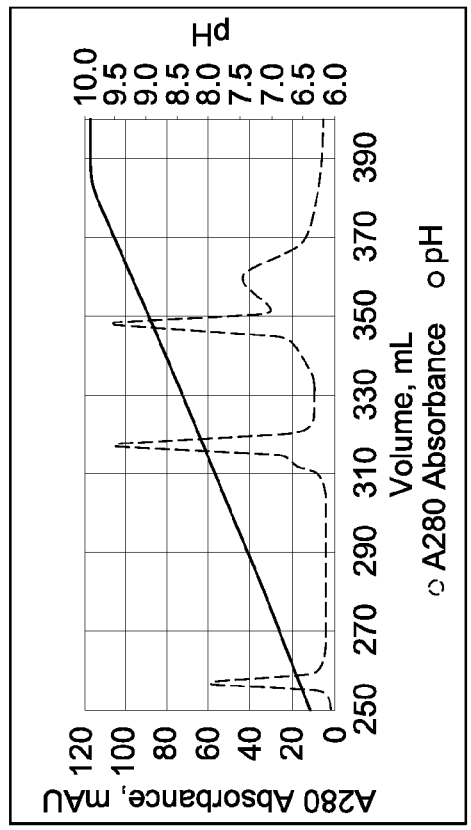

Linear pH gradient separation of mixtures of common-light-chain IgG4 bispecific heterodimer and parental homodimeric antibody species (formats as described in Scheme B of Compositions and Formats tested in the Examples, above) with varying theoretical differences in heavy chain pI using a strong cation exchanger Mono S 10/100 GL column and a linear pH gradient with starting buffer A: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH4.0 and final buffer: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH11.0. Flow rate 4 ml/min. FIG. 18A: common-light-chain bispecific homodimers and heterodimer with calculated theoretical differences in heavy chain pI of 1.68 (calculated theoretical pI HC1=7.05; calculated theoretical pI HC2=8.73) were purified using a 15 column volume step gradient of 32% B, followed by a 20 column volume linear gradient from 32% B to 71% B, followed by a 15 column volume hold of 71% B. FIG. 18B: common-light-chain bispecific homodimers and heterodimer with calculated theoretical differences in heavy chain pI of 1.99 (calculated theoretical pI HC1=6.74; calculated theoretical pI HC2=8.73) were purified using a 15 column volume step gradient of 22% B, followed by a 20 column volume linear gradient from 22% B to 75% B, followed by a 15 column volume hold of 75% B. FIG. 18C: common-light-chain bispecific homodimers and heterodimer with calculated theoretical differences in heavy chain pI of 1.77 (calculated theoretical pI HC1=7.27; calculated theoretical pI HC2=9.04) were purified using a 15 column volume step gradient of 25% B, followed by a 20 column volume linear gradient from 25% B to 83% B, followed by a 15 column volume hold of 83% B. FIG. 18D: common-light-chain bispecific homodimers and heterodimer with calculated theoretical differences in heavy chain pI of 1.94 (calculated theoretical pI HC1=6.74; calculated theoretical pI HC2=8.68) were purified using a 15 column volume step gradient of 21% B, followed by a 20 column volume linear gradient from 21% B to 75% B, followed by a 15 column volume hold of 75% B.

The results demonstrate that MAIs of the IgG4 isotype format were readily purified from parental homodimeric IgG4 isotype species at all pI differences tested.

Example 11

Figure 19A:
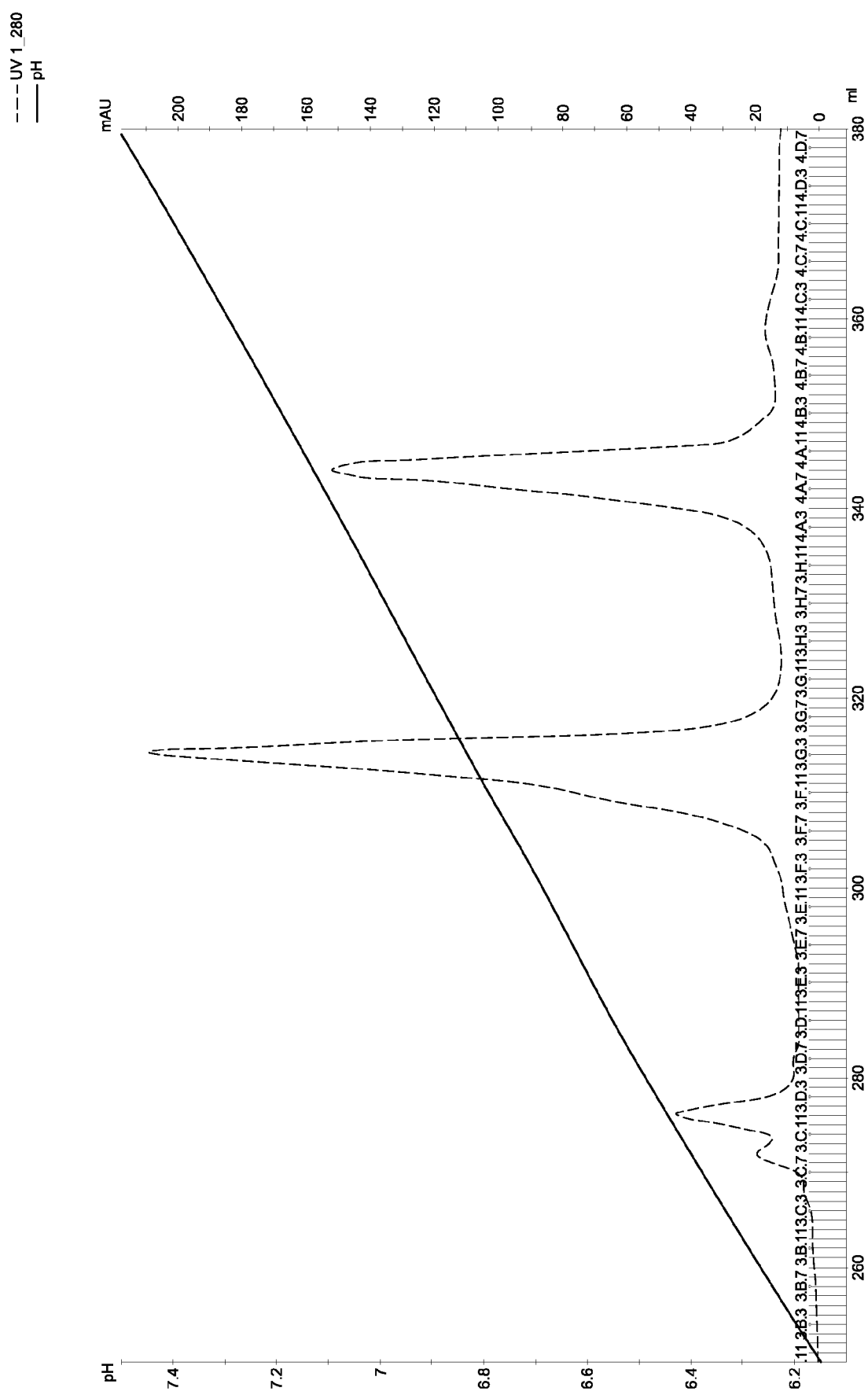
FIGS. 19A and 19B schematic representations of independent cation exchange chromatography experiments as described in Example 11. A280=absorbance units measured at a wavelength of 280 nm; ΔpI=difference in calculated isoelectric point between the two different heavy chains; run duration=elution volume in milliliters (mL). The MAI was in the hybrid native IgG1/native IgG4 format, the first parental homodimeric antibody species was in the native IgG1 format and the second parental homodimeric antibody species was in the native IgG4 format.
Figure 19B:
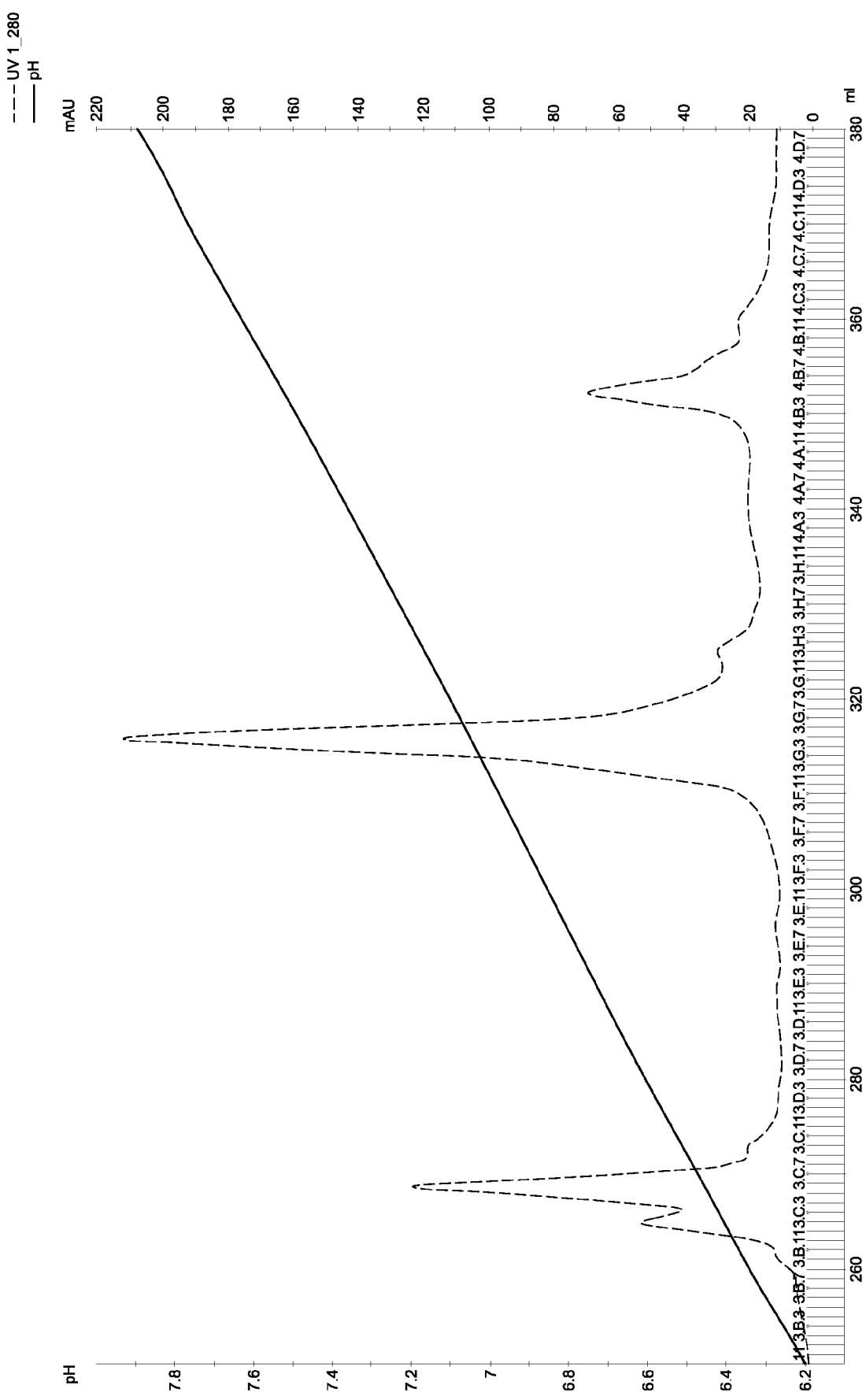

Linear pH gradient separation of mixtures of common-light-chain bispecific IgG1/IgG4 hybrid heterodimer, and IgG1 and IgG4 homodimeric antibody species (formats as described in Scheme C of Compositions and Formats tested in the Examples, above) with varying theoretical differences in heavy chain pI using a strong cation exchanger Mono S 10/100 GL column and a linear pH gradient with starting buffer A: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH4.0 and final buffer: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl. pH11.0. Flow rate 4 ml/min. FIG. 19A: common-light-chain bispecific IgG1 and IgG4 homodimers and IgG1/IgG4 heterodimer with calculated theoretical differences in heavy chain pI of 2.2 (calculated theoretical pI HC1 (IgG4)=7.05; calculated theoretical pI HC2 (IgG1)=9.22) were purified using a 15 column volume step gradient of 24.5% B, followed by a 20 column volume linear gradient from 24.5% B to 51% B, followed by a 15 column volume hold of 51% B. FIG. 19B: common-light-chain bispecific IgG1 and IgG4 homodimers and IgG1/IgG4 heterodimer with calculated theoretical differences in heavy chain pI of 2.4 (calculated theoretical pI HC1 (IgG4)=7.05; calculated theoretical pI HC2 (IgG1)=9.46) were purified using a 15 column volume step gradient of 24.5% B, followed by a 20 column volume linear gradient from 24.5% B to 58% B, followed by a 15 column volume hold of 58% B. The large difference in pI between IgG1 and IgG4 backbones leads to excellent separation of the IgG1 and IgG4 homodimers from the heterodimer.

The results demonstrate that MAIs of the hybrid IgG1/IgG4 isotype format were readily purified from parental homodimeric IgG4 isotype species at all pI differences tested.

Example 12

Figure 20A:
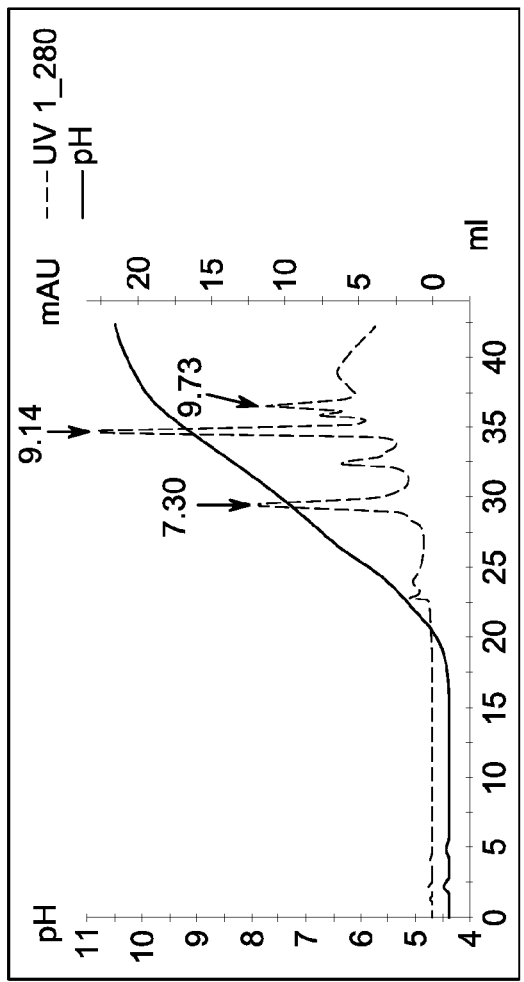
FIGS. 20A and 20B, 21A and 21B, and 22A and 22B depict the results of the experiments described in Example 13.
Figure 20B:
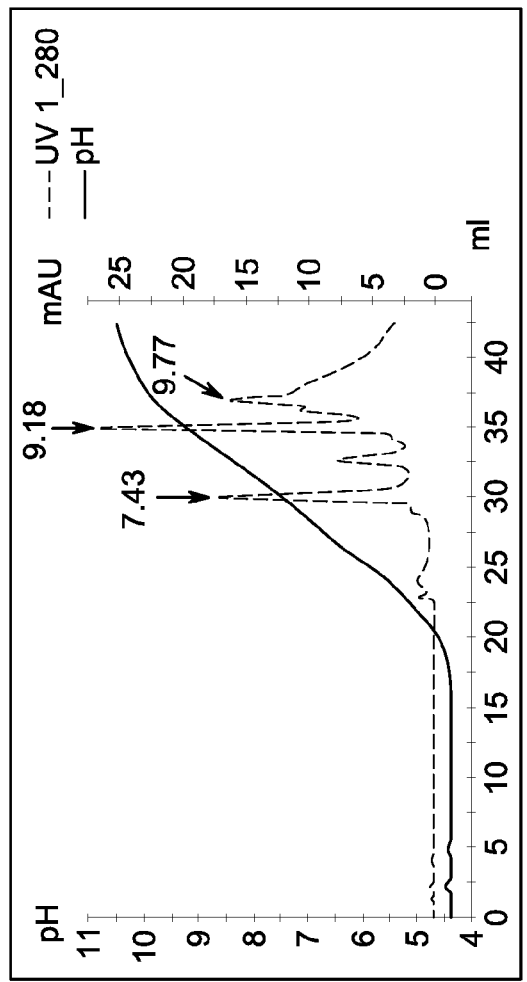

In certain instances, very broad elution profiles had been observed, as illustrated in FIGS. 20A and 20B, which depict the elution profiles of each of two different mixtures of parental homodimeric species and the corresponding MAI (formats as described in Scheme D of Compositions and Formats tested in the Examples, above). The gradients and eluant compositions were as described in Examples 1 through 9. In the experiment depicted in FIG. 20A, two different IgG4 homodimers (homodimeric parental species) with calculated theoretical differences in full IgG pI of 1.81 (calculated theoretical pI of IgG4 homodimeric parental species A=7.41; calculated theoretical pI of IgG4 homodimeric parental species B=9.22) and the corresponding MAI with a calculated whole IgG4 pI of 8.87, were subjected to cation exchange chromatography using a strong cation exchanger Mono S 5/50 GL column and a linear pH gradient with starting buffer A: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH4.0 and final buffer: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH11.0. The observed pH at which each various species in the first mixture eluted as in FIG. 20A was 7.30 (homodimeric parental species A), 9.73 (homodimeric parental species B), and 9.14 (the MAI (heterodimeric parental species)). FIG. 20B depicts the results of a similar experiment using different IgG4 homodimeric parental species A and B (but which, coincidentally, had the same calculated theoretical pIs as calculated for the parental species depicted in FIG. 20A). The MAI depicted in FIG. 20B had a calculated pI=8.76. The observed pH at which each various species in the first mixture eluted as in FIG. 20B was 7.43 (homodimeric parental species A), 9.77 (homodimeric parental species B), and 9.18 (the MAI (heterodimeric parental species)).

As in the previous Examples, all samples and columns used in the studies depicted in FIGS. 20A and 20B were prepared and equilibrated at pH 4. It was thus desirable to determine if certain modified elution conditions and components might better resolve or separate species in mixtures for which such broad elution profiles are observed or anticipated based on the nature of the species in a given mixture.

Accordingly, experiments were undertaken using the same homodimeric parental species and MAIs used to generate the data depicted in FIGS. 20A and 20B, except that a step pH gradient phase was included in the elution portion, in which the pH of the eluant was increased from about pH 4 to about pH 6.5 within a very small eluant volume (i.e., within very few elution fraction). Additionally, the sample mixture containing both homodimeric parental species and the heterodimeric MAI (formats as described in Scheme D of Compositions and Formats tested in the Examples, above) was prepared and equilibrated on the column at pH 6 prior to generating the step gradient, which eluted the lowest pI homodimeric species. This then allowed for the resolving and separation of the remaining MAI from the second homodimeric species by using a shallow linear gradient phase (from pH 7.8 through pH 9.65 as in FIG. 21A, and from pH 7.94 through pH 9.68 as in FIG. 21B).

Figure 21A:
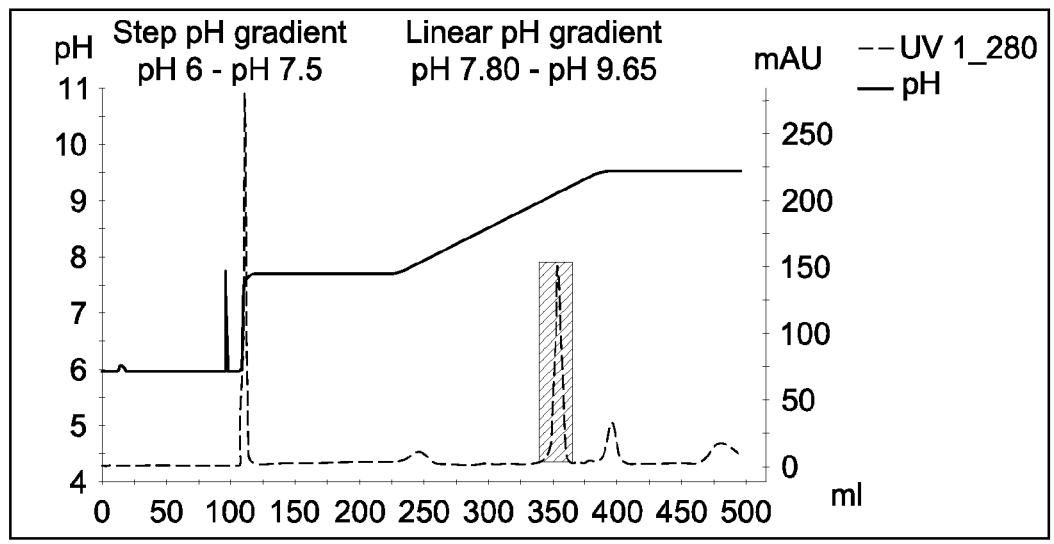
Figure 21B:
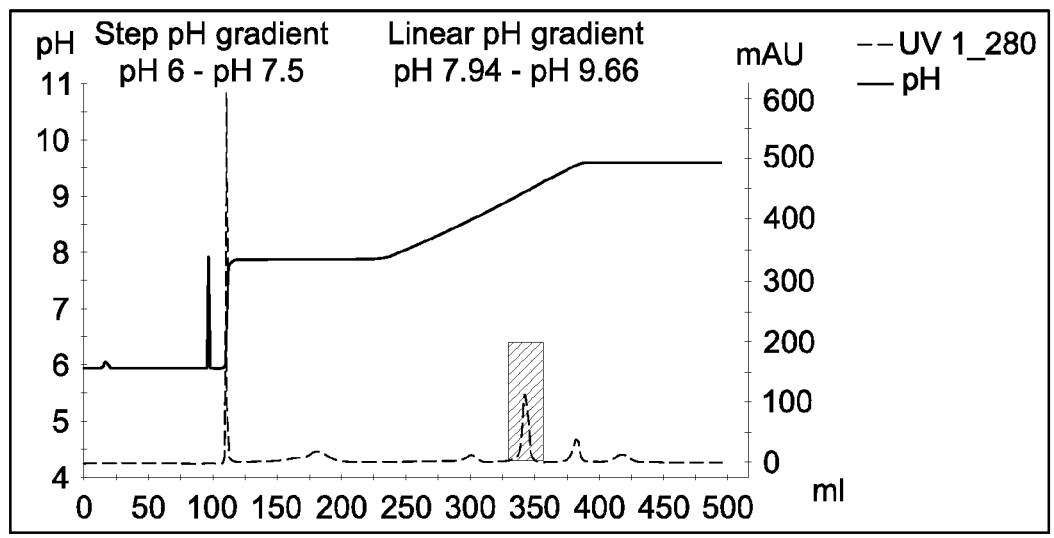
Figure 22A:
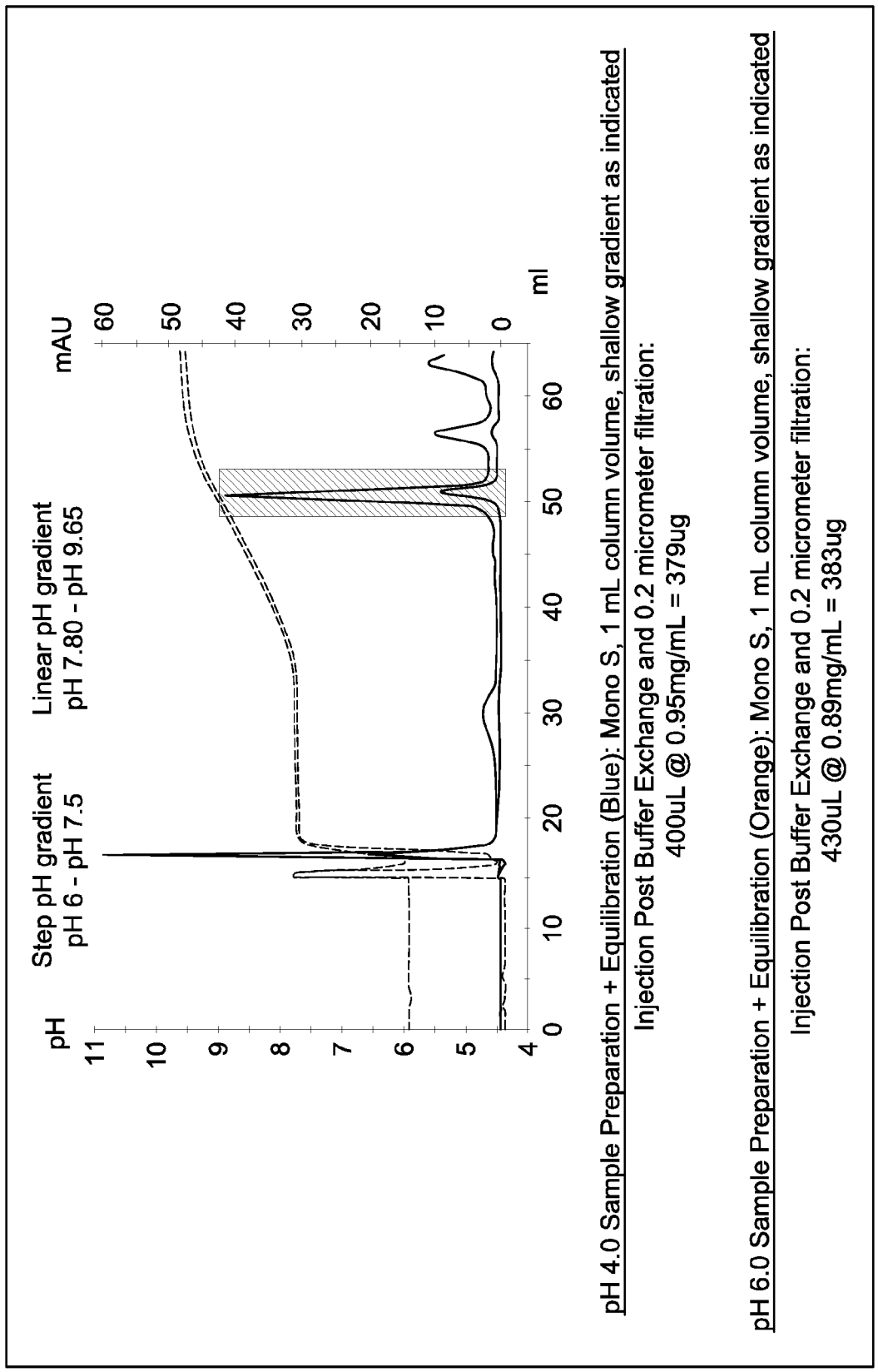
Figure 22B:
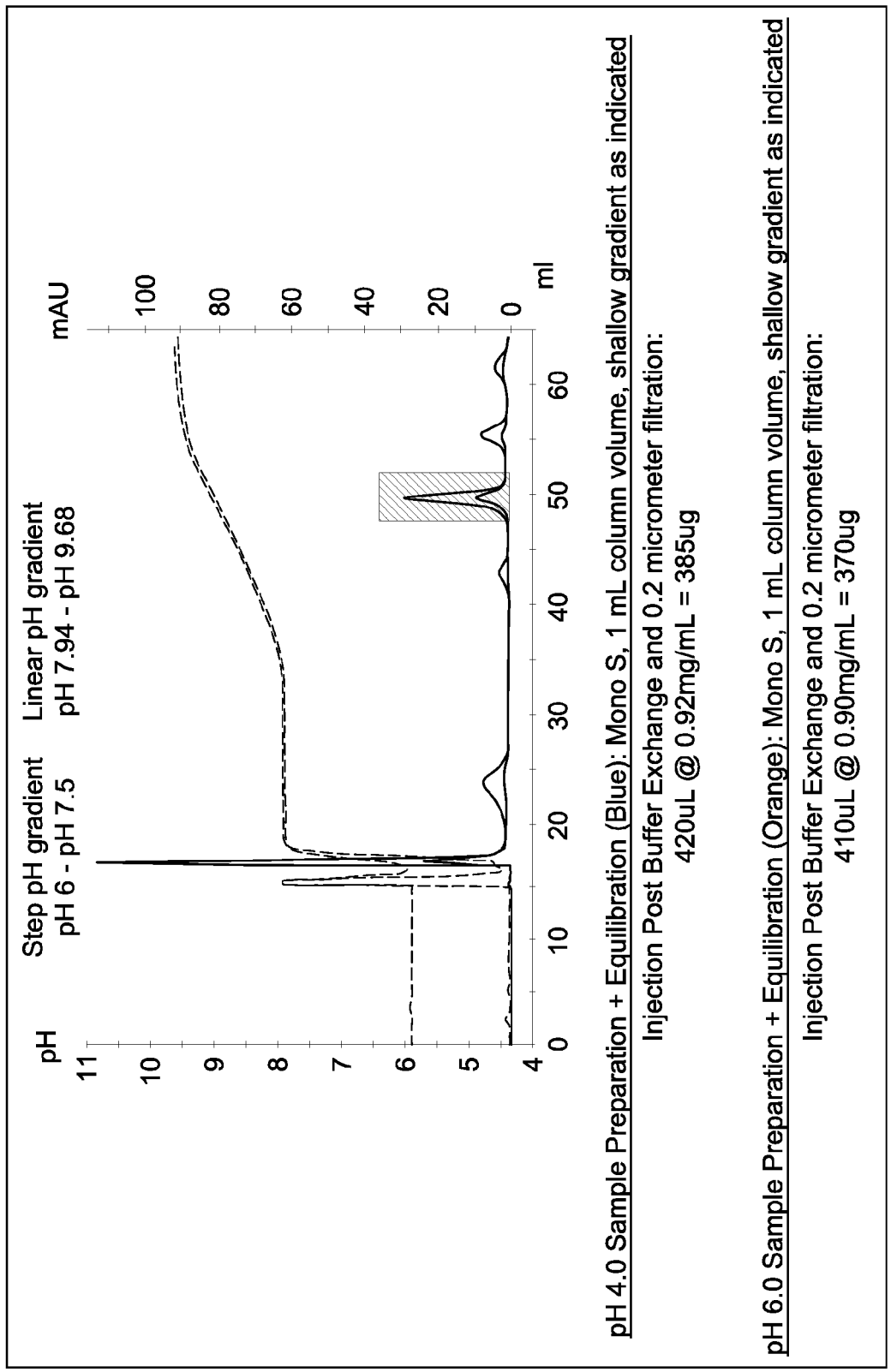

As depicted in FIGS. 22A and 22B the same two sample mixtures used to generate the data in FIG. 21A and FIG. 21B were employed in two similar dual phase (i.e., step pH gradient then linear pH gradient schemes) elution experiments; one beginning at pH 4, the other beginning at pH 6. The results, depicted in FIGS. 22A and 22B, demonstrate that elutions which begin at milder pH (e.g., pH 6 versus pH 4), resolution, separation, and elution of the MAIs from their respective corresponding homodimeric parental species is enhanced relative to elutions beginning at more extreme pH (i.e., beginning at pH 4 versus pH 6).

Example 13

It was desirable to next determine if employing milder beginning pHs of sample mixtures (e.g., pH 6 versus lower pH's) and shallow linear pH gradients (i.e., gradients applied over relatively large eluant volumes (large numbers of fractions/fraction volumes), would result in the resolution and separation of MAIs from corresponding homodimeric parental species that have calculated and/or experimental pIs that are very close in value to one another.

Figure 23:
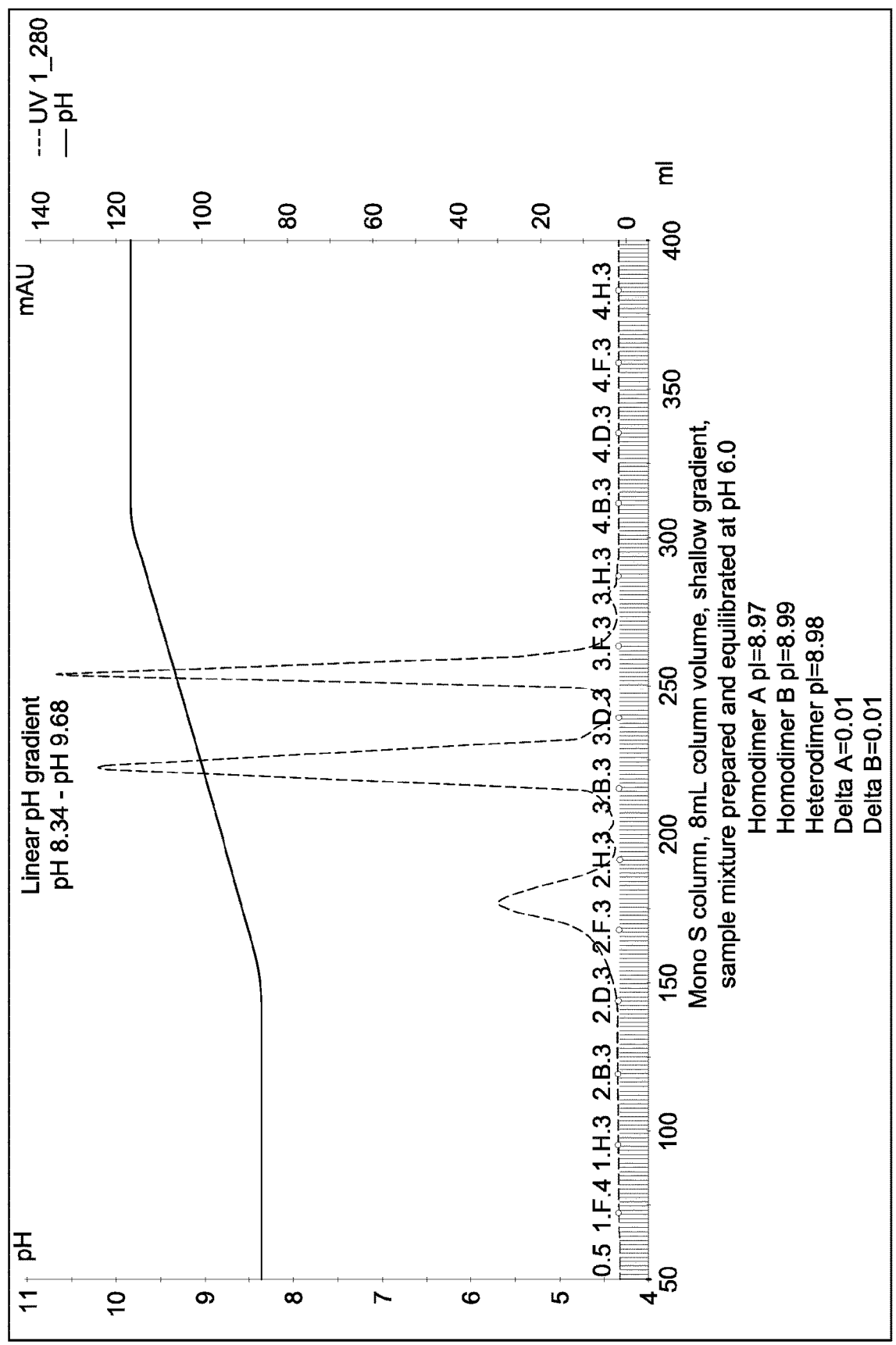
FIG. 23 depicts the results of the experiments described in Example 13.

Accordingly, a sample mixture containing both homodimeric parental species and the heterodimeric MAI (formats as described in Scheme D of Compositions and Formats tested in the Examples, above), wherein calculated theoretical whole IgG4 pI of each homodimeric parental species was 8.97 and 8.99, respectively, and the calculated theoretical whole IgG4 pI of the MAI was 8.98, were prepared and the column equilibrated at pH 6.0, and then subjected to cation exchange chromatography using a strong cation exchanger Mono S 10/100 GL column and a linear pH gradient with starting buffer A: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH8.34 and final buffer: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH9.86. The observed pH at which each various species in the first mixture eluted as in FIG. 20A was 7.30 (homodimeric parental species A), 9.73 (homodimeric parental species B), and 9.14 (the MAI (heterodimeric parental species was subjected to the elution conditions depicted in FIG. 23.

The results indicate that an MAI with a pI as little as 0.01 pH units different from each corresponding parental homodimeric species can be resolved and separated from both such homodimeric parental species using the disclosed methods.

Example 14

Figure 24:
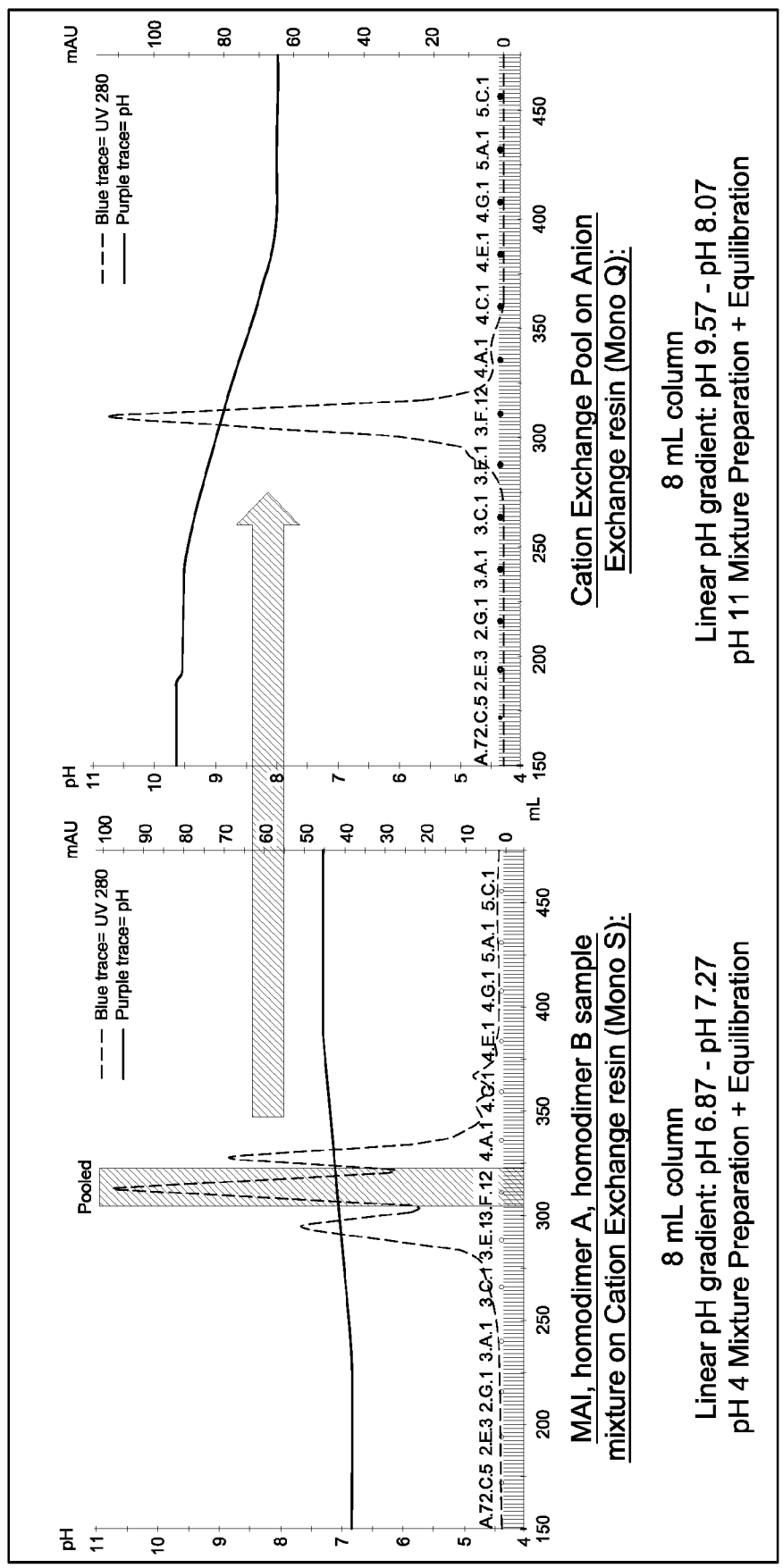
FIG. 24 depicts the results of the experiments described in Example 14.

It had been observed that, for certain sample mixtures, neither cation exchange nor anion exchange, alone, was sufficient to separate certain MAIs from their homodimeric parental species to satisfactory purity. It was then desirable to assess whether the resolution and purification of such MAIs could be improved to satisfaction by subjecting a set of pooled fractions corresponding to the MAI-eluting peak of a cation exchange procedure to a subsequent anion exchange procedure, each procedure as described above in Examples 1-9 and as indicated in FIG. 24.

More specifically, two different 10 milligram sample aliquots of an MAI/homodimeric parental species mixture of the format as described in Scheme A of Compositions and Formats tested in the Examples, above, were injected into the cation exchange column in order to generate sufficient eluate for the subsequence anion exchange procedure. The calculated theoretical whole IgG pI of each homodimeric parental species was 9.19 and 9.09, respectively, and the calculated theoretical whole IgG1 pI of the MAI was 9.09. The sample mixture was prepared and the column equilibrated at pH 6.0, and then subjected to cation exchange chromatography using a strong cation exchanger Mono S 10/100 GL column and a linear pH gradient with starting buffer A: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH 6.87 and final buffer: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH 7.27. The pools containing the presumptive heterodimer (MAI)-containing middle peak as depicted in the left portion of FIG. 24 were collected, pooled, and then injected into the anion exchange column and eluted using a linear pH gradient with starting buffer A: 9.8 mM methylamine, 9.1 mM 1,2-ethanediamine, 6.4 mM 1-methylpiperazine, 13.7 mM 1,4-dimethylpiperazine, 5.8 mM bis-tris, 7.7 mM hydroxylamine, and 10 mM sodium chloride at pH=9.57; and final buffer B: 9.8 mM methylamine, 9.1 mM 1,2-ethanediamine, 6.4 mM 1-methylpiperazine, 13.7 mM 1,4-dimethylpiperazine, 5.8 mM bis-tris, 7.7 mM hydroxylamine, and 10 mM sodium chloride at pH=8.07. Mass spectroscopy analysis of a specimen of the presumptive MAI-containing pool from the initial cation exchange procedure revealed that the peak contained significant amounts of one of the homodimeric parental species. Mass spectroscopy analysis of the presumptive MAI-containing peak that eluted from the subsequent anion exchange column revealed that the pooled fractions corresponding to this peak were contained the MAI and were essentially devoid of either homodimeric parental species.

The results demonstrate that, for certain mixtures, using both cation exchange and anion exchange sequentially can enhance resolution and separation of MAIs from their corresponding homodimeric parental species.

Example 15

It was next desirable to determine whether, for certain MAI and corresponding homodimeric parental species mixtures, it might be advantageous to employ different buffer systems or eluants, which are designed more specifically for use with anion exchange resins.

Figure 25A:
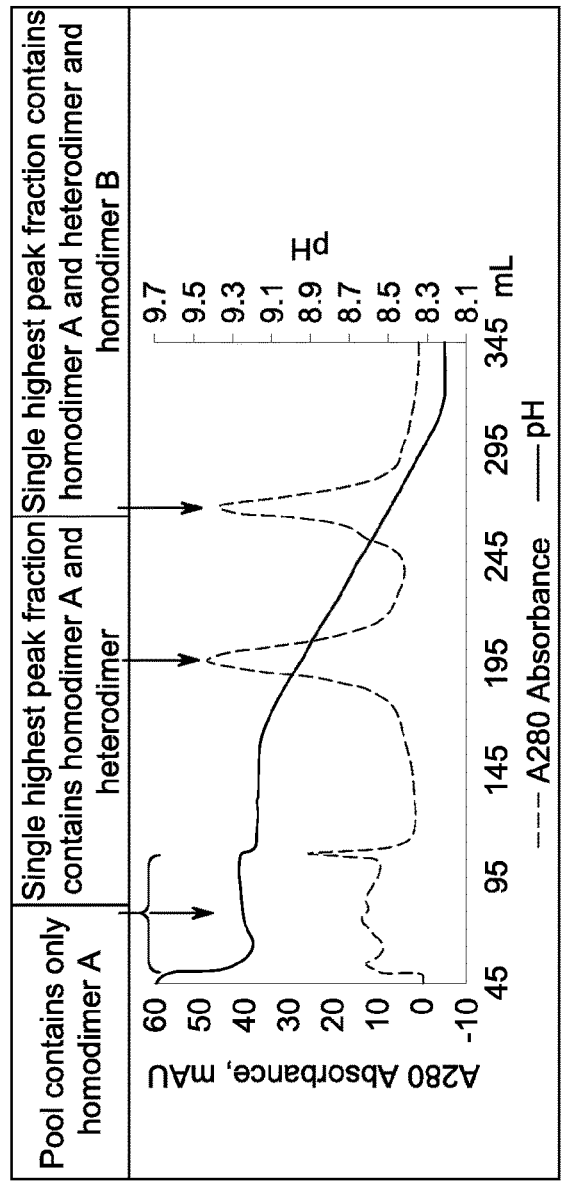
FIGS. 25A and 25B depict the results of the experiments described in Example 15.
Figure 25B:
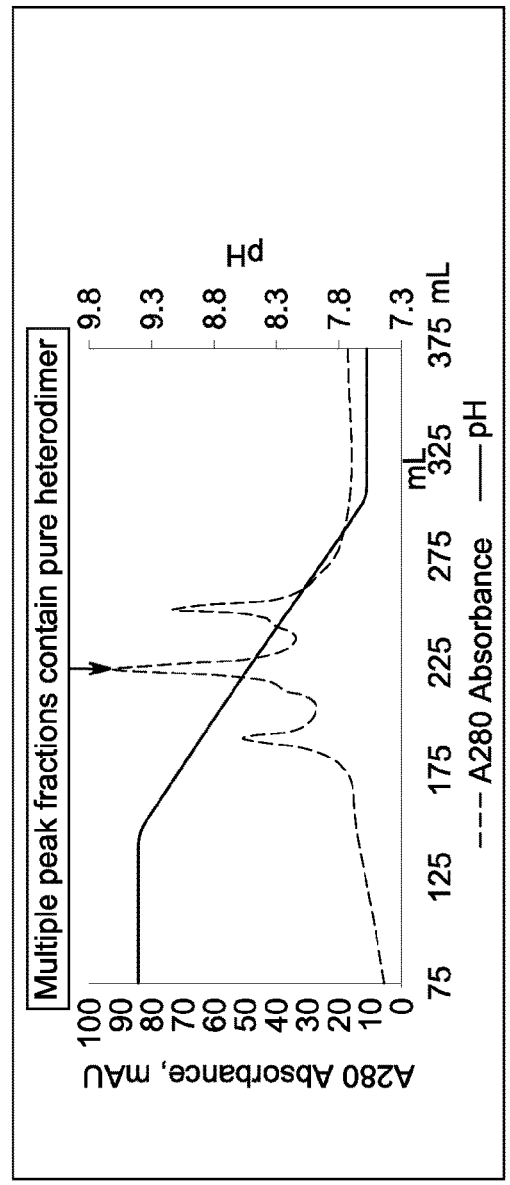

Accordingly, an experiment was designed in which an MAI/homodimeric parental species mixture of the format as described in Scheme A of Compositions and Formats tested in the Examples, above, was subjected to anion exchange chromatography using the following cation exchange buffer system: starting buffer A: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH 9.20 and final buffer B: 15.6 mM CAPS, 9.4 mM CHES, 4.6 mM TAPS, 9.9 mM HEPPSO, 8.7 mM MOPSO, 11 mM MES, 13 mM acetic acid, 9.9 mM formic acid, 10 mM NaCl, pH 8.20, under conditions as indicated in FIG. 25A. All three of the peaks illustrated in FIG. 25A were analyzed by mass spectroscopy to determine peak composition, which was observed to be as indicated in FIG. 25A. A separate aliquot of the same MAI/homodimeric parental species mixture was then subjected to anion exchange chromatography using the following anion exchange buffer system: starting buffer A: 9.8 mM methylamine, 9.1 mM 1,2-ethanediamine, 6.4 mM 1-methylpiperazine, 13.7 mM 1,4-dimethylpiperazine, 5.8 mM bis-tris, 7.7 mM hydroxylamine, and 10 mM sodium chloride at pH=9.34; and final buffer B: 9.8 mM methylamine, 9.1 mM 1,2-ethanediamine, 6.4 mM 1-methylpiperazine, 13.7 mM 1,4-dimethylpiperazine, 5.8 mM bis-tris, 7.7 mM hydroxylamine, and 10 mM sodium chloride at pH=7.53 under conditions as indicated in FIG. 25B. All three of the peaks illustrated in FIG. 25B were analyzed by mass spectroscopy to determine peak composition, which was observed to be as indicated in FIG. 25B.

The results indicate that, for certain MAI/homodimeric parental species mixtures, using anion exchange buffer systems or eluants when employing anion exchange chromatographic procedures may resolve and separate MAIs from the homodimeric parental species to levels of purity that markedly improved relative to that observed when using cation exchange buffer systems or eluants when employing anion exchange chromatographic procedures.

Other chromatographic materials that may be employed with similar results to that demonstrated in the Examples above are provided in FIG. 26A and FIG. 26B.

Whereas particular embodiments of the invention have been described above for purposes of illustration, it will be appreciated by those skilled in the art that numerous variations of the details may be made without departing from the invention as described in the appended claims.

What is claimed is:

1. A method of purifying a multi specific antibody of interest (MAI), wherein the MAI comprises a heterodimer comprising a first heavy chain polypeptide comprising a first heavy chain variable region and a second heavy chain polypeptide comprising a second heavy chain variable region, wherein the first and the second variable regions have different antigen specificities and different isoelectric points, the method comprising:

i) obtaining a composition comprising the MAI, a first parental homodimeric antibody species comprising either at least one copy of the first heavy chain polypeptide or at least two copies of the first heavy chain polypeptide, and a second parental homodimeric antibody species comprising either at least one copy of the second heavy chain polypeptide or at least two copies of the second heavy chain polypeptide; and ii) performing ion exchange chromatography whereby the MAI is separated from the first and the second parental homodimeric antibody species, wherein the performing step ii) comprises:

a. contacting the composition with an ion exchange chromatographic material forming a composition-ion exchange chromatographic material complex, and preparing or equilibrating either:

ai. the composition; or
      aii. the composition-ion exchange chromatographic material complex;
   in a first sample of an eluant at a desired starting pH prior to performing the elution, and b. performing an elution step wherein the ion exchange chromatographic material-composition complex is contacted with a sample of eluant, wherein the eluant comprises at least two buffering agents that each have a different negative log acid dissociation constant (pKa), which agents are selected from either:
      bi. CAPS, CHES, TAPS, HEPPSO, MOPSO, MES, acetic acid, formic acid and at least one salt; or
      bii. methylamine, 1,2-ethanediamine, 1-methylpiperazine, 1,4-dimethylpiperazine, 2-[Bis(2-hydroxyethyl)amino]-2-(hydroxymethyl)propane-1,3-diol (bis-tris), hydroxylamine, and at least one salt; and c. flowing a volume of a second sample of the eluant that is prepared at a desired ending pH through the ion exchange chromatographic material-composition complex;
   wherein the MAI, the first parental homodimeric antibody species, and the second parental homodimeric antibody species elute from the ion exchange chromatographic material in distinguishable elution volumes, allowing for the purification of the MAI;

and further wherein the method provides for the purification and separation of said MAI from the first and second parental homodimeric antibody species when the difference in the isoelectric point between the first and the second variable regions is less than 0.5 pH units.

2. The method according to claim 1, wherein a pH gradient is generated as the eluant flows through the ion exchange chromatographic material-composition complex.

3. The method according to claim 1, with the proviso that the eluant does not include any of the following: imidazole, piperazine, or tris(hydroxymethyl)aminomethane (TRIS).

4. The method according to claim 1, wherein the eluant comprises at least one salt selected from the group consisting of NaCl, KCl, and $Na_2SO_4$.

5. The method according to claim 1, wherein the different isoelectric points are actual isoelectric points or calculated isoelectric points and either:
   a. the difference in the actual isoelectric point of the first heavy chain polypeptide and the actual isoelectric point of the second heavy chain polypeptide is less than 0.50 pH unit, less than 0.45 pH unit; less than 0.40 pH unit; less than 0.35 pH unit; less than 0.30 pH unit; less than 0.25 pH unit; less than 0.20 pH unit; less than 0.15 pH unit; less than 0.14 pH unit; less than 0.13 pH unit; less than 0.12 pH unit; less than 0.11 pH unit; less than 0.10 pH unit; less than 0.09 pH unit; less than 0.08 pH unit; less than 0.07 pH unit; less than 0.06 pH unit; less than 0.04 pH unit; less than 0.03 pH unit; less than 0.025 pH unit; less than 0.02 pH unit; or pH values that are between any of the preceding values;
   b. the difference in the actual isoelectric point of the first parental homodimeric antibody species and the actual isoelectric point of the second parental homodimeric antibody species is less than 0.50 pH unit; less than 0.45 pH unit; less than 0.40 pH unit; less than 0.35 pH unit; less than 0.30 pH unit; less than 0.25 pH unit; less than 0.20 pH unit; less than 0.15 pH unit; less than 0.14 pH unit; less than 0.13 pH unit; less than 0.12 pH unit; less than 0.11 pH unit; less than 0.10 pH unit; less than 0.09 pH unit; less than 0.08 pH unit; less than 0.07 pH unit; less than 0.06 pH unit; less than 0.04 pH unit; less than 0.03 pH unit; less than 0.025 pH unit; less than 0.02 pH unit; or pH values that are between any of the preceding values;
   c. the difference in the calculated isoelectric point of the first heavy chain polypeptide and the calculated isoelectric point of the second heavy chain polypeptide is less than 0.50 pH unit; less than 0.45 pH unit; less than 0.40 pH unit; less than 0.35 pH unit; less than 0.30 pH unit; less than 0.25 pH unit; less than 0.20 pH unit; less than 0.15 pH unit; less than 0.14 pH unit; less than 0.13 pH unit; less than 0.12 pH unit; less than 0.11 pH unit; less than 0.10 pH unit; less than 0.09 pH unit; less than 0.08 pH unit; less than 0.07 pH unit; less than 0.06 pH unit; less than 0.04 pH unit; less than 0.03 pH unit; less than 0.025 pH unit; less than 0.02 pH unit; or pH values that are between any of the preceding values; or
   d. the difference in the calculated isoelectric point of the first parental homodimeric antibody species and the calculated isoelectric point of the second parental homodimeric antibody species is less than 0.50 pH unit; less than 0.45 pH unit; less than 0.40 pH unit; less than 0.35 pH unit; less than 0.30 pH unit; less than 0.25 pH unit; less than 0.20 pH unit; less than 0.15 pH unit; less than 0.14 pH unit; less than 0.13 pH unit; less than 0.12 pH unit; less than 0.11 pH unit; less than 0.10 pH unit; less than 0.09 pH unit; less than 0.08 pH unit; less than 0.07 pH unit; less than 0.06 pH unit; less than 0.04 pH unit; less than 0.03 pH unit; less than 0.025 pH unit; less than 0.02 pH unit; or pH values that are between any of the preceding values.

6. The method according to claim 1, wherein (i) the desired starting pH is less than 9.0; less than 8.5; less than 8.0; less than 7.5; less than 7.0; less than 6.5; less than 6.0; less than 5.5; less than 5.0; less than 4.5; less than 4.0; less than 3.5; or less than 3.0; or pH values that are between any of the preceding values; and/or (ii) the desired ending pH is more than 7.0; more than 7.5; more than 8.0; more than 8.5; more than 9.0; more than 9.5; more than 10.0; more than 10.5; more than 11.0; more than 11.5; more than 12.0; more than 12.5; more than 13.0; more than 13.5; or pH values that are between any of the preceding values.

7. The method according to claim 1, wherein the eluant comprises at least two buffering agents and wherein the acid dissociation constant (pKa) of each buffering agent is between about 3 and 11.

8. The method according to claim 1, wherein the MAI further comprises (i) a third polypeptide comprising a first light chain variable region; or (ii) a third polypeptide and a fourth polypeptide, each of which comprises a second light chain variable region.

9. The method according to claim 1, wherein the first heavy chain polypeptide and the second heavy chain polypeptide each further comprise an Fc region selected from:
   (i) a wild-type Fc region;
   (ii) an IgG1 isotype Fc region, an IgG2 isotype Fc region, an IgG3 isotype Fc region, or an IgG4 isotype Fc region; and/or
   (iii) an Fc region that has not been engineered in order to alter the isoelectric point of the first parental homodimeric antibody species, the second parental homodimeric antibody species, or the MAI.

10. The method according to claim 1, wherein:
   (i) the MAI is in a native antibody format; at least the first parental homodimeric antibody species is in a native format; at least the second parental homodimeric antibody species is in a native format; the first parental homodimeric antibody species is in a native format and the second parental homodimeric antibody species is in a native format; or the MAI is in a native antibody format, the first parental homodimeric antibody species is in a native format, and the second parental homodimeric antibody species is in a native format; and/or
   (ii) the MAI is in an IgG1 format, an IgG2 format, an IgG3 format, or an IgG4 format; the first parental homodimeric antibody species is in an IgG1 format, an IgG2 format, an IgG3 format, or an IgG4 format; the second parental homodimeric antibody species is in an IgG1 format, an IgG2 format, an IgG3 format, or an IgG4 format; the first parental homodimeric antibody species and the second parental homodimeric antibody species are in an IgG1 format, an IgG2 format, an IgG3 format, or an IgG4 format; or the MAI, the first parental homodimeric antibody species and the second parental homodimeric antibody species are in an IgG1 format, an IgG2 format, an IgG3 format, or an IgG4 format; or a hybrid format, wherein said native antibody refers to an antibody having a tetrameric structure comprised of two heavy chains and two light chains wherein said heavy chains and lights chains are associated with each other as in an antibody of a particular isotype which is naturally occurring in a particular animal species.

11. The method according to claim 1, wherein the ionic strength of the eluant remains about the same throughout the elution step.

12. The method according to claim 1, wherein the composition is obtained from a prokaryotic host cell or a eukaryotic host cell that expresses nucleic acid sequences encoding the first heavy chain polypeptide and the second heavy chain polypeptide.

13. The method according to claim 1, wherein each sample of the eluant comprises at least one salt at a concentration of about 10 mM.

14. The method according to claim 1, wherein each sample of the eluant comprises NaCl at a concentration of about 10 mM.

15. A method of purifying a multispecific antibody of interest (MAI), wherein the MAI comprises a heterodimer comprising a first heavy chain polypeptide comprising a first heavy chain variable region and a second heavy chain polypeptide comprising a second heavy chain variable region, wherein the first and the second variable regions have different antigen specificities and different isoelectric points, the method comprising:
  i) obtaining a composition comprising the MAI, a first parental homodimeric antibody species comprising either at least one copy of the first heavy chain polypeptide or at least two copies of the first heavy chain polypeptide, and a second parental homodimeric antibody species comprising either at least one copy of the second heavy chain polypeptide or at least two copies of the second heavy chain polypeptide; and
  ii) performing ion exchange chromatography whereby the MAI is separated from the first and the second parental homodimeric antibody species, wherein the performing step ii) comprises:
    a. contacting the composition with an ion exchange chromatographic material forming a composition-ion exchange chromatographic material complex, and preparing or equilibrating either:
      ai. the composition; or
      aii. the composition-ion exchange chromatographic material complex;
    in a first sample of an eluant at a desired starting pH prior to performing the elution, and
    b. performing an elution step wherein the ion exchange chromatographic material-composition complex is contacted with a sample of eluant, wherein the eluant comprises at least two buffering agents that each have a different negative log acid dissociation constant (pKa), which agents are selected from either:
      bi. CAPS, CHES, TAPS, HEPPSO, MOPSO, MES, acetic acid, formic acid and at least one salt; or
      bii. methylamine, 1,2-ethanediamine, 1-methylpiperazine, 1,4-dimethylpiperazine, 2-[Bis(2-hydroxyethyl)amino]-2-(hydroxymethyl)propane-1,3-diol (bis-tris), hydroxylamine, and at least one salt; and
    c. flowing a volume of a second sample of the eluant that is prepared at a desired ending pH through the ion exchange chromatographic material-composition complex;
  wherein the MAI, the first parental homodimeric antibody species, and the second parental homodimeric antibody species elute from the ion exchange chromatographic material in distinguishable elution volumes, allowing for the purification of the MAI;
  wherein the ionic strength of the eluant remains essentially the same throughout the elution step;
  and further wherein the eluant does not include imidazole.

16. The method according to claim 15, wherein the eluant comprises at least one salt selected from the group consisting of NaCl, KCl, and $Na_2SO_4$.

17. The method according to claim 15, wherein each sample of the eluant comprises at least one salt at a concentration of about 10 mM.

18. The method according to claim 15, wherein each sample of the eluant comprises NaCl at a concentration of about 10 mM.

19. The method according to claim 15, with the proviso that the eluant does not include any of the following: imidazole, piperazine, or tris(hydroxymethyl)aminomethane (TRIS).

20. A method of purifying a multispecific antibody of interest (MAI), wherein the MAI comprises a heterodimer comprising a first heavy chain polypeptide comprising a first heavy chain variable region and a second heavy chain polypeptide comprising a second heavy chain variable region, wherein the first and the second variable regions have different antigen specificities and different isoelectric points, the method comprising:
  i) obtaining a composition comprising the MAI, a first parental homodimeric antibody species comprising either at least one copy of the first heavy chain polypeptide or at least two copies of the first heavy chain polypeptide, and a second parental homodimeric antibody species comprising either at least one copy of the second heavy chain polypeptide or at least two copies of the second heavy chain polypeptide; and
  ii) performing ion exchange chromatography whereby the MAI is separated from the first and the second parental homodimeric antibody species, wherein the performing step ii) comprises:
    a. contacting the composition with an ion exchange chromatographic material forming a composition-ion exchange chromatographic material complex, and preparing or equilibrating either:
      ai. the composition; or
      aii. the composition-ion exchange chromatographic material complex;
    in a first sample of an eluant at a desired starting pH prior to performing the elution, and
    b. performing an elution step wherein the ion exchange chromatographic material-composition complex is contacted with a sample of eluant, wherein the eluant comprises at least two buffering agents that each have a different negative log acid dissociation constant (pKa), which agents are selected from either:
      bi. CAPS, CHES, TAPS, HEPPSO, MOPSO, MES, acetic acid, formic acid and at least one salt; or
      bii. methylamine, 1,2-ethanediamine, 1-methylpiperazine, 1,4-dimethylpiperazine, 2-[Bis(2-hydroxyethyl)amino]-2-(hydroxymethyl)propane-1,3-diol (bis-tris), hydroxylamine, and at least one salt; and
    c. flowing a volume of a second sample of the eluant that is prepared at a desired ending pH through the ion exchange chromatographic material-composition complex;
  wherein the MAI, the first parental homodimeric antibody species, and the second parental homodimeric antibody species elute from the ion exchange chromatographic material in distinguishable elution volumes, allowing for the purification of the MAI;
  and further wherein the first heavy chain polypeptide and/or the second heavy chain polypeptide of the MAI are not engineered or mutated for the purpose of enhancing the separation, resolution, or purification of the MAI from the parental homodimeric antibody species prior to purification or expression of the MAI.

21. The method according to claim 20, wherein the first heavy chain polypeptide and the second heavy chain polypeptide each further comprise an Fc region selected from:
   (i) a wild-type Fc region;
   (ii) an IgG1 isotype Fc region, an IgG2 isotype Fc region, an IgG3 isotype Fc region, or an IgG4 isotype Fc region; and/or
   (iii) an Fc region that has not been engineered in order to alter the isoelectric point of the first parental homodimeric antibody species, the second parental homodimeric antibody species, or the MAI.

22. The method according to claim 20, wherein:
   (i) the MAI is in a native antibody format; at least the first parental homodimeric antibody species is in a native format; at least the second parental homodimeric antibody species is in a native format; the first parental homodimeric antibody species is in a native format and the second parental homodimeric antibody species is in a native format; or the MAI is in a native antibody format, the first parental homodimeric antibody species is in a native format, and the second parental homodimeric antibody species is in a native format; and/or
   (ii) the MAI is in an IgG1 format, an IgG2 format, an IgG3 format, or an IgG4 format; the first parental homodimeric antibody species is in an IgG1 format, an IgG2 format, an IgG3 format, or an IgG4 format; the second parental homodimeric antibody species is in an IgG1 format, an IgG2 format, an IgG3 format, or an IgG4 format; the first parental homodimeric antibody species and the second parental homodimeric antibody species are in an IgG1 format, an IgG2 format, an IgG3 format, or an IgG4 format; or the MAI, the first parental homodimeric antibody species and the second parental homodimeric antibody species are in an IgG1 format, an IgG2 format, an IgG3 format, or an IgG4 format; or a hybrid format, wherein said native antibody refers to an antibody having a tetrameric structure comprised of two heavy chains and two light chains wherein said heavy chains and lights chains are associated with each other as in an antibody of a particular isotype which is naturally occurring in a particular animal species.

* * * * *

SEQUENCE LISTING

```
<160> NUMBER OF SEQ ID NOS: 43

<210> SEQ ID NO 1
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(150)
<223> OTHER INFORMATION: This sequence may encompass 1-75 "Gly Ser"
      repeating units wherein some positions may not be present

<400> SEQUENCE: 1

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser Gly Ser
            20                  25                  30

Gly Ser Gly Ser Gly Ser Gly Ser Gly Ser Gly Ser Gly Ser Gly Ser
        35                  40                  45

Gly Ser Gly Ser Gly Ser Gly Ser Gly Ser Gly Ser Gly Ser Gly Ser
    50                  55                  60

Gly Ser Gly Ser Gly Ser Gly Ser Gly Ser Gly Ser Gly Ser Gly Ser
65                  70                  75                  80
```

Gly Ser Gly Ser Gly Ser Gly Ser Gly Ser Gly Ser
            85                  90                  95

Gly Ser Gly Ser Gly Ser Gly Ser Gly Ser Gly Ser
        100                 105                 110

Gly Ser Gly Ser Gly Ser Gly Ser Gly Ser Gly Ser
        115                 120                 125

Gly Ser Gly Ser Gly Ser Gly Ser Gly Ser Gly Ser
        130                 135                 140

Gly Ser Gly Ser Gly Ser
145             150

<210> SEQ ID NO 2
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(225)
<223> OTHER INFORMATION: This sequence may encompass 1-75 "Gly Gly Ser"
      repeating units wherein some positions may not be present

<400> SEQUENCE: 2

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
        35                  40                  45

Gly Gly Ser Gly Gly Ser Gly Gly Ser Gly Gly Ser Gly Gly Ser Gly
    50                  55                  60

Gly Ser Gly Gly Ser Gly Gly Ser Gly Gly Ser Gly Gly Ser Gly Gly
65                  70                  75                  80

Ser Gly Gly Ser Gly Gly Ser Gly Gly Ser Gly Gly Ser Gly Gly Ser
            85                  90                  95

Gly Gly Ser Gly Gly Ser Gly Gly Ser Gly Gly Ser Gly Gly Ser Gly
        100                 105                 110

Gly Ser Gly Gly Ser Gly Gly Ser Gly Gly Ser Gly Gly Ser Gly Gly
    115                 120                 125

Ser Gly Gly Ser Gly Gly Ser Gly Gly Ser Gly Gly Ser Gly Gly Ser
130                 135                 140

Gly Gly Ser Gly Gly Ser Gly Gly Ser Gly Gly Ser Gly Gly Ser Gly
145                 150                 155                 160

Gly Ser Gly Gly Ser Gly Gly Ser Gly Gly Ser Gly Gly Ser Gly Gly
            165                 170                 175

Ser Gly Gly Ser Gly Gly Ser Gly Gly Ser Gly Gly Ser Gly Gly Ser
        180                 185                 190

Gly Gly Ser Gly Gly Ser Gly Gly Ser Gly Gly Ser Gly Gly Ser Gly
    195                 200                 205

Gly Ser Gly Gly Ser Gly Gly Ser Gly Gly Ser Gly Gly Ser Gly Gly
        210                 215                 220

Ser
225

<210> SEQ ID NO 3
<211> LENGTH: 300

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(300)
<223> OTHER INFORMATION: This sequence may encompass 1-75 "Gly Gly Gly
      Ser" repeating units wherein some positions may not be present

<400> SEQUENCE: 3

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Ser Gly Gly Gly Ser
        35                  40                  45

Gly Gly Gly Ser Gly Gly Gly Ser Gly Gly Gly Ser Gly Gly Gly Ser
    50                  55                  60

Gly Gly Gly Ser Gly Gly Gly Ser Gly Gly Gly Ser Gly Gly Gly Ser
65                  70                  75                  80

Gly Gly Gly Ser Gly Gly Gly Ser Gly Gly Gly Ser Gly Gly Gly Ser
                85                  90                  95

Gly Gly Gly Ser Gly Gly Gly Ser Gly Gly Gly Ser Gly Gly Gly Ser
            100                 105                 110

Gly Gly Gly Ser Gly Gly Gly Ser Gly Gly Gly Ser Gly Gly Gly Ser
        115                 120                 125

Gly Gly Gly Ser Gly Gly Gly Ser Gly Gly Gly Ser Gly Gly Gly Ser
    130                 135                 140

Gly Gly Gly Ser Gly Gly Gly Ser Gly Gly Gly Ser Gly Gly Gly Ser
145                 150                 155                 160

Gly Gly Gly Ser Gly Gly Gly Ser Gly Gly Gly Ser Gly Gly Gly Ser
                165                 170                 175

Gly Gly Gly Ser Gly Gly Gly Ser Gly Gly Gly Ser Gly Gly Gly Ser
            180                 185                 190

Gly Gly Gly Ser Gly Gly Gly Ser Gly Gly Gly Ser Gly Gly Gly Ser
        195                 200                 205

Gly Gly Gly Ser Gly Gly Gly Ser Gly Gly Gly Ser Gly Gly Gly Ser
    210                 215                 220

Gly Gly Gly Ser Gly Gly Gly Ser Gly Gly Gly Ser Gly Gly Gly Ser
225                 230                 235                 240

Gly Gly Gly Ser Gly Gly Gly Ser Gly Gly Gly Ser Gly Gly Gly Ser
                245                 250                 255

Gly Gly Gly Ser Gly Gly Gly Ser Gly Gly Gly Ser Gly Gly Gly Ser
            260                 265                 270

Gly Gly Gly Ser Gly Gly Gly Ser Gly Gly Gly Ser Gly Gly Gly Ser
        275                 280                 285

Gly Gly Gly Ser Gly Gly Gly Ser Gly Gly Gly Ser
    290                 295                 300

<210> SEQ ID NO 4
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<221> NAME/KEY: MISC_FEATURE
<222> LOCATION: (1)..(375)
<223> OTHER INFORMATION: This sequence may encompass 1-75 "Gly Gly Gly Gly Ser" repeating units wherein some positions may not be present

<400> SEQUENCE: 4

```
Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Ser Gly Gly Gly Ser Gly Gly Gly
            35                  40                  45

Gly Ser Gly Gly Gly Ser Gly Gly Gly Ser Gly Gly Gly Gly
        50                  55                  60

Ser Gly Gly Gly Ser Gly Gly Gly Ser Gly Gly Gly Gly Ser
65                  70                  75                  80

Gly Gly Gly Ser Gly Gly Gly Ser Gly Gly Gly Ser Gly Gly
            85                  90                  95

Gly Gly Ser Gly Gly Gly Ser Gly Gly Gly Ser Gly Gly Gly
            100                 105                 110

Gly Ser Gly Gly Gly Ser Gly Gly Gly Ser Gly Gly Gly Gly
        115                 120                 125

Ser Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser
145                 150                 155                 160

Gly Gly Gly Gly Ser Gly Gly Gly Gly Ser Gly Gly Gly Ser Gly
                165                 170                 175

Gly Gly Gly Ser Gly Gly Gly Ser Gly Gly Gly Ser Gly Gly
            180                 185                 190

Gly Gly Ser Gly Gly Gly Ser Gly Gly Gly Ser Gly Gly Gly
            195                 200                 205

Gly Ser Gly Gly Gly Ser Gly Gly Gly Ser Gly Gly Gly Gly
        210                 215                 220

Ser Gly Gly Gly Ser Gly Gly Gly Ser Gly Gly Gly Gly Ser
225                 230                 235                 240

Gly Gly Gly Gly Ser Gly Gly Gly Gly Ser Gly Gly Gly Ser Gly
                245                 250                 255

Gly Gly Gly Ser Gly Gly Gly Ser Gly Gly Gly Ser Gly Gly
            260                 265                 270

Gly Gly Ser Gly Gly Gly Ser Gly Gly Gly Ser Gly Gly Gly
            275                 280                 285

Gly Ser Gly Gly Gly Ser Gly Gly Gly Ser Gly Gly Gly Gly
        290                 295                 300

Ser Gly Gly Gly Ser Gly Gly Gly Ser Gly Gly Gly Gly Ser
305                 310                 315                 320

Gly Gly Gly Gly Ser Gly Gly Gly Gly Ser Gly Gly Gly Ser Gly
                325                 330                 335

Gly Gly Gly Ser Gly Gly Gly Ser Gly Gly Gly Ser Gly Gly
            340                 345                 350

Gly Gly Ser Gly Gly Gly Ser Gly Gly Gly Ser Gly Gly Gly
            355                 360                 365

Gly Ser Gly Gly Gly Ser
        370                 375
```

<210> SEQ ID NO 5
<211> LENGTH: 675
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(675)
<223> OTHER INFORMATION: This sequence may encompass 1-75 "Gly Gly Gly
      Gly Ser Gly Gly Gly Gly" repeating units wherein some positions
      may not be present

<400> SEQUENCE: 5

Gly Gly Gly Gly Ser Gly Gly Gly Gly Gly Gly Ser Gly Gly
1               5                   10                  15

Gly Gly Gly Gly Gly Ser Gly Gly Gly Gly Gly Gly Gly Ser
            20                  25                  30

Gly Gly Gly Gly Gly Gly Gly Ser Gly Gly Gly Gly Gly Gly
        35                  40                  45

Gly Ser Gly Gly Gly Gly Gly Gly Ser Gly Gly Gly Gly Gly
    50                  55                  60

Gly Gly Ser Gly Gly Gly Gly Gly Gly Ser Gly Gly Gly Gly
65                  70                  75                  80

Gly Gly Gly Gly Gly Ser Gly Gly Gly Gly Gly Gly Ser Gly
                85                  90                  95

Gly Gly Gly Gly Gly Gly Ser Gly Gly Gly Gly Gly Gly Gly
            100                 105                 110

Ser Gly Gly Gly Gly Gly Gly Ser Gly Gly Gly Gly Gly Gly
        115                 120                 125

Gly Gly Ser Gly Gly Gly Gly Gly Gly Ser Gly Gly Gly Gly
    130                 135                 140

Gly Gly Gly Gly Ser Gly Gly Gly Gly Gly Gly Ser Gly Gly
145                 150                 155                 160

Gly Gly Gly Gly Gly Ser Gly Gly Gly Gly Gly Gly Gly Ser
                165                 170                 175

Gly Gly Gly Gly Gly Gly Gly Ser Gly Gly Gly Gly Gly Gly
            180                 185                 190

Gly Ser Gly Gly Gly Gly Gly Gly Ser Gly Gly Gly Gly Gly
        195                 200                 205

Gly Gly Ser Gly Gly Gly Gly Gly Gly Ser Gly Gly Gly Gly
    210                 215                 220

Gly Gly Gly Gly Gly Ser Gly Gly Gly Gly Gly Gly Ser Gly
225                 230                 235                 240

Gly Gly Gly Gly Gly Gly Ser Gly Gly Gly Gly Gly Gly Gly
                245                 250                 255

Ser Gly Gly Gly Gly Gly Gly Ser Gly Gly Gly Gly Gly Gly
            260                 265                 270

Gly Gly Ser Gly Gly Gly Gly Gly Gly Ser Gly Gly Gly Gly
        275                 280                 285

Gly Gly Gly Gly Ser Gly Gly Gly Gly Gly Gly Ser Gly Gly
    290                 295                 300

Gly Gly Gly Gly Ser Gly Gly Gly Gly Gly Gly Gly Gly Ser
305                 310                 315                 320

Gly Gly Gly Gly Gly Gly Gly Gly Ser Gly Gly Gly Gly Gly
                325                 330                 335

Gly Ser Gly Gly Gly Gly Gly Gly Ser Gly Gly Gly Gly
            340                 345                 350

Gly Gly Gly Ser Gly Gly Gly Gly Gly Gly Ser Gly Gly Gly
        355                 360                 365

Gly Gly Gly Gly Gly Ser Gly Gly Gly Gly Gly Gly Ser Gly
370                 375                 380

Gly Gly Gly Gly Gly Gly Ser Gly Gly Gly Gly Gly Gly Gly
385                 390                 395                 400

Ser Gly Gly Gly Gly Gly Gly Gly Ser Gly Gly Gly Gly Gly
            405                 410                 415

Gly Gly Ser Gly Gly Gly Gly Gly Gly Ser Gly Gly Gly Gly
        420                 425                 430

Gly Gly Gly Gly Ser Gly Gly Gly Gly Gly Gly Ser Gly Gly
    435                 440                 445

Gly Gly Gly Gly Gly Ser Gly Gly Gly Gly Gly Gly Gly Ser
450                 455                 460

Gly Gly Gly Gly Gly Gly Gly Ser Gly Gly Gly Gly Gly Gly
465                 470                 475                 480

Gly Ser Gly Gly Gly Gly Gly Gly Gly Ser Gly Gly Gly Gly
            485                 490                 495

Gly Gly Gly Ser Gly Gly Gly Gly Gly Gly Ser Gly Gly Gly
        500                 505                 510

Gly Gly Gly Gly Ser Gly Gly Gly Gly Gly Gly Ser Gly
    515                 520                 525

Gly Gly Gly Gly Gly Ser Gly Gly Gly Gly Gly Gly Gly
        530                 535                 540

Ser Gly Gly Gly Gly Gly Gly Gly Ser Gly Gly Gly Gly Gly
545                 550                 555                 560

Gly Gly Ser Gly Gly Gly Gly Gly Gly Ser Gly Gly Gly Gly
            565                 570                 575

Gly Gly Gly Gly Ser Gly Gly Gly Gly Gly Gly Ser Gly Gly
        580                 585                 590

Gly Gly Gly Gly Gly Ser Gly Gly Gly Gly Gly Gly Gly Ser
    595                 600                 605

Gly Gly Gly Gly Gly Gly Gly Ser Gly Gly Gly Gly Gly Gly
610                 615                 620

Gly Ser Gly Gly Gly Gly Gly Gly Gly Ser Gly Gly Gly Gly
625                 630                 635                 640

Gly Gly Gly Ser Gly Gly Gly Gly Gly Gly Ser Gly Gly Gly
            645                 650                 655

Gly Gly Gly Gly Gly Ser Gly Gly Gly Gly Gly Gly Ser Gly
        660                 665                 670

Gly Gly Gly
    675

<210> SEQ ID NO 6
<211> LENGTH: 1050
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(1050)
<223> OTHER INFORMATION: This sequence may encompass 1-75 "Gly Gly Gly Gly Ser Gly Gly Gly Gly Ser Gly Gly Gly Gly" repeating units
wherein some positions may not be present

<400> SEQUENCE: 6

Gly Gly Gly Gly Ser Gly Gly Gly Ser Gly Gly Gly Gly Gly
1               5                   10                  15

Gly Gly Ser Gly Gly Gly Ser Gly Gly Gly Gly Gly Gly
            20              25                  30

Ser Gly Gly Gly Gly Ser Gly Gly Gly Gly Gly Gly Ser Gly
        35                  40                  45

Gly Gly Gly Ser Gly Gly Gly Gly Gly Gly Ser Gly Gly Gly
            50                  55                  60

Gly Ser Gly Gly Gly Gly Gly Gly Ser Gly Gly Gly Ser
65              70                  75              80

Gly Gly Gly Gly Gly Gly Gly Ser Gly Gly Gly Ser Gly Gly
                85                  90                  95

Gly Gly Gly Gly Gly Ser Gly Gly Gly Ser Gly Gly Gly
                100                 105                 110

Gly Gly Gly Gly Ser Gly Gly Gly Ser Gly Gly Gly Gly
                115                 120                 125

Gly Gly Ser Gly Gly Gly Ser Gly Gly Gly Gly Gly Gly
        130                 135                 140

Ser Gly Gly Gly Ser Gly Gly Gly Gly Gly Gly Ser Gly
145                 150                 155             160

Gly Gly Gly Ser Gly Gly Gly Gly Gly Gly Ser Gly Gly
                165                 170             175

Gly Ser Gly Gly Gly Gly Gly Gly Ser Gly Gly Gly Ser
        180                 185                 190

Gly Gly Gly Gly Gly Gly Ser Gly Gly Gly Ser Gly Gly
            195                 200             205

Gly Gly Gly Gly Gly Ser Gly Gly Gly Ser Gly Gly Gly Gly
            210                 215             220

Gly Gly Gly Gly Ser Gly Gly Gly Ser Gly Gly Gly Gly Gly
225                 230                 235             240

Gly Gly Ser Gly Gly Gly Ser Gly Gly Gly Gly Gly Gly
            245                 250             255

Ser Gly Gly Gly Gly Ser Gly Gly Gly Gly Gly Gly Ser Gly
            260                 265             270

Gly Gly Gly Ser Gly Gly Gly Gly Gly Gly Ser Gly Gly Gly
            275                 280             285

Gly Ser Gly Gly Gly Gly Gly Gly Ser Gly Gly Gly Ser
            290                 295             300

Gly Gly Gly Gly Gly Gly Gly Ser Gly Gly Gly Ser Gly Gly
305                 310             315             320

Gly Gly Gly Gly Gly Ser Gly Gly Gly Ser Gly Gly Gly Gly
                325                 330             335

Gly Gly Gly Gly Ser Gly Gly Gly Ser Gly Gly Gly Gly Gly
                340                 345             350

Gly Gly Ser Gly Gly Gly Ser Gly Gly Gly Gly Gly Gly
            355                 360             365

Ser Gly Gly Gly Ser Gly Gly Gly Gly Gly Gly Ser Gly
            370                 375             380

Gly Gly Gly Ser Gly Gly Gly Gly Gly Gly Ser Gly Gly Gly
                385                 390             395             400

-continued

Gly Ser Gly Gly Gly Gly Gly Gly Gly Ser Gly Gly Gly Ser
              405                 410                 415
Gly Gly Gly Gly Gly Gly Gly Ser Gly Gly Gly Ser Gly Gly
              420                 425                 430
Gly Gly Gly Gly Gly Ser Gly Gly Gly Ser Gly Gly Gly Gly
              435                 440                 445
Gly Gly Gly Gly Ser Gly Gly Gly Ser Gly Gly Gly Gly Gly
              450                 455                 460
Gly Gly Ser Gly Gly Gly Ser Gly Gly Gly Gly Gly Gly Gly
465                 470                 475                 480
Ser Gly Gly Gly Ser Gly Gly Gly Gly Gly Gly Gly Ser Gly
              485                 490                 495
Gly Gly Ser Gly Gly Gly Gly Gly Gly Gly Ser Gly Gly Gly
              500                 505                 510
Gly Ser Gly Gly Gly Gly Gly Gly Gly Ser Gly Gly Gly Ser
              515                 520                 525
Gly Gly Gly Gly Gly Gly Ser Gly Gly Gly Ser Gly Gly Gly
              530                 535                 540
Gly Gly Gly Gly Gly Ser Gly Gly Gly Ser Gly Gly Gly Gly
545                 550                 555                 560
Gly Gly Gly Gly Ser Gly Gly Gly Ser Gly Gly Gly Gly Gly
              565                 570                 575
Gly Gly Ser Gly Gly Gly Ser Gly Gly Gly Gly Gly Gly Gly
              580                 585                 590
Ser Gly Gly Gly Ser Gly Gly Gly Gly Gly Gly Gly Ser Gly
              595                 600                 605
Gly Gly Ser Gly Gly Gly Gly Gly Gly Gly Ser Gly Gly Gly
              610                 615                 620
Gly Ser Gly Gly Gly Gly Gly Gly Gly Ser Gly Gly Gly Ser
625                 630                 635                 640
Gly Gly Gly Gly Gly Gly Gly Ser Gly Gly Gly Ser Gly Gly
              645                 650                 655
Gly Gly Gly Gly Gly Gly Ser Gly Gly Gly Ser Gly Gly Gly
              660                 665                 670
Gly Gly Gly Gly Ser Gly Gly Gly Ser Gly Gly Gly Gly Gly
              675                 680                 685
Gly Gly Ser Gly Gly Gly Ser Gly Gly Gly Gly Gly Gly Gly
              690                 695                 700
Ser Gly Gly Gly Ser Gly Gly Gly Gly Gly Gly Gly Ser Gly
705                 710                 715                 720
Gly Gly Gly Ser Gly Gly Gly Gly Gly Gly Gly Ser Gly Gly
              725                 730                 735
Gly Ser Gly Gly Gly Gly Gly Gly Gly Ser Gly Gly Gly Ser
              740                 745                 750
Gly Gly Gly Gly Gly Gly Gly Ser Gly Gly Gly Ser Gly Gly
              755                 760                 765
Gly Gly Gly Gly Gly Gly Ser Gly Gly Gly Ser Gly Gly Gly
              770                 775                 780
Gly Gly Gly Gly Ser Gly Gly Gly Ser Gly Gly Gly Gly Gly
785                 790                 795                 800
Gly Gly Ser Gly Gly Gly Gly Ser Gly Gly Gly Gly Gly Gly
              805                 810                 815

Ser Gly Gly Gly Gly Ser Gly Gly Gly Gly Ser Gly
                820                 825                 830

Gly Gly Gly Ser Gly Gly Gly Gly Gly Gly Ser Gly Gly
        835                 840                 845

Gly Ser Gly Gly Gly Gly Gly Gly Gly Ser Gly Gly Gly Ser
    850                 855                 860

Gly Gly Gly Gly Gly Gly Gly Ser Gly Gly Gly Ser Gly Gly
865                 870                 875                 880

Gly Gly Gly Gly Gly Ser Gly Gly Gly Ser Gly Gly Gly
                885                 890                 895

Gly Gly Gly Gly Ser Gly Gly Gly Ser Gly Gly Gly Gly
            900                 905                 910

Gly Gly Ser Gly Gly Gly Gly Ser Gly Gly Gly Gly Gly
        915                 920                 925

Ser Gly Gly Gly Gly Ser Gly Gly Gly Gly Gly Gly Ser Gly
    930                 935                 940

Gly Gly Gly Ser Gly Gly Gly Gly Gly Gly Ser Gly Gly
945                 950                 955                 960

Gly Ser Gly Gly Gly Gly Gly Gly Ser Gly Gly Gly Ser
            965                 970                 975

Gly Gly Gly Gly Gly Gly Ser Gly Gly Gly Ser Gly Gly
        980                 985                 990

Gly Gly Gly Gly Gly Ser Gly  Gly Gly Gly Ser Gly  Gly Gly Gly
                995                 1000                1005

Gly Gly  Gly Gly Ser Gly Gly  Gly Gly Ser Gly Gly  Gly Gly Gly
    1010                1015                1020

Gly Gly  Gly Ser Gly Gly Gly  Gly Ser Gly Gly Gly  Gly Gly Gly
    1025                1030                1035

Gly Gly  Ser Gly Gly Gly Gly  Ser Gly Gly Gly Gly
    1040                1045                1050

<210> SEQ ID NO 7
<211> LENGTH: 1425
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(1425)
<223> OTHER INFORMATION: This sequence may encompass 1-75 "Gly Gly Gly
      Gly Ser Gly Gly Gly Gly Ser Gly Gly Gly Gly Ser Gly Gly Gly Gly"
      repeating units wherein some positions may not be present

<400> SEQUENCE: 7

Gly Gly Gly Gly Ser Gly Gly Gly Gly Ser Gly Gly Gly Gly Ser Gly
1               5                   10                  15

Gly Gly Gly Gly Gly Gly Ser Gly Gly Gly Gly Ser Gly Gly Gly
            20                  25                  30

Gly Ser Gly Gly Gly Gly Gly Gly Gly Gly Gly Ser Gly Gly Gly Ser
        35                  40                  45

Gly Gly Gly Gly Ser Gly Gly Gly Gly Gly Gly Gly Ser Gly Gly
    50                  55                  60

Gly Gly Ser Gly Gly Gly Gly Ser Gly Gly Gly Gly Gly Gly Gly Gly
65                  70                  75                  80

Ser Gly Gly Gly Gly Ser Gly Gly Gly Gly Ser Gly Gly Gly Gly Gly
                85                  90                  95

-continued

Gly Gly Gly Ser Gly Gly Gly Ser Gly Gly Gly Ser Gly
            100                 105                 110

Gly Gly Gly Gly Gly Ser Gly Gly Gly Ser Gly Gly Gly
            115                 120                 125

Ser Gly Gly Gly Gly Gly Gly Gly Ser Gly Gly Gly Ser Gly
            130                 135                 140

Gly Gly Ser Gly Gly Gly Gly Gly Gly Ser Gly Gly Gly
145                 150                 155             160

Gly Ser Gly Gly Gly Ser Gly Gly Gly Gly Gly Gly Ser
            165                 170                 175

Gly Gly Gly Gly Ser Gly Gly Gly Ser Gly Gly Gly Gly
            180                 185                 190

Gly Gly Ser Gly Gly Gly Ser Gly Gly Gly Ser Gly Gly Gly
            195                 200                 205

Gly Gly Gly Gly Gly Ser Gly Gly Gly Ser Gly Gly Gly Ser
            210                 215                 220

Gly Gly Gly Gly Gly Gly Gly Ser Gly Gly Gly Ser Gly Gly
225                 230                 235             240

Gly Gly Ser Gly Gly Gly Gly Gly Gly Gly Ser Gly Gly Gly
            245                 250                 255

Ser Gly Gly Gly Gly Ser Gly Gly Gly Gly Gly Gly Ser Gly
            260                 265                 270

Gly Gly Ser Gly Gly Gly Ser Gly Gly Gly Gly Gly Gly
            275                 280                 285

Gly Ser Gly Gly Gly Gly Ser Gly Gly Gly Ser Gly Gly Gly
            290                 295                 300

Gly Gly Gly Gly Ser Gly Gly Gly Ser Gly Gly Gly Ser Gly
305                 310                 315             320

Gly Gly Gly Gly Gly Gly Ser Gly Gly Gly Ser Gly Gly Gly
            325                 330                 335

Gly Ser Gly Gly Gly Gly Gly Gly Gly Ser Gly Gly Gly Ser
            340                 345                 350

Gly Gly Gly Gly Ser Gly Gly Gly Gly Gly Gly Ser Gly Gly
            355                 360                 365

Gly Gly Ser Gly Gly Gly Ser Gly Gly Gly Gly Gly Gly Gly
            370                 375                 380

Ser Gly Gly Gly Gly Ser Gly Gly Gly Ser Gly Gly Gly Gly
385                 390                 395             400

Gly Gly Gly Ser Gly Gly Gly Gly Gly Ser Gly Gly Ser Gly
            405                 410                 415

Gly Gly Gly Gly Gly Ser Gly Gly Gly Gly Ser Gly Gly Gly Gly
            420                 425                 430

Ser Gly Gly Gly Gly Gly Gly Gly Ser Gly Gly Gly Ser Gly
435                 440                 445

Gly Gly Gly Ser Gly Gly Gly Gly Gly Gly Gly Ser Gly Gly Gly
            450                 455                 460

Gly Ser Gly Gly Gly Gly Ser Gly Gly Gly Gly Gly Gly Ser
465                 470                 475             480

Gly Gly Gly Gly Ser Gly Gly Gly Gly Ser Gly Gly Gly Gly
            485                 490                 495

Gly Gly Ser Gly Gly Gly Gly Ser Gly Gly Gly Ser Gly Gly Gly
            500                 505                 510

-continued

Gly Gly Gly Gly Ser Gly Gly Gly Ser Gly Gly Ser
        515             520             525
Gly Gly Gly Gly Gly Gly Gly Ser Gly Gly Gly Ser Gly Gly
        530             535             540
Gly Gly Ser Gly Gly Gly Gly Gly Gly Ser Gly Gly Gly Gly
545             550             555             560
Ser Gly Gly Gly Ser Gly Gly Gly Gly Gly Gly Ser Gly
        565             570             575
Gly Gly Gly Ser Gly Gly Gly Gly Ser Gly Gly Gly Gly Gly
        580             585             590
Gly Ser Gly Gly Gly Ser Gly Gly Gly Ser Gly Gly Gly Gly
        595             600             605
Gly Gly Gly Gly Ser Gly Gly Gly Gly Ser Gly Gly Gly Ser Gly
        610             615             620
Gly Gly Gly Gly Gly Gly Ser Gly Gly Gly Ser Gly Gly Gly
625             630             635             640
Gly Ser Gly Gly Gly Gly Gly Gly Gly Ser Gly Gly Gly Ser
        645             650             655
Gly Gly Gly Gly Ser Gly Gly Gly Gly Gly Gly Ser Gly Gly
        660             665             670
Gly Gly Ser Gly Gly Gly Gly Ser Gly Gly Gly Gly Gly Gly
        675             680             685
Ser Gly Gly Gly Gly Ser Gly Gly Gly Ser Gly Gly Gly Gly
        690             695             700
Gly Gly Gly Ser Gly Gly Gly Ser Gly Gly Gly Ser Gly Gly
705             710             715             720
Gly Gly Gly Gly Gly Ser Gly Gly Gly Ser Gly Gly Gly Gly
        725             730             735
Ser Gly Gly Gly Gly Gly Gly Gly Ser Gly Gly Gly Ser Gly
        740             745             750
Gly Gly Gly Ser Gly Gly Gly Gly Gly Gly Ser Gly Gly
        755             760             765
Gly Ser Gly Gly Gly Ser Gly Gly Gly Gly Gly Gly Ser
        770             775             780
Gly Gly Gly Gly Ser Gly Gly Gly Ser Gly Gly Gly Gly Gly
785             790             795             800
Gly Gly Ser Gly Gly Gly Ser Gly Gly Gly Ser Gly Gly Gly
        805             810             815
Gly Gly Gly Gly Gly Ser Gly Gly Gly Ser Gly Gly Gly Ser
        820             825             830
Gly Gly Gly Gly Gly Gly Gly Ser Gly Gly Gly Ser Gly Gly
        835             840             845
Gly Gly Ser Gly Gly Gly Gly Gly Gly Ser Gly Gly Gly Gly
        850             855             860
Ser Gly Gly Gly Gly Ser Gly Gly Gly Gly Gly Gly Ser Gly
865             870             875             880
Gly Gly Gly Ser Gly Gly Gly Gly Ser Gly Gly Gly Gly Gly
        885             890             895
Gly Ser Gly Gly Gly Gly Ser Gly Gly Gly Gly Ser Gly Gly Gly
        900             905             910
Gly Gly Gly Gly Ser Gly Gly Gly Ser Gly Gly Gly Ser Gly
        915             920             925
Gly Gly Gly Gly Gly Gly Gly Ser Gly Gly Gly Gly Ser Gly Gly Gly

-continued

```
            930                 935                 940
Gly Ser Gly Gly Gly Gly Gly Gly Ser Gly Gly Gly Ser
945                 950                 955                 960
Gly Gly Gly Gly Ser Gly Gly Gly Gly Gly Gly Ser Gly Gly
                965                 970                 975
Gly Gly Ser Gly Gly Gly Gly Ser Gly Gly Gly Gly Gly Gly
                980                 985                 990
Ser Gly Gly Gly Gly Ser Gly Gly Gly Gly Ser Gly Gly Gly Gly Gly
        995                 1000                1005
Gly Gly Gly Ser Gly Gly Gly Gly Ser Gly Gly Gly Gly Ser Gly
        1010                1015                1020
Gly Gly Gly Gly Gly Gly Gly Ser Gly Gly Gly Gly Ser Gly Gly
        1025                1030                1035
Gly Gly Ser Gly Gly Gly Gly Gly Gly Gly Ser Gly Gly Gly
        1040                1045                1050
Gly Ser Gly Gly Gly Gly Ser Gly Gly Gly Gly Gly Gly Gly
        1055                1060                1065
Ser Gly Gly Gly Gly Ser Gly Gly Gly Gly Ser Gly Gly Gly Gly
        1070                1075                1080
Gly Gly Gly Gly Ser Gly Gly Gly Gly Ser Gly Gly Gly Ser
        1085                1090                1095
Gly Gly Gly Gly Gly Gly Gly Ser Gly Gly Gly Gly Ser Gly
        1100                1105                1110
Gly Gly Gly Ser Gly Gly Gly Gly Gly Gly Gly Gly Ser Gly Gly
        1115                1120                1125
Gly Gly Ser Gly Gly Gly Gly Ser Gly Gly Gly Gly Gly Gly Gly
        1130                1135                1140
Gly Ser Gly Gly Gly Gly Ser Gly Gly Gly Gly Ser Gly Gly Gly
        1145                1150                1155
Gly Gly Gly Gly Gly Ser Gly Gly Gly Gly Ser Gly Gly Gly Gly
        1160                1165                1170
Ser Gly Gly Gly Gly Gly Gly Gly Ser Gly Gly Gly Gly Ser
        1175                1180                1185
Gly Gly Gly Gly Ser Gly Gly Gly Gly Gly Gly Gly Ser Gly
        1190                1195                1200
Gly Gly Gly Ser Gly Gly Gly Ser Gly Gly Gly Gly Gly Gly
        1205                1210                1215
Gly Gly Ser Gly Gly Gly Gly Ser Gly Gly Gly Gly Ser Gly Gly
        1220                1225                1230
Gly Gly Gly Gly Gly Gly Ser Gly Gly Gly Gly Ser Gly Gly Gly
        1235                1240                1245
Gly Ser Gly Gly Gly Gly Gly Gly Gly Gly Ser Gly Gly Gly Gly
        1250                1255                1260
Ser Gly Gly Gly Gly Ser Gly Gly Gly Gly Gly Gly Gly Ser
        1265                1270                1275
Gly Gly Gly Gly Ser Gly Gly Gly Gly Ser Gly Gly Gly Gly
        1280                1285                1290
Gly Gly Gly Ser Gly Gly Gly Gly Ser Gly Gly Gly Gly Ser Gly
        1295                1300                1305
Gly Gly Gly Gly Gly Gly Gly Ser Gly Gly Gly Gly Ser Gly Gly
        1310                1315                1320
Gly Gly Ser Gly Gly Gly Gly Gly Gly Gly Gly Ser Gly Gly Gly
        1325                1330                1335
```

```
Gly Ser Gly Gly Gly Gly Ser Gly Gly Gly Gly Gly Gly Gly
    1340            1345                1350

Ser Gly Gly Gly Gly Ser Gly Gly Gly Gly Ser Gly Gly Gly Gly
    1355                1360                1365

Gly Gly Gly Gly Ser Gly Gly Gly Gly Ser Gly Gly Gly Gly Ser
    1370                1375                1380

Gly Gly Gly Gly Gly Gly Gly Ser Gly Gly Gly Gly Ser Gly
    1385                1390                1395

Gly Gly Gly Ser Gly Gly Gly Gly Gly Gly Gly Ser Gly Gly
    1400            1405                1410

Gly Gly Ser Gly Gly Gly Gly Ser Gly Gly Gly Gly
    1415            1420                1425

<210> SEQ ID NO 8
<211> LENGTH: 1800
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(1800)
<223> OTHER INFORMATION: This sequence may encompass 1-75 "Gly Gly Gly
      Gly Ser Gly Gly Gly Gly Ser Gly Gly Gly Gly Ser Gly Gly Gly
      Gly Ser Gly Gly Gly Gly" repeating units wherein
      some positions may not be present

<400> SEQUENCE: 8

Gly Gly Gly Gly Ser Gly Gly Gly Gly Ser Gly Gly Gly Gly Ser Gly
1               5                   10                  15

Gly Gly Gly Ser Gly Gly Gly Gly Gly Gly Gly Ser Gly Gly Gly
            20                  25                  30

Gly Ser Gly Gly Gly Gly Ser Gly Gly Gly Gly Ser Gly Gly Gly
        35                  40                  45

Gly Gly Gly Gly Ser Gly Gly Gly Gly Ser Gly Gly Gly Gly Ser Gly
    50                  55                  60

Gly Gly Gly Ser Gly Gly Gly Gly Gly Gly Gly Ser Gly Gly Gly
65                  70                  75                  80

Gly Ser Gly Gly Gly Gly Ser Gly Gly Gly Gly Ser Gly Gly Gly
        85                  90                  95

Gly Gly Gly Gly Ser Gly Gly Gly Gly Ser Gly Gly Gly Gly Ser Gly
            100                 105                 110

Gly Gly Gly Ser Gly Gly Gly Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Gly Gly Gly Gly Ser Gly Gly Gly Gly Ser Gly Gly Gly Gly Ser Gly
145                 150                 155                 160

Gly Gly Gly Ser Gly Gly Gly Gly Gly Gly Gly Ser Gly Gly Gly
            165                 170                 175

Gly Ser Gly Gly Gly Gly Ser Gly Gly Gly Gly Ser Gly Gly Gly Gly
            180                 185                 190

Gly Gly Gly Gly Ser Gly Gly Gly Gly Ser Gly Gly Gly Gly Ser Gly
        195                 200                 205

Gly Gly Gly Ser Gly Gly Gly Gly Gly Gly Gly Ser Gly Gly Gly
    210                 215                 220
```

-continued

Gly Ser Gly Gly Gly Ser Gly Gly Gly Ser Gly Gly Gly Gly
225                 230                 235                 240

Gly Gly Gly Gly Ser Gly Gly Gly Ser Gly Gly Gly Gly Ser Gly
            245                 250                 255

Gly Gly Gly Ser Gly Gly Gly Gly Gly Gly Ser Gly Gly Gly
            260                 265                 270

Gly Ser Gly Gly Gly Ser Gly Gly Gly Ser Gly Gly Gly Gly
        275                 280                 285

Gly Gly Gly Ser Gly Gly Gly Ser Gly Gly Gly Gly Ser Gly
        290                 295                 300

Gly Gly Gly Ser Gly Gly Gly Gly Gly Gly Ser Gly Gly Gly
305                 310                 315                 320

Gly Ser Gly Gly Gly Ser Gly Gly Gly Ser Gly Gly Gly Gly
            325                 330                 335

Gly Gly Gly Gly Ser Gly Gly Gly Ser Gly Gly Gly Gly Ser Gly
            340                 345                 350

Gly Gly Gly Ser Gly Gly Gly Gly Gly Gly Ser Gly Gly Gly
355                 360                 365

Gly Ser Gly Gly Gly Ser Gly Gly Gly Ser Gly Gly Gly Gly
        370                 375                 380

Gly Gly Gly Gly Ser Gly Gly Gly Ser Gly Gly Gly Gly Ser Gly
385                 390                 395                 400

Gly Gly Gly Ser Gly Gly Gly Gly Gly Gly Ser Gly Gly Gly
            405                 410                 415

Gly Ser Gly Gly Gly Ser Gly Gly Gly Ser Gly Gly Gly Gly
        420                 425                 430

Gly Gly Gly Gly Ser Gly Gly Gly Ser Gly Gly Gly Gly Ser Gly
            435                 440                 445

Gly Gly Gly Ser Gly Gly Gly Gly Gly Gly Ser Gly Gly Gly
450                 455                 460

Gly Ser Gly Gly Gly Ser Gly Gly Gly Ser Gly Gly Gly Gly
465                 470                 475                 480

Gly Gly Gly Gly Ser Gly Gly Gly Ser Gly Gly Gly Gly Ser Gly
            485                 490                 495

Gly Gly Gly Ser Gly Gly Gly Gly Gly Gly Ser Gly Gly Gly
            500                 505                 510

Gly Ser Gly Gly Gly Ser Gly Gly Gly Ser Gly Gly Gly Gly
        515                 520                 525

Gly Gly Gly Gly Ser Gly Gly Gly Ser Gly Gly Gly Gly Ser Gly
            530                 535                 540

Gly Gly Gly Ser Gly Gly Gly Gly Gly Gly Ser Gly Gly Gly
545                 550                 555                 560

Gly Ser Gly Gly Gly Gly Ser Gly Gly Gly Ser Gly Gly Gly Gly
            565                 570                 575

Gly Gly Gly Gly Ser Gly Gly Gly Ser Gly Gly Gly Gly Ser Gly
            580                 585                 590

Gly Gly Gly Ser Gly Gly Gly Gly Gly Gly Ser Gly Gly Gly
            595                 600                 605

Gly Ser Gly Gly Gly Gly Ser Gly Gly Gly Ser Gly Gly Gly Gly
        610                 615                 620

Gly Gly Gly Gly Ser Gly Gly Gly Gly Ser Gly Gly Gly Ser Gly
625                 630                 635                 640

Gly Gly Gly Ser Gly Gly Gly Gly Gly Gly Gly Ser Gly Gly Gly

-continued

```
                645                 650                 655
Gly Ser Gly Gly Gly Ser Gly Gly Gly Ser Gly Gly Gly Gly
                660                 665                 670
Gly Gly Gly Gly Ser Gly Gly Gly Ser Gly Gly Gly Ser Gly
                675                 680                 685
Gly Gly Gly Ser Gly Gly Gly Gly Gly Gly Ser Gly Gly Gly
                690                 695                 700
Gly Ser Gly Gly Gly Ser Gly Gly Gly Ser Gly Gly Gly Gly
705                 710                 715                 720
Gly Gly Gly Gly Ser Gly Gly Gly Ser Gly Gly Gly Ser Gly
                725                 730                 735
Gly Gly Gly Ser Gly Gly Gly Gly Gly Gly Ser Gly Gly Gly
                740                 745                 750
Gly Ser Gly Gly Gly Ser Gly Gly Gly Ser Gly Gly Gly Gly
                755                 760                 765
Gly Gly Gly Gly Ser Gly Gly Gly Ser Gly Gly Gly Ser Gly
                770                 775                 780
Gly Gly Gly Ser Gly Gly Gly Gly Gly Gly Ser Gly Gly Gly
785                 790                 795                 800
Gly Ser Gly Gly Gly Ser Gly Gly Gly Ser Gly Gly Gly Gly
                805                 810                 815
Gly Gly Gly Gly Ser Gly Gly Gly Ser Gly Gly Gly Ser Gly
                820                 825                 830
Gly Gly Gly Ser Gly Gly Gly Gly Gly Gly Ser Gly Gly Gly
                835                 840                 845
Gly Ser Gly Gly Gly Ser Gly Gly Gly Ser Gly Gly Gly Gly
                850                 855                 860
Gly Gly Gly Gly Ser Gly Gly Gly Ser Gly Gly Gly Ser Gly
865                 870                 875                 880
Gly Gly Gly Ser Gly Gly Gly Gly Gly Gly Ser Gly Gly Gly
                885                 890                 895
Gly Ser Gly Gly Gly Gly Ser Gly Gly Gly Ser Gly Gly Gly
                900                 905                 910
Gly Gly Gly Gly Ser Gly Gly Gly Gly Ser Gly Gly Gly Ser Gly
                915                 920                 925
Gly Gly Gly Ser Gly Gly Gly Gly Gly Gly Ser Gly Gly Gly
                930                 935                 940
Gly Ser Gly Gly Gly Gly Ser Gly Gly Gly Ser Gly Gly Gly
945                 950                 955                 960
Gly Gly Gly Gly Ser Gly Gly Gly Ser Gly Gly Gly Ser Gly
                965                 970                 975
Gly Gly Gly Ser Gly Gly Gly Gly Gly Gly Ser Gly Gly Gly
                980                 985                 990
Gly Ser Gly Gly Gly Gly Ser Gly  Gly Gly Gly Ser Gly  Gly Gly Gly
                995                 1000                1005
Gly Gly  Gly Gly Ser Gly Gly  Gly Gly Ser Gly  Gly Gly Ser
                1010                1015                1020
Gly Gly  Gly Gly Ser Gly Gly  Gly Gly Gly Gly  Gly Ser Gly
                1025                1030                1035
Gly Gly  Gly Ser Gly Gly Gly  Gly Ser Gly Gly  Gly Ser Gly
                1040                1045                1050
Gly Gly  Gly Gly Gly Gly Gly  Ser Gly Gly Gly  Gly  Ser Gly Gly
                1055                1060                1065
```

-continued

Gly Gly Ser Gly Gly Gly Gly Ser Gly Gly Gly Gly Gly
    1070            1075             1080

Gly Ser Gly Gly Gly Gly Ser Gly Gly Gly Ser Gly Gly Gly
    1085            1090             1095

Gly Ser Gly Gly Gly Gly Gly Gly Gly Ser Gly Gly Gly Gly
    1100            1105             1110

Ser Gly Gly Gly Gly Ser Gly Gly Gly Ser Gly Gly Gly Gly
    1115            1120             1125

Gly Gly Gly Gly Ser Gly Gly Gly Gly Ser Gly Gly Gly Ser
    1130            1135             1140

Gly Gly Gly Gly Ser Gly Gly Gly Gly Gly Gly Gly Ser Gly
    1145            1150             1155

Gly Gly Gly Ser Gly Gly Gly Gly Ser Gly Gly Gly Gly Ser Gly
    1160            1165             1170

Gly Gly Gly Gly Gly Gly Ser Gly Gly Gly Ser Gly Gly
    1175            1180             1185

Gly Gly Ser Gly Gly Gly Gly Ser Gly Gly Gly Gly Gly Gly
    1190            1195             1200

Gly Ser Gly Gly Gly Gly Ser Gly Gly Gly Ser Gly Gly Gly
    1205            1210             1215

Gly Ser Gly Gly Gly Gly Gly Gly Gly Ser Gly Gly Gly Gly
    1220            1225             1230

Ser Gly Gly Gly Gly Ser Gly Gly Gly Ser Gly Gly Gly Gly
    1235            1240             1245

Gly Gly Gly Gly Ser Gly Gly Gly Gly Ser Gly Gly Gly Ser
    1250            1255             1260

Gly Gly Gly Gly Ser Gly Gly Gly Gly Gly Gly Gly Ser Gly
    1265            1270             1275

Gly Gly Gly Ser Gly Gly Gly Gly Ser Gly Gly Gly Gly Ser Gly
    1280            1285             1290

Gly Gly Gly Gly Gly Gly Gly Ser Gly Gly Gly Ser Gly Gly
    1295            1300             1305

Gly Gly Ser Gly Gly Gly Gly Ser Gly Gly Gly Gly Gly Gly
    1310            1315             1320

Gly Ser Gly Gly Gly Gly Ser Gly Gly Gly Ser Gly Gly Gly
    1325            1330             1335

Gly Ser Gly Gly Gly Gly Gly Gly Gly Ser Gly Gly Gly Gly
    1340            1345             1350

Ser Gly Gly Gly Gly Ser Gly Gly Gly Ser Gly Gly Gly Gly
    1355            1360             1365

Gly Gly Gly Gly Ser Gly Gly Gly Gly Ser Gly Gly Gly Ser
    1370            1375             1380

Gly Gly Gly Gly Ser Gly Gly Gly Gly Gly Gly Gly Ser Gly
    1385            1390             1395

Gly Gly Gly Ser Gly Gly Gly Gly Ser Gly Gly Gly Gly Ser Gly
    1400            1405             1410

Gly Gly Gly Gly Gly Gly Gly Ser Gly Gly Gly Gly Ser Gly Gly
    1415            1420             1425

Gly Gly Ser Gly Gly Gly Gly Ser Gly Gly Gly Gly Gly Gly
    1430            1435             1440

Gly Ser Gly Gly Gly Gly Ser Gly Gly Gly Ser Gly Gly Gly
    1445            1450             1455

Gly Ser Gly Gly Gly Gly Gly Gly Gly Ser Gly Gly Gly Gly
1460                1465                1470

Ser Gly Gly Gly Gly Ser Gly Gly Gly Gly Ser Gly Gly Gly Gly
1475                1480                1485

Gly Gly Gly Gly Ser Gly Gly Gly Gly Ser Gly Gly Gly Gly Ser
1490                1495                1500

Gly Gly Gly Gly Ser Gly Gly Gly Gly Gly Gly Gly Ser Gly
1505                1510                1515

Gly Gly Gly Ser Gly Gly Gly Gly Ser Gly Gly Gly Gly Ser Gly
1520                1525                1530

Gly Gly Gly Gly Gly Gly Gly Ser Gly Gly Gly Gly Ser Gly Gly
1535                1540                1545

Gly Gly Ser Gly Gly Gly Gly Ser Gly Gly Gly Gly Gly Gly Gly
1550                1555                1560

Gly Ser Gly Gly Gly Gly Ser Gly Gly Gly Gly Ser Gly Gly Gly
1565                1570                1575

Gly Ser Gly Gly Gly Gly Gly Gly Gly Ser Gly Gly Gly Gly
1580                1585                1590

Ser Gly Gly Gly Gly Ser Gly Gly Gly Gly Ser Gly Gly Gly Gly
1595                1600                1605

Gly Gly Gly Gly Ser Gly Gly Gly Gly Ser Gly Gly Gly Gly Ser
1610                1615                1620

Gly Gly Gly Gly Ser Gly Gly Gly Gly Gly Gly Gly Ser Gly
1625                1630                1635

Gly Gly Gly Ser Gly Gly Gly Gly Ser Gly Gly Gly Gly Ser Gly
1640                1645                1650

Gly Gly Gly Gly Gly Gly Gly Ser Gly Gly Gly Gly Ser Gly Gly
1655                1660                1665

Gly Gly Ser Gly Gly Gly Gly Ser Gly Gly Gly Gly Gly Gly Gly
1670                1675                1680

Gly Ser Gly Gly Gly Gly Ser Gly Gly Gly Gly Ser Gly Gly Gly
1685                1690                1695

Gly Ser Gly Gly Gly Gly Gly Gly Gly Ser Gly Gly Gly Gly
1700                1705                1710

Ser Gly Gly Gly Gly Ser Gly Gly Gly Gly Ser Gly Gly Gly Gly
1715                1720                1725

Gly Gly Gly Gly Ser Gly Gly Gly Gly Ser Gly Gly Gly Gly Ser
1730                1735                1740

Gly Gly Gly Gly Ser Gly Gly Gly Gly Gly Gly Gly Ser Gly
1745                1750                1755

Gly Gly Gly Ser Gly Gly Gly Gly Ser Gly Gly Gly Gly Ser Gly
1760                1765                1770

Gly Gly Gly Gly Gly Gly Gly Ser Gly Gly Gly Gly Ser Gly Gly
1775                1780                1785

Gly Gly Ser Gly Gly Gly Gly Ser Gly Gly Gly Gly
1790                1795                1800

<210> SEQ ID NO 9
<211> LENGTH: 2175
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(2175)
<223> OTHER INFORMATION: This sequence may encompass 1-75 "Gly Gly Gly Gly Ser Gly Gly Gly Gly Ser Gly Gly Gly Gly Ser Gly Gly Gly Gly Ser Gly Gly Gly Gly Ser Gly Gly Gly Gly" repeating units wherein some positions may not be present

<400> SEQUENCE: 9

```
Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
            20                  25                  30
Gly Ser Gly Gly Gly Ser Gly Gly Gly Ser Gly Gly Gly Gly
        35                  40                  45
Ser Gly Gly Gly Gly Ser Gly Gly Gly Gly Gly Gly Ser Gly
    50                  55                  60
Gly Gly Gly Ser Gly Gly Gly Ser Gly Gly Gly Ser Gly Gly
65                  70                  75                  80
Gly Gly Ser Gly Gly Gly Gly Gly Ser Gly Gly Gly
            85                  90                  95
Ser Gly Gly Gly Ser Gly Gly Gly Ser Gly Gly Gly Ser
            100                 105                 110
Gly Gly Gly Gly Gly Gly Gly Ser Gly Gly Gly Ser Gly Gly
            115                 120                 125
Gly Gly Ser Gly Gly Gly Ser Gly Gly Gly Ser Gly Gly Gly
        130                 135                 140
Gly Gly Gly Gly Gly Ser Gly Gly Gly Ser Gly Gly Gly Gly Ser
145                 150                 155                 160
Gly Gly Gly Gly Ser Gly Gly Gly Ser Gly Gly Gly Gly
            165                 170                 175
Gly Gly Ser Gly Gly Gly Ser Gly Gly Gly Ser Gly Gly Gly
            180                 185                 190
Gly Ser Gly Gly Gly Ser Gly Gly Gly Gly Gly Gly Ser
        195                 200                 205
Gly Gly Gly Gly Ser Gly Gly Gly Ser Gly Gly Gly Ser Gly
    210                 215                 220
Gly Gly Gly Ser Gly Gly Gly Gly Gly Ser Gly Gly Gly
225                 230                 235                 240
Gly Ser Gly Gly Gly Ser Gly Gly Gly Ser Gly Gly Gly Gly
            245                 250                 255
Ser Gly Gly Gly Gly Gly Gly Ser Gly Gly Gly Gly Ser Gly
            260                 265                 270
Gly Gly Ser Gly Gly Gly Ser Gly Gly Gly Ser Gly Gly
        275                 280                 285
Gly Gly Gly Gly Gly Gly Ser Gly Gly Gly Ser Gly Gly Gly
            290                 295                 300
Ser Gly Gly Gly Gly Ser Gly Gly Gly Ser Gly Gly Gly Gly
305                 310                 315                 320
Gly Gly Gly Ser Gly Gly Gly Ser Gly Gly Gly Ser Gly Gly
            325                 330                 335
Gly Gly Ser Gly Gly Gly Ser Gly Gly Gly Gly Gly Gly
        340                 345                 350
Ser Gly Gly Gly Gly Ser Gly Gly Gly Ser Gly Gly Gly Ser
    355                 360                 365
Gly Gly Gly Gly Ser Gly Gly Gly Gly Gly Gly Ser Gly Gly
            370                 375                 380
```

```
Gly Gly Ser Gly Gly Gly Ser Gly Gly Gly Ser Gly Gly
385                 390                 395                 400

Gly Ser Gly Gly Gly Gly Gly Gly Ser Gly Gly Gly Ser
    405                 410                 415

Gly Gly Gly Gly Ser Gly Gly Gly Ser Gly Gly Gly Ser Gly
420                 425                 430

Gly Gly Gly Gly Gly Gly Ser Gly Gly Gly Ser Gly Gly
    435                 440                 445

Gly Ser Gly Gly Gly Gly Ser Gly Gly Gly Ser Gly Gly Gly
    450                 455                 460

Gly Gly Gly Gly Ser Gly Gly Gly Ser Gly Gly Gly Ser Gly
465                 470                 475                 480

Gly Gly Gly Ser Gly Gly Gly Ser Gly Gly Gly Gly Gly
            485                 490                 495

Gly Ser Gly Gly Gly Ser Gly Gly Gly Ser Gly Gly Gly
            500                 505                 510

Ser Gly Gly Gly Gly Ser Gly Gly Gly Gly Gly Ser Gly
        515                 520                 525

Gly Gly Gly Ser Gly Gly Gly Ser Gly Gly Gly Ser Gly Gly
530                 535                 540

Gly Gly Ser Gly Gly Gly Gly Gly Gly Ser Gly Gly Gly Gly
545                 550                 555                 560

Ser Gly Gly Gly Gly Ser Gly Gly Gly Ser Gly Gly Gly Ser
            565                 570                 575

Gly Gly Gly Gly Gly Gly Gly Ser Gly Gly Gly Ser Gly Gly
            580                 585                 590

Gly Gly Ser Gly Gly Gly Ser Gly Gly Gly Ser Gly Gly Gly
        595                 600                 605

Gly Gly Gly Gly Gly Ser Gly Gly Gly Ser Gly Gly Gly Ser
        610                 615                 620

Gly Gly Gly Gly Ser Gly Gly Gly Ser Gly Gly Gly Gly Gly
625                 630                 635                 640

Gly Gly Ser Gly Gly Gly Gly Ser Gly Gly Gly Ser Gly Gly
            645                 650                 655

Gly Ser Gly Gly Gly Gly Ser Gly Gly Gly Gly Gly Gly Ser
        660                 665                 670

Gly Gly Gly Gly Ser Gly Gly Gly Ser Gly Gly Gly Ser Gly
            675                 680                 685

Gly Gly Gly Ser Gly Gly Gly Gly Gly Gly Ser Gly Gly Gly
        690                 695                 700

Gly Ser Gly Gly Gly Gly Ser Gly Gly Gly Ser Gly Gly Gly
705                 710                 715                 720

Ser Gly Gly Gly Gly Gly Gly Gly Ser Gly Gly Gly Ser Gly
        725                 730                 735

Gly Gly Gly Ser Gly Gly Gly Gly Ser Gly Gly Gly Ser Gly
            740                 745                 750

Gly Gly Gly Gly Gly Gly Ser Gly Gly Gly Ser Gly Gly Gly
            755                 760                 765

Ser Gly Gly Gly Gly Ser Gly Gly Gly Ser Gly Gly Gly Gly
        770                 775                 780

Gly Gly Gly Ser Gly Gly Gly Gly Ser Gly Gly Gly Ser Gly Gly
785                 790                 795                 800
```

Gly Gly Ser Gly Gly Gly Ser Gly Gly Gly Gly Gly Gly
            805                 810                 815

Ser Gly Gly Gly Ser Gly Gly Gly Ser Gly Gly Gly Ser
            820                 825                 830

Gly Gly Gly Gly Ser Gly Gly Gly Gly Gly Gly Ser Gly Gly
            835                 840                 845

Gly Gly Ser Gly Gly Gly Ser Gly Gly Gly Ser Gly Gly Gly
    850                 855                 860

Gly Ser Gly Gly Gly Gly Gly Gly Ser Gly Gly Gly Ser
865             870                 875                 880

Gly Gly Gly Gly Ser Gly Gly Gly Ser Gly Gly Gly Ser Gly
            885                 890                 895

Gly Gly Gly Gly Gly Gly Ser Gly Gly Gly Ser Gly Gly Gly
            900                 905                 910

Gly Ser Gly Gly Gly Ser Gly Gly Gly Ser Gly Gly Gly Gly
            915                 920                 925

Gly Gly Gly Ser Gly Gly Gly Ser Gly Gly Gly Ser Gly
    930                 935                 940

Gly Gly Gly Ser Gly Gly Gly Ser Gly Gly Gly Gly Gly
945                 950                 955                 960

Gly Ser Gly Gly Gly Gly Ser Gly Gly Gly Ser Gly Gly Gly
            965                 970                 975

Ser Gly Gly Gly Ser Gly Gly Gly Gly Gly Gly Ser Gly
            980                 985                 990

Gly Gly Gly Ser Gly Gly Gly Gly Ser Gly Gly Gly Ser Gly Gly
            995                 1000                1005

Gly Gly Ser Gly Gly Gly Gly Gly Gly Gly Ser Gly Gly Gly
    1010                1015                1020

Gly Ser Gly Gly Gly Gly Ser Gly Gly Gly Gly Ser Gly Gly Gly
    1025                1030                1035

Gly Ser Gly Gly Gly Gly Gly Gly Gly Ser Gly Gly Gly Gly
    1040                1045                1050

Ser Gly Gly Gly Gly Ser Gly Gly Gly Ser Gly Gly Gly Gly
    1055                1060                1065

Ser Gly Gly Gly Gly Gly Gly Gly Ser Gly Gly Gly Ser
    1070                1075                1080

Gly Gly Gly Gly Ser Gly Gly Gly Ser Gly Gly Gly Ser
    1085                1090                1095

Gly Gly Gly Gly Gly Gly Gly Ser Gly Gly Gly Gly Ser Gly
    1100                1105                1110

Gly Gly Gly Ser Gly Gly Gly Ser Gly Gly Gly Gly Ser Gly
    1115                1120                1125

Gly Gly Gly Gly Gly Gly Ser Gly Gly Gly Gly Ser Gly Gly
    1130                1135                1140

Gly Gly Ser Gly Gly Gly Gly Ser Gly Gly Gly Gly Ser Gly Gly
    1145                1150                1155

Gly Gly Gly Gly Gly Gly Ser Gly Gly Gly Gly Ser Gly Gly Gly
    1160                1165                1170

Gly Ser Gly Gly Gly Gly Ser Gly Gly Gly Gly Ser Gly Gly Gly
    1175                1180                1185

Gly Gly Gly Gly Gly Gly Ser Gly Gly Gly Ser Gly Gly Gly Gly
    1190                1195                1200

Ser Gly Gly Gly Gly Gly Ser Gly Gly Gly Gly Ser Gly Gly Gly Gly

-continued

Gly Gly Gly Gly Ser Gly Gly Gly Ser Gly Gly Gly Ser
1205             1210            1215

Gly Gly Gly Gly Ser Gly Gly Gly Ser Gly Gly Gly Ser
1220             1225            1230

Gly Gly Gly Gly Ser Gly Gly Gly Ser Gly Gly Gly Gly
1235             1240            1245

Gly Gly Gly Ser Gly Gly Gly Ser Gly Gly Gly Ser Gly
1250             1255            1260

Gly Gly Gly Ser Gly Gly Gly Ser Gly Gly Gly Gly Gly
1265             1270            1275

Gly Gly Ser Gly Gly Gly Gly Ser Gly Gly Gly Ser Gly Gly
1280             1285            1290

Gly Gly Ser Gly Gly Gly Gly Ser Gly Gly Gly Gly Gly Gly
1295             1300            1305

Gly Ser Gly Gly Gly Gly Ser Gly Gly Gly Gly Ser Gly Gly Gly
1310             1315            1320

Gly Ser Gly Gly Gly Gly Ser Gly Gly Gly Gly Gly Gly Gly Gly
1325             1330            1335

Ser Gly Gly Gly Gly Ser Gly Gly Gly Ser Gly Gly Gly Gly
1340             1345            1350

Ser Gly Gly Gly Gly Ser Gly Gly Gly Gly Gly Gly Gly Ser
1355             1360            1365

Gly Gly Gly Gly Ser Gly Gly Gly Gly Ser Gly Gly Gly Ser
1370             1375            1380

Gly Gly Gly Gly Ser Gly Gly Gly Gly Gly Gly Gly Ser Gly
1385             1390            1395

Gly Gly Gly Ser Gly Gly Gly Gly Ser Gly Gly Gly Ser Gly
1400             1405            1410

Gly Gly Gly Ser Gly Gly Gly Gly Gly Gly Gly Ser Gly Gly
1415             1420            1425

Gly Gly Ser Gly Gly Gly Gly Ser Gly Gly Gly Ser Gly Gly
1430             1435            1440

Gly Gly Ser Gly Gly Gly Gly Gly Gly Gly Gly Ser Gly Gly Gly
1445             1450            1455

Gly Ser Gly Gly Gly Gly Ser Gly Gly Gly Gly Ser Gly Gly Gly
1460             1465            1470

Gly Ser Gly Gly Gly Gly Gly Gly Gly Gly Ser Gly Gly Gly Gly
1475             1480            1485

Ser Gly Gly Gly Gly Ser Gly Gly Gly Ser Gly Gly Gly Gly
1490             1495            1500

Ser Gly Gly Gly Gly Gly Gly Gly Ser Gly Gly Gly Ser
1505             1510            1515

Gly Gly Gly Gly Ser Gly Gly Gly Gly Ser Gly Gly Gly Ser
1520             1525            1530

Gly Gly Gly Gly Gly Gly Gly Ser Gly Gly Gly Gly Ser Gly
1535             1540            1545

Gly Gly Gly Ser Gly Gly Gly Gly Ser Gly Gly Gly Gly Ser Gly
1550             1555            1560

Gly Gly Gly Gly Gly Gly Ser Gly Gly Gly Ser Gly Gly
1565             1570            1575

Gly Gly Ser Gly Gly Gly Gly Ser Gly Gly Gly Gly Ser Gly Gly
1580             1585            1590

Gly Gly Gly Gly Gly Gly Ser Gly Gly Gly Gly Ser Gly Gly Gly
1595             1600            1605

Gly Ser Gly Gly Gly Gly Ser Gly Gly Gly Ser Gly Gly
1610             1615             1620

Gly Gly Gly Gly Gly Ser Gly Gly Gly Gly Ser Gly Gly Gly
1625             1630             1635

Ser Gly Gly Gly Gly Ser Gly Gly Gly Gly Ser Gly Gly Gly
1640             1645             1650

Gly Gly Gly Gly Ser Gly Gly Gly Gly Ser Gly Gly Gly Ser
1655             1660             1665

Gly Gly Gly Gly Ser Gly Gly Gly Gly Ser Gly Gly Gly Gly
1670             1675             1680

Gly Gly Gly Ser Gly Gly Gly Gly Ser Gly Gly Gly Ser Gly
1685             1690             1695

Gly Gly Gly Ser Gly Gly Gly Gly Ser Gly Gly Gly Gly Gly
1700             1705             1710

Gly Gly Ser Gly Gly Gly Gly Ser Gly Gly Gly Gly Ser Gly Gly
1715             1720             1725

Gly Gly Ser Gly Gly Gly Gly Ser Gly Gly Gly Gly Gly Gly Gly
1730             1735             1740

Gly Ser Gly Gly Gly Gly Ser Gly Gly Gly Gly Ser Gly Gly Gly
1745             1750             1755

Gly Ser Gly Gly Gly Gly Ser Gly Gly Gly Gly Gly Gly Gly Gly
1760             1765             1770

Ser Gly Gly Gly Gly Ser Gly Gly Gly Gly Ser Gly Gly Gly Gly
1775             1780             1785

Ser Gly Gly Gly Gly Ser Gly Gly Gly Gly Gly Gly Gly Ser
1790             1795             1800

Gly Gly Gly Gly Ser Gly Gly Gly Gly Ser Gly Gly Gly Gly Ser
1805             1810             1815

Gly Gly Gly Gly Ser Gly Gly Gly Gly Gly Gly Gly Ser Gly
1820             1825             1830

Gly Gly Gly Ser Gly Gly Gly Gly Ser Gly Gly Gly Gly Ser Gly
1835             1840             1845

Gly Gly Gly Ser Gly Gly Gly Gly Gly Gly Gly Ser Gly Gly
1850             1855             1860

Gly Gly Ser Gly Gly Gly Gly Ser Gly Gly Gly Gly Ser Gly Gly
1865             1870             1875

Gly Gly Ser Gly Gly Gly Gly Gly Gly Gly Gly Ser Gly Gly Gly
1880             1885             1890

Gly Ser Gly Gly Gly Gly Ser Gly Gly Gly Gly Ser Gly Gly Gly
1895             1900             1905

Gly Ser Gly Gly Gly Gly Gly Gly Gly Gly Ser Gly Gly Gly Gly
1910             1915             1920

Ser Gly Gly Gly Gly Ser Gly Gly Gly Gly Ser Gly Gly Gly Gly
1925             1930             1935

Ser Gly Gly Gly Gly Gly Gly Gly Ser Gly Gly Gly Gly Ser
1940             1945             1950

Gly Gly Gly Gly Ser Gly Gly Gly Gly Ser Gly Gly Gly Gly Ser
1955             1960             1965

Gly Gly Gly Gly Gly Gly Gly Ser Gly Gly Gly Gly Ser Gly
1970             1975             1980

Gly Gly Gly Ser Gly Gly Gly Gly Ser Gly Gly Gly Gly Ser Gly
1985             1990             1995

Gly Gly Gly Gly Gly Gly Gly Ser Gly Gly Gly Gly Ser Gly Gly
        2000                2005                2010

Gly Gly Ser Gly Gly Gly Gly Ser Gly Gly Gly Gly Ser Gly Gly
        2015                2020                2025

Gly Gly Gly Gly Gly Ser Gly Gly Gly Gly Ser Gly Gly Gly
        2030                2035                2040

Gly Ser Gly Gly Gly Gly Ser Gly Gly Gly Gly Ser Gly Gly Gly
        2045                2050                2055

Gly Gly Gly Gly Ser Gly Gly Gly Gly Ser Gly Gly Gly Gly
        2060                2065                2070

Ser Gly Gly Gly Gly Ser Gly Gly Gly Gly Ser Gly Gly Gly Gly
        2075                2080                2085

Gly Gly Gly Gly Ser Gly Gly Gly Gly Ser Gly Gly Gly Gly Ser
        2090                2095                2100

Gly Gly Gly Gly Ser Gly Gly Gly Gly Ser Gly Gly Gly Gly Gly
        2105                2110                2115

Gly Gly Gly Ser Gly Gly Gly Gly Ser Gly Gly Gly Gly Ser Gly
        2120                2125                2130

Gly Gly Gly Ser Gly Gly Gly Gly Ser Gly Gly Gly Gly Gly Gly
        2135                2140                2145

Gly Gly Ser Gly Gly Gly Gly Ser Gly Gly Gly Gly Ser Gly Gly
        2150                2155                2160

Gly Gly Ser Gly Gly Gly Gly Ser Gly Gly Gly Gly
        2165                2170                2175

<210> SEQ ID NO 10
<211> LENGTH: 2550
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(2550)
<223> OTHER INFORMATION: This sequence may encompass 1-75 "Gly Gly Gly
      Gly Ser Gly Gly Gly Gly Ser Gly Gly Gly Gly Ser Gly Gly Gly Gly
      Ser Gly Gly Gly Gly Ser Gly Gly Gly Gly Ser Gly Gly Gly Gly"
      repeating units wherein some positions may not be present

<400> SEQUENCE: 10

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Gly Gly Gly Ser Gly Gly Gly Gly Ser Gly Gly Gly Gly
        35                  40                  45

Ser Gly Gly Gly Gly Ser Gly Gly Gly Gly Ser Gly Gly Gly Ser
    50                  55                  60

Gly Gly Gly Gly Gly Gly Gly Ser Gly Gly Gly Gly Ser Gly Gly
65                  70                  75                  80

Gly Gly Ser Gly Gly Gly Gly Ser Gly Gly Gly Gly Ser Gly Gly
            85                  90                  95

Gly Ser Gly Gly Gly Gly Gly Gly Gly Ser Gly Gly Gly Gly Ser
            100                 105                 110

Gly Gly Gly Gly Ser Gly Gly Gly Gly Ser Gly Gly Gly Ser Gly
        115                 120                 125

Gly Gly Gly Ser Gly Gly Gly Gly Gly Gly Gly Gly Ser Gly Gly Gly

```
                130                 135                 140
Gly Ser Gly Gly Gly Gly Ser Gly Gly Gly Ser Gly Gly Gly
145                 150                 155                 160

Ser Gly Gly Gly Gly Ser Gly Gly Gly Gly Gly Gly Ser Gly
                165                 170                 175

Gly Gly Gly Ser Gly Gly Gly Gly Ser Gly Gly Gly Ser Gly
            180                 185                 190

Gly Gly Ser Gly Gly Gly Gly Ser Gly Gly Gly Gly Gly Gly
        195                 200                 205

Ser Gly Gly Gly Gly Ser Gly Gly Gly Ser Gly Gly Gly Ser
    210                 215                 220

Gly Gly Gly Gly Ser Gly Gly Gly Gly Ser Gly Gly Gly Gly
225                 230                 235                 240

Gly Gly Ser Gly Gly Gly Gly Ser Gly Gly Gly Ser Gly Gly
                245                 250                 255

Gly Gly Ser Gly Gly Gly Gly Ser Gly Gly Gly Ser Gly Gly
            260                 265                 270

Gly Gly Gly Gly Ser Gly Gly Gly Ser Gly Gly Gly Ser Gly
        275                 280                 285

Gly Gly Gly Ser Gly Gly Gly Ser Gly Gly Gly Ser Gly Gly
    290                 295                 300

Gly Gly Gly Gly Gly Ser Gly Gly Gly Ser Gly Gly Gly Gly
305                 310                 315                 320

Ser Gly Gly Gly Gly Ser Gly Gly Gly Ser Gly Gly Gly Ser
                325                 330                 335

Gly Gly Gly Gly Gly Gly Gly Ser Gly Gly Gly Ser Gly Gly
            340                 345                 350

Gly Gly Ser Gly Gly Gly Ser Gly Gly Gly Ser Gly Gly Gly
        355                 360                 365

Gly Ser Gly Gly Gly Gly Gly Gly Ser Gly Gly Gly Gly Ser
    370                 375                 380

Gly Gly Gly Gly Ser Gly Gly Gly Ser Gly Gly Gly Ser Gly
385                 390                 395                 400

Gly Gly Gly Ser Gly Gly Gly Gly Gly Gly Ser Gly Gly Gly
                405                 410                 415

Gly Ser Gly Gly Gly Gly Ser Gly Gly Gly Ser Gly Gly Gly
            420                 425                 430

Ser Gly Gly Gly Gly Ser Gly Gly Gly Gly Gly Gly Ser Gly
        435                 440                 445

Gly Gly Gly Ser Gly Gly Gly Ser Gly Gly Gly Ser Gly Gly
    450                 455                 460

Gly Gly Ser Gly Gly Gly Ser Gly Gly Gly Gly Gly Gly Gly
465                 470                 475                 480

Ser Gly Gly Gly Gly Ser Gly Gly Gly Ser Gly Gly Gly Ser
                485                 490                 495

Gly Gly Gly Gly Ser Gly Gly Gly Gly Ser Gly Gly Gly Gly
            500                 505                 510

Gly Gly Ser Gly Gly Gly Gly Ser Gly Gly Gly Ser Gly Gly
        515                 520                 525

Gly Ser Gly Gly Gly Ser Gly Gly Gly Ser Gly Gly Gly Gly
    530                 535                 540

Gly Gly Gly Gly Ser Gly Gly Gly Gly Ser Gly Gly Gly Ser Gly
545                 550                 555                 560
```

```
Gly Gly Gly Ser Gly Gly Gly Ser Gly Gly Gly Ser Gly Gly
            565             570             575
Gly Gly Gly Gly Gly Gly Ser Gly Gly Gly Ser Gly Gly Gly
                580             585             590
Ser Gly Gly Gly Gly Ser Gly Gly Gly Ser Gly Gly Gly Ser
    595             600             605
Gly Gly Gly Gly Gly Gly Gly Ser Gly Gly Gly Ser Gly Gly
        610             615             620
Gly Gly Ser Gly Gly Gly Ser Gly Gly Gly Ser Gly Gly Gly
625             630             635             640
Gly Ser Gly Gly Gly Gly Gly Gly Ser Gly Gly Gly Gly Ser
        645             650             655
Gly Gly Gly Gly Ser Gly Gly Gly Ser Gly Gly Gly Ser Gly
            660             665             670
Gly Gly Gly Ser Gly Gly Gly Gly Gly Gly Ser Gly Gly Gly
            675             680             685
Gly Ser Gly Gly Gly Ser Gly Gly Gly Ser Gly Gly Gly Gly
    690             695             700
Ser Gly Gly Gly Ser Gly Gly Gly Gly Gly Gly Ser Gly Gly
705             710             715             720
Gly Gly Ser Gly Gly Gly Gly Ser Gly Gly Gly Ser Gly Gly
            725             730             735
Gly Gly Ser Gly Gly Gly Ser Gly Gly Gly Gly Gly Gly Gly
            740             745             750
Ser Gly Gly Gly Ser Gly Gly Gly Ser Gly Gly Gly Gly Ser
    755             760             765
Gly Gly Gly Gly Ser Gly Gly Gly Ser Gly Gly Gly Gly Gly
770             775             780
Gly Gly Ser Gly Gly Gly Ser Gly Gly Gly Ser Gly Gly Gly
785             790             795             800
Gly Ser Gly Gly Gly Gly Ser Gly Gly Gly Ser Gly Gly Gly
        805             810             815
Gly Gly Gly Gly Ser Gly Gly Gly Ser Gly Gly Gly Ser Gly
            820             825             830
Gly Gly Gly Ser Gly Gly Gly Ser Gly Gly Gly Ser Gly Gly
            835             840             845
Gly Gly Gly Gly Gly Ser Gly Gly Gly Ser Gly Gly Gly Gly
        850             855             860
Ser Gly Gly Gly Gly Ser Gly Gly Gly Gly Ser Gly Gly Ser
865             870             875             880
Gly Gly Gly Gly Gly Gly Gly Ser Gly Gly Gly Ser Gly Gly
            885             890             895
Gly Gly Ser Gly Gly Gly Ser Gly Gly Gly Ser Gly Gly Gly
            900             905             910
Gly Ser Gly Gly Gly Gly Gly Gly Gly Ser Gly Gly Gly Ser
        915             920             925
Gly Gly Gly Gly Ser Gly Gly Gly Ser Gly Gly Gly Ser Gly
            930             935             940
Gly Gly Ser Gly Gly Gly Gly Gly Gly Gly Ser Gly Gly Gly
945             950             955             960
Gly Ser Gly Gly Gly Gly Ser Gly Gly Gly Ser Gly Gly Gly
        965             970             975
```

```
Ser Gly Gly Gly Gly Ser Gly Gly Gly Gly Gly Gly Ser Gly
        980                 985                 990

Gly Gly Gly Ser Gly Gly Gly Gly  Ser Gly Gly Gly  Ser Gly Gly
        995                 1000                1005

Gly Gly  Ser Gly Gly Gly Gly  Ser Gly Gly Gly  Gly Gly Gly
        1010                1015                1020

Gly Ser  Gly Gly Gly Gly Ser  Gly Gly Gly Gly Ser  Gly Gly Gly
        1025                1030                1035

Gly Ser  Gly Gly Gly Gly Ser  Gly Gly Gly Gly Ser  Gly Gly Gly
        1040                1045                1050

Gly Gly  Gly Gly Gly Ser Gly  Gly Gly Ser Gly  Gly Gly Gly
        1055                1060                1065

Ser Gly  Gly Gly Gly Ser Gly  Gly Gly Ser Gly  Gly Gly Gly
        1070                1075                1080

Ser Gly  Gly Gly Gly Gly Gly  Gly Gly Ser Gly  Gly Gly Ser
        1085                1090                1095

Gly Gly  Gly Gly Ser Gly Gly  Gly Gly Ser Gly Gly  Gly Gly Ser
        1100                1105                1110

Gly Gly  Gly Gly Ser Gly Gly  Gly Gly Gly Gly  Gly Ser Gly
        1115                1120                1125

Gly Gly  Gly Ser Gly Gly Gly  Gly Ser Gly Gly Gly  Gly Ser Gly
        1130                1135                1140

Gly Gly  Gly Ser Gly Gly Gly  Gly Ser Gly Gly Gly  Gly Gly Gly
        1145                1150                1155

Gly Gly  Ser Gly Gly Gly Gly  Ser Gly Gly Gly Gly  Ser Gly Gly
        1160                1165                1170

Gly Gly  Ser Gly Gly Gly Gly  Ser Gly Gly Gly Gly  Ser Gly Gly
        1175                1180                1185

Gly Gly  Gly Gly Gly Ser  Gly Gly Gly Ser  Gly Gly Gly
        1190                1195                1200

Gly Ser  Gly Gly Gly Gly Ser  Gly Gly Gly Gly Ser  Gly Gly Gly
        1205                1210                1215

Gly Ser  Gly Gly Gly Gly Gly  Gly Gly Gly Ser Gly  Gly Gly Gly
        1220                1225                1230

Ser Gly  Gly Gly Gly Ser Gly  Gly Gly Gly Ser Gly  Gly Gly Gly
        1235                1240                1245

Ser Gly  Gly Gly Gly Ser Gly  Gly Gly Gly Gly Gly  Gly Gly Ser
        1250                1255                1260

Gly Gly  Gly Gly Ser Gly Gly  Gly Gly Ser Gly Gly  Gly Gly Ser
        1265                1270                1275

Gly Gly  Gly Gly Ser Gly Gly  Gly Gly Ser Gly Gly  Gly Gly Gly
        1280                1285                1290

Gly Gly  Gly Ser Gly Gly Gly  Gly Ser Gly Gly Gly  Gly Ser Gly
        1295                1300                1305

Gly Gly  Gly Ser Gly Gly Gly  Gly Ser Gly Gly Gly  Gly Ser Gly
        1310                1315                1320

Gly Gly  Gly Gly Gly Gly Gly  Ser Gly Gly Gly  Ser Gly Gly
        1325                1330                1335

Gly Gly  Ser Gly Gly Gly Gly  Ser Gly Gly Gly Gly  Ser Gly Gly
        1340                1345                1350

Gly Gly  Ser Gly Gly Gly Gly  Gly Gly Gly Gly Ser  Gly Gly Gly
        1355                1360                1365

Gly Ser  Gly Gly Gly Gly Ser  Gly Gly Gly Gly Ser  Gly Gly Gly
```

```
                      1370                1375                1380

Gly Ser Gly Gly Gly Gly Ser Gly Gly Gly Gly Gly Gly Gly
    1385                1390                1395

Ser Gly Gly Gly Gly Ser Gly Gly Gly Ser Gly Gly Gly Gly
    1400                1405                1410

Ser Gly Gly Gly Gly Ser Gly Gly Gly Ser Gly Gly Gly Gly
    1415                1420                1425

Gly Gly Gly Gly Ser Gly Gly Gly Gly Ser Gly Gly Gly Ser
    1430                1435                1440

Gly Gly Gly Gly Ser Gly Gly Gly Gly Ser Gly Gly Gly Ser
    1445                1450                1455

Gly Gly Gly Gly Gly Gly Gly Gly Ser Gly Gly Gly Ser Gly
    1460                1465                1470

Gly Gly Gly Ser Gly Gly Gly Gly Ser Gly Gly Gly Ser Gly
    1475                1480                1485

Gly Gly Gly Ser Gly Gly Gly Gly Gly Gly Gly Ser Gly Gly
    1490                1495                1500

Gly Gly Ser Gly Gly Gly Gly Ser Gly Gly Gly Ser Gly Gly
    1505                1510                1515

Gly Gly Ser Gly Gly Gly Gly Ser Gly Gly Gly Gly Gly Gly
    1520                1525                1530

Gly Ser Gly Gly Gly Gly Ser Gly Gly Gly Gly Ser Gly Gly Gly
    1535                1540                1545

Gly Ser Gly Gly Gly Gly Ser Gly Gly Gly Gly Ser Gly Gly Gly
    1550                1555                1560

Gly Gly Gly Gly Gly Ser Gly Gly Gly Gly Ser Gly Gly Gly Gly
    1565                1570                1575

Ser Gly Gly Gly Gly Ser Gly Gly Gly Ser Gly Gly Gly Gly
    1580                1585                1590

Ser Gly Gly Gly Gly Gly Gly Gly Ser Gly Gly Gly Gly Ser
    1595                1600                1605

Gly Gly Gly Gly Ser Gly Gly Gly Gly Ser Gly Gly Gly Ser
    1610                1615                1620

Gly Gly Gly Gly Ser Gly Gly Gly Gly Gly Gly Gly Ser Gly
    1625                1630                1635

Gly Gly Gly Ser Gly Gly Gly Gly Ser Gly Gly Gly Ser Gly
    1640                1645                1650

Gly Gly Gly Ser Gly Gly Gly Gly Ser Gly Gly Gly Gly Gly Gly
    1655                1660                1665

Gly Gly Ser Gly Gly Gly Gly Ser Gly Gly Gly Gly Ser Gly Gly
    1670                1675                1680

Gly Gly Ser Gly Gly Gly Gly Ser Gly Gly Gly Gly Ser Gly Gly
    1685                1690                1695

Gly Gly Gly Gly Gly Gly Ser Gly Gly Gly Gly Ser Gly Gly Gly
    1700                1705                1710

Gly Ser Gly Gly Gly Gly Ser Gly Gly Gly Gly Ser Gly Gly Gly
    1715                1720                1725

Gly Ser Gly Gly Gly Gly Gly Gly Gly Gly Ser Gly Gly Gly Gly
    1730                1735                1740

Ser Gly Gly Gly Gly Ser Gly Gly Gly Gly Ser Gly Gly Gly Gly
    1745                1750                1755

Ser Gly Gly Gly Gly Ser Gly Gly Gly Gly Gly Gly Gly Ser
    1760                1765                1770
```

```
Gly Gly Gly Gly Ser Gly Gly  Gly Gly Ser Gly  Gly Gly Ser
    1775            1780              1785

Gly Gly Gly Gly Ser Gly Gly  Gly Ser Gly Gly   Gly Gly Gly
    1790            1795              1800

Gly Gly Gly Ser Gly Gly Gly  Ser Gly Gly Gly   Ser Gly Gly
    1805            1810              1815

Gly Gly Gly Ser Gly Gly Gly  Ser Gly Gly Gly   Gly Ser Gly
    1820            1825              1830

Gly Gly Gly Gly Gly Gly Gly  Ser Gly Gly Gly   Ser Gly Gly
    1835            1840              1845

Gly Gly Ser Gly Gly Gly Gly  Ser Gly Gly Gly   Ser Gly Gly
    1850            1855              1860

Gly Gly Ser Gly Gly Gly Gly  Gly Gly Gly Ser   Gly Gly Gly
    1865            1870              1875

Gly Ser Gly Gly Gly Gly Ser  Gly Gly Gly Ser   Gly Gly Gly
    1880            1885              1890

Gly Ser Gly Gly Gly Gly Ser  Gly Gly Gly Gly   Gly Gly Gly
    1895            1900              1905

Ser Gly Gly Gly Gly Ser Gly  Gly Gly Gly Ser Gly  Gly Gly Gly
    1910            1915              1920

Ser Gly Gly Gly Gly Ser Gly  Gly Gly Gly Ser Gly  Gly Gly Gly
    1925            1930              1935

Gly Gly Gly Gly Ser Gly Gly  Gly Gly Ser Gly   Gly Gly Ser
    1940            1945              1950

Gly Gly Gly Gly Ser Gly Gly  Gly Gly Ser Gly   Gly Gly Ser
    1955            1960              1965

Gly Gly Gly Gly Gly Gly Gly  Gly Ser Gly Gly   Gly Gly Ser Gly
    1970            1975              1980

Gly Gly Gly Ser Gly Gly Gly  Gly Ser Gly Gly   Gly Gly Ser Gly
    1985            1990              1995

Gly Gly Gly Ser Gly Gly Gly  Gly Gly Gly Gly   Ser Gly Gly
    2000            2005              2010

Gly Gly Ser Gly Gly Gly Gly  Ser Gly Gly Gly   Ser Gly Gly
    2015            2020              2025

Gly Gly Ser Gly Gly Gly Gly  Ser Gly Gly Gly   Gly Gly Gly
    2030            2035              2040

Gly Ser Gly Gly Gly Gly Ser  Gly Gly Gly Gly Ser  Gly Gly Gly
    2045            2050              2055

Gly Ser Gly Gly Gly Gly Ser  Gly Gly Gly Gly Ser  Gly Gly Gly
    2060            2065              2070

Gly Gly Gly Gly Gly Ser Gly  Gly Gly Gly Ser Gly  Gly Gly Gly
    2075            2080              2085

Ser Gly Gly Gly Gly Ser Gly  Gly Gly Gly Ser Gly  Gly Gly Gly
    2090            2095              2100

Ser Gly Gly Gly Gly Gly Gly  Gly Gly Ser Gly   Gly Gly Ser
    2105            2110              2115

Gly Gly Gly Gly Ser Gly Gly  Gly Gly Ser Gly   Gly Gly Ser
    2120            2125              2130

Gly Gly Gly Gly Ser Gly Gly  Gly Gly Gly Gly   Gly Ser Gly
    2135            2140              2145

Gly Gly Gly Ser Gly Gly Gly  Gly Ser Gly Gly   Gly Gly Ser Gly
    2150            2155              2160
```

```
Gly Gly Gly Ser Gly Gly Gly  Ser Gly Gly Gly  Gly Gly Gly
    2165                2170                2175

Gly Gly Ser Gly Gly Gly Gly  Ser Gly Gly Gly  Ser Gly Gly
    2180                2185                2190

Gly Gly Ser Gly Gly Gly Gly  Ser Gly Gly Gly  Ser Gly Gly
    2195                2200                2205

Gly Gly Gly Gly Gly Gly Ser  Gly Gly Gly Ser  Gly Gly Gly
    2210                2215                2220

Gly Ser Gly Gly Gly Gly Ser  Gly Gly Gly Ser  Gly Gly Gly
    2225                2230                2235

Gly Ser Gly Gly Gly Gly Gly  Gly Gly Ser Gly  Gly Gly Gly
    2240                2245                2250

Ser Gly Gly Gly Gly Ser Gly  Gly Gly Ser Gly  Gly Gly Gly
    2255                2260                2265

Ser Gly Gly Gly Gly Ser Gly  Gly Gly Gly Gly  Gly Gly Ser
    2270                2275                2280

Gly Gly Gly Gly Ser Gly Gly  Gly Gly Ser Gly  Gly Gly Gly Ser
    2285                2290                2295

Gly Gly Gly Gly Ser Gly Gly  Gly Gly Ser Gly  Gly Gly Gly
    2300                2305                2310

Gly Gly Gly Ser Gly Gly Gly  Gly Ser Gly Gly  Gly Gly Ser Gly
    2315                2320                2325

Gly Gly Gly Ser Gly Gly Gly  Gly Ser Gly Gly  Gly Gly Ser Gly
    2330                2335                2340

Gly Gly Gly Gly Gly Gly Gly  Ser Gly Gly Gly  Ser Gly Gly
    2345                2350                2355

Gly Gly Ser Gly Gly Gly Gly  Ser Gly Gly Gly  Ser Gly Gly
    2360                2365                2370

Gly Gly Ser Gly Gly Gly Gly  Gly Gly Gly Ser  Gly Gly Gly
    2375                2380                2385

Gly Ser Gly Gly Gly Gly Ser  Gly Gly Gly Ser  Gly Gly Gly
    2390                2395                2400

Gly Ser Gly Gly Gly Gly Ser  Gly Gly Gly Gly  Gly Gly Gly
    2405                2410                2415

Ser Gly Gly Gly Gly Ser Gly  Gly Gly Ser Gly  Gly Gly Gly
    2420                2425                2430

Ser Gly Gly Gly Gly Ser Gly  Gly Gly Ser Gly  Gly Gly Gly
    2435                2440                2445

Gly Gly Gly Gly Ser Gly Gly  Gly Gly Ser Gly  Gly Gly Gly Ser
    2450                2455                2460

Gly Gly Gly Gly Ser Gly Gly  Gly Gly Ser Gly  Gly Gly Gly Ser
    2465                2470                2475

Gly Gly Gly Gly Gly Gly Gly  Gly Ser Gly Gly  Gly Gly Ser Gly
    2480                2485                2490

Gly Gly Gly Ser Gly Gly Gly  Gly Ser Gly Gly  Gly Gly Ser Gly
    2495                2500                2505

Gly Gly Gly Ser Gly Gly Gly  Gly Gly Gly Gly  Ser Gly Gly
    2510                2515                2520

Gly Gly Ser Gly Gly Gly Gly  Ser Gly Gly Gly  Ser Gly Gly
    2525                2530                2535

Gly Gly Ser Gly Gly Gly Gly  Ser Gly Gly Gly  Gly
    2540                2545                2550
```

```
<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Gly
1

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Lys Gly Gly Gly Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Gly Asn Gly Ser Gly Gly
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Gly Cys Gly Gly Gly Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16
```

Gly Pro Asn Gly Gly
1               5

<210> SEQ ID NO 17
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(150)
<223> OTHER INFORMATION: This sequence may encompass 1-75 "Gly Glu"
      repeating units wherein some positions may not be present

<400> SEQUENCE: 17

Gly Glu Gly Glu Gly Glu Gly Glu Gly Glu Gly Glu Gly Glu Gly Glu
1               5                   10                  15

Gly Glu Gly Glu Gly Glu Gly Glu Gly Glu Gly Glu Gly Glu Gly Glu
            20                  25                  30

Gly Glu Gly Glu Gly Glu Gly Glu Gly Glu Gly Glu Gly Glu Gly Glu
        35                  40                  45

Gly Glu Gly Glu Gly Glu Gly Glu Gly Glu Gly Glu Gly Glu Gly Glu
    50                  55                  60

Gly Glu Gly Glu Gly Glu Gly Glu Gly Glu Gly Glu Gly Glu Gly Glu
65                  70                  75                  80

Gly Glu Gly Glu Gly Glu Gly Glu Gly Glu Gly Glu Gly Glu Gly Glu
                85                  90                  95

Gly Glu Gly Glu Gly Glu Gly Glu Gly Glu Gly Glu Gly Glu Gly Glu
            100                 105                 110

Gly Glu Gly Glu Gly Glu Gly Glu Gly Glu Gly Glu Gly Glu Gly Glu
        115                 120                 125

Gly Glu Gly Glu Gly Glu Gly Glu Gly Glu Gly Glu Gly Glu Gly Glu
    130                 135                 140

Gly Glu Gly Glu Gly Glu
145                 150

<210> SEQ ID NO 18
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(225)
<223> OTHER INFORMATION: This sequence may encompass 1-75 "Gly Gly Glu"
      repeating units wherein some positions may not be present

<400> SEQUENCE: 18

Gly Gly Glu Gly Gly Glu Gly Gly Glu Gly Gly Glu Gly Gly Glu Gly
1               5                   10                  15

Gly Glu Gly Gly Glu Gly Gly Glu Gly Gly Glu Gly Gly Glu Gly Gly
            20                  25                  30

Glu Gly Gly Glu Gly Gly Glu Gly Gly Glu Gly Gly Glu Gly Gly Glu
        35                  40                  45

Gly Gly Glu Gly Gly Glu Gly Gly Glu Gly Gly Glu Gly Gly Glu Gly
    50                  55                  60

Gly Glu Gly Gly Glu Gly Gly Glu Gly Gly Glu Gly Gly Glu Gly Gly

```
                65                  70                  75                  80
Glu Gly Gly Glu Gly Gly Gly Glu Gly Gly Glu Gly Gly Gly Glu
                    85                  90                  95
Gly Gly Glu Gly Gly Glu Gly Gly Gly Glu Gly Gly Gly Glu Gly
                    100                 105                 110
Gly Gly Glu Gly Gly Gly Glu Gly Gly Glu Gly Gly Gly Glu Gly
                    115                 120                 125
Glu Gly Gly Glu Gly Gly Gly Glu Gly Gly Glu Gly Gly Gly Glu
            130                 135                 140
Gly Gly Glu Gly Gly Glu Gly Gly Gly Glu Gly Gly Gly Glu Gly
145                 150                 155                 160
Gly Gly Glu Gly Gly Glu Gly Gly Gly Glu Gly Gly Glu Gly Gly
                    165                 170                 175
Glu Gly Gly Glu Gly Gly Glu Gly Gly Gly Glu Gly Gly Gly Glu
                    180                 185                 190
Gly Gly Glu Gly Gly Glu Gly Gly Gly Glu Gly Gly Gly Glu Gly
                    195                 200                 205
Gly Glu Gly Gly Glu Gly Gly Glu Gly Gly Glu Gly Gly Glu Gly
            210                 215                 220
Glu
225

<210> SEQ ID NO 19
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(300)
<223> OTHER INFORMATION: This sequence may encompass 1-75 "Gly Gly Gly
      Glu" repeating units wherein some positions may not be present

<400> SEQUENCE: 19

Gly Gly Gly Glu Gly Gly Gly Glu Gly Gly Gly Glu Gly Gly Gly Glu
1               5                   10                  15
Gly Gly Gly Glu Gly Gly Gly Glu Gly Gly Gly Glu Gly Gly Gly Glu
            20                  25                  30
Gly Gly Gly Glu Gly Gly Gly Glu Gly Gly Gly Glu Gly Gly Gly Glu
        35                  40                  45
Gly Gly Gly Glu Gly Gly Gly Glu Gly Gly Gly Glu Gly Gly Gly Glu
    50                  55                  60
Gly Gly Gly Glu Gly Gly Gly Glu Gly Gly Gly Glu Gly Gly Gly Glu
65                  70                  75                  80
Gly Gly Gly Glu Gly Gly Gly Glu Gly Gly Gly Glu Gly Gly Gly Glu
                85                  90                  95
Gly Gly Gly Glu Gly Gly Gly Glu Gly Gly Gly Glu Gly Gly Gly Glu
            100                 105                 110
Gly Gly Gly Glu Gly Gly Gly Glu Gly Gly Gly Glu Gly Gly Gly Glu
        115                 120                 125
Gly Gly Gly Glu Gly Gly Gly Glu Gly Gly Gly Glu Gly Gly Gly Glu
    130                 135                 140
Gly Gly Gly Glu Gly Gly Gly Glu Gly Gly Gly Glu Gly Gly Gly Glu
145                 150                 155                 160
Gly Gly Gly Glu Gly Gly Gly Glu Gly Gly Gly Glu Gly Gly Gly Glu
```

```
                        165                 170                 175
Gly Gly Gly Glu Gly Gly Gly Glu Gly Gly Gly Glu Gly Gly Gly Glu
                180                 185                 190

Gly Gly Gly Glu Gly Gly Gly Glu Gly Gly Gly Glu Gly Gly Gly Glu
                195                 200                 205

Gly Gly Gly Glu Gly Gly Gly Glu Gly Gly Gly Glu Gly Gly Gly Glu
                210                 215                 220

Gly Gly Gly Glu Gly Gly Gly Glu Gly Gly Gly Glu Gly Gly Gly Glu
225                 230                 235                 240

Gly Gly Gly Glu Gly Gly Gly Glu Gly Gly Gly Glu Gly Gly Gly Glu
                245                 250                 255

Gly Gly Gly Glu Gly Gly Gly Glu Gly Gly Gly Glu Gly Gly Gly Glu
                260                 265                 270

Gly Gly Gly Glu Gly Gly Gly Glu Gly Gly Gly Glu Gly Gly Gly Glu
                275                 280                 285

Gly Gly Gly Glu Gly Gly Gly Glu Gly Gly Gly Glu
                290                 295                 300

<210> SEQ ID NO 20
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(375)
<223> OTHER INFORMATION: This sequence may encompass 1-75 "Gly Gly Gly
      Gly Glu" repeating units wherein some positions may not be present

<400> SEQUENCE: 20

Gly Gly Gly Gly Glu Gly Gly Gly Glu Gly Gly Gly Glu Gly
1               5                   10                  15

Gly Gly Gly Glu Gly Gly Gly Glu Gly Gly Gly Glu Gly Gly
                20                  25                  30

Gly Gly Glu Gly Gly Gly Glu Gly Gly Gly Glu Gly Gly Gly
            35                  40                  45

Gly Glu Gly Gly Gly Glu Gly Gly Gly Glu Gly Gly Gly Gly
        50                  55                  60

Glu Gly Gly Gly Glu Gly Gly Gly Glu Gly Gly Gly Gly Glu
65                  70                  75                  80

Gly Gly Gly Gly Glu Gly Gly Gly Glu Gly Gly Gly Gly Glu Gly
                85                  90                  95

Gly Gly Glu Gly Gly Gly Gly Glu Gly Gly Gly Gly Glu Gly Gly
            100                 105                 110

Gly Gly Glu Gly Gly Gly Gly Glu Gly Gly Gly Gly Glu Gly Gly
            115                 120                 125

Gly Glu Gly Gly Gly Gly Glu Gly Gly Gly Gly Glu Gly Gly Gly
        130                 135                 140

Glu Gly Gly Gly Gly Glu Gly Gly Gly Gly Glu Gly Gly Gly Glu
145                 150                 155                 160

Gly Gly Gly Gly Glu Gly Gly Gly Gly Glu Gly Gly Gly Glu Gly
                165                 170                 175

Gly Gly Gly Glu Gly Gly Gly Gly Glu Gly Gly Gly Glu Gly Gly
                180                 185                 190

Gly Gly Glu Gly Gly Gly Gly Glu Gly Gly Gly Gly Glu Gly Gly Gly
```

```
                195                 200                 205
Gly Glu Gly Gly Gly Glu Gly Gly Gly Gly Glu Gly Gly Gly Gly
            210                 215                 220
Glu Gly Gly Gly Gly Glu Gly Gly Gly Glu Gly Gly Gly Gly Glu
225                 230                 235                 240
Gly Gly Gly Gly Glu Gly Gly Gly Glu Gly Gly Gly Gly Glu Gly
            245                 250                 255
Gly Gly Gly Glu Gly Gly Gly Glu Gly Gly Gly Gly Glu Gly Gly
            260                 265                 270
Gly Gly Glu Gly Gly Gly Glu Gly Gly Gly Glu Gly Gly Gly Gly
            275                 280                 285
Gly Glu Gly Gly Gly Glu Gly Gly Gly Glu Gly Gly Gly Gly Gly
            290                 295                 300
Glu Gly Gly Gly Glu Gly Gly Gly Glu Gly Gly Gly Gly Glu
305                 310                 315                 320
Gly Gly Gly Gly Glu Gly Gly Gly Glu Gly Gly Gly Gly Glu Gly
            325                 330                 335
Gly Gly Gly Glu Gly Gly Gly Glu Gly Gly Gly Gly Glu Gly Gly
            340                 345                 350
Gly Gly Glu Gly Gly Gly Glu Gly Gly Gly Gly Glu Gly Gly Gly
            355                 360                 365
Gly Glu Gly Gly Gly Gly Glu
            370                 375
```

<210> SEQ ID NO 21
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(150)
<223> OTHER INFORMATION: This sequence may encompass 1-75 "Gly Asp"
      repeating units wherein some positions may not be present

<400> SEQUENCE: 21

```
Gly Asp Gly Asp Gly Asp Gly Asp Gly Asp Gly Asp Gly Asp Gly Asp
1               5                   10                  15
Gly Asp Gly Asp Gly Asp Gly Asp Gly Asp Gly Asp Gly Asp
            20                  25                  30
Gly Asp Gly Asp Gly Asp Gly Asp Gly Asp Gly Asp Gly Asp
            35                  40                  45
Gly Asp Gly Asp Gly Asp Gly Asp Gly Asp Gly Asp Gly Asp
        50                  55                  60
Gly Asp Gly Asp Gly Asp Gly Asp Gly Asp Gly Asp Gly Asp Gly Asp
65                  70                  75                  80
Gly Asp Gly Asp Gly Asp Gly Asp Gly Asp Gly Asp Gly Asp
            85                  90                  95
Gly Asp Gly Asp Gly Asp Gly Asp Gly Asp Gly Asp Gly Asp
            100                 105                 110
Gly Asp Gly Asp Gly Asp Gly Asp Gly Asp Gly Asp Gly Asp
            115                 120                 125
Gly Asp Gly Asp Gly Asp Gly Asp Gly Asp Gly Asp Gly Asp
            130                 135                 140
Gly Asp Gly Asp Gly Asp
```

145             150

<210> SEQ ID NO 22
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(225)
<223> OTHER INFORMATION: This sequence may encompass 1-75 "Gly Gly Asp"
      repeating units wherein some positions may not be present

<400> SEQUENCE: 22

Gly Gly Asp Gly Gly Asp Gly Gly Asp Gly Gly Asp Gly Gly Asp Gly
1               5                   10                  15

Gly Asp Gly Gly Asp Gly Gly Asp Gly Gly Asp Gly Gly Asp Gly Gly
                20                  25                  30

Asp Gly Gly Asp Gly Gly Asp Gly Gly Asp Gly Gly Asp Gly Gly Asp
            35                  40                  45

Gly Gly Asp Gly Gly Asp Gly Gly Asp Gly Gly Asp Gly Gly Asp Gly
        50                  55                  60

Gly Asp Gly Gly Asp Gly Gly Asp Gly Gly Asp Gly Gly Asp Gly Gly
65                  70                  75                  80

Asp Gly Gly Asp Gly Gly Asp Gly Gly Asp Gly Gly Asp Gly Gly Asp
                85                  90                  95

Gly Gly Asp Gly Gly Asp Gly Gly Asp Gly Gly Asp Gly Gly Asp Gly
                100                 105                 110

Gly Asp Gly Gly Asp Gly Gly Asp Gly Gly Asp Gly Gly Asp Gly Gly
            115                 120                 125

Asp Gly Gly Asp Gly Gly Asp Gly Gly Asp Gly Gly Asp Gly Gly Asp
        130                 135                 140

Gly Gly Asp Gly Gly Asp Gly Gly Asp Gly Gly Asp Gly Gly Asp Gly
145                 150                 155                 160

Gly Asp Gly Gly Asp Gly Gly Asp Gly Gly Asp Gly Gly Asp Gly Gly
                165                 170                 175

Asp Gly Gly Asp Gly Gly Asp Gly Gly Asp Gly Gly Asp Gly Gly Asp
                180                 185                 190

Gly Gly Asp Gly Gly Asp Gly Gly Asp Gly Gly Asp Gly Gly Asp Gly
            195                 200                 205

Gly Asp Gly Gly Asp Gly Gly Asp Gly Gly Asp Gly Gly Asp Gly Gly
        210                 215                 220

Asp
225

<210> SEQ ID NO 23
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(300)
<223> OTHER INFORMATION: This sequence may encompass 1-75 "Gly Gly Gly
      Asp" repeating units wherein some positions may not be present

<400> SEQUENCE: 23

```
Gly Gly Gly Asp Gly Gly Gly Asp Gly Gly Gly Asp Gly Gly Gly Asp
1               5                   10                  15

Gly Gly Gly Asp Gly Gly Gly Asp Gly Gly Gly Asp Gly Gly Gly Asp
            20                  25                  30

Gly Gly Gly Asp Gly Gly Gly Asp Gly Gly Gly Asp Gly Gly Gly Asp
        35                  40                  45

Gly Gly Gly Asp Gly Gly Gly Asp Gly Gly Gly Asp Gly Gly Gly Asp
    50                  55                  60

Gly Gly Gly Asp Gly Gly Gly Asp Gly Gly Gly Asp Gly Gly Gly Asp
65                  70                  75                  80

Gly Gly Gly Asp Gly Gly Gly Asp Gly Gly Gly Asp Gly Gly Gly Asp
            85                  90                  95

Gly Gly Gly Asp Gly Gly Gly Asp Gly Gly Gly Asp Gly Gly Gly Asp
        100                 105                 110

Gly Gly Gly Asp Gly Gly Gly Asp Gly Gly Gly Asp Gly Gly Gly Asp
    115                 120                 125

Gly Gly Gly Asp Gly Gly Gly Asp Gly Gly Gly Asp Gly Gly Gly Asp
130                 135                 140

Gly Gly Gly Asp Gly Gly Gly Asp Gly Gly Gly Asp Gly Gly Gly Asp
145                 150                 155                 160

Gly Gly Gly Asp Gly Gly Gly Asp Gly Gly Gly Asp Gly Gly Gly Asp
            165                 170                 175

Gly Gly Gly Asp Gly Gly Gly Asp Gly Gly Gly Asp Gly Gly Gly Asp
        180                 185                 190

Gly Gly Gly Asp Gly Gly Gly Asp Gly Gly Gly Asp Gly Gly Gly Asp
    195                 200                 205

Gly Gly Gly Asp Gly Gly Gly Asp Gly Gly Gly Asp Gly Gly Gly Asp
210                 215                 220

Gly Gly Gly Asp Gly Gly Gly Asp Gly Gly Gly Asp Gly Gly Gly Asp
225                 230                 235                 240

Gly Gly Gly Asp Gly Gly Gly Asp Gly Gly Gly Asp Gly Gly Gly Asp
            245                 250                 255

Gly Gly Gly Asp Gly Gly Gly Asp Gly Gly Gly Asp Gly Gly Gly Asp
        260                 265                 270

Gly Gly Gly Asp Gly Gly Gly Asp Gly Gly Gly Asp Gly Gly Gly Asp
    275                 280                 285

Gly Gly Gly Asp Gly Gly Gly Asp Gly Gly Gly Asp
290                 295                 300

<210> SEQ ID NO 24
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(375)
<223> OTHER INFORMATION: This sequence may encompass 1-75 "Gly Gly Gly
      Gly Asp" repeating units wherein some positions may not be present

<400> SEQUENCE: 24

Gly Gly Gly Gly Asp Gly Gly Gly Gly Asp Gly Gly Gly Gly Asp Gly
1               5                   10                  15

Gly Gly Gly Asp Gly Gly Gly Gly Asp Gly Gly Gly Gly Asp Gly Gly
            20                  25                  30
```

Gly Gly Asp Gly Gly Gly Gly Asp Gly Gly Gly Gly Asp Gly Gly
                35                  40                  45
Gly Asp Gly Gly Gly Gly Asp Gly Gly Gly Gly Asp Gly Gly Gly
 50                  55                  60
Asp Gly Gly Gly Gly Asp Gly Gly Gly Gly Asp Gly Gly Gly Gly Asp
 65                  70                  75                  80
Gly Gly Gly Gly Asp Gly Gly Gly Gly Asp Gly Gly Gly Gly Asp Gly
                 85                  90                  95
Gly Gly Gly Asp Gly Gly Gly Gly Asp Gly Gly Gly Gly Asp Gly Gly
            100                 105                 110
Gly Gly Asp Gly Gly Gly Gly Asp Gly Gly Gly Gly Asp Gly Gly Gly
        115                 120                 125
Gly Asp Gly Gly Gly Gly Asp Gly Gly Gly Gly Asp Gly Gly Gly Gly
    130                 135                 140
Asp Gly Gly Gly Gly Asp Gly Gly Gly Gly Asp Gly Gly Gly Gly Asp
145                 150                 155                 160
Gly Gly Gly Gly Asp Gly Gly Gly Gly Asp Gly Gly Gly Gly Asp Gly
                165                 170                 175
Gly Gly Gly Asp Gly Gly Gly Gly Asp Gly Gly Gly Gly Asp Gly Gly
            180                 185                 190
Gly Gly Asp Gly Gly Gly Gly Asp Gly Gly Gly Gly Asp Gly Gly Gly
        195                 200                 205
Gly Asp Gly Gly Gly Gly Asp Gly Gly Gly Gly Asp Gly Gly Gly Gly
    210                 215                 220
Asp Gly Gly Gly Gly Asp Gly Gly Gly Gly Asp Gly Gly Gly Gly Asp
225                 230                 235                 240
Gly Gly Gly Gly Asp Gly Gly Gly Gly Asp Gly Gly Gly Gly Asp Gly
                245                 250                 255
Gly Gly Gly Asp Gly Gly Gly Gly Asp Gly Gly Gly Gly Asp Gly Gly
            260                 265                 270
Gly Gly Asp Gly Gly Gly Gly Asp Gly Gly Gly Gly Asp Gly Gly Gly
        275                 280                 285
Gly Asp Gly Gly Gly Gly Asp Gly Gly Gly Gly Asp Gly Gly Gly Gly
    290                 295                 300
Asp Gly Gly Gly Gly Asp Gly Gly Gly Gly Asp Gly Gly Gly Gly Asp
305                 310                 315                 320
Gly Gly Gly Gly Asp Gly Gly Gly Gly Asp Gly Gly Gly Gly Asp Gly
                325                 330                 335
Gly Gly Gly Asp Gly Gly Gly Gly Asp Gly Gly Gly Gly Asp Gly Gly
            340                 345                 350
Gly Gly Asp Gly Gly Gly Gly Asp Gly Gly Gly Gly Asp Gly Gly Gly
        355                 360                 365
Gly Asp Gly Gly Gly Gly Asp
    370                 375

<210> SEQ ID NO 25
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(150)
<223> OTHER INFORMATION: This sequence may encompass 1-75 "Gly Lys"
      repeating units wherein some positions may not be present

<400> SEQUENCE: 25

```
Gly Lys Gly Lys Gly Lys Gly Lys Gly Lys Gly Lys Gly Lys Gly Lys
1               5                   10                  15
Gly Lys Gly Lys Gly Lys Gly Lys Gly Lys Gly Lys Gly Lys Gly Lys
            20                  25                  30
Gly Lys Gly Lys Gly Lys Gly Lys Gly Lys Gly Lys Gly Lys Gly Lys
        35                  40                  45
Gly Lys Gly Lys Gly Lys Gly Lys Gly Lys Gly Lys Gly Lys Gly Lys
    50                  55                  60
Gly Lys Gly Lys Gly Lys Gly Lys Gly Lys Gly Lys Gly Lys Gly Lys
65                  70                  75                  80
Gly Lys Gly Lys Gly Lys Gly Lys Gly Lys Gly Lys Gly Lys Gly Lys
                85                  90                  95
Gly Lys Gly Lys Gly Lys Gly Lys Gly Lys Gly Lys Gly Lys Gly Lys
            100                 105                 110
Gly Lys Gly Lys Gly Lys Gly Lys Gly Lys Gly Lys Gly Lys Gly Lys
        115                 120                 125
Gly Lys Gly Lys Gly Lys Gly Lys Gly Lys Gly Lys Gly Lys Gly Lys
    130                 135                 140
Gly Lys Gly Lys Gly Lys
145             150
```

<210> SEQ ID NO 26
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(225)
<223> OTHER INFORMATION: This sequence may encompass 1-75 "Gly Gly Lys"
      repeating units wherein some positions may not be present

<400> SEQUENCE: 26

```
Gly Gly Lys Gly Gly Lys Gly Gly Lys Gly Gly Lys Gly Gly Lys Gly
1               5                   10                  15
Gly Lys Gly Gly Lys Gly Gly Lys Gly Gly Lys Gly Gly Lys Gly Gly
            20                  25                  30
Lys Gly Gly Lys Gly Gly Lys Gly Gly Lys Gly Gly Lys Gly Gly Lys
        35                  40                  45
Gly Gly Lys Gly Gly Lys Gly Gly Lys Gly Gly Lys Gly Gly Lys Gly
    50                  55                  60
Gly Lys Gly Gly Lys Gly Gly Lys Gly Gly Lys Gly Gly Lys Gly Gly
65                  70                  75                  80
Lys Gly Gly Lys Gly Gly Lys Gly Gly Lys Gly Gly Lys Gly Gly Lys
                85                  90                  95
Gly Gly Lys Gly Gly Lys Gly Gly Lys Gly Gly Lys Gly Gly Lys Gly
            100                 105                 110
Gly Lys Gly Gly Lys Gly Gly Lys Gly Gly Lys Gly Gly Lys Gly Gly
        115                 120                 125
Lys Gly Gly Lys Gly Gly Lys Gly Gly Lys Gly Gly Lys Gly Gly Lys
    130                 135                 140
Gly Gly Lys Gly Gly Lys Gly Gly Lys Gly Gly Lys Gly Gly Lys Gly
145             150                 155                 160
```

Gly Lys Gly Gly Lys Gly Gly Gly Lys Gly Gly Lys Gly
                165                 170                 175

Lys Gly Gly Lys Gly Gly Lys Gly Gly Lys Gly Gly Gly Lys
            180                 185                 190

Gly Gly Lys Gly Gly Lys Gly Gly Lys Gly Gly Gly Lys Gly
        195                 200                 205

Gly Lys Gly Lys Gly Gly Lys Gly Gly Gly Lys Gly Gly
    210                 215                 220

Lys
225

<210> SEQ ID NO 27
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(300)
<223> OTHER INFORMATION: This sequence may encompass 1-75 "Gly Gly Gly
      Lys" repeating units wherein some positions may not be present

<400> SEQUENCE: 27

Gly Gly Gly Lys Gly Gly Gly Lys Gly Gly Lys Gly Gly Gly Lys
1               5                   10                  15

Gly Gly Gly Lys Gly Gly Gly Lys Gly Gly Lys Gly Gly Gly Lys
            20                  25                  30

Gly Gly Gly Lys Gly Gly Gly Lys Gly Gly Lys Gly Gly Gly Lys
        35                  40                  45

Gly Gly Gly Lys Gly Gly Gly Lys Gly Gly Lys Gly Gly Gly Lys
    50                  55                  60

Gly Gly Gly Lys Gly Gly Gly Lys Gly Gly Lys Gly Gly Gly Lys
65                  70                  75                  80

Gly Gly Gly Lys Gly Gly Gly Lys Gly Gly Lys Gly Gly Gly Lys
                85                  90                  95

Gly Gly Gly Lys Gly Gly Gly Lys Gly Gly Lys Gly Gly Gly Lys
            100                 105                 110

Gly Gly Gly Lys Gly Gly Gly Lys Gly Gly Lys Gly Gly Gly Lys
        115                 120                 125

Gly Gly Gly Lys Gly Gly Gly Lys Gly Gly Lys Gly Gly Gly Lys
    130                 135                 140

Gly Gly Gly Lys Gly Gly Gly Lys Gly Gly Lys Gly Gly Gly Lys
145                 150                 155                 160

Gly Gly Gly Lys Gly Gly Gly Lys Gly Gly Lys Gly Gly Gly Lys
                165                 170                 175

Gly Gly Gly Lys Gly Gly Gly Lys Gly Gly Lys Gly Gly Gly Lys
            180                 185                 190

Gly Gly Gly Lys Gly Gly Gly Lys Gly Gly Lys Gly Gly Gly Lys
        195                 200                 205

Gly Gly Gly Lys Gly Gly Gly Lys Gly Gly Lys Gly Gly Gly Lys
    210                 215                 220

Gly Gly Gly Lys Gly Gly Gly Lys Gly Gly Lys Gly Gly Gly Lys
225                 230                 235                 240

Gly Gly Gly Lys Gly Gly Gly Lys Gly Gly Lys Gly Gly Gly Lys
                245                 250                 255

```
Gly Gly Gly Lys Gly Gly Gly Lys Gly Gly Gly Lys Gly Gly Gly Lys
                260                 265                 270

Gly Gly Gly Lys Gly Gly Gly Lys Gly Gly Gly Lys Gly Gly Gly Lys
        275                 280                 285

Gly Gly Gly Lys Gly Gly Gly Lys Gly Gly Gly Lys
    290                 295                 300

<210> SEQ ID NO 28
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(375)
<223> OTHER INFORMATION: This sequence may encompass 1-75 "Gly Gly Gly
      Gly Lys" repeating units wherein some positions may not be present

<400> SEQUENCE: 28

Gly Gly Gly Gly Lys Gly Gly Gly Gly Lys Gly Gly Gly Gly Lys Gly
1               5                   10                  15

Gly Gly Gly Lys Gly Gly Gly Gly Lys Gly Gly Gly Gly Lys Gly Gly
            20                  25                  30

Gly Gly Lys Gly Gly Gly Gly Lys Gly Gly Gly Gly Lys Gly Gly Gly
        35                  40                  45

Gly Lys Gly Gly Gly Gly Lys Gly Gly Gly Gly Lys Gly Gly Gly Gly
    50                  55                  60

Lys Gly Gly Gly Gly Lys Gly Gly Gly Gly Lys Gly Gly Gly Gly Lys
65                  70                  75                  80

Gly Gly Gly Gly Lys Gly Gly Gly Gly Lys Gly Gly Gly Gly Lys Gly
                85                  90                  95

Gly Gly Gly Lys Gly Gly Gly Gly Lys Gly Gly Gly Gly Lys Gly Gly
            100                 105                 110

Gly Gly Lys Gly Gly Gly Gly Lys Gly Gly Gly Gly Lys Gly Gly Gly
        115                 120                 125

Gly Lys Gly Gly Gly Gly Lys Gly Gly Gly Gly Lys Gly Gly Gly Gly
    130                 135                 140

Lys Gly Gly Gly Gly Lys Gly Gly Gly Gly Lys Gly Gly Gly Gly Lys
145                 150                 155                 160

Gly Gly Gly Gly Lys Gly Gly Gly Gly Lys Gly Gly Gly Gly Lys Gly
                165                 170                 175

Gly Gly Gly Lys Gly Gly Gly Gly Lys Gly Gly Gly Gly Lys Gly Gly
            180                 185                 190

Gly Gly Lys Gly Gly Gly Gly Lys Gly Gly Gly Gly Lys Gly Gly Gly
        195                 200                 205

Gly Lys Gly Gly Gly Gly Lys Gly Gly Gly Gly Lys Gly Gly Gly Gly
    210                 215                 220

Lys Gly Gly Gly Gly Lys Gly Gly Gly Gly Lys Gly Gly Gly Gly Lys
225                 230                 235                 240

Gly Gly Gly Gly Lys Gly Gly Gly Gly Lys Gly Gly Gly Gly Lys Gly
                245                 250                 255

Gly Gly Gly Lys Gly Gly Gly Gly Lys Gly Gly Gly Gly Lys Gly Gly
            260                 265                 270

Gly Gly Lys Gly Gly Gly Gly Lys Gly Gly Gly Gly Lys Gly Gly Gly
        275                 280                 285
```

Gly Lys Gly Gly Gly Lys Gly Gly Gly Lys Gly Gly Gly
        290                 295                 300

Lys Gly Gly Gly Lys Gly Gly Gly Lys Gly Gly Gly Lys
305                 310                 315                 320

Gly Gly Gly Lys Gly Gly Gly Lys Gly Gly Gly Lys Gly
            325                 330                 335

Gly Gly Lys Gly Gly Gly Lys Gly Gly Gly Lys Gly Gly
        340                 345                 350

Gly Gly Lys Gly Gly Gly Lys Gly Gly Gly Lys Gly Gly
            355                 360                 365

Gly Lys Gly Gly Gly Gly Lys
    370                 375

<210> SEQ ID NO 29
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(150)
<223> OTHER INFORMATION: This sequence may encompass 1-75 "Gly Arg"
      repeating units wherein some positions may not be present

<400> SEQUENCE: 29

Gly Arg Gly Arg Gly Arg Gly Arg Gly Arg Gly Arg Gly Arg Gly Arg
1               5                   10                  15

Gly Arg Gly Arg Gly Arg Gly Arg Gly Arg Gly Arg Gly Arg Gly Arg
            20                  25                  30

Gly Arg Gly Arg Gly Arg Gly Arg Gly Arg Gly Arg Gly Arg Gly Arg
        35                  40                  45

Gly Arg Gly Arg Gly Arg Gly Arg Gly Arg Gly Arg Gly Arg Gly Arg
    50                  55                  60

Gly Arg Gly Arg Gly Arg Gly Arg Gly Arg Gly Arg Gly Arg Gly Arg
65                  70                  75                  80

Gly Arg Gly Arg Gly Arg Gly Arg Gly Arg Gly Arg Gly Arg Gly Arg
                85                  90                  95

Gly Arg Gly Arg Gly Arg Gly Arg Gly Arg Gly Arg Gly Arg Gly Arg
            100                 105                 110

Gly Arg Gly Arg Gly Arg Gly Arg Gly Arg Gly Arg Gly Arg Gly Arg
        115                 120                 125

Gly Arg Gly Arg Gly Arg Gly Arg Gly Arg Gly Arg Gly Arg Gly Arg
    130                 135                 140

Gly Arg Gly Arg Gly Arg
145                 150

<210> SEQ ID NO 30
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(225)
<223> OTHER INFORMATION: This sequence may encompass 1-75 "Gly Gly Arg"
      repeating units wherein some positions may not be present

<400> SEQUENCE: 30

```
Gly Gly Arg Gly Gly Arg Gly Gly Arg Gly Gly Arg Gly
1               5                   10                  15

Gly Arg Gly Gly Arg Gly Gly Arg Gly Gly Arg Gly Gly
            20                  25                  30

Arg Gly Gly Arg Gly Gly Arg Gly Gly Arg Gly Gly Arg
            35                  40                  45

Gly Gly Arg Gly Gly Arg Gly Gly Arg Gly Gly Arg Gly
    50                  55                  60

Gly Arg Gly Gly Arg Gly Gly Arg Gly Gly Arg Gly Gly
65                  70                  75                  80

Arg Gly Gly Arg Gly Gly Arg Gly Gly Arg Gly Gly Arg
            85                  90                  95

Gly Gly Arg Gly Gly Arg Gly Gly Arg Gly Gly Arg Gly
            100                 105                 110

Gly Arg Gly Gly Arg Gly Gly Arg Gly Gly Arg Gly Gly
            115                 120                 125

Arg Gly Gly Arg Gly Gly Arg Gly Gly Arg Gly Gly Arg
    130                 135                 140

Gly Gly Arg Gly Gly Arg Gly Gly Arg Gly Gly Arg Gly
145                 150                 155                 160

Gly Arg Gly Gly Arg Gly Gly Arg Gly Gly Arg Gly Gly
            165                 170                 175

Arg Gly Gly Arg Gly Gly Arg Gly Gly Arg Gly Gly Arg
            180                 185                 190

Gly Gly Arg Gly Gly Arg Gly Gly Arg Gly Gly Arg Gly
            195                 200                 205

Gly Arg Gly Gly Arg Gly Gly Arg Gly Gly Arg Gly Gly
    210                 215                 220

Arg
225

<210> SEQ ID NO 31
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(300)
<223> OTHER INFORMATION: This sequence may encompass 1-75 "Gly Gly Gly
      Arg" repeating units wherein some positions may not be present

<400> SEQUENCE: 31

Gly Gly Gly Arg Gly Gly Gly Arg Gly Gly Gly Arg Gly Gly Gly Arg
1               5                   10                  15

Gly Gly Gly Arg Gly Gly Gly Arg Gly Gly Gly Arg Gly Gly Gly Arg
            20                  25                  30

Gly Gly Gly Arg Gly Gly Gly Arg Gly Gly Gly Arg Gly Gly Gly Arg
        35                  40                  45

Gly Gly Gly Arg Gly Gly Gly Arg Gly Gly Gly Arg Gly Gly Gly Arg
    50                  55                  60

Gly Gly Gly Arg Gly Gly Gly Arg Gly Gly Gly Arg Gly Gly Gly Arg
65                  70                  75                  80

Gly Gly Gly Arg Gly Gly Gly Arg Gly Gly Gly Arg Gly Gly Gly Arg
            85                  90                  95
```

```
Gly Gly Gly Arg Gly Gly Gly Arg Gly Gly Gly Arg
            100                 105             110

Gly Gly Gly Arg Gly Gly Gly Arg Gly Gly Gly Arg
            115                 120             125

Gly Gly Gly Arg Gly Gly Gly Arg Gly Gly Gly Arg
            130                 135             140

Gly Gly Gly Arg Gly Gly Gly Arg Gly Gly Gly Arg
145                     150                 155             160

Gly Gly Gly Arg Gly Gly Gly Arg Gly Gly Gly Arg
            165                 170             175

Gly Gly Gly Arg Gly Gly Gly Arg Gly Gly Gly Arg
            180                 185             190

Gly Gly Gly Arg Gly Gly Gly Arg Gly Gly Gly Arg
            195                 200             205

Gly Gly Gly Arg Gly Gly Gly Arg Gly Gly Gly Arg
            210                 215             220

Gly Gly Gly Arg Gly Gly Gly Arg Gly Gly Gly Arg
225                     230                 235             240

Gly Gly Gly Arg Gly Gly Gly Arg Gly Gly Gly Arg
            245                 250             255

Gly Gly Gly Arg Gly Gly Gly Arg Gly Gly Gly Arg
            260                 265             270

Gly Gly Gly Arg Gly Gly Gly Arg Gly Gly Gly Arg
            275                 280             285

Gly Gly Gly Arg Gly Gly Gly Gly Gly Arg
            290                 295             300

<210> SEQ ID NO 32
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(375)
<223> OTHER INFORMATION: This sequence may encompass 1-75 "Gly Gly Gly
      Gly Arg" repeating units wherein some positions may not be present

<400> SEQUENCE: 32

Gly Gly Gly Gly Arg Gly Gly Gly Gly Arg Gly Gly Gly Gly Arg Gly
1               5                   10                  15

Gly Gly Arg Gly Gly Gly Gly Arg Gly Gly Gly Gly Arg Gly Gly
            20                  25                  30

Gly Gly Arg Gly Gly Gly Gly Arg Gly Gly Gly Gly Arg Gly Gly
            35                  40                  45

Gly Arg Gly Gly Gly Gly Arg Gly Gly Gly Gly Arg Gly Gly Gly Gly
            50                  55                  60

Arg Gly Gly Gly Gly Arg Gly Gly Gly Gly Arg Gly Gly Gly Gly Arg
65                  70                  75                  80

Gly Gly Gly Gly Arg Gly Gly Gly Gly Arg Gly Gly Gly Gly Arg Gly
                85                  90                  95

Gly Gly Gly Arg Gly Gly Gly Gly Arg Gly Gly Gly Gly Arg Gly Gly
            100                 105             110

Gly Gly Arg Gly Gly Gly Gly Arg Gly Gly Gly Gly Arg Gly Gly Gly
            115                 120             125
```

Gly Arg Gly Gly Gly Arg Gly Gly Gly Arg Gly Gly Gly
    130             135             140

Arg Gly Gly Gly Arg Gly Gly Gly Arg Gly Gly Gly Arg
145             150             155             160

Gly Gly Gly Gly Arg Gly Gly Gly Arg Gly Gly Gly Arg Gly
            165             170             175

Gly Gly Gly Arg Gly Gly Gly Arg Gly Gly Gly Arg Gly Gly
        180             185             190

Gly Gly Arg Gly Gly Gly Arg Gly Gly Gly Arg Gly Gly Gly
    195             200             205

Gly Arg Gly Gly Gly Arg Gly Gly Gly Arg Gly Gly Gly
    210             215             220

Arg Gly Gly Gly Arg Gly Gly Gly Arg Gly Gly Gly Arg
225             230             235             240

Gly Gly Gly Gly Arg Gly Gly Gly Arg Gly Gly Gly Arg Gly
            245             250             255

Gly Gly Gly Arg Gly Gly Gly Arg Gly Gly Gly Arg Gly Gly
        260             265             270

Gly Gly Arg Gly Gly Gly Arg Gly Gly Gly Arg Gly Gly Gly
    275             280             285

Gly Arg Gly Gly Gly Arg Gly Gly Gly Arg Gly Gly Gly
    290             295             300

Arg Gly Gly Gly Arg Gly Gly Gly Arg Gly Gly Gly Arg
305             310             315             320

Gly Gly Gly Gly Arg Gly Gly Gly Arg Gly Gly Gly Arg Gly
            325             330             335

Gly Gly Gly Arg Gly Gly Gly Arg Gly Gly Gly Arg Gly Gly
        340             345             350

Gly Gly Arg Gly Gly Gly Arg Gly Gly Gly Arg Gly Gly Gly
    355             360             365

Gly Arg Gly Gly Gly Arg
    370             375

<210> SEQ ID NO 33
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(375)
<223> OTHER INFORMATION: This sequence may encompass 1-75 "Glu Ala Ala
      Ala Lys" repeating units wherein some positions may not be present

<400> SEQUENCE: 33

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys Glu Ala
            20                  25                  30

Ala Ala Lys Glu Ala Ala Ala Lys Glu Ala Ala Ala Lys Glu Ala Ala
        35                  40                  45

Ala Lys Glu Ala Ala Ala Lys Glu Ala Ala Ala Lys Glu Ala Ala Ala
    50                  55                  60

Lys Glu Ala Ala Ala Lys Glu Ala Ala Ala Lys Glu Ala Ala Ala Lys
65                  70                  75                  80

Glu Ala Ala Ala Lys Glu Ala Ala Ala Lys Glu Ala Ala Ala Lys Glu
                85                  90                  95

Ala Ala Ala Lys Glu Ala Ala Ala Lys Glu Ala Ala Ala Lys Glu Ala
            100                 105                 110

Ala Ala Lys Glu Ala Ala Ala Lys Glu Ala Ala Ala Lys Glu Ala Ala
        115                 120                 125

Ala Lys Glu Ala Ala Ala Lys Glu Ala Ala Ala Lys Glu Ala Ala Ala
    130                 135                 140

Lys Glu Ala Ala Ala Lys Glu Ala Ala Ala Lys Glu Ala Ala Ala Lys
145                 150                 155                 160

Glu Ala Ala Ala Lys Glu Ala Ala Ala Lys Glu Ala Ala Ala Lys Glu
                165                 170                 175

Ala Ala Ala Lys Glu Ala Ala Ala Lys Glu Ala Ala Ala Lys Glu Ala
            180                 185                 190

Ala Ala Lys Glu Ala Ala Ala Lys Glu Ala Ala Ala Lys Glu Ala Ala
        195                 200                 205

Ala Lys Glu Ala Ala Ala Lys Glu Ala Ala Ala Lys Glu Ala Ala Ala
    210                 215                 220

Lys Glu Ala Ala Ala Lys Glu Ala Ala Ala Lys Glu Ala Ala Ala Lys
225                 230                 235                 240

Glu Ala Ala Ala Lys Glu Ala Ala Ala Lys Glu Ala Ala Ala Lys Glu
                245                 250                 255

Ala Ala Ala Lys Glu Ala Ala Ala Lys Glu Ala Ala Ala Lys Glu Ala
            260                 265                 270

Ala Ala Lys Glu Ala Ala Ala Lys Glu Ala Ala Ala Lys Glu Ala Ala
        275                 280                 285

Ala Lys Glu Ala Ala Ala Lys Glu Ala Ala Ala Lys Glu Ala Ala Ala
    290                 295                 300

Lys Glu Ala Ala Ala Lys Glu Ala Ala Ala Lys Glu Ala Ala Ala Lys
305                 310                 315                 320

Glu Ala Ala Ala Lys Glu Ala Ala Ala Lys Glu Ala Ala Ala Lys Glu
                325                 330                 335

Ala Ala Ala Lys Glu Ala Ala Ala Lys Glu Ala Ala Ala Lys Glu Ala
            340                 345                 350

Ala Ala Lys Glu Ala Ala Ala Lys Glu Ala Ala Ala Lys Glu Ala Ala
        355                 360                 365

Ala Lys Glu Ala Ala Ala Lys
    370                 375

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Ala Ala Ala Lys Glu Ala Ala Ala Lys Glu Ala Ala Ala Lys
1               5                   10                  15

<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Glu Ala Ala Ala Lys Glu Ala Ala Ala Lys Glu Ala Ala Ala Lys Glu
1               5                   10                  15

Ala Ala Ala Lys
            20

<210> SEQ ID NO 36
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Glu Ala Ala Ala Lys Glu Ala Ala Lys Glu Ala Ala Ala Lys Glu
1               5                   10                  15

Ala Ala Ala Lys Glu Ala Ala Ala Lys
            20                  25

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Gly Gly Ser
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 38

His His His His His His
1               5

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 39

His His His His His His His His His His
1               5                   10

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Ile Ala Glu Tyr
1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Ala Gln Tyr
1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Ser Lys Tyr
1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Val Ala Lys His
1
```